(12) United States Patent
Buschmann et al.

(10) Patent No.: US 8,859,535 B2
(45) Date of Patent: Oct. 14, 2014

(54) HYDROXY SUBSTITUTED ISOQUINOLINONE DERIVATIVES

(75) Inventors: Nicole Buschmann, Basel (CH); Pascal Furet, Thann (FR); Philipp Holzer, Sissach (CH); Joerg Kallen, Basel (CH); Keiichi Masuya, Basel (CH); Stefan Stutz, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/127,155

(22) PCT Filed: Jun. 19, 2012

(86) PCT No.: PCT/EP2012/061752
§ 371 (c)(1),
(2), (4) Date: Dec. 17, 2013

(87) PCT Pub. No.: WO2012/175520
PCT Pub. Date: Dec. 27, 2012

(65) Prior Publication Data
US 2014/0135306 A1    May 15, 2014

Related U.S. Application Data

(60) Provisional application No. 61/498,802, filed on Jun. 20, 2011.

(51) Int. Cl.
| | |
|---|---|
| C07D 409/10 | (2006.01) |
| A61K 31/472 | (2006.01) |
| A61K 31/4725 | (2006.01) |
| C07D 217/24 | (2006.01) |
| C07D 401/04 | (2006.01) |
| C07D 401/10 | (2006.01) |
| C07D 401/14 | (2006.01) |
| C07D 405/10 | (2006.01) |
| C07D 405/14 | (2006.01) |
| C07D 491/08 | (2006.01) |
| C07D 493/08 | (2006.01) |
| C07D 451/14 | (2006.01) |
| C07D 413/08 | (2006.01) |
| C07D 451/02 | (2006.01) |

(52) U.S. Cl.
CPC .......... *A61K 31/4725* (2013.01); *C07D 405/10* (2013.01); *C07D 491/08* (2013.01); *C07D 401/10* (2013.01); *C07D 401/14* (2013.01); *C07D 493/08* (2013.01); *C07D 409/10* (2013.01); *A61K 31/472* (2013.01); *C07D 451/14* (2013.01); *C07D 401/04* (2013.01); *C07D 413/08* (2013.01); *C07D 451/02* (2013.01); *C07D 405/14* (2013.01); *C07D 217/24* (2013.01)
USPC .................. 514/210.18; 514/309; 514/210.21; 514/304; 514/305; 546/141; 546/126; 546/133

(58) Field of Classification Search
None
See application file for complete search history.

(56) References Cited

FOREIGN PATENT DOCUMENTS

| | | |
|---|---|---|
| WO | 2005117876 | 12/2005 |
| WO | 2006097337 | 9/2006 |
| WO | 2011076786 | 6/2011 |

*Primary Examiner* — Janet L Andres
*Assistant Examiner* — Timothy R Rozof
(74) *Attorney, Agent, or Firm* — Scott W. Reid

(57) ABSTRACT

The invention relates to compounds of formula (I): as defined in the application. Such compounds are suitable for the treatment of a disorder or disease which is mediated by the activity of MDM2 and/or MDM4, or variants thereof.

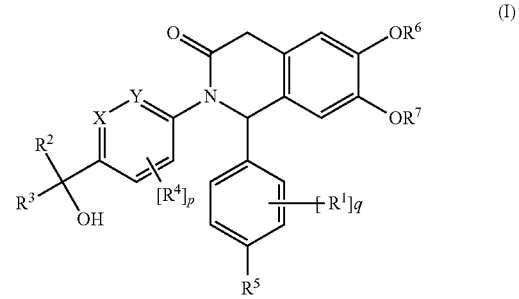

18 Claims, No Drawings

HYDROXY SUBSTITUTED ISOQUINOLINONE DERIVATIVES

The present invention relates to hydroxy substituted isoquinolinone derivatives capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor supressor. "MDM2" (originally from the oncogene "murine double minute 2") refers both to the name of the gene as well as the protein encoded by that gene. MDM2 protein functions both as an E3 ubiquitin ligase that recognizes the N-terminal transactivation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to cancers such as tumors, leukemias or other proliferative diseases.

WO2008/034039 discloses tetrahydroisoquinoline compounds as ligands binding to the HDM2 protein. WO 03/095625 discloses benzodiazepine compounds that bind to HDM2 and interfere with its interaction with proteins such as p53.

There is a need for new drugs that are capable of interfering with the interaction between p53 and MDM2 or especially oncogenic variants thereof and that thus allow p53 to exert its beneficial effect against uncontrolled tumor growth, allowing it e.g. to accumulate, to arrest the cell cycle and/or to cause apoptosis of affected cells.

It has now been found that a novel class of hydroxy substituted isoquinolinone derivatives show potent inhibition of the MDM2/p53 interaction (this term including in particular Hdm2/p53 interaction) and the corresponding compounds thus represent a novel type of compound that are useful in the treatment of a number of disorders, such as proliferative diseases, especially cancer. The invention relates therefore to these compounds as drugs as well as to the other inventive embodiments indicated herein.

The compounds of the invention also show inhibition of the MDM4/p53 interaction (this term including in particular Hdm4/p53 interaction).

Particularly interesting compounds of the invention herein are highly potent in the p53-Hdm2 inhibition (TR-FRET) Assay described herein. Compounds of particular interest possess favourable pharmacokinetic properties. They provide an optimum balance of several pharmaceutically advantageous properties including potency, desirable molecular weight, lipophilicity and solubility. They should be non-toxic and demonstrate few side-effects. Furthermore, the ideal drug candidate will exist in a physical form that is stable, non-hygroscopic and easily formulated.

The invention therefore provides a compound of the formula (I):

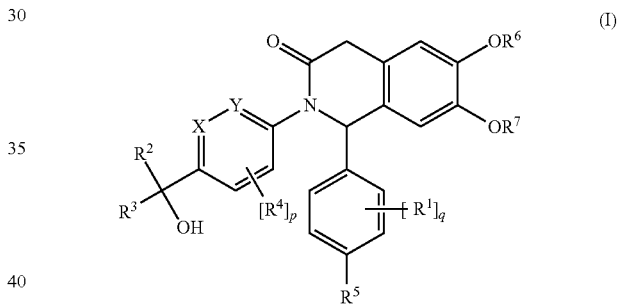

wherein
either X is N and Y is CH, or X is CH and Y is N, or both X and Y are CH;
$R^1$ is halogen or cyano;
q is 0, 1 or 2;
$R^2$ is selected from
 phenyl, wherein said phenyl is optionally substituted with from 1 to 4 substituents independently selected from $(C_1-C_4)$alkyl, $(C_1-C_4)$alkoxy-, $(C_1-C_4)$alkylC(O)—, $(C_1-C_4)$alkoxyC(O)—, halo, CN, OH, —$(CH_2)_v$—N$(R^8)$C(O)—$(C_1-C_7)$alkyl and $R^8(R^9)$N—C(O)—, wherein v is 0, 1 or 2,
 $(CH_2)_b$—N$(R^8)$C(O)—$(C_1-C_7)$alkyl, b is 0, 1 or 2,
 $(C_1-C_7)$alkyl, wherein said $(C_1-C_7)$alkyl is optionally substituted with from 1 to 4 substituents independently selected from hydroxy, halo, CN and OH,
 $(C_3-C_{10})$cycloalkyl$^1$, wherein said $(C_3-C_{10})$cycloalkyl$^1$ is optionally substituted with from 1 to 4 substituents independently selected from halo, =O, —$(C_1-C_7)$alkyl, $(C_1-C_4)$alkoxy-, $(C_1-C_4)$alkylC(O)—, $(C_1-C_4)$alkoxyC(O)—, HO—C(O)—, halo-C(O)—, $R^8(R^9)$N—C(O)—, or heterocyclyl$^1$, said heterocyclyl$^1$ being optionally substituted by 1 or 2 —$(C_1-C_4)$alkyl substituents,
 heteroaryl$^1$, wherein said heteroaryl$^1$ is optionally substituted with from 1 to 4 substituents independently selected from $(C_1-C_4)$alkyl, $(C_1-C_4)$alkoxy-, $(C_1-C_4)$alkylC(O)—, $(C_1-C_4)$alkoxyC(O)—, halo, CN, OH, —$(CH_2)_v$—N(R$^8$)C(O)—$(C_1-C_7)$alkyl and R$^8$(R$^9$)N—C(O)—, heterocyclyl$^3$, wherein said heterocyclyl$^3$ is optionally substituted by 1, 2, 3 or 4 $(C_1-C_3)$alkyl substituents, and is optionally substituted at 1 or 2 ring C atoms with =O, and wherein when heterocyclyl$^3$ contains a S atom in the ring, said S atom may optionally be substituted with 1 or 2 =O substituents, and heterocyclyl$^2$, wherein said heterocyclyl$^2$ is optionally substituted at a ring N atom with a substituent selected from:

$(C_1-C_7)$alkyl, $(C_1-C_4)$alkoxy-, $(C_1-C_4)$alkylC(O)—, or $(C_1-C_4)$alkoxyC(O)—, wherein said $(C_1-C_7)$alkyl, $(C_1-C_4)$alkoxy-, $(C_1-C_4)$alkylC(O)— and $(C_1-C_4)$alkoxyC(O)— are each optionally substituted at alkyl by from 1 to 4 substituents independently selected from halo, —CN, OH, $(C_1-C_4)$alkoxy-, $(C_1-C_4)$alkylC(O)—, $(C_1-C_4)$alkoxyC(O)— and $(C_1-C_4)$alkyl-C(O)—O—, HC(O)—, halo-C(O)—, R$^8$(R$^9$)N—C(O)—, $(C_3-C_7)$cycloalkyl-C(O)—, $(C_1-C_4)$alkylS(O)$_t$—, OH, CN, =O, heterocyclyl$^1$, said heterocyclyl$^1$ being optionally substituted by 1 or 2 $(C_1-C_4)$alkyl substituents, $(C_4-C_6)$cycloalkyl$^2$, said $(C_4-C_6)$cycloalkyl$^2$ being optionally substituted with one or two substituents independently selected from halo, $(C_1-C_4)$alkyl, =O, OH, and $(CH_2)_r$-phenyl, wherein r is 1 or 2, and wherein said heterocyclyl$^2$ is optionally further substituted at a ring C atom with 1, 2 or 3 $(C_1-C_3)$alkyl substituents and wherein said heterocyclyl$^2$ is optionally substituted at 1 or 2 ring C atoms with =O, or optionally substituted at a ring S atom with 1 or 2 =O;

R$^3$ is $(C_1-C_3)$alkyl or H, wherein said $(C_1-C_3)$alkyl is optionally substituted with from one to 3 substituents independently selected from halo and OH;

or R$^2$ and R$^3$ together with the carbon atom to which they are attached form:

a 4, 5 or 6 membered fully saturated carbocyclic ring, wherein said carbocyclic ring is optionally substituted with from 1 to 4 substituents independently selected from halo, =O, —$(C_1-C_3)$alkyl, $(C_1-C_3)$alkoxy-, $(C_1-C_3)$alkylC(O)—, $(C_1-C_3)$alkoxyC(O)—, or heterocyclic ring A, comprising 3 carbon atoms and one nitrogen atom, wherein the arrow indicates the point of attachment to the rest of the molecule,

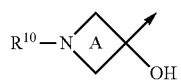

wherein R$^{10}$ is H, $(C_1-C_4)$alkylC(O)—, $(C_1-C_4)$alkoxyC(O)—, R$^8$(R$^9$)N—C(O)—, $(C_3-C_7)$cycloalkyl-C(O)—, $(C_1-C_4)$alkylS(O)$_p$, $(C_1-C_7)$alkyl, (said $(C_1-C_7)$alkyl being optionally substituted by from 1 to 4 substituents independently selected from halo and OH);

t is 0, 1 or 2;

R$^4$ is halo, methyl or methoxy;

p is 0, 1 or 2;

R$^5$ is halo or cyano;

R$^6$ is $(C_1-C_7)$alkyl, wherein optionally one, several, or all of the hydrogen atoms are replaced with deuterium, and wherein said $(C_1-C_7)$alkyl is optionally substituted with from 1 to 4 halo substituents, $(C_1-C_4)$alkoxy$(C_1-C_4)$alkyl-, heteroaryl$^1$$(C_1-C_7)$alkyl-, heterocyclyl$^1$$(C_1-C_7)$alkyl-, R$^8$(R$^9$)N—C(O)—$(CH_2)_n$—, R$^8$(R$^9$)N—$(CH_2)_n$—, n is 1 or 2;

R$^7$ is $(C_1-C_7)$alkyl wherein optionally one, several, or all of the hydrogen atoms are replaced with deuterium;

R$^8$ is H or $(C_1-C_4)$alkyl;

R$^9$ is H or $(C_1-C_4)$alkyl;

$(C_3-C_{10})$cycloalkyl$^1$ is a fully saturated ring or ring system containing 3, 4, 5, 6, 7, 8, 9 or 10 ring carbon atoms, which can comprise fused and/or bridged rings;

$(C_4-C_6)$cycloalkyl$^2$ is a fully saturated monocyclic ring containing 4, 5 or 6 ring carbon atoms;

heterocyclyl$^1$ is a 4, 5 or 6 membered saturated or partially unsaturated monocyclic group comprising ring carbon atoms and 1 or 2 ring heteroatoms independently selected from N, O and S;

heteroaryl$^1$ is a 5 or 6 membered fully unsaturated or partially unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;

heterocyclyl$^2$ is a 4, 5, 6, 7, 8 or 9 membered fully saturated or partially unsaturated monocyclic, bicyclic or multicyclic group, which can comprise fused and/or bridged rings, and which comprises 1 ring N atom and optionally 1 ring S atom or optionally 1 ring O atom;

heterocyclyl$^3$ is a 4, 5, 6, 7, 8 or 9 membered fully saturated or partially unsaturated monocyclic, bicyclic or multicyclic group, which can comprise fused and/or bridged rings, and which comprises 1 ring S heteroatom or 1 ring O heteroatom;

or a salt thereof, with the proviso that the compound of formula (I) is not 7-((R)-sec-Butoxy)-1-(4-chloro-phenyl)-2-[4-(1-hydroxy-ethyl)-phenyl]-6-methoxy-1,4-dihydro-2H-isoquinolin-3-one:

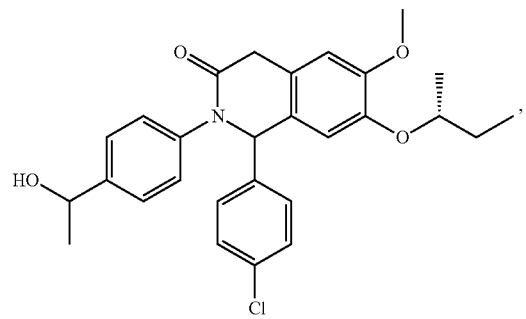 [SMILES: CC[C@@H](C)Oc1cc2c(cc1OC)CC(=O)N(c1ccc(C(C)O)cc1)C2c1ccc(Cl)cc1]

Unless specified otherwise, the term "compounds of the present invention" refers to compounds of formula (I) and subformulae thereof (add other additional genus structures as necessary), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates), as well as N-oxides of the compounds of formula (I).

Various embodiments of the invention are described herein. It will be recognized that features specified in each embodiment may be combined with other specified features to provide further embodiments.

In an embodiment of the invention there is provided a compound of formula (I) wherein both X and Y are CH.

Another embodiment provides a compound of formula (I) wherein q is 0.

In another embodiment, $R^2$ is selected from
  phenyl, wherein said phenyl is optionally substituted with from 1 to 4 substituents independently selected from $(C_1-C_4)$alkyl, $(C_1-C_4)$alkoxy-, $(C_1-C_4)$alkylC(O)—, $(C_1-C_4)$alkoxyC(O)—, halo, CN, OH, —$(CH_2)_v$—N($R^8$)C(O)—$(C_1-C_7)$alkyl and $R^8(R^9)$N—C(O)—, wherein v is 0, 1 or 2,
  —$(CH_2)_b$—N($R^8$)C(O)—$(C_1-C_7)$alkyl, b is 0, 1 or 2,
  $(C_3-C_{10})$cycloalkyl$^1$, wherein said $(C_3-C_{10})$cycloalkyl$^1$ is optionally substituted with from 1 to 4 substituents independently selected from halo, =O, —$(C_1-C_7)$alkyl, $(C_1-C_4)$alkoxy-, $(C_1-C_4)$alkylC(O)—, $(C_1-C_4)$alkoxyC(O)—, HO—C(O)—, halo-C(O)—, $R^8(R^9)$N—C(O)—, or heterocyclyl$^1$, said heterocyclyl$^1$ being optionally substituted by 1 or 2 —$(C_1-C_4)$alkyl substituents,
  heteroaryl$^1$, wherein said heteroaryl$^1$ is optionally substituted with from 1 to 4 substituents independently selected from $(C_1-C_4)$alkyl, $(C_1-C_4)$alkoxy-, $(C_1-C_4)$alkylC(O)—, $(C_1-C_4)$alkoxyC(O)—, halo, CN, OH, —$(CH_2)_v$—N($R^8$)C(O)—$(C_1-C_7)$alkyl and $R^8(R^9)$N—C(O)—,
  heterocyclyl$^3$, wherein said heterocyclyl$^3$ is optionally substituted by 1, 2, 3 or 4 $(C_1-C_3)$alkyl substituents, and is optionally substituted at 1 or 2 ring C atoms with =O, and wherein when heterocyclyl$^3$ contains a S atom in the ring, said S atom may optionally be substituted with 1 or 2 =O substituents,
and
  heterocyclyl$^2$, wherein said heterocyclyl$^2$ is optionally substituted at a ring N atom with a substituent selected from:
    $(C_1-C_7)$alkyl, $(C_1-C_4)$alkoxy-, $(C_1-C_4)$alkylC(O)—, or $(C_1-C_4)$alkoxyC(O)—,
  wherein said $(C_1-C_7)$alkyl, $(C_1-C_4)$alkoxy-, $(C_1-C_4)$alkylC(O)— and $(C_1-C_4)$alkoxyC(O)— are each optionally substituted at alkyl by from 1 to 4 substituents independently selected from halo, —CN, OH, $(C_1-C_4)$alkoxy-, $(C_1-C_4)$alkylC(O)—, $(C_1-C_4)$alkoxyC(O)— and $(C_1-C_4)$alkyl-C(O)—O—,
    HC(O)—, halo-C(O)—, $R^8(R^9)$N—C(O)—, $(C_3-C_7)$cycloalkyl-C(O)—, $(C_1-C_4)$alkylS(O)$_t$—, OH, CN, =O,
    heterocyclyl$^1$, said heterocyclyl$^1$ being optionally substituted by 1 or 2 $(C_1-C_4)$alkyl substituents,
    $(C_4-C_6)$cycloalkyl$^2$, said $(C_4-C_6)$cycloalkyl$^2$ being optionally substituted with one or two substituents independently selected from halo, $(C_1-C_4)$alkyl, =O, OH, and —$(CH_2)_r$-phenyl, wherein r is 1 or 2,
  and wherein said heterocyclyl$^2$ is optionally further substituted at a ring C atom with 1, 2 or 3 $(C_1-C_3)$alkyl substituents and wherein said heterocyclyl$^2$ is optionally substituted at 1 or 2 ring C atoms with =O, or optionally substituted at a ring S atom with 1 or 2 =O;
In another embodiment $R^2$ is phenyl, wherein said phenyl is optionally substituted with from 1 to 4 substituents independently selected from $(C_1-C_4)$alkoxy-, halo and —$(CH_2)_v$—N($R^8$)C(O)—$(C_1-C_7)$alkyl, in particular wherein v is 0.

In another embodiment, $R^2$ is —$(CH_2)$—N($R^8$)C(O)—$(C_1-C_4)$alkyl.

In another embodiment $R^2$ is $(C_1-C_2)$alkyl, wherein said $(C_1-C_2)$alkyl is optionally substituted with a hydroxy substituent.

In another embodiment $R^2$ is $(C_3-C_{10})$cycloalkyl$^1$, wherein said $(C_3-C_{10})$cycloalkyl$^1$ is optionally substituted with from 1 to 4 substituents independently selected from halo, =O, $(C_1-C_4)$alkoxyC(O)—, HO—C(O)—, $R^8(R^9)$N—C(O)—.

In another embodiment $R^2$ is heteroaryl$^1$, wherein said heteroaryl$^1$ is optionally substituted with from 1 substituent selected from methyl and methoxy.

In another embodiment $R^2$ is heterocyclyl$^2$ or heterocyclyl$^3$ as defined in any of the embodiments herein, with optional substituents as defined herein.

In a further embodiment $R^2$ is heterocyclyl$^2$, wherein said heterocyclyl$^2$ is optionally substituted at a ring N atom with a substituent selected from:
    $(C_1-C_4)$alkyl, $(C_1-C_4)$alkylC(O)— or $(C_1-C_4)$alkoxyC(O)—,
  wherein said $(C_1-C_7)$alkyl, $(C_1-C_4)$alkylC(O)— and $(C_1-C_4)$alkoxyC(O)— are each optionally substituted at alkyl by from 1 to 4 substituents independently selected from halo, —CN, OH, $(C_1-C_4)$alkylC(O)—, $(C_1-C_4)$alkoxyC(O)— and $(C_1-C_4)$alkyl-C(O)—O—;
    HC(O)—, halo-C(O)—, $R^8(R^9)$N—C(O)—, $(C_3-C_7)$cycloalkyl-C(O)—, $(C_1-C_4)$alkylS(O)$_t$—, =O;
    heterocyclyl$^1$, said heterocyclyl$^1$ being optionally substituted by 1 or 2 $(C_1-C_4)$alkyl substituents;
    $(C_4-C_6)$cycloalkyl$^2$, said $(C_4-C_6)$cycloalkyl$^2$ being optionally substituted with one or two substituents independently selected from halo, $(C_1-C_4)$alkyl or =O;
    —$(CH_2)_r$-phenyl, wherein r is 1,
    and wherein said heterocyclyl$^2$ is optionally further substituted at a ring C atom with 1, 2 or 3 $(C_1-C_3)$alkyl substituents,
    and wherein said heterocyclyl$^2$ is optionally substituted at 1 or 2 ring C atoms with =O, or optionally substituted at a ring S atom with 1 or 2 =O;
or $R^2$ is heterocyclyl$^3$, wherein said heterocyclyl$^3$ is optionally substituted by 1, 2, 3 or 4 $(C_1-C_3)$alkyl substituents, and wherein when heterocyclyl$^3$ contains a S atom in the ring, said S atom may optionally be substituted with 1 or 2 =O substituents.

In a further embodiment $R^2$ is heterocyclyl$^2$, wherein said heterocyclyl$^2$ is piperidinyl, azetidinyl, aza-bicyclooctyl, aza-bicyclononyl or oxa-aza-bicyclononyl, optionally substituted with:
    $CH_3$—C(O)—, said $CH_3$—C(O)—, being optionally substituted with 1, 2 or 3 fluoro substituents, CN, or OH,
    $(C_1-C_4)$alkyl, said $(C_1-C_4)$alkyl optionally substituted with 1, 2 or 3 fluoro, 1 or 2 OH, wherein $(C_1-C_4)$alkyl is in particular t-butyl, isopropyl, n-propyl, ethyl or methyl,
    piperidinyl, said piperidinyl being optionally substituted with methyl or ethyl, or
    t-butoxy-C(O)—, =O, $CH_3$—NH—C(O)—, $CH_3$—N($CH_3$)—C(O)—, $NH_2$—C(O)—, $(C_1-C_2)$alkylS(O)$_2$—, methoxy-C(O)—, cyclopropyl-C(O)—, isopropoxy-C(O)—, isopropyl-NH—C(O)—, HC(O)—, FC(O)—, $CH_3$—C(O)—O—$CH_2$—C(O)—, oxetanyl, cyclobutanyl, tetrahydrofuranyl or cyclohexyl,
or $R^2$ is heterocyclyl$^3$, wherein said heterocyclyl$^3$ is
    tetrahydropyranyl, said tetrahydropyranyl being optionally substituted by 1, 2, 3 or 4 methyl, tetrahydrofuranyl, oxabicycloheptyl, dioxohydrothiopyranyl, oxohydrothiopyranyl, oxabicyclooctyl, oxabicyclononyl, dioxo-thia-bicyclooctyl, dioxo-thia-bicyclononyl or oxa-bicyclooctyl;

In a particular embodiment $R^2$ is piperidinyl, preferably piperidin-4-yl, substituted at N by $CH_3$—C(O)—, said $CH_3$—C(O)—, being optionally substituted with 1, 2 or 3 fluoro substituents, $(C_1-C_4)$alkyl, said $(C_1-C_4)$alkyl optionally substituted with 1, 2 or 3 fluoro, 1 or 2 OH, wherein $(C_1-C_4)$alkyl is in particular t-butyl, isopropyl, n-propyl, ethyl or methyl, or t-butoxy-C(O)—, =O, $CH_3$—NH—C(O)—, $CH_3$—N($CH_3$)—C(O)— or $NH_2$—C(O)—, $(C_1-C_2)$alkylS$(O)_2$—, methoxy-C(O)—, cyclopropyl-C(O)—, isopropoxy-C(O)—, isopropyl-NH—C(O)—, HC(O)—, FC(O)—, $CH_3$—C(O)—O—$CH_2$—C(O)—, oxetanyl, cyclobutanyl, tetrahydrofuranyl or cyclohexyl.

In a more particular embodiment $R^2$ is piperidinyl, preferably piperidin-4-yl, substituted at N by oxetanyl.

In another particular embodiment $R^2$ is tetrahydropyranyl.

In another embodiment there is provided a compound of formula (I) wherein $R^3$ is $(C_1-C_3)$alkyl, in particular methyl.

Another embodiment provides a compound of formula (I) wherein $R^2$ and $R^3$ together with the carbon atom to which they are attached form:

a 4 or 5 membered fully saturated carbocyclic ring, or
heterocyclic ring A, wherein $R^{10}$ is H, t-butoxy-C(O)—, $CH_3$—C(O)—, $CH_3$—O—C(O)—, $CH_3$—NH—C(O)—, $CH_3$—N($CH_3$)—C(O)—, $NH_2$—C(O)—, cyclopropyl-C(O)— or $(C_1-C_2)$alkylS$(O)_2$—.

Another embodiment provides a compound of formula (I) wherein $R^5$ is chloro.

Another embodiment provides a compound of formula (I) wherein p is 0.

Another embodiment provides a compound of formula (I) wherein $R^6$ is $(C_1-C_7)$alkyl, wherein optionally one, several, or all of the hydrogen atoms are replaced with deuterium, and wherein said $(C_1-C_7)$alkyl is optionally substituted with from 1 to 4 halo substituents. In particular, $R^6$ is methyl, wherein optionally one, several, or all of the hydrogen atoms are replaced with deuterium. More particularly $R^6$ is methyl.

Another embodiment provides a compound of formula (I) wherein $R^7$ is $(C_1-C_7)$alkyl, and in particular $(C_1-C_3)$alkyl. More particularly, $R^7$ is isopropyl.

Another embodiment provides a compound of formula (I) wherein $R^8$ is H or methyl.

Another embodiment provides a compound of formula (I) wherein $R^9$ is H or $(C_1-C_4)$alkyl, particularly H or methyl.

In a further embodiment, the stereochemistry of the compound of formula (I) is as shown in formula (Ia) below:

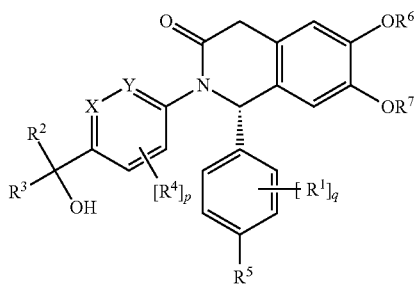

In another embodiment, the chirality of the stereocentre as shown in formula (II) (when $R^2$ and $R^3$ are not the same group) is S, wherein * marks the point of attachment to the rest of the molecule.

In another particular embodiment of the invention there is provided a compound of formula (I) as described herein, with the proviso that $R^2$ is not:

$(C_1-C_7)$alkyl, wherein said $(C_1-C_7)$alkyl is optionally substituted with from 1 to 4 substituents independently selected from hydroxy, halo, CN and OH.

In another particular embodiment of the invention there is provided a compound of formula (I) as described herein, wherein $R^3$ is methyl, and wherein $R^2$ is as described herein with the proviso that $R^2$ is not:

$(C_1-C_7)$alkyl, wherein said $(C_1-C_7)$alkyl is optionally substituted with from 1 to 4 substituents independently selected from hydroxy, halo, CN and OH.

Another particular embodiment of the invention is directed to a compound of formula (I) as described herein, with the proviso that $R^2$ is not:

$(C_1-C_7)$alkyl, wherein said $(C_1-C_7)$alkyl is optionally substituted with from 1 to 4 substituents independently selected from hydroxy, halo, CN and OH, when $R^3$ is H.

In another particular embodiment of the invention there is provided a compound of formula (I) as described herein, with the proviso that $R^2$ is not:

$(C_1-C_7)$alkyl, wherein said $(C_1-C_7)$alkyl is optionally substituted with from 1 to 4 substituents independently selected from hydroxy, halo, CN and OH, when $R^3$ is H, and wherein $R^7$ is, in particular, isopropyl.

For purposes of interpreting this specification, terms used in the singular will also include the plural and vice versa.

In the above definitions, halo means fluoro, chloro or bromo. Particularly fluoro or chloro, especially fluoro.

Alkyl, and alkoxy groups, containing the requisite number of carbon atoms, can be unbranched or branched. Examples of alkyl include, but are not limited to, methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

=O means an oxo substituent. For example, a heterocyclyl ring substituted by an =O substituent means there is an oxo substituent directly on ring.

Specific preferred compounds according to the invention are those listed in the Examples section below.

In another embodiment there is provided a compound of formula (I), or a salt thereof, preferably a pharmaceutically acceptable salt thereof, selected from the following list:

1: (S)-1-(4-Chloro-phenyl)-2-{4-[1-hydroxy-1-(3-methoxy-phenyl)-ethyl]-phenyl}-7-isopropoxy-6-methoxy-1,4-dihydro-2H-isoquinolin-3-one 2: (S)-1-(4-Chloro-phenyl)-2-{4-[hydroxy-(3-methoxy-phenyl)-methyl]-phenyl}-7-isopropoxy-6-methoxy-1,4-dihydro-2H-isoquinolin-3-one 3: (S)-1-(4-Chloro-phenyl)-2-[4-(1-hydroxy-1-methyl-propyl)-phenyl]-7-isopropoxy-6-methoxy-1,4-dihydro-2H-isoquinolin-3-one 4: (S)-1-(4-Chloro-phenyl)-2-{4-[hydroxy-(4-methoxy-phenyl)-methyl]-phenyl}-7-isopropoxy-6-methoxy-1,4-dihydro-2H-isoquinolin-3-one 5: (S)-1-(4-Chloro-phenyl)-2-{4-[1-hydroxy-1-(4-methoxy-phenyl)-ethyl]-phenyl}-7-isopropoxy-6-methoxy-1,4-dihydro-2H-isoquinolin-3-one 6: (S)-1-(4-Chloro-phenyl)-2-{4-[1-(4-fluoro-phenyl)-1-hydroxy-ethyl]-phenyl}-7-isopropoxy-6-methoxy-1,4-dihydro-2H-isoquinolin-3-one 7: (S)-1-(4-Chloro-phenyl)-7-isopropoxy-6-methoxy-2-{4-[2,2,2-trifluoro-1-hydroxy-1-(4-methoxy-phenyl)-ethyl]-phenyl}-1,4-dihydro-2H-isoquinolin-3-one 8: (S)-1-(4-Chloro-phenyl)-2-[4-(cyclohexyl-hydroxy-methyl)-phenyl]-7-isopropoxy-6-methoxy-1,4-dihydro-2H-isoquinolin-3-one 9: (S)-1-(4-Chloro-phenyl)-2-[6-(1-hydroxy-1-methyl-propyl)-pyridin-3-yl]-7-isopropoxy-6-methoxy-1,4-dihydro-2H-isoquinolin-3-one 10: (S)-1-(4-Chloro-phenyl)-2-[5-(1-hydroxy-1-methyl-propyl)-pyridin-2-yl]-7-isopropoxy-6-methoxy-1,4-dihydro-2H-isoquinolin-3-one 11: (S)-1-(4-Chloro-phenyl)-2-[4-(1-hydroxy-1-methyl-ethyl)-phenyl]-7-isopropoxy-6-methoxy-1,4-dihydro-2H-isoquinolin-3-one 12: (S)-1-(4-Chloro-phenyl)-2-[5-(1-hydroxy-1-pyridin-4-yl-ethyl)-pyridin-2-yl]-7-isopropoxy-6-methoxy-1,4-dihydro-2H-isoquinolin-3-one 13: (S)-1-(4-Chloro-phenyl)-2-{4-[1-hydroxy-1-(1-methyl-1H-imidazol-4-yl)-ethyl]-phenyl}-7-isopropoxy-6-methoxy-1,4-dihydro-2H-isoquinolin-3-one 14: (S)-1-(4-Chloro-phenyl)-2-{4-[1-hydroxy-1-(1-methyl-1H-pyrazol-3-yl)-ethyl]-phenyl}-7-isopropoxy-6-methoxy-1,4-dihydro-2H-isoquinolin-3-one 15: (S)-1-(4-Chloro-phenyl)-2-[5-(1-hydroxy-1-pyridin-3-yl-ethyl)-pyridin-2-yl]-7-isopropoxy-6-methoxy-1,4-dihydro-2H-isoquinolin-3-one 16: (S)-1-(4-Chloro-phenyl)-2-[4-(1-hydroxy-1-pyridin-3-yl-ethyl)-phenyl]-7-isopropoxy-6-methoxy-1,4-dihydro-2H-isoquinolin-3-one 17: (S)-1-(4-Chloro-phenyl)-2-[4-(1-hydroxy-1-pyridin-4-yl-ethyl)-phenyl]-7-isopropoxy-6-methoxy-1,4-dihydro-2H-isoquinolin-3-one 18: (S)-1-(4-Chloro-phenyl)-2-[4-(1-hydroxy-1-pyridin-2-yl-ethyl)-phenyl]-7-isopropoxy-6-methoxy-1,4-dihydro-2H-isoquinolin-3-one 19: (S)-1-(4-Chloro-phenyl)-2-{4-[1-(3,4-difluoro-phenyl)-1-hydroxy-ethyl]-phenyl}-7-isopropoxy-6-methoxy-1,4-dihydro-2H-isoquinolin-3-one 20: (S)-1-(4-Chloro-phenyl)-2-[2-fluoro-4-(1-hydroxy-1-pyridin-3-yl-ethyl)-phenyl]-7-isopropoxy-6-methoxy-1,4-dihydro-2H-isoquinolin-3-one 21: N-[4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-phenyl]-acetamide 22: (S)-1-(4-Chloro-phenyl)-2-{4-[1-(3,5-dimethoxy-phenyl)-1-hydroxy-ethyl]-phenyl}-7-isopropoxy-6-methoxy-1,4-dihydro-2H-isoquinolin-3-one 23: (S)-1-(4-Chloro-phenyl)-2-{4-[1-hydroxy-1-(6-methoxy-pyridin-3-yl)-ethyl]-phenyl}-7-isopropoxy-6-methoxy-1,4-dihydro-2H-isoquinolin-3-one 24: N-[4-(1-{5-[(S)-1-(4-Chloro-phenyl)-7-isopropoxy-6-methoxy-3-oxo-3,4-dihydro-1H-isoquinolin-2-yl]-pyridin-2-yl}-1-hydroxy-ethyl)-phenyl]-acetamide 25: N-[4-(1-{6-[(S)-1-(4-Chloro-phenyl)-7-isopropoxy-6-methoxy-3-oxo-3,4-dihydro-1H-isoquinolin-2-yl]-pyridin-3-yl}-1-hydroxy-ethyl)-phenyl]-acetamide 26: N-[4-((S)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-phenyl]-acetamide 27: N-[4-((R)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-phenyl]-acetamide 28: N-[4-(1-{4-[(S)-1-(4-Chloro-phenyl)-7-isopropoxy-6-methoxy-3-oxo-3,4-dihydro-1H-isoquinolin-2-yl]-2-fluoro-phenyl}-1-hydroxy-ethyl)-phenyl]-acetamide 29: N-(2-{4-[(S)-1-(4-Chloro-phenyl)-7-isopropoxy-6-methoxy-3-oxo-3,4-dihydro-1H-isoquinolin-2-yl]-phenyl}-2-hydroxy-propyl)-acetamide 30: (S)-1-(4-Chloro-phenyl)-2-{4-[1-hydroxy-1-(tetrahydro-pyran-4-yl)-ethyl]-phenyl}-7-isopropoxy-6-methoxy-1,4-dihydro-2H-isoquinolin-3-one 31: (S)-2-{4-[1-(1-Acetyl-piperidin-4-yl)-1-hydroxy-ethyl]-phenyl}-1-(4-chloro-phenyl)-7-isopropoxy-6-methoxy-1,4-dihydro-2H-isoquinolin-3-one 32: (S)-1-(4-Chloro-phenyl)-2-{4-[(S)-1-hydroxy-1-(tetrahydro-pyran-4-yl)-ethyl]-phenyl}-7-isopropoxy-6-methoxy-1,4-dihydro-2H-isoquinolin-3-one 33: (S)-1-(4-Chloro-phenyl)-2-{4-[(R)-1-hydroxy-1-(tetrahydro-pyran-4-yl)-ethyl]-phenyl}-7-isopropoxy-6-methoxy-1,4-dihydro-2H-isoquinolin-3-one 34: (S)-1-(4-Chloro-phenyl)-2-{4-[1-hydroxy-1-(1-methyl-piperidin-4-yl)-ethyl]-phenyl}-7-isopropoxy-6-methoxy-1,4-dihydro-2H-isoquinolin-3-one 35: (S)-1-(4-Chloro-phenyl)-2-{3-fluoro-4-[1-hydroxy-1-(tetrahydro-pyran-4-yl)-ethyl]-phenyl}-7-isopropoxy-6-methoxy-1,4-dihydro-2H-isoquinolin-3-one 36: (S)-1-(4-Chloro-phenyl)-2-{4-[1-hydroxy-1-(tetrahydro-pyran-4-yl)-ethyl]-2-methoxy-phenyl}-7-isopropoxy-6-methoxy-1,4-dihydro-2H-isoquinolin-3-one 37: (S)-1-(4-Chloro-phenyl)-2-{5-[1-hydroxy-1-(tetrahydro-pyran-4-yl)-ethyl]-pyridin-2-yl}-7-isopropoxy-6-methoxy-1,4-dihydro-2H-isoquinolin-3-one 38: (S)-1-(4-Chloro-phenyl)-2-{3-fluoro-4-[(R)-1-hydroxy-1-(tetrahydro-pyran-4-yl)-ethyl]-phenyl}-7-isopropoxy-6-methoxy-1,4-dihydro-2H-isoquinolin-3-one 39: (S)-1-(4-Chloro-phenyl)-2-{3-fluoro-4-[(S)-1-hydroxy-1-(tetrahydro-pyran-4-yl)-ethyl]-phenyl}-7-isopropoxy-6-methoxy-1,4-dihydro-2H-isoquinolin-3-one 40: (S)-1-(4-Chloro-phenyl)-2-{4-[hydroxy-(tetrahydro-pyran-4-yl)-methyl]-phenyl}-7-isopropoxy-6-methoxy-1,4-dihydro-2H-isoquinolin-3-one 41: (S)-1-(4-Chloro-phenyl)-2-[4-(1,3-dihydroxy-1-methyl-propyl)-phenyl]-7-isopropoxy-6-methoxy-1,4-dihydro-2H-isoquinolin-3-one 42: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid tert-butyl ester 43: (S)-1-(4-Chloro-phenyl)-2-[4-(1-hydroxy-1-piperidin-4-yl-ethyl)-phenyl]-7-isopropoxy-6-methoxy-1,4-dihydro-2H-isoquinolin-3-one 44: (S)-1-(4-Chloro-phenyl)-2-{4-[1,2-dihydroxy-1-(4-methoxy-phenyl)-ethyl]-phenyl}-7-isopropoxy-6-methoxy-1,4-dihydro-2H-isoquinolin-3-one 45: (S)-1-(4-Chloro-phenyl)-2-{4-[1-(4,4-difluoro-cyclohexyl)-1-hydroxy-ethyl]-phenyl}-7-isopropoxy-6-methoxy-1,4-dihydro-2H-isoquinolin-3-one 46: (S)-1-(4-Chloro-phenyl)-2-{4-[(R)-1-(4,4-difluoro-cyclohexyl)-1-hydroxy-ethyl]-phenyl}-7-isopropoxy-6-methoxy-1,4-dihydro-2H-isoquinolin-3-one 47: (S)-1-(4-Chloro-phenyl)-2-{4-[(S)-1-(4,4-difluoro-cyclohexyl)-1-hydroxy-ethyl]-phenyl}-7-isopropoxy-6-methoxy-1,4-dihydro-2H-isoquinolin-3-one 48: (S)-1-(4-Chloro-phenyl)-2-{4-[1-hydroxy-1-(tetrahydro-furan-3-yl)-ethyl]-phenyl}-7-isopropoxy-6-methoxy-1,4-dihydro-2H-isoquinolin-3-one 49: (S)-1-(4-Chloro-phenyl)-2-{4-[1-hydroxy-1-(2-oxo-piperidin-4-yl)-ethyl]-phenyl}-7-isopropoxy-6-methoxy-1,4-dihydro-2H-isoquinolin-3-one 50: (S)-1-(4-Chloro-phenyl)-2-[4-(1-hydroxy-cyclopentyl)-phenyl]-7-isopropoxy-6-methoxy-1,4-dihydro-2H-isoquinolin-3-one 51: (S)-1-(4-Chloro-phenyl)-2-[4-(1-hydroxy-cyclobutyl)-phenyl]-7-isopropoxy-6-methoxy-1,4-dihydro-2H-isoquinolin-3-one 52: (S)-2-{4-[1-(1-Acetyl-piperidin-4-yl)-1-hydroxy-ethyl]-phenyl}-7-((R)-sec-butoxy)-1-(4-chloro-phenyl)-6-methoxy-1,4-dihydro-2H-isoquinolin-3-one 53: (S)-2-{4-[(S)-1-(1-Acetyl-piperidin-4-yl)-1-hydroxy-ethyl]-phenyl}-1-(4-chloro-phenyl)-7-isopropoxy-6-methoxy-1,4-dihydro-2H-isoquinolin-3-one 54: (S)-2-{4-[(R)-1-(1-Acetyl-piperidin-4-yl)-1-hydroxy-ethyl]-phenyl}-1-(4-chloro-phenyl)-7-isopropoxy-6-methoxy-1,4-dihydro-2H-isoquinolin-3-one 55: 3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid tert-butyl ester 56: (S)-1-(4-Chloro-phenyl)-2-[4-(3-hydroxy-azetidin-3-yl)-phenyl]-7-isopropoxy-6-methoxy-1,4-dihydro-2H-isoquinolin-3-one 57: (S)-2-[4-(1-Acetyl-3-hydroxy-azetidin-3-yl)-phenyl]-1-(4-chloro-phenyl)-7-isopropoxy-6-methoxy-1,4-dihydro-2H-isoquinolin-3-one 58: 3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid methyl ester 59: 3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid dimethylamide 60: 3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid methylamide 61: (S)-1-(4-Chloro-phenyl)-2-[4-(1-cyclopropanecarbonyl-3-hydroxy-azetidin-3-yl)-phenyl]-7-isopropoxy-6-methoxy-1,4-dihydro-2H-isoquinolin-3-one 62: (S)-1-(4-Chloro-phenyl)-2-[4-(3-hydroxy-1-methanesulfonyl-azetidin-3-yl)-phenyl]-7-isopropoxy-6-methoxy-1,4-dihydro-2H-isoquinolin-3-one 63: (S)-1-(4-Chloro-phenyl)-2-[4-(1-cyclohexyl-1-hydroxy-ethyl)-phenyl]-7-isopropoxy-6-methoxy-1,4-dihydro-2H-isoquinolin-3-one 64: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-azetidine-1-carboxylic acid tert-butyl ester 65: (S)-2-[4-(1-Azetidin-3-yl-1-hydroxy-ethyl)-phenyl]-1-(4-chloro-phenyl)-7-isopropoxy-6-methoxy-1,4-dihydro-2H-isoquinolin-3-one 66: (S)-2-{4-[1-(1-Acetyl-azetidin-3-yl)-1-hydroxy-ethyl]-phenyl}-1-(4-chloro-phenyl)-7-isopropoxy-6-methoxy-1,4-dihydro-2H-isoquinolin-3-one 67: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-azetidine-1-carboxylic acid methylamide 68: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-azetidine-1-carboxylic acid dimethylamide 69: (S)-1-(4-Chloro-phenyl)-2-(4-{1-hydroxy-1-[1-(3,3,3-trifluoro-propyl)-azetidin-3-yl]-ethyl}-phenyl)-7-isopropoxy-6-methoxy-1,4-dihydro-2H-isoquinolin-3-one 70: (S)-1-(4-Chloro-phenyl)-2-{4-[1-hydroxy-1-(1-methyl-azetidin-3-yl)-ethyl]-phenyl}-7-isopropoxy-6-methoxy-1,4-dihydro-2H-isoquinolin-3-one 71: (S)-1-(4-Chloro-phenyl)-2-{4-[1-(1-ethyl-azetidin-3-yl)-1-hydroxy-ethyl]-phenyl}-7-isopropoxy-6-methoxy-1,4-dihydro-2H-isoquinolin-3-one 72: (S)-1-(4-Chloro-phenyl)-2-{4-[1-hydroxy-1-(1-isopropyl-azetidin-3-yl)-ethyl]-phenyl}-7-isopropoxy-6-methoxy-1,4-dihydro-2H-isoquinolin-3-one 73: (S)-1-(4-Chloro-phenyl)-2-{4-[1-hydroxy-1-(1-methanesulfonyl-azetidin-3-yl)-ethyl]-phenyl}-7-isopropoxy-6-methoxy-1,4-dihydro-2H-isoquinolin-3-one 74: (S)-1-(4-Chloro-phenyl)-2-(4-{1-hydroxy-1-[1-(2,2,2-trifluoro-ethyl)-azetidin-3-yl]-ethyl}-phenyl)-7-isopropoxy-6-methoxy-1,4-dihydro-2H-isoquinolin-3-one 75: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid amide 76: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid methyl ester 77: (S)-1-(4-Chloro-phenyl)-2-(4-{1-hydroxy-1-[1-(2,2,2-trifluoro-ethyl)-piperidin-4-yl]-ethyl}-phenyl)-7-isopropoxy-6-methoxy-1,4-dihydro-2H-isoquinolin-3-one 78: (S)-1-(4-Chloro-phenyl)-2-{4-[1-hydroxy-1-(1-isopropyl-piperidin-4-yl)-ethyl]-phenyl}-7-isopropoxy-6-methoxy-1,4-dihydro-2H-isoquinolin-3-one 79: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid methylamide 80: S)-1-(4-Chloro-phenyl)-2-{4-[1-(1-cyclopropanecarbonyl-piperidin-4-yl)-1-hydroxy-ethyl]-phenyl}-7-isopropoxy-6-methoxy-1,4-dihydro-2H-isoquinolin-3-one 81: (S)-1-(4-Chloro-phenyl)-2-{4-[1-hydroxy-1-(1-methanesulfonyl-piperidin-4-yl)-ethyl]-phenyl}-7-isopropoxy-6-methoxy-1,4-dihydro-2H-isoquinolin-3-one 82: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid dimethylamide 83: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid isopropyl ester 84: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid isopropylamide 85: (S)-1-(4-Chloro-phenyl)-2-{4-[1-(1-ethyl-piperidin-4-yl)-1-hydroxy-ethyl]-phenyl}-7-isopropoxy-6-methoxy-1,4-dihydro-2H-isoquinolin-3-one 86: S)-1-(4-Chloro-phenyl)-2-(4-{1-hydroxy-1-[1-(3,3,3-trifluoro-propyl)-piperidin-4-yl]-ethyl}-phenyl)-7-isopropoxy-6-methoxy-1,4-dihydro-2H-isoquinolin-3-one 87: (S)-1-(4-Chloro-phenyl)-2-(4-{1-[1-(2,2-difluoroacetyl)-piperidin-4-yl]-1-hydroxy-ethyl}-phenyl)-7-isopropoxy-6-methoxy-1,4-dihydro-2H-isoquinolin-3-one 88: 3-[4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidin-1-yl]-3-oxo-propionitrile 89: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde 90: 4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbonyl fluoride 91: Acetic acid 2-[4-(1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-piperidin-1-yl]-2-oxo-ethyl ester 92: (S)-1-(4-Chloro-phenyl)-2-(4-{1-hydroxy-1-[1-(2-hydroxy-acetyl)-piperidin-4-yl]-ethyl}-phenyl)-7-isopropoxy-6-methoxy-1,4-dihydro-2H-isoquinolin-3-one 93: (S)-1-(4-Chloro-phenyl)-2-(4-{1-hydroxy-1-[1-(2-hydroxy-ethyl)-piperidin-4-yl]-ethyl}-phenyl)-7-isopropoxy-6-methoxy-1,4-dihydro-2H-isoquinolin-3-one 94: (S)-1-(4-Chloro-phenyl)-2-{4-[(S)-1-hydroxy-1-(1-methyl-piperidin-4-yl)-ethyl]-phenyl}-7-isopropoxy-6-methoxy-1,4-dihydro-2H-isoquinolin-3-one 95: (S)-1-(4-Chloro-phenyl)-2-{4-[(R)-1-hydroxy-1-(1-methyl-piperidin-4-yl)-ethyl]-phenyl}-7-isopropoxy-6-methoxy-1,4-dihydro-2H-isoquinolin-3-one 96: (S)-1-(4-Chloro-phenyl)-2-{4-[1-hydroxy-1-(1-oxetan-3-yl-piperidin-4-yl)-ethyl]-phenyl}-7-isopropoxy-6-methoxy-1,4-dihydro-2H-isoquinolin-3-one 97: (S)-1-(4-Chloro-phenyl)-2-{4-[1-(1-cyclobutyl-piperidin-4-yl)-1-hydroxy-ethyl]-phenyl}-7-isopropoxy-6-methoxy-1,4-dihydro-2H-isoquinolin-3-one 98: (S)-1-(4-Chloro-phenyl)-2-(4-{1-hydroxy-1-[1-(tetrahydro-pyran-4-yl)-azetidin-3-yl]-ethyl}-phenyl)-7-isopropoxy-6-methoxy-1,4-dihydro-2H-isoquinolin-3-one 99: (S)-1-(4-Chloro-phenyl)-2-{4-[1-(1-cyclohexyl-azetidin-3-yl)-1-hydroxy-ethyl]-phenyl}-7-isopropoxy-6-methoxy-1,4-dihydro-2H-isoquinolin-3-one 100: (S)-1-(4-Chloro-phenyl)-2-(4-{1-[1-(1-ethyl-piperidin-4-yl)-azetidin-3-yl]-1-hydroxy-ethyl}-phenyl)-7-isopropoxy-6-methoxy-1,4-dihydro-2H-isoquinolin-3-one 101: (S)-1-(4-Chloro-phenyl)-2-(4-{1-hydroxy-1-[1-(1-methyl-piperidin-4-yl)-azetidin-3-yl]-ethyl}-phenyl)-7-isopropoxy-6-methoxy-1,4-dihydro-2H-isoquinolin-3-one 102: (S)-1-(4-Chloro-phenyl)-2-(4-{1-hydroxy-1-[1-(2-hydroxy-acetyl)-azetidin-3-yl]-ethyl}-phenyl)-7-isopropoxy-6-methoxy-1,4-dihydro-2H-isoquinolin-3-one 103: (S)-1-(4-Chloro-phenyl)-2-{4-[1-hydroxy-1-(1-oxetan-3-yl-azetidin-3-yl)-ethyl]-phenyl}-7-isopropoxy-6-methoxy-1,4-dihydro-2H-isoquinolin-3-one 104: (S)-2-{4-[1-(8-Acetyl-8-aza-bicyclo[3.2.1]oct-3-yl)-1-hydroxy-ethyl]-phenyl}-1-(4-chloro-phenyl)-7-isopropoxy-6-methoxy-1,4-dihydro-2H-isoquinolin-3-one 105: (S)-1-(4-Chloro-phenyl)-2-{4-[1-hydroxy-1-(8-methyl-8-aza-bicyclo[3.2.1]oct-3-yl)-ethyl]-phenyl}-7-isopropoxy-6-methoxy-1,4-dihydro-2H-isoquinolin-3-one 106: (S)-1-(4-Chloro-phenyl)-2-(4-{1-hydroxy-1-[8-(2,2,2-trifluoro-ethyl)-8-aza-bicyclo[3.2.1]oct-3-yl]-ethyl}-phenyl)-7-isopropoxy-6-methoxy-1,4-dihydro-2H-isoquinolin-3-one 107: (S)-1-(4-Chloro-phenyl)-2-{4-[1-hydroxy-1-(8-methanesulfonyl-8-aza-bicyclo[3.2.1]oct-3-yl)-ethyl]-phenyl}-7-isopropoxy-6-methoxy-1,4-dihydro-2H-isoquinolin-3-one 108: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carboxylic acid dimethylamide 109: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carboxylic acid methylamide 110: (S)-1-(4-Chloro-phenyl)-2-{4-[1-hydroxy-1-(8-isopropyl-8-aza-bicyclo[3.2.1]oct-3-yl)-ethyl]-phenyl}-7-isopropoxy-6-methoxy-1,4-dihydro-2H-isoquinolin-3-one 111: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carbaldehyde 112: (S)-1-(4-Chloro-phenyl)-2-{4-[1-(8-ethyl-8-aza-bicyclo[3.2.1]oct-3-yl)-1-hydroxy-ethyl]-phenyl}-7-isopropoxy-6-methoxy-1,4-dihydro-2H-isoquinolin-3-one 113: (S)-1-(4-Chloro-phenyl)-2-(4-{1-hydroxy-1-[8-(2-hydroxy-ethyl)-8-aza-bicyclo[3.2.1]oct-3-yl]-ethyl}-phenyl)-7-isopropoxy-6-methoxy-1,4-dihydro-2H-isoquinolin-3-one 114: (S)-1-(4-Chloro-phenyl)-2-(4-{1-hydroxy-1-[8-(2-hydroxy-acetyl)-8-aza-bicyclo[3.2.1]oct-3-yl]-ethyl}-phenyl)-7-isopropoxy-6-methoxy-1,4-dihydro-2H-isoquinolin-3-one 115: (S)-1-(4-Chloro-phenyl)-2-{4-[1-hydroxy-1-(8-oxetan-3-yl-8-aza-bicyclo[3.2.1]oct-3-yl)-ethyl]-phenyl}-7-isopropoxy-6-methoxy-1,4-dihydro-2H-isoquinolin-3-one 116: (S)-2-{4-[1-(9-Aza-bicyclo[3.3.1]non-3-yl)-1-hydroxy-ethyl]-phenyl}-1-(4-chloro-phenyl)-7-isopropoxy-6-methoxy-1,4-dihydro-2H-isoquinolin-3-one 117: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-9-aza-bicyclo[3.3.1]nonane-9-carbaldehyde 118: (S)-1-(4-Chloro-phenyl)-2-(4-{1-hydroxy-1-[9-(2,2,2-trifluoro-ethyl)-9-aza-bicyclo[3.3.1]non-3-yl]-ethyl}-phenyl)-7-isopropoxy-6-methoxy-1,4-dihydro-2H-isoquinolin-3-one 119: 3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-9-aza-bicyclo[3.3.1]nonane-9-carboxylic acid methylamide 120: (S)-1-(4-Chloro-phenyl)-2-{4-[1-hydroxy-1-(9-oxetan-3-yl-9-aza-bicyclo[3.3.1]non-3-yl)-ethyl]-phenyl}-7-isopropoxy-6-methoxy-1,4-dihydro-2H-isoquinolin-3-one 121: Acetic acid 2-[3-(1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-9-aza-bicyclo[3.3.1]non-9-yl]-2-oxo-ethyl ester 122: (S)-1-(4-Chloro-phenyl)-2-{4-[1-(9-ethyl-9-aza-bicyclo[3.3.1]non-3-yl)-1-hydroxy-ethyl]-phenyl}-7-isopropoxy-6-methoxy-1,4-dihydro-2H-isoquinolin-3-one 123: (S)-1-(4-Chloro-phenyl)-2-(4-{1-hydroxy-1-[9-(2-hydroxy-acetyl)-9-aza-bicyclo[3.3.1]non-3-yl]-ethyl}-phenyl)-7-isopropoxy-6-methoxy-1,4-dihydro-2H-isoquinolin-3-one 124: 4-((R)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde 125: 4-((S)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde 126: (S)-1-(4-Chloro-phenyl)-2-{4-[(R)-1-hydroxy-1-(1-oxetan-3-yl-piperidin-4-yl)-ethyl]-phenyl}-7-isopropoxy-6-methoxy-1,4-dihydro-2H-isoquinolin-3-one 127: (S)-1-(4-Chloro-phenyl)-2-{4-[(S)-1-hydroxy-1-(1-oxetan-3-yl-piperidin-4-yl)-ethyl]-phenyl}-7-isopropoxy-6-methoxy-1,4-dihydro-2H-isoquinolin-3-one 128: Acetic acid 2-[4-((S)-1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-piperidin-1-yl]-2-oxo-ethyl ester 129: Acetic acid 2-[4-((R)-1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-piperidin-1-yl]-2-oxo-ethyl ester
130: (S)-1-(4-Chloro-phenyl)-2-(4-{1-[1-((R)-2,3-dihydroxy-propyl)-piperidin-4-yl]-1-hydroxy-ethyl}-phenyl)-7-isopropoxy-6-methoxy-1,4-dihydro-2H-isoquinolin-3-one
131: (S)-1-(4-Chloro-phenyl)-2-(4-{(S)-1-hydroxy-1-[1-(2-hydroxy-ethyl)-piperidin-4-yl]-ethyl}-phenyl)-7-isopropoxy-6-methoxy-1,4-dihydro-2H-isoquinolin-3-one
132: (S)-1-(4-Chloro-phenyl)-2-(4-{(R)-1-hydroxy-1-[1-(2-hydroxy-ethyl)-piperidin-4-yl]-ethyl}-phenyl)-7-isopropoxy-6-methoxy-1,4-dihydro-2H-isoquinolin-3-one
133: (S)-1-(4-Chloro-phenyl)-2-(4-{(S)-1-hydroxy-1-[1-(2-hydroxy-acetyl)-piperidin-4-yl]-ethyl}-phenyl)-7-isopropoxy-6-methoxy-1,4-dihydro-2H-isoquinolin-3-one
134: (S)-1-(4-Chloro-phenyl)-2-(4-{(R)-1-hydroxy-1-[1-(2-hydroxy-acetyl)-piperidin-4-yl]-ethyl}-phenyl)-7-isopropoxy-6-methoxy-1,4-dihydro-2H-isoquinolin-3-one
135: (S)-1-(4-Chloro-phenyl)-2-{4-[1-hydroxy-1-(7-oxa-bicyclo[2.2.1]hept-1-yl)-ethyl]-phenyl}-7-isopropoxy-6-methoxy-1,4-dihydro-2H-isoquinolin-3-one
136: (S)-1-(4-Chloro-phenyl)-2-{4-[(R)-1-hydroxy-1-(7-oxa-bicyclo[2.2.1]hept-1-yl)-ethyl]-phenyl}-7-isopropoxy-6-methoxy-1,4-dihydro-2H-isoquinolin-3-one
137: (S)-1-(4-Chloro-phenyl)-2-{4-[(S)-1-hydroxy-1-(7-oxa-bicyclo[2.2.1]hept-1-yl)-ethyl]-phenyl}-7-isopropoxy-6-methoxy-1,4-dihydro-2H-isoquinolin-3-one
138: (S)-2-[4-(1-Bicyclo[2.2.1]hept-1-yl-1-hydroxy-ethyl)-phenyl]-1-(4-chloro-phenyl)-7-isopropoxy-6-methoxy-1,4-dihydro-2H-isoquinolin-3-one
139: (S)-2-[4-((S)-1-Bicyclo[2.2.1]hept-1-yl-1-hydroxy-ethyl)-phenyl]-1-(4-chloro-phenyl)-7-isopropoxy-6-methoxy-1,4-dihydro-2H-isoquinolin-3-one
140: (S)-2-[4-((R)-1-Bicyclo[2.2.1]hept-1-yl-1-hydroxy-ethyl)-phenyl]-1-(4-chloro-phenyl)-7-isopropoxy-6-methoxy-1,4-dihydro-2H-isoquinolin-3-one
141: (S)-2-[4-(1-Adamantan-1-yl-1-hydroxy-ethyl)-phenyl]-1-(4-chloro-phenyl)-7-isopropoxy-6-methoxy-1,4-dihydro-2H-isoquinolin-3-one
142: (S)-2-[4-((S)-1-Adamantan-1-yl-1-hydroxy-ethyl)-phenyl]-1-(4-chloro-phenyl)-7-isopropoxy-6-methoxy-1,4-dihydro-2H-isoquinolin-3-one
143: (S)-2-[4-((R)-1-Adamantan-1-yl-1-hydroxy-ethyl)-phenyl]-1-(4-chloro-phenyl)-7-isopropoxy-6-methoxy-1,4-dihydro-2H-isoquinolin-3-one
144: (S)-2-[4-(1-Adamantan-2-yl-1-hydroxy-ethyl)-phenyl]-1-(4-chloro-phenyl)-7-isopropoxy-6-methoxy-1,4-dihydro-2H-isoquinolin-3-one
145: (S)-1-(4-Chloro-phenyl)-2-{4-[1-hydroxy-1-(tetrahydro-pyran-4-yl)-ethyl]-phenyl}-7-isopropoxy-6-(2-methoxy-ethoxy)-1,4-dihydro-2H-isoquinolin-3-one
146: (S)-1-(4-Chloro-phenyl)-2-{4-[1-hydroxy-1-(tetrahydro-pyran-4-yl)-ethyl]-phenyl}-7-isopropoxy-6-(pyridin-2-ylmethoxy)-1,4-dihydro-2H-isoquinolin-3-one
147: (S)-1-(4-Chloro-phenyl)-2-{4-[1-hydroxy-1-(tetrahydro-pyran-4-yl)-ethyl]-phenyl}-7-isopropoxy-6-(oxetan-3-ylmethoxy)-1,4-dihydro-2H-isoquinolin-3-one
148: 2-((S)-1-(4-Chloro-phenyl)-2-{4-[1-hydroxy-1-(tetrahydro-pyran-4-yl)-ethyl]-phenyl}-7-isopropoxy-3-oxo-1,2,3,4-tetrahydro-isoquinolin-6-yloxy)-N-methyl-acetamide
149: 2-((S)-1-(4-Chloro-phenyl)-2-{4-[1-hydroxy-1-(tetrahydro-pyran-4-yl)-ethyl]-phenyl}-7-isopropoxy-3-oxo-1,2,3,4-tetrahydro-isoquinolin-6-yloxy)-N,N-dimethyl-acetamide
150: (S)-1-(4-Chloro-phenyl)-2-{4-[1-(1,1-dioxo-hexahydro-1-thiopyran-4-yl)-1-hydroxy-ethyl]-phenyl}-7-isopropoxy-6-d$^3$-methoxy-1,4-dihydro-2H-isoquinolin-3-one
151: 4-(1-{4-[(S)-1-(4-Chloro-phenyl)-7-isopropoxy-6-d$^3$-methoxy-3-oxo-3,4-dihydro-1H-isoquinolin-2-yl]-phenyl}-1-hydroxy-ethyl)-piperidine-1-carbaldehyde
152: (S)-1-(4-Chloro-phenyl)-2-{4-[(R)-1-(1,1-dioxo-hexahydro-1-thiopyran-4-yl)-1-hydroxy-ethyl]-phenyl}-7-isopropoxy-6-d$^3$-methoxy-1,4-dihydro-2H-isoquinolin-3-one
153: (S)-1-(4-Chloro-phenyl)-2-{4-[(S)-1-(1,1-dioxo-hexahydro-1-thiopyran-4-yl)-1-hydroxy-ethyl]-phenyl}-7-isopropoxy-6-d$^3$-methoxy-1,4-dihydro-2H-isoquinolin-3-one
154: 4-((R)-1-{4-[(S)-1-(4-Chloro-phenyl)-7-isopropoxy-6-d$^3$-methoxy-3-oxo-3,4-dihydro-1H-isoquinolin-2-yl]-phenyl}-1-hydroxy-ethyl)-piperidine-1-carbaldehyde
155: 4-((S)-1-{4-[(S)-1-(4-Chloro-phenyl)-7-isopropoxy-6-d$^3$-methoxy-3-oxo-3,4-dihydro-1H-isoquinolin-2-yl]-phenyl}-1-hydroxy-ethyl)-piperidine-1-carbaldehyde
156: (S)-1-(4-Chloro-phenyl)-2-{4-[1-hydroxy-1-(3-oxa-7-aza-bicyclo[3.3.1]non-9-yl)-ethyl]-phenyl}-7-isopropoxy-6-methoxy-1,4-dihydro-2H-isoquinolin-3-one
157: 9-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-3-oxa-7-aza-bicyclo[3.3.1]nonane-7-carbaldehyde
158: (S)-1-(4-Chloro-phenyl)-2-{4-[1-hydroxy-1-(8-oxabicyclo[3.2.1]oct-3-yl)-ethyl]-phenyl}-7-isopropoxy-6-methoxy-1,4-dihydro-2H-isoquinolin-3-one
159: (S)-1-(4-Chloro-phenyl)-2-{4-[(S)-1-hydroxy-1-(8-oxabicyclo[3.2.1]oct-3-yl)-ethyl]-phenyl}-7-isopropoxy-6-methoxy-1,4-dihydro-2H-isoquinolin-3-one
160: (S)-1-(4-Chloro-phenyl)-2-{4-[(R)-1-hydroxy-1-(8-oxa-bicyclo[3.2.1]oct-3-yl)-ethyl]-phenyl}-7-isopropoxy-6-methoxy-1,4-dihydro-2H isoquinolin-3-one
161: (S)-1-(4-Chloro-phenyl)-2-{4-[1-hydroxy-1-(9-oxa-bicyclo[3.3.1]non-3-yl)-ethyl]-phenyl}-7-isopropoxy-6-methoxy-1,4-dihydro-2H-isoquinolin-3-one
162: S)-1-(4-Chloro-phenyl)-2-{4-[1-hydroxy-1-(2,2,6,6-tetramethyl-tetrahydro-pyran-4-yl)-ethyl]-phenyl}-7-isopropoxy-6-methoxy-1,4-dihydro-2H-isoquinolin-3-one
163: (S)-1-(4-Chloro-phenyl)-2-{4-[(S)-1-hydroxy-1-(2,2,6,6-tetramethyl-tetrahydro-pyran-4-yl)-ethyl]-phenyl}-7-isopropoxy-6-methoxy-1,4-dihydro-2H-isoquinolin-3-one
164: (S)-1-(4-Chloro-phenyl)-2-{4-[(R)-1-hydroxy-1-(2,2,6,6-tetramethyl-tetrahydro-pyran-4-yl)-ethyl]-phenyl}-7-isopropoxy-6-methoxy-1,4-dihydro-2H-isoquinolin-3-one
165: 1-(4-Chloro-phenyl)-6-difluoromethoxy-2-{4-[1-hydroxy-1-(tetrahydro-pyran-4-yl)-ethyl]-phenyl}-7-isopropoxy-1,4-dihydro-2H-isoquinolin-3-one
166: (S)-1-(4-Chloro-phenyl)-2-{4-[1-(1,1-dioxo-hexahydro-1-thiopyran-4-yl)-1-hydroxy-ethyl]-phenyl}-7-isopropoxy-6-methoxy-1,4-dihydro-2H-isoquinolin-3-one
167: (S)-1-(4-Chloro-phenyl)-2-{4-[(R)-1-(1,1-dioxo-hexahydro-1-thiopyran-4-yl)-1-hydroxy-ethyl]-phenyl}-7-isopropoxy-6-methoxy-1,4-dihydro-2H-isoquinolin-3-one
168: (S)-1-(4-Chloro-phenyl)-2-{4-[(S)-1-(1,1-dioxo-hexahydro-1-thiopyran-4-yl)-1-hydroxy-ethyl]-phenyl}-7-isopropoxy-6-methoxy-1,4-dihydro-2H-isoquinolin-3-one 169: (S)-1-(4-Chloro-phenyl)-2-{4-[1-hydroxy-1-(1-oxo-hexahydro-1-thiopyran-4-yl)-ethyl]-phenyl}-7-isopropoxy-6-methoxy-1,4-dihydro-2H-isoquinolin-3-one
170: (S)-1-(4-Chloro-phenyl)-2-{4-[(R)-1-hydroxy-1-(1-oxo-hexahydro-thiopyran-4-yl)-ethyl]-phenyl}-7-isopropoxy-6-methoxy-1,4-dihydro-2H-isoquinolin-3-one
171: (S)-1-(4-Chloro-phenyl)-2-{4-[(S)-1-hydroxy-1-(1-oxo-hexahydro-1-thiopyran-4-yl)-ethyl]-phenyl}-7-isopropoxy-6-methoxy-1,4-dihydro-2H-isoquinolin-3-one
172: (S)-1-(4-Chloro-phenyl)-2-{4-[1-(8,8-dioxo-8-thia-bicyclo[3.2.1]oct-3-yl)-1-hydroxy-ethyl]-phenyl}-7-isopropoxy-6-methoxy-1,4-dihydro-2H-isoquinolin-3-one
173: (S)-1-(4-Chloro-phenyl)-2-{4-[(R)-1-(8,8-dioxo-8-thia-bicyclo[3.2.1]oct-3-yl)-1-hydroxy-ethyl]-phenyl}-7-isopropoxy-6-methoxy-1,4-dihydro-2H-isoquinolin-3-one
174: (S)-1-(4-Chloro-phenyl)-2-{4-[(S)-1-(8,8-dioxo-8-thia-bicyclo[3.2.1]oct-3-yl)-1-hydroxy-ethyl]-phenyl}-7-isopropoxy-6-methoxy-1,4-dihydro-2H-isoquinolin-3-one
175: (S)-1-(4-Chloro-phenyl)-2-{4-[1-(9,9-dioxo-9-thia-bicyclo[3.3.1]non-3-yl)-1-hydroxy-ethyl]-phenyl}-7-isopropoxy-6-methoxy-1,4-dihydro-2H-isoquinolin-3-one
176: (S)-1-(4-Chloro-phenyl)-2-{4-[(R)-1-(9,9-dioxo-9-thia-bicyclo[3.3.1]non-3-yl)-1-hydroxy-ethyl]-phenyl}-7-isopropoxy-6-methoxy-1,4-dihydro-2H-isoquinolin-3-one
177: (S)-1-(4-Chloro-phenyl)-2-{4-[(S)-1-(9,9-dioxo-9-thia-bicyclo[3.3.1]non-3-yl)-1-hydroxy-ethyl]-phenyl}-7-isopropoxy-6-methoxy-1,4-dihydro-2H-isoquinolin-3-one
178: (S)-1-(4-Chloro-phenyl)-2-{4-[1-hydroxy-1-(2-oxa-bicyclo[2.2.2]oct-4-yl)-ethyl]-phenyl}-7-isopropoxy-6-methoxy-1,4-dihydro-2H-isoquinolin-3-one
179: (S)-3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid tert-butyl ester
180: (S)-1-(4-Chloro-phenyl)-2-[4-((S)-1-hydroxy-1-piperidin-3-yl-ethyl)-phenyl]-7-isopropoxy-6-methoxy-1,4-dihydro-2H-isoquinolin-3-one
181: (S)-1-(4-Chloro-phenyl)-2-{4-[1-hydroxy-1-((S)-1-methyl-piperidin-3-yl)-ethyl]-phenyl}-7-isopropoxy-6-methoxy-1,4-dihydro-2H-isoquinolin-3-one
182: (S)-3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde, and
183: (S)-1-(4-Chloro-phenyl)-2-{4-[1-hydroxy-1-((S)-1-oxetan-3-yl-piperidin-3-yl)-ethyl]-phenyl}-7-isopropoxy-6-methoxy-1,4-dihydro-2H-isoquinolin-3-one As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}F$, $^{32}F$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

p53 refers to the human protein itself as described by Matlashewski et al. in EMBO J. 3, 3257-62 (1984) or related family members (e.g. p73 as described in Kaghad et al. in Cell 90, 809-19 (1997) and p63 as described in Yang et al in Mol Cell 2, 305-16 (1998)) (named also p53 wild type herein) or to any variant thereof (e.g. a splice variant, mutant, fragment or isoform due to deletion, insertion and/or exchange of one or more, e.g. one to 200, of the amino acids) that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof. Where not mentioned otherwise, p53 generally relates to TP53, p53, TP73, p73, TP63, TP73L, p63, or variants thereof, respectively, as just defined.

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Research Park, Madison Wis., USA, which uses the algorithm of Smith and Waterman (Adv. Appl. Math. 2: 482-489 (1981), especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression. Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor inducing agent, an oncogene.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by MDM2 and/or MDM4, or (ii) associated with MDM2 and/or MDM4 activity, or (iii) characterized by activity (normal or abnormal) of MDM2 and/or MDM4, or (2) reducing or inhibiting the activity of MDM2 and/or MDM4, or (3) reducing or inhibiting the expression of MDM2 and/or MDM4. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of MDM2 and/or MDM4; or at least partially reducing or inhibiting the expression of MDM2 and/or MDM4.

In a further embodiment, the compounds of formula (I) are particularly useful for the treatment of disorders of diseases associated with the activity of MDM2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another embodiment of the invention there is provided a pharmaceutical composition comprising a therapeutically effective amount of a compound of formula (I) as defined herein, and one or more pharmaceutically acceptable carriers.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compounds of formula I in free form or in salt form exhibit valuable pharmacological properties, e.g. MDM2 and/or MDM4 modulating properties, e.g. as indicated in tests as provided in the next sections, and are therefore indicated for therapy.

Having regard to their inhibitory effect on p53/MDM2 and/or p53/MDM4 interaction, compounds of the formula (I) in free or pharmaceutically acceptable salt form, are useful in the treatment of conditions which are mediated by the activity (including normal activity or especially overactivity) of MDM2 and/or MDM4, or variants thereof, respectively, as described, such as proliferative conditions, e.g. by activation of the P53/MDM2 interaction, and/or that are responsive (meaning especially in a therapeutically beneficial way) to inhibition of the p53/MDM2 interaction, most especially a disease or disorder as mentioned hereinbelow.

Compounds of formula (I) are believed to be useful in the treatment of a disease based on dysregulation of cell cycle, such as a proliferative disorder or disease, for example cancer or tumour diseases. In particular, such diseases or disorders include benign or malignant tumors, a sarcoma, such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia or a lymphoma, such as of B- or T-cell origin, and metastases in other organs), viral infections (e.g. herpes, papilloma, HIV, Kaposi's, viral hepatitis).

In particular, compounds of formula (I) are believed to be useful to treat a sarcoma such as liposarcoma, rhabdomyosarcoma or osteosarcoma, or a melanoma, leukemia or lymphoma.

Thus, as a further embodiment, the present invention provides the use of a compound of formula (I) in therapy. In a further embodiment, the therapy is selected from a disease which may be treated by inhibition of the MDM2/p53 and/or MDM4/p53 interaction, in particular the diseases or disorders listed herein.

The invention also provides a compound of the formula (I) as defined herein, for use as a pharmaceutical, in particular for use in the treatment of a disorder or a disease mediated by the activity of MDM2 and/or MDM4, in particular for a disease or disorder mentioned herein.

The invention also provides the use of a compound of formula (I) as defined herein, for the manufacture of a medicament for the treatment of a disorder or a disease in a subject mediated by the activity of MDM2 and/or MDM4, more particularly for a disease or disorder mentioned herein.

In another embodiment, the invention provides a method of treating a disease or disorder which is treated by inhibition of the MDM2/p53 and/or MDM4/p53 interaction, comprising administration of a therapeutically acceptable amount of a compound of formula (I), in particular a method of treating the diseases or disorders listed herein.

In another embodiment, the invention provides a method of modulating MDM2 and/or MDM4 activity in a subject, comprising the step of administering to a subject a therapeutically effective amount of a compound of formula (I) as defined herein.

The compounds of the formula (I) have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side.

The invention also relates to the use of a compound of the formula (I) (or a pharmaceutical formulation comprising a compound of the formula (I)) in the treatment of one or more of the diseases mentioned above and below where the disease(s) respond or responds (in a beneficial way, e.g. by partial or complete removal of one or more of its symptoms up to complete cure or remission) to an inhibition of the MDM2/p53 and/or MDM4/p53 interaction, especially where the involved MDM2 or MDM4 and/or variant shows (e.g. in the context of other regulatory mechanisms, due to overexpression, to mutation or the like) inadequately high or more higher than normal activity.

The invention can also relate to the use of a compound of the formula (I) to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the induction of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agents or treatments, such as side effects resulting in mucositis, stomatitis, xerostomia, gastrointestinal disorders and/or alopecia.

The efficacy of the compounds of the formula (I) and salts thereof as modulators affecting the interaction between can be demonstrated as shown in WO 98/01467 (which especially regarding the assays is included herein by reference) or preferably follows:

Assays

Time Resolved Fluorescence Energy Transfer (TR-FRET) Assay

The inhibition of p53-MDM2 and p53-MDM4 interactions is measured by time resolved fluorescence energy transfer (TR-FRET). Fluorescence energy transfer (or Foerster resonance energy transfer) describes an energy transfer between donor and acceptor fluorescent molecules. For this assay, human MDM2 protein (amino acids 2-188) and human MDM4 protein (amino acids 2-185), tagged with a C-terminal biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 620 nm. The ratiometric FRET assay readout is calculated from the raw data of the two distinct fluorescence signals measured in time resolved mode (fluorescence 665 nm/fluorescence 620 nm×1000).

The test is performed in white 384-well plates (Greiner Bio-One, reference 781207) in a total volume of 60 μL by adding 1 μL of compounds tested at different concentrations diluted in 100% DMSO (1.7% final DMSO concentration) in reaction buffer (PBS, 125 mM NaCl, 0.001% Novexin (consists of carbohydrate polymers), designed to increase the solubility and stability of proteins; Expedeon Ltd., Cambridgeshire, United Kingdom), 0.01% Gelatin, 0.01% 0.2%, Pluronic F-127 (block copolymer from ethylenoxide and propyleneoxide), 1 mM DTT). After addition of 1.25 nM MDM2-biotinylated or 2.5 nM MDM4-biotinylated (internal preparations), and 0.625 nM Europium labeled streptavidin (Perkin Elmer), the solution is pre-incubated for 15 minutes at room temperature, then 10 nM Cy5-p53 peptide (internal preparation) is added before an incubation at room temperature for 15 minutes prior to reading the plate. For measurement of samples, a Victor II microplate reader (Perkin Elmer) is used with the following settings: Excitation 340 nm, Emission Donor 620 nm and Emission Acceptor 665 nm. $IC_{50}$ values are calculated by curve fitting using XLfit. If not specified, reagents are purchased from Sigma-Aldrich Chemie GmBH, Buchs, Switzerland.

This assay was used to evaluate compounds displaying inhibition of p53-MDM2 interaction and p53-MDM4 interaction at $IC_{50}$s of 0.005 to 50 μM (p53-MDM2 Assay 1 and p53-MDM4 Assay 1, respectively). For selected compounds displaying $IC_{50}$s between 0.05 and 5 nM on MDM2, a slightly modified assay is used with the following adaptations: 0.1 nM MDM2, 0.1 nM Europium labeled streptavidin and Tecan genios Pro is used as a microplate reader for the fluorescence measurements (p53-MDM2 Assay 2).

The present invention also relates to novel aspects of the above described assays. Inhibitions of p53-Hdm2 and p53-Hdm4 by representative compounds in the present invention are displayed herein.

Cellular Proliferation Assay in SJSA-1 and SAOS-2 Cells Based on YO-PRO®-1 Iodide Staining The effect of PPI (protein-protein interaction) inhibitors on cell growth of p53 wild-type or mutant cells is assessed in a proliferation assay based on YO-PRO®-1 iodide staining (J Immunol Methods. 1995; 185(2):249-58). The principal of this assay is the use of the DNA-intercalating dye YO-PRO®-1 iodide which upon binding to DNA emits a strong fluorescence signal. In addition, the dye is membrane-impermeant and thus, apoptotic cells can be distinguished from the viable cell population during the same assay. In the absence of cell permeabilization, the dye is only entering into cells that are beginning to undergo apoptosis. After treatment of the cells with a lysis buffer, the total cell number can be estimated.

To test PPI inhibitors on cell growth, SJSA-1 cells (p53 wild-type cells) and SAOS-2 cells (p53 null cells) are plated out into 96-well micro-titer plates and treated with decreasing concentrations of the compounds. After a 72 hour incubation period, 2.5 µM YO-PRO®-1 iodide is directly added to the cells and a first read-out is performed using a standard fluorescence plate reader (filter setting 485/530 nm) revealing the relative number of apoptotic cells. Subsequently, cells are permeabilized by directly adding lysis buffer containing the detergent NP40, EDTA and EGTA to obtain final concentrations of 0.01% and 5 mM, respectively. After complete permeabilization, the total cell number is quantified during a second read using the fluorescence plate reader with the same settings.

In Vivo Experiments

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, $3\times10^6$ cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated.

As an alternative to cell line SJSA-1, other cell lines may also be used in the same manner, for example, the HCT116 colon carcinoma cell line (ATCC No. CCL-247);

the LNCaP clone FGC prostate carcinoma cell line (ATCC No. CRL-1740);

the RKO colon carcinoma cell line (ATCC No. CRL-2577);

the HT1080 fibrosarcoma cell line (ATCC No. CCL-121);

the A375 malignant melanoma cell line (ATCC No. CRL-1619), the NCI-H460 large cell lung carcinoma cell line (ATCC No. HTB-177);

the JEG-3 choriocarcinoma (ATCC No. HTB-36)

the ZR-75-1 breast ductal carcinoma (ATCC No. CRL-1500)

A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, antileukemia compounds, ribonucleotide reductase inhibittors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. under TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g. in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™) cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of PI3K, such as BEZ235, BKM120 or BYL719;

n) compounds targeting, decreasing or inhibiting the activity of the cyclin dependent kinase family, such as PD 0332991, or compounds inhibiting the Ras/Raf/MEK pathway such as RAF265, or a MEK inhibitor.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1, erbitux, bevacizumab (Avastin™) rituximab (Rituxan™), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the formula (I) can be used in combination with standard leukemia therapies, especially in combination with therapies used for the treatment of AML. In particular, compounds of the formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The above-mentioned compounds, which can be used in combination with a compound of the formula (I), can be prepared and administered as described in the art, such as in the documents cited above.

A compound of the formula (I) can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of the formula (I) can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Compounds of particular interest as combinations partners as selected from the group of rapalogs such as RAD001, mTOR/PI3K inhibitors such as BEZ235, pan PI3K inhibitors such as BKM120, p110alpha inhibitors such as BYL719, anti-Notch mAb, CDK4 inhibitors such as LEE011, B-RAF inhibitors such as RAF265, MEK inhibitors, TNKS (Tankyrase) inhibitors, smoothened inhibitors such as LDE225, WNT inhibitors, c-Met inhibitors, PARP inhibitors, and Nilotinib.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by inhibition of the MDM2/p53 and/or MDM4/p53 interaction. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by inhibition of the MDM2/p53 and/or MDM4/p53 interaction, wherein the medicament is prepared for administration with another therapeutic agent. The invention also provides the use of another therapeutic agent for treating a disease or condition mediated by inhibition of the MDM2/p53 and/or MDM4/p53 interaction, wherein the medicament is administered with a compound of formula (I).

The invention also provides a compound of formula (I) for use in a method of treating a disease or condition mediated by inhibition of the MDM2/p53 and/or MDM4/p53 interaction, wherein the compound of formula (I) is prepared for administration with another therapeutic agent. The invention also provides another therapeutic agent for use in a method of treating a disease or condition mediated by inhibition of the MDM2/p53 and/or MDM4/p53 interaction, wherein the other therapeutic agent is prepared for administration with a compound of formula (I). The invention also provides a compound of formula (I) for use in a method of treating a disease or condition mediated by inhibition of the MDM2/p53 and/or MDM4/p53 interaction, wherein the compound of formula (I) is administered with another therapeutic agent. The invention also provides another therapeutic agent for use in a method of treating a disease or condition mediated by inhibition of the MDM2/p53 and/or MDM4/p53 interaction, wherein the other therapeutic agent is administered with a compound of formula (I).

The invention also provides the use of a compound of formula (I) for treating a disease or condition mediated by inhibition of the MDM2/p53 and/or MDM4/p53 interaction, wherein the patient has previously (e.g. within 24 hours) been treated with another therapeutic agent. The invention also provides the use of another therapeutic agent for treating a disease or condition mediated by inhibition of the MDM2/p53 and/or MDM4/p53 interaction, wherein the patient has previously (e.g. within 24 hours) been treated with a compound of formula (I).

Typically, the compounds of formula (I) can be prepared according to the Schemes provided infra.

General synthesis scheme A:

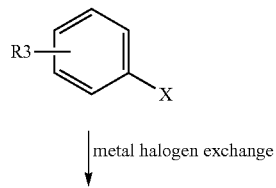

metal halogen exchange

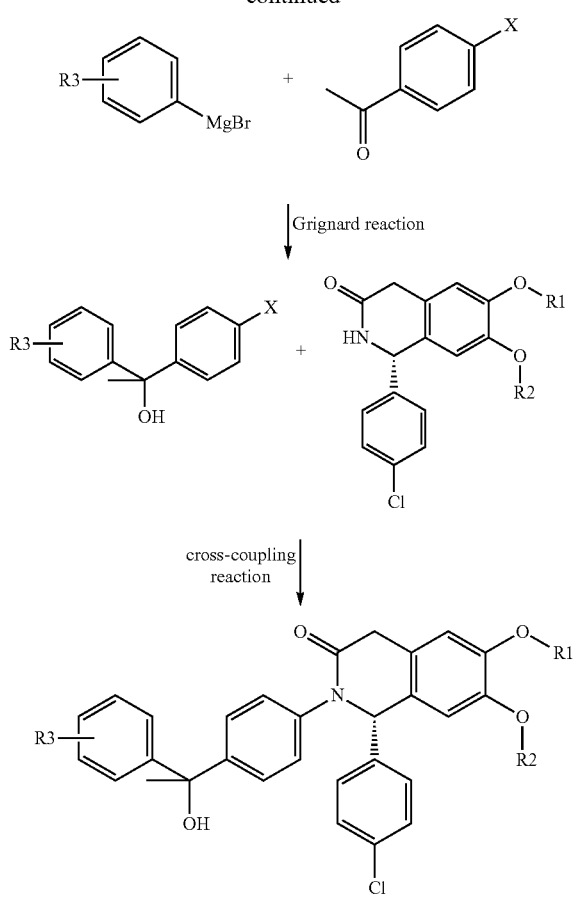
Scheme A illustrates one method of preparing compounds of the invention (e.g. examples 1-5).
General synthesis scheme B:
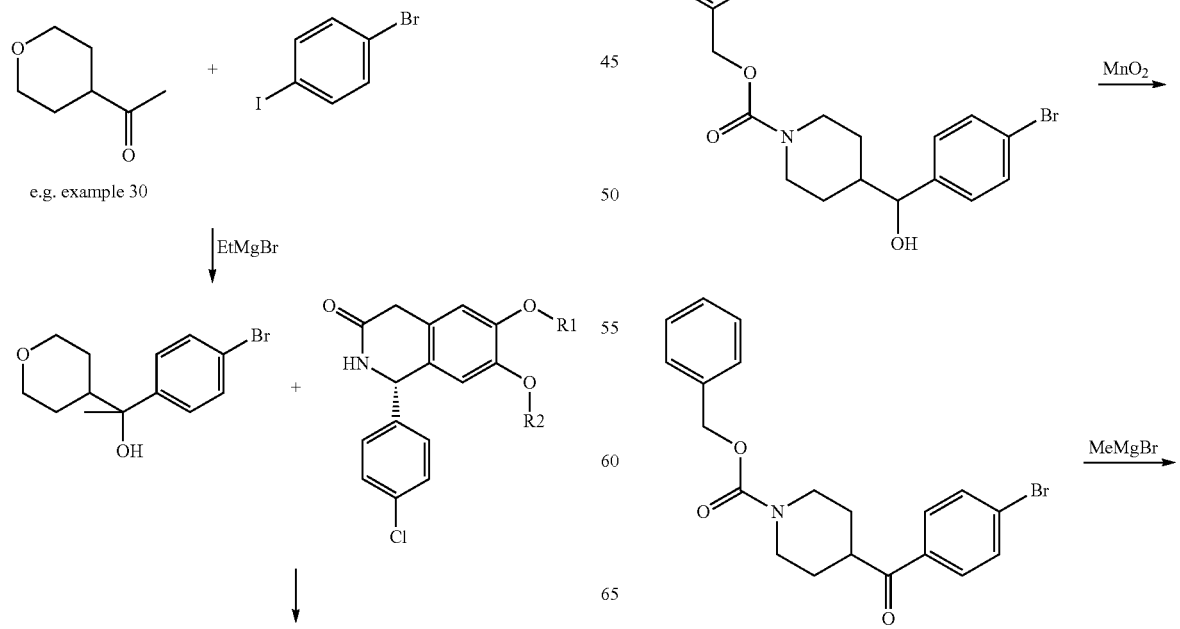
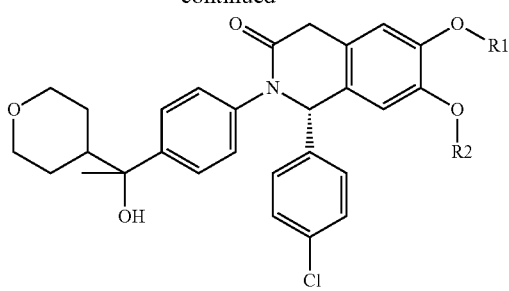
Scheme B illustrates an alternative method of preparing compounds of the invention (e.g. example 30)
General synthesis scheme C:
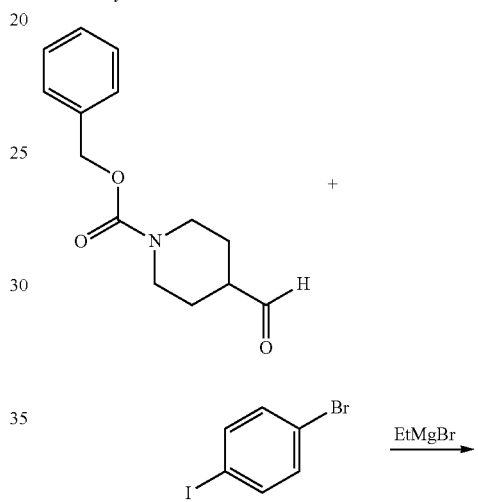

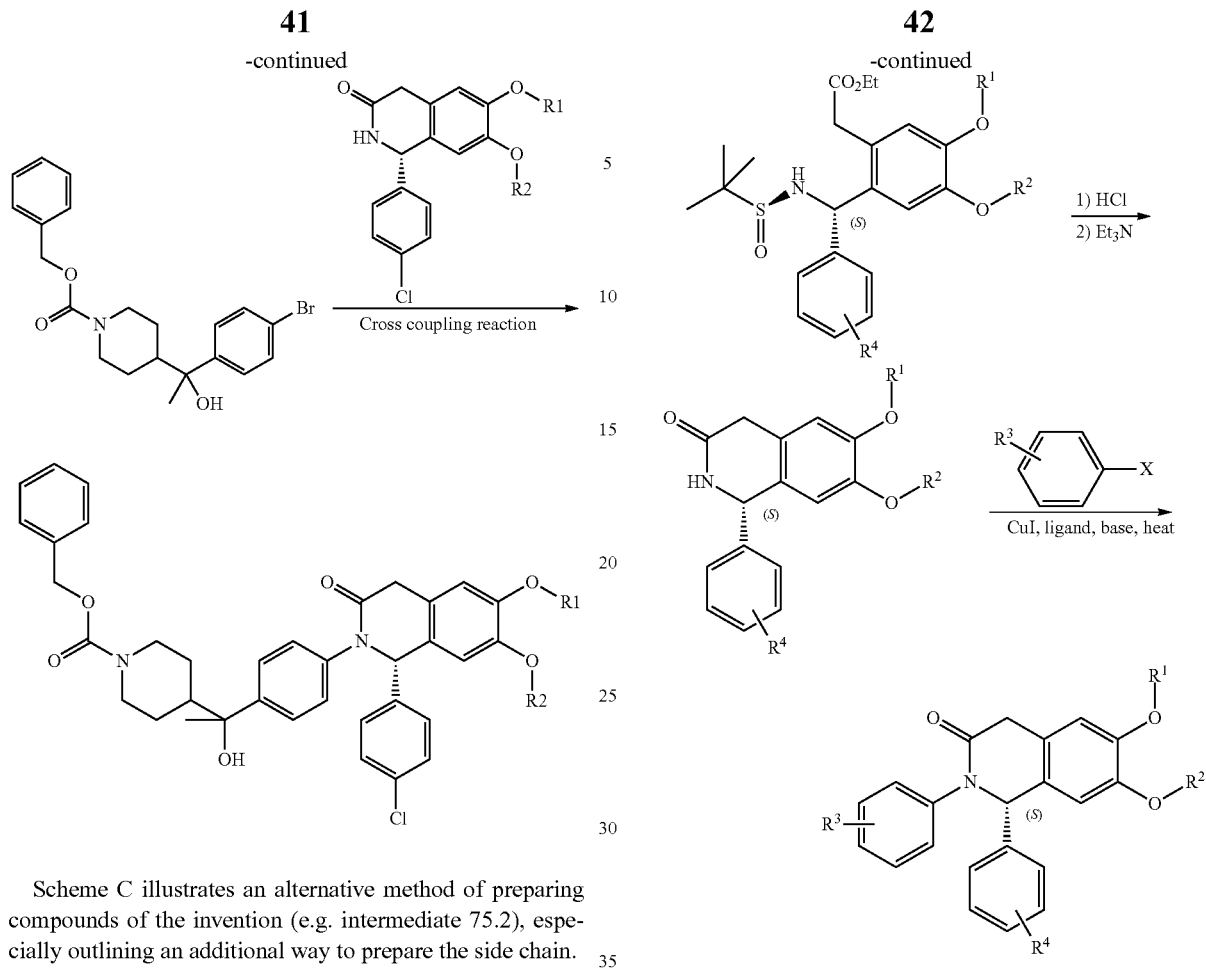

Scheme C illustrates an alternative method of preparing compounds of the invention (e.g. intermediate 75.2), especially outlining an additional way to prepare the side chain.

General Synthetic Scheme D (synthesis of chiral core intermediate):

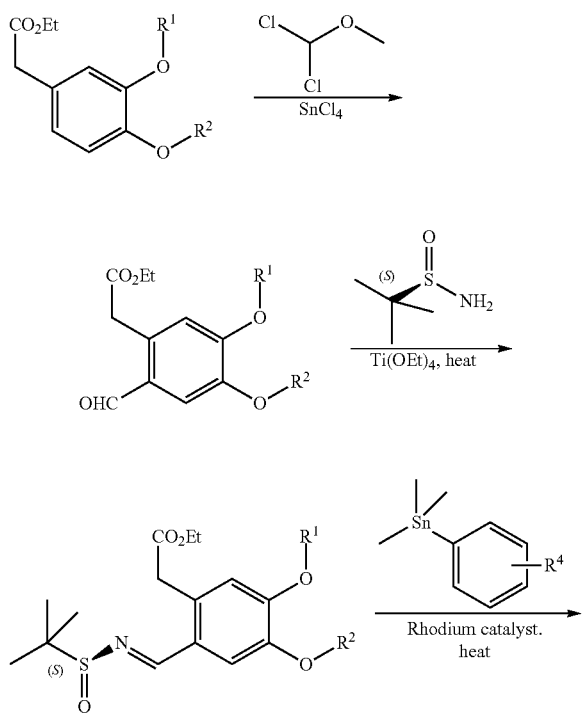

(3,4-Dialkoxy-phenyl)-acetic acid ethyl ester was treated with dichloro-methoxy-methane in typically DCM by slowly added SnCl$_4$ (1M solution in DCM), over typically 30 minutes. After the complete addition, the reaction was typically stirred at 0° C. for 1.5 hrs. The chiral auxiliar group was added following the procedure from Davis et a. (Frank A. Davis, Pradyumna K. Mohanty; *J. Org. Chem.*, 2002, 67, 4, 1290) using typically a Lewis acid such as Ti(OEt)$_4$ and typically an aprotic solvent such as DCM. The enantioselevtive addition of the aryl group followed the procedure from Oi et al (S. Oi, M. Moro, H. Fukurhara, T. Kawanishi, Y. Inoue, *Tetrahedron*, 59, 2003, 4351). The tin reagent was added to a solution of starting material (sulfoximine) in an organic solvent such as THF, dioxane or acetonitrile, but typically THF in the presence of a rhodium catalyst, such as bis(acetonitrile)(1,5-cyclooctadiene)rhodium(I)tetrafluoroborate. The reaction is carried out typically at elevated temperature such as 60° C. Other reagents than the tin reagents can be utilized such as the corresponding borate salts.

Deprotection of the sulfoxamine group was typically done under acidic conditions using acids such as HCl (e.g. 1.25 M in ethanol) in an organic solvent such as an alcohol, typically methanol. The free amine was evaporated to dryness, re-dissolved in typically methanol and a base is added, typically triethylamine and the reaction is stirred at typically room temperature.

The cross-coupling reaction is carried out following Buchwald's condition for the C—N amidation reaction, typically following Buchwald literature procedure (A. Klapars, Xiaohua Huang, S. L. Buchwald; *J. Am. Chem. Soc.*, 2002, 124, 7421). Under an inert argon atmosphere and using degassed aprotic solvents encompassing toluene, dioxane, THF and DMF, but typically dioxane, the starting materials (isoquinolinone and aryl halide) are mixed in the presence of a copper source, such as Cu powder, CuI, CuCN, Cu$_2$O, CuCl$_2$, but typically CuI and an diamine ligand, such as ethylenediamine, or other 1,2-diamine ligands, but typically trans-1,2-cyclohexanediamine in the presence of a base, such as K$_3$PO$_4$, K$_2$CO$_3$ or CsCO$_3$, but typically K$_3$PO$_4$. The reaction is heated to typically 100-110° C. and stirred for 4 to 16 hours depending the progress of the reaction.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

The R groups in the above-mentioned general schemes are illustrative only. They may or may not have the same meanings as R groups in embodiments of the invention herein.

General Analytical Methods.

1H-NMR measurements were performed on a Bruker Ultrashield™ 400 (400 MHz), Bruker Ultrashield™ 600 (600 MHz) or a 500 MHz DRX Bruker CryoProbe (500 MHz) spectrometer using or not trimethylsilane as an internal standard. Chemical shifts (d-values) are reported in ppm downfield from tetramethylsilane, coupling constants (J) are given in Hz, spectra splitting pattern are designated as singulet (s), doublet (d), doublet doublet (dd), triplet (t), quadruplet (q), multiplet or more overlapping signals (m), broad signal (br). Solvents are given in parentheses.

TLC were performed with precoated silica gel 60 F$_{254}$ glass plates (Merck, Darmstadt, Germany) using the respective named solvent systems. Visualization was generally done by UV light (254 nm).

LC-MS spectra were recorded on a Waters 2795 Alliance HT instrument with a Sunfire™ C18, 4.6×20 mm, 3.5 µm column, eluting with a linear gradient of 5 to 100% MeCN (+0.1% TFA) in water (+0.1% TFA) in 4 min with a flow rate of 3 ml/min at 45° C., with positive ion electrospray ionization (Micromass ZQ Detector): ($^A$t$_{Ret}$)

Preparative RP-HPLC purifications were performed using optimized gradient elution (CH$_3$CN/water with 0.1% TFA) with a Waters HPLC prep-system equipped with a UV detector Waters 2487 Dual Absorbance Detector, a MS detector Waters micromassZQ, and a reversed phase column Sun-Fire™ Prep, C18 OBD, 100×30 mm, 5 µm, or 100×19 mm, 5 µm.

HPLC retention times ($^X$R$_{Ret}$) were reported in min and were recorded using the following conditions:

Retention times for system A ($^B$t$_{Ret}$) were measured with a Thermo Finnigan instrument equipped with an UV 6000LP Photodiode Array Detector (DAD detection at 218 nm), eluting with an isocratic from 0-8.0 min of 2 to 100% MeCN (0.1% HCOOH) in water (+0.1% HCOOH), 8.0-10.0 min. 100% MeCN (0.1% HCOOH) then 10.0-11.0 min of 100% to 2% MeCN (+0.1% HCOOH) with a flow rate of 2.0 ml/min at 30° C. The column was a Chromolith Performance RP-18e, 4.6×100 mm (Merck)

Retention times for system B ($^C$t$_{Ret}$) were measured with a Agilent 1100 instrument equipped with an Agilent 1100 series Dioden Array Detector (DAD detection at 215 nm), eluting with an isocratic from 0-8.0 min of 2 to 100% MeCN (0.1% TFA) in water (+0.1% TFA), 8.0-10.0 min. 100% MeCN (0.1% TFA), 10.0-11.0 min of 100% to 2% MeCN (+0.1 TFA) then 11.0-13.0 min of 2% MeCN (+0.1% TFA) with a flow rate of 2.0 ml/min at 25° C. The column was a Chromolith Performance RP-18e, 4.6×100 mm (Merck)

Retention times for system C ($^D$t$_{Ret}$) were measured with a Agilent 1100 instrument equipped with an Agilent 1100 series Dioden Array Detector (DAD detection at 215 nm), eluting with an isocratic from 0-5.0 min of 2 to 100% MeCN (0.1% TFA) in water (+0.1% TFA), 5.0-6.5 min. 100% MeCN (0.1% TFA) then 6.5-7.0 min of 100% to 2% MeCN (+0.1% TFA) with a flow rate of 1.0 ml/min at 30° C. The column was a Nucleosil 100-3C18 HD, 4×70 mm.

Retention times for system D ($^E$t$_{Ret}$) were measured with a Agilent 1100 instrument equipped with an Agilent 1100 series Dioden Array Detector (DAD detection at 215 nm), eluting with an isocratic from 0-7.0 min of 2 to 100% MeCN (0.1% TFA) in water (+0.1% TFA), 7.0-9.0 min. 100% MeCN (0.1% TFA), 9.0-10.0 min of 100% to 2% MeCN (+0.1 TFA) with a flow rate of 1.0 ml/min at 30° C. The column was a Nucleosil 100-3 C18 HD, 4×125 mm (Macherey-Nagel)

Retention times for system E ($^F$t$_{Ret}$) were measured with a Waters 2690 instrument equipped with an Waters 996 series Photodiode Array Detector (detection at 215 nm and 254 nm), eluting with an isocratic from 1.0-11.0 min of 2 to 100% MeCN (0.1% TFA) in water (+0.1% TFA) then 11.0-13.0 min of 100% MeCN (+0.1% TFA) with a flow rate of 1.0 ml/min at 35° C. The column was Column Engineering, Inc., Matrix C18 4.6×150 mm (Lot#205), 3.0 µm

EXAMPLES

The following examples are intended to illustrate the invention and are not to be construed as being limitations thereon. Temperatures are given in degrees centrigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Where no specific source is indicated, starting materials and solvents are obtainable from customary suppliers, such as Sigma-Aldrich, Fluke, Alfa Aesar, Merck, or from providers indicated specifically. Further, the compounds of the present invention can be produced by organic synthesis methods known to one of ordinary skill in the art as shown in the following examples.

ABBREVIATIONS

| | |
|---|---|
| Ac | acetyl |
| AcOEt or EtOAc | ethyl acetate |
| AcOH | acetic acid |
| aq. | aqueous |
| API-MS | Atmospheric Pressure Ionization Mass Spectroscopy |
| BH$_3$•THF | borane tetrahydrofuran complex |
| Boc | t-butoxycarbonyl |

-continued

| | |
|---|---|
| brine | saturated aqueous sodium chloride solution at RT |
| $^t$Bu | t-butyl |
| CDCl$_3$ | deuteriated chloroform |
| CD$_3$OD | deuteriated methanol |
| Celite | trademark of Celite Corp. (World Minerals Inc.), Santa Barbara, CA, USA, for filtering aid based on kieselguhr |
| CHCl$_3$ | chloroform |
| conc. | concentrated |
| Cs$_2$CO$_3$ | cesium carbonate |
| CuI | copper(I) iodide |
| Cu$_2$O | copper(I) oxide |
| DCM | dichloromethane |
| DIPEA | diisopropylethylamine |
| DMAP | 4-dimethylaminopyridine |
| DME | 1,2-dimethoxyethane |
| DMF | N,N-dimethylformamide |
| DMSO | dimethylsulfoxide |
| DTAD | di-t-butyl azodicarboxylate |
| equiv. | equivallent |
| Et | ethyl |
| Et$_3$N | triethylamine |
| Et$_2$O | diethyl ether |
| EtOH | ethanol |
| Fe | iron metal |
| g | gramm(s) |
| h | hour(s) |
| HATU | O-(7-azabenzotriazol-1-yl)-N,N,N',N'-tetramethyluronium-hexafluorophosphat |
| HCl | hydrogen chloride |
| HNO$_3$ | nitric acid |
| HPLC | high-pressure liquid chromatography |
| H$_2$SO$_4$ | sulfuric acid |
| iPr | isopropyl |
| K$_2$CO$_3$ | potassium carbonate |
| KOH | potassium hydroxide |
| K$_3$PO$_4$ | potassium phosphate |
| LC-MS | liquid chromatography mass spectroscopy |
| LiBH$_4$ | lithium borohydride |
| LiOH | lithium hydroxide |
| M | molar |
| Me | methyl |
| MeCN | acetonitrile |
| mg | milligram(s) |
| MeI | methyl iodide |
| MeOH | methanol |
| min | minute(s) |
| ml or mL | milliliter(s) |
| mmol | millimole(s) |
| MnO$_2$ | manganese(IV) oxide |
| MS | mass spectrometry |
| NaBH$_4$ | sodium borohydride |
| NaBH$_3$CN | sodium cyanoborohydride |
| NaBH(OAc)$_3$ | sodium triacetoxyborohydride |
| Na$_2$CO$_3$ | sodium carbonate |
| NaH | sodium hydride |
| NaHCO$_3$ | sodium bicarbonate |
| NaN$_3$ | sodium azide |
| NaOCN | sodium cyanate |
| NaOH | sodium hydroxide |
| Na$_2$SO$_4$ | sodium sulfate |
| NH$_3$ | ammoniac |
| NH$_4$Cl | ammonium chloride |
| NMM | 4-methylmorpholine |
| NMR | nuclear magnetic resonance |
| PDC | pyridinium dichromate |
| Pd/C | palladium over charcoal |
| PdCl$_2$(PPh$_3$)$_2$ | dichlorobis(triphenylphosphine)-palladium (II) |
| Pd(PPh$_3$)$_4$ | tetrakis(triphenylphosphine)palladium |
| Ph | phenyl |
| PPh$_3$ | triphenylphosphine |
| prep-HPLC | preparative high-pressure liquid chromatography |
| PTSA | p-toluenesulfonic acid |
| quant. | quantitative |
| R$_F$ | retention factor |
| RT | room temperature |
| SiO$_2$ | silica |
| SnCl$_2$ | stannous chloride or Tin(II) chloride |
| SnCl$_4$ | Tin(IV) chloride |
| SOCl$_2$ | thionyl chloride |
| TBDMSCl | tert-butyldimethylsilyl chloride |
| TBME | tert-butyl-dimethyl ether |
| TFA | trifluoroacetic acid |
| THF | tetrahydrofurane |
| Ti(OEt)$_4$ | titanium(IV) ethoxide |
| Ti(OiPr)$_4$ | titanium(IV) isopropoxide |
| TLC | thin layer chromatography |
| t$_{Ret}$ | retention time |

Example 1

(S)-1-(4-Chloro-phenyl)-2-{4-[1-hydroxy-1-(3-methoxy-phenyl)-ethyl]-phenyl}-7-isopropoxy-6-methoxy-1,4-dihydro-2H-isoquinolin-3-one

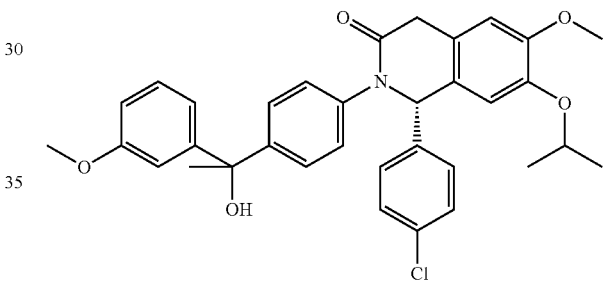

A dry 10 ml microwave vial was charged with K$_3$PO$_4$ (123 mg, 0.578 mmol), (S)-1-(4-chlorophenyl)-7-isopropoxy-6-methoxy-1,2-dihydroisoquinolin-3(4H)-one (100 mg, 0.289 mmol), 1-(4-iodophenyl)-1-(3-methoxyphenyl)ethanol (113 mg, 0.318 mmol), trans-1,2-diaminocyclohexane (6.95 µl, 0.058 mmol) and dioxane (3 ml). The reaction mixture was degassed with argon in a sonic bath during 5 minutes. Then copper(I)iodide (11.01 mg, 0.058 mmol) was added. The vial was sealed and heated for 8 hrs to 100° C. in a metal heating block. The reaction mixture was diluted with ethyl acetate and the organic phase was washed with aqueous NaHCO$_3$ solution and brine. The organic phase was dried over Na$_2$SO$_4$, filtered and concentrated in vacuo to obtain a brown oil as crude material which was purified by preparative HPLC (reversed phase). Fractions containing the products were pooled and worked up (addition of NaHCO$_3$, removal of acetonitrile followed by extraction with DCM). The residue was dissolved in 1,4-dioxane and freeze dried overnight to obtain the title compound as yellowish solid.

HPLC: $^A$t$_{Ret}$=2.14 min; LC-MS: m/z 572.14 [M+H]$^+$

1H-NMR (600 MHz, DMSO-d$_6$): δ 7.36 (d, 2H), 7.33 (s, 4H), 7.16 (t, 1H), 7.07 (s, 1H), 7.06 (d, 2H), 6.95 (m, 1H), 6.92 (d, 1H), 6.82 (s, 1H), 6.71 (dd 1H), 6.05 (s, 1H), 4.43 (quint, 1H), 3.70 (dd, 2H), 3.69 (d, 6H), 1.76 (s, 3H), 1.21 (d, 3H), 1.18 (d, 3H)

Intermediate 1.1

1-(4-iodophenyl)-1-(3-methoxyphenyl)ethanol

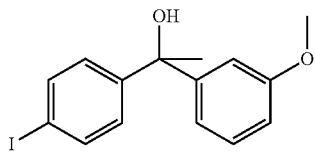 [SMILES: COc1cccc(C(C)(O)c2ccc(I)cc2)c1]

A solution of 4-iodoacetophenone (2 g, 7.97 mmol) in THF (20 ml) was immersed in an ice-bath and (3-methoxyphenyl)magnesium bromide 1M in THF (23.90 ml, 23.90 mmol) was added slowly by syringe. The reaction mixture was stirred at r.t. for 3 hrs. The reaction mixture was quenched with 20 ml aqueous saturated NH$_4$Cl solution and diluted with ethyl acetate. The organic phase was separated and washed with brine. The organic phase was dried over Na$_2$SO$_4$, filtered and concentrated in vacuo to obtain the crude product which was purified by automated column chromatography (n-heptane (isom. mixture)/ethyl acetate). Organic solvents were removed to obtain title compound as yellowish oil.

HPLC: $^A t_{Ret}$=1.92 min; LC-MS: m/z 337.0 [M–H$_2$O+H]$^+$

Intermediate 1.2

(S)-1-(4-Chloro-phenyl)-7-isopropoxy-6-methoxy-1,4-dihydro-2H-isoquinolin-3-one

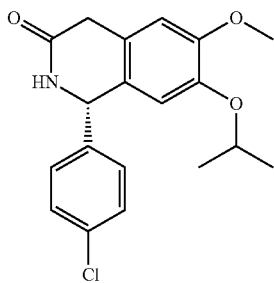 [SMILES: COc1cc2c(cc1OC(C)C)[C@H](c1ccc(Cl)cc1)NC(=O)C2]

A solution of intermediate 1.3 (3.96 g, 7.98 mmol) in 1.25M HCl in MeOH (128 ml) was stirred at RT for 30 min. The reaction mixture was evaporated to dryness and the resulting residue was dissolved in MeOH (40 ml). Et$_3$N (5.56 ml, 39.9 mmol) was added at RT then the mixture was stirred for 15 min and evaporated to dryness. The resulting crude material was purified by Combi-Flash Companion™ (Isco Inc.) column chromatography (SiO$_2$; gradient elution, [heptane/DCM 1:1]/TBME 9:1→100% TBME) to yield the title compound (2.51 g, 7.24 mmol, 91%, ee 92%) as an off-white solid.

TLC: R$_F$=0.13 (heptane/DCM/TBME 1:1:2);

HPLC: $^A t_{Ret}$=2.03 min; LC-MS: m/z 346.4 [M+H]$^+$

1H-NMR (400 MHz, DMSO-d$_6$): δ 1.16 (d, J=6.1, 3H), 1.21 (d, J=6.1, 3H), 3.36 (d, J=19.8, 1H), 3.51 (d, J=19.8, 1H), 3.72 (s, 3H), 4.40 (spt, J=6.1, 1H), 5.55 (d, J=3.4, 1H), 6.79 (s, 1H), 6.84 (s, 1H), 7.26-7.33 (m, 2H), 7.35-7.42 (m, 2H), 8.49 (d, J=3.9, 1H).

Intermediate 1.3

{2-[(S)-(4-Chloro-phenyl)-((S)-2-methyl-propane-2-sulfinylamino)-methyl]-4-isopropoxy-5-methoxy-phenyl}-acetic acid ethyl ester

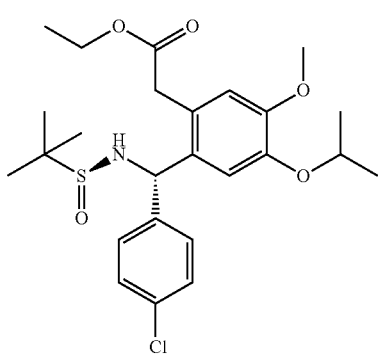 [SMILES: CCOC(=O)Cc1cc(OC)c(OC(C)C)cc1[C@@H](N[S@@](=O)C(C)(C)C)c1ccc(Cl)cc1]

A 250-mL flask was charged with intermediate 1.5 (10.97 g, 28.6 mmol) and anhydrous THF (50 ml) then evacuated under vacuum and back-filled with argon (3×). Intermediate 1.4 (15.75 g, 57.2 mmol) and bis(acetonitrile)(1,5-cyclooctadiene)rhodium(I)tetrafluoroborate (1.09 g, 2.86 mmol) were successively added at RT and the resulting orange suspension was heated at 60° C. and stirred for 2 h. Additional bis(acetonitrile)(1,5-cyclooctadiene)rhodium(I)tetrafluoroborate (1.09 g, 2.86 mmol) was added at 60° C. and the mixture was further stirred for 4 h. The reaction mixture was cooled to RT, diluted with AcOEt and washed with water. The organic phase was dried over Na$_2$SO$_4$, filtered and evaporated to dryness. The resulting crude material was purified by Combi-Flash Companion™ (Isco Inc.) column chromatography (SiO$_2$; gradient elution, heptane/AcOEt 95:5→3:7) to yield the title compound (3.96 g, 7.98 mmol, 28%) as a brownish resin.

TLC: R$_F$=0.29 (heptane/AcOEt 1:1)

HPLC: $^A t_{Ret}$=2.70 min; LC-MS: m/z 496.3 [M+H]$^+$

1H-NMR (400 MHz, DMSO-d$_6$): δ 1.10-1.19 (m, 15H), 1.23 (d, J=5.9, 3H), 3.57 (d, J=16.4, 1H), 3.68 (d, J=16.1, 1H), 3.73 (s, 3H), 3.93-4.05 (m, 2H), 4.37-4.45 (m, 1H), 5.62 (d, J=6.1, 1H), 5.82 (d, J=6.1, 1H), 6.82 (s, 1H), 6.94 (s, 1H), 7.25-7.30 (m, 2H), 7.36-7.41 (m, 2H).

Intermediate 1.4

(4-Chloro-phenyl)-trimethyl-stannane

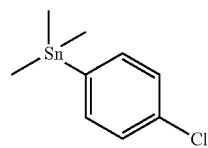

To a 1M solution of trimethyltin chloride in THF (92 ml, 92 mmol) was slowly added a 1M solution of 4-chlorophenylmagnesium bromide in Et$_2$O (92 ml, 92 mmol) over a 40 min period at −10° C. so that the temperature never exceed 0° C. After the addition, the cooling bath was removed and the resulting suspension was stirred at RT for 1 h. A saturated aqueous solution of NH$_4$Cl (14 ml) was added followed by water until complete dissolution of the precipitate. The mixture was transferred into a separating funnel and extracted with Et₂O (3×). The combined organic fractions were dried over Na₂SO₄, filtered and evaporated to dryness. The resulting crude material was purified by Combi-Flash Companion™ (Isco Inc.) column chromatography (SiO₂; isocratic elution with cyclohexane) to yield the title compound (24.47 g, 89 mmol, 97%) as a colorless oil.

TLC: $R_F$=0.76 (cyclohexane/AcOEt 95:5)
HPLC: $^A t_{Ret}$=3.25 min
1H-NMR (400 MHz, CDCl₃): δ 0.31 (s, 9H) 7.32-7.36 (m, 2H) 7.41-7.45 (m, 2H).

Intermediate 1.5

(4-Isopropoxy-5-methoxy-2-{[(E)-(S)-2-methyl-propane-2-sulfinylimino]-methyl}-phenyl)-acetic acid ethyl ester

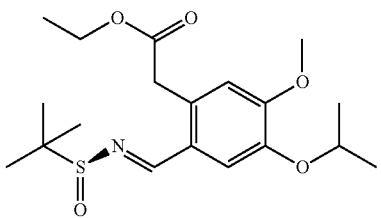 [SMILES: CCOC(=O)Cc1cc(OC)c(OC(C)C)cc1/C=N/[S@@](=O)C(C)(C)C]

To a solution of intermediate 1.6 (9.14 g, 32.6 mmol) and (S)-(−)-2-methyl-2-propanesulfinamide (5.93 g, 48.9 mmol) in DCM (200 ml) was added Ti(OEt)₄ (27.3 ml, 130 mmol) at 0° C. (ice bath). The reaction mixture was heated at reflux, stirred for 5 h then cooled to RT and quenched by the careful addition of water (14.7 ml). The resulting white precipitate was filtered through a Celite pad, the filter cake was washed with DCM and the filtrate then evaporated to dryness. The resulting crude material was purified by Combi-Flash Companion™ (Isco Inc.) column chromatography (SiO₂; gradient elution, heptane/AcOEt 95:5→1:1) to yield the title compound (11.07 g, 28.9 mmol, 89%) as a yellow oil.

TLC: $R_F$=0.40 (heptane/AcOEt 1:1);
HPLC: $^A t_{Ret}$=2.35 min; LC-MS: m/z 384.5 [M+H]⁺;
1H-NMR (400 MHz, DMSO-d₆): δ 1.17 (t, J=7.1, 3H) 1.15 (s, 9H) 1.27 (d, J=6.1, 6H) 3.83 (s, 3H) 3.94-4.07 (m, 4H) 4.58-4.66 (m, 1H) 7.04 (s, 1H) 7.50 (s, 1H) 8.49 (s, 1H).

Intermediate 1.6

(2-Formyl-4-isopropoxy-5-methoxy-phenyl)-acetic acid ethyl ester

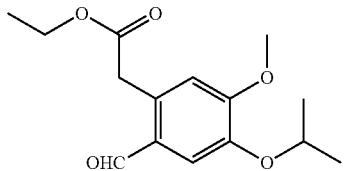 [SMILES: CCOC(=O)Cc1cc(OC)c(OC(C)C)cc1C=O]

To a solution of intermediate 1.7 (11.94 g, 47.3 mmol) and dichloro-methoxy-methane (8.56 ml, 95 mmol) in DCM (350 ml) was slowly added SnCl₄ (1M solution in DCM, 95 ml, 95 mmol) over a 45 min period at 0° C. (ice bath). After the addition, the reaction mixture was further stirred at 0° C. for 45 min then poured into water and extracted with DCM (2×). The organic phase was washed with a 2M aqueous Na₂CO₃ solution, then dried over Na₂SO₄, filtered and evaporated to dryness. The resulting crude material was purified by Combi-Flash Companion™ (Isco Inc.) column chromatography (SiO₂; gradient elution, heptane/AcOEt 95:5→1:1) to yield the title compound (11.13 g, 39.7 mmol, 84%) as a yellow oil which crystallized on standing into an off-white solid. TLC: $R_F$=0.50 (heptane/AcOEt 1:1);

HPLC: $^A t_{Ret}$=1.93 min; LC-MS: m/z 281.4 [M+H]⁺;
1H-NMR (400 MHz, DMSO-d₆): δ 1.18 (t, J=7.1, 3H) 1.28 (d, J=6.1, 6H) 3.84 (s, 3H) 4.01 (s, 2H) 4.07 (q, J=7.1, 2H) 4.56-4.68 (m, 1H) 7.03 (s, 1H) 7.45 (s, 1H) 9.93 (s, 1H).

Intermediate 1.7

(4-Isopropoxy-3-methoxy-phenyl)-acetic acid ethyl ester

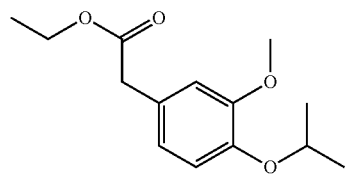 [SMILES: CCOC(=O)Cc1ccc(OC(C)C)c(OC)c1]

A mixture of ethyl (4-hydroxy-3-methoxy-phenyl)-acetic acid ethyl ester (11.22 g, 53.4 mmol) and K₂CO₃ (22.13 g, 160 mmol) in DMF (100 ml) was heated at 60° C. 2-Iodopropane (9.06 ml, 91 mmol) was added and the mixture was vigorously stirred at 60° C. for 5 h. The reaction mixture was cooled to RT, diluted with AcOEt and washed with water. The aqueous phase was separated and further extracted with AcOEt. The combined organic fractions were dried over Na₂SO₄, filtered and evaporated to dryness. The resulting crude material was purified by Combi-Flash Companion™ (Isco Inc.) column chromatography (SiO₂; gradient elution, heptane/AcOEt 98:2→3:1) to yield the title compound (11.94 g, 47.3 mmol, 89%) as a colorless oil.

TLC: $R_F$=0.44 (heptane/AcOEt 7:3);
HPLC: $^A t_{Ret}$=2.14 min; LC-MS: m/z 253.4 [M+H]⁺;
1H-NMR (400 MHz, CDCl₃): δ 1.28 (t, J=7.1, 3H), 1.38 (d, J=6.1, 6H), 3.56 (s, 2H), 3.87 (s, 3H), 4.17 (q, J=7.1, 2H), 4.50 (h, J=6.1, 1H), 6.77-6.89 (m, 3H).

Example 2

(S)-1-(4-Chloro-phenyl)-2-{4-[hydroxy-(3-methoxy-phenyl)-methyl]-phenyl}-7-isopropoxy-6-methoxy-1,4-dihydro-2H-isoquinolin-3-one

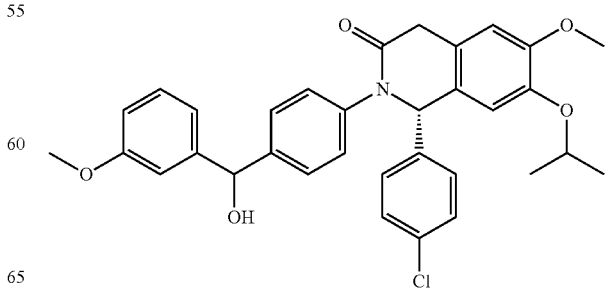

Example 2 was obtained analogously to example 1 except in step 1.1, 4-iodobenzaldehyde was used instead of 4-iodoacetophenone.

HPLC: $^At_{Ret}$=2.05 min; LC-MS: m/z 558.1 [M+H]$^+$

1H-NMR (400 MHz, DMSO-d$_6$): δ 7.34 (s, 4H), 7.33 (d, 2H), 7.19 (t, 1H), 7.06 (s, 1H), 6.94 (s, 1H), 6.90 (d, 1H), 6.84 (s, 1H), 6.75 (d 1H), 6.06 (s, 1H), 5.89 (hept, 1H), 5.62 (m, 1H), 4.44 (m, 1H), 3.86 (d, 1H), 3.71 (d, 6H), 3.58 (d, 1H), 3.56 (s, 2H), 1.23 (d, 3H), 1.19 (d, 3H)

Example 3

(S)-1-(4-Chloro-phenyl)-2-[4-(1-hydroxy-1-methyl-propyl)-phenyl]-7-isopropoxy-6-methoxy-1,4-dihydro-2H-isoquinolin-3-one

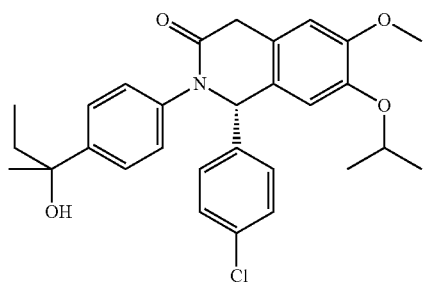

Example 3 was obtained analogously to example 1 except in step 1.1, ethylmagnesium bromide was used instead of (3-methoxyphenyl)magnesium bromide HPLC: $^At_{Ret}$=1.19 min; LC-MS: m/z 494.3 [M+H]$^+$ 1H-NMR (600 MHz, DMSO-d$_6$): δ 7.36 (s, 6H), 7.09 (m, 3H), 6.85 (s, 1H), 6.08 (s, 1H), 4.82 (s, 1H), 4.45 (hept, 1H), 3.86 (d, 1H), 3.72 (s, 3H), 3.59 (d, 1H), 3.56 (s, 3H), 1.64 (m, 2H), 1.24 (d, 3H), 1.20 (d, 3H)

Example 4

(S)-1-(4-Chloro-phenyl)-2-{4-[hydroxy-(4-methoxy-phenyl)-methyl]-phenyl}-7-isopropoxy-6-methoxy-1,4-dihydro-2H-isoquinolin-3-one

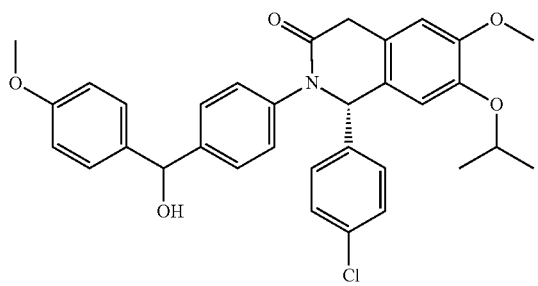 [SMILES: COc1ccc(C(O)c2ccc(N3C(=O)Cc4cc(OC)c(OC(C)C)cc4[C@@H]3c3ccc(Cl)cc3)cc2)cc1]

Example 4 was obtained analogously to example 1 except in step 1.1, 4-iodobenzaldehyde was used instead of 4-iodoacetophenone and (4-methoxyphenyl)magnesium bromide was used instead of (3-methoxyphenyl)magnesium bromide.

HPLC: $^At_{Ret}$=1.20 min; LC-MS: m/z 558.1 [M+H]$^+$

1H-NMR (600 MHz, DMSO-d$_6$): δ 7.34 (s, 4H), 7.30 (d, 2H), 7.24 (d, 2H), 7.08 (d, 2H), 7.06 (s, 1H), 6.84 (s, 1H), 6.06 (s, 1H), 5.79 (t, 1H), 4.60 (s, 1H), 4.44 (quint, 1H), 3.87 (d, 1H), 3.72 (s, 3H), 3.70 (s, 3H), 3.58 (d, 1H), 3.56 (s, 2H), 1.23 (d, 3H), 1.19 (d, 3H)

Example 5

(S)-1-(4-Chloro-phenyl)-2-{4-[1-hydroxy-1-(4-methoxy-phenyl)-ethyl]-phenyl}-7-isopropoxy-6-methoxy-1,4-dihydro-2H-isoquinolin-3-one

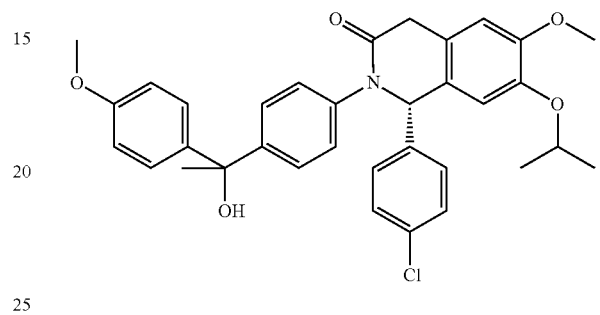

Example 5 was obtained analogously to example 1 except in step 1.1, (4-methoxyphenyl)magnesium bromide was used instead of (3-methoxyphenyl)magnesium bromide.

HPLC: $^At_{Ret}$=1.24 min; LC-MS: m/z 572.1 [M+H]$^+$

1H-NMR (600 MHz, DMSO-d$_6$): δ 7.35 (s, 4H), 7.35 (d, 2H), 7.29 (d, 2H), 7.09 (s, 1H), 7.07 (d, 2H), 6.83 (s, 1H), 6.81 (d, 2H), 6.06 (s, 1H), 5.62 (s, 1H), 4.44 (quint, 1H), 3.58 (d, 1H), 3.56 (s, 2H), 1.77 (s, 3H), 1.23 (d, 3H), 1.19 (d, 3H)

Example 6

(S)-1-(4-Chloro-phenyl)-2-{4-[1-(4-fluoro-phenyl)-1-hydroxy-ethyl]-phenyl}-7-isopropoxy-6-methoxy-1,4-dihydro-2H-isoquinolin-3-one

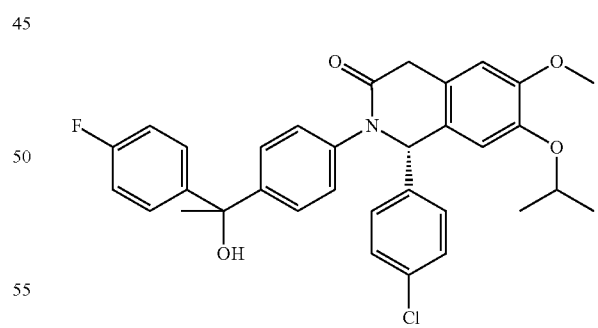

Example 6 was obtained analogously to example 1 except in step 1.1, (4-fluorophenyl)magnesium bromide was used instead of 4-methoxyphenyl)magnesium bromide.

HPLC: $^At_{Ret}$=1.25 min; LC-MS: m/z 560.0 [M+H]$^+$

1H-NMR (600 MHz, DMSO-d$_6$): δ 7.45-7.35 (m, 7H), 7.12-7.05 (m, 5H), 6.82 (s, 1H), 5.8 (s, 2H), 4.45 (quint, 1H), 3.86 (d, 1H), 3.74 (s, 3H), 3.60 (d, 1H), 1.8 (s, 3H), 1.23 (d, 3H), 1.19 (d, 3H)

Example 7

(S)-1-(4-Chloro-phenyl)-7-isopropoxy-6-methoxy-2-{4-[2,2,2-trifluoro-1-hydroxy-1-(4-methoxy-phenyl)-ethyl]-phenyl}-1,4-dihydro-2H-isoquinolin-3-one

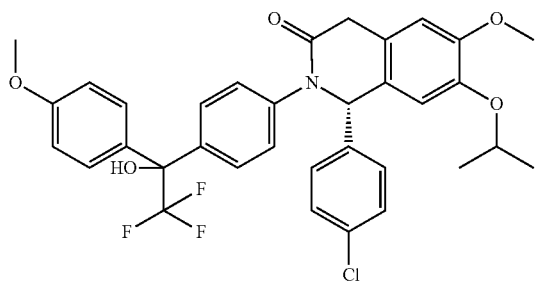 [SMILES: COc1ccc(C(O)(c2ccc(N3C(=O)Cc4cc(OC)c(OC(C)C)cc4[C@@H]3c3ccc(Cl)cc3)cc2)C(F)(F)F)cc1]

Example 7 was obtained analogously to example 1 except in step 1.1, 4'-bromo-2,2,2-trifluoroacetophenone and (4-methoxyphenyl)magnesium bromide were used instead of 4-iodoacetophenone and (3-methoxyphenyl)magnesium bromide.

HPLC: $^A t_{Ret}$=1.29 min; LC-MS: m/z 626.2 [M+H]$^+$

1H-NMR (600 MHz, DMSO-d$_6$): δ 7.40-7.33 (m, 6H), 7.31-7.25 (m, 3H), 7.21 (d, 2H), 7.12 (s, 1H), 6.93 (d, 2H), 6.84 (s, 1H), 6.14 (s, 1H), 4.45 (quint, 1H), 3.83 (d, 1H), 3.74 (s, 3H), 3.71 (s, 3H), 3.60 (d, 1H), 1.23 (d, 1H), 1.19 (d, 3H)

Example 8

(S)-1-(4-Chloro-phenyl)-2-[4-(cyclohexyl-hydroxy-methyl)-phenyl]-7-isopropoxy-6-methoxy-1,4-dihydro-2H-isoquinolin-3-one

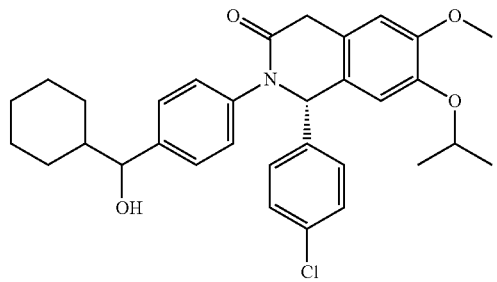 [SMILES: COc1cc2c(cc1OC(C)C)[C@H](c1ccc(Cl)cc1)N(c1ccc(C(O)C3CCCCC3)cc1)C(=O)C2]

Example 8 was obtained analogously to example 1 except in step 1.1, 4-bromobenzaldehyde was used instead of 4-iodoacetophenone and that cyclohexylmagnesium chloride was used instead of (3-methoxyphenyl)magnesium bromide.

HPLC: $^A t_{Ret}$=1.31 min; LC-MS: m/z 534.3 [M+H]$^+$

1H-NMR (600 MHz, DMSO-d$_6$): δ 7.36 (d, 4H), 7.23 (d, 2H), 7.11 (d, 3H), 6.86 (s, 1H), 6.10 (s, 1H), 5.10-5.07 (m, 1H), 4.46 (quint, 1H), 4.22-4.18 (m, 1H), 3.89 (d, 1H), 3.74 (s, 3H), 3.61 (d, 1H), 1.79 (br d, 1H), 1.67 (br d, 1H), 1.64-1.55 (m, 2H), 1.45-1.37 (m, 1H), 1.29 (br d, 3H), 1.25 (d, 3H), 1.21 (d, 3H), 1.00 (m, 5H)

Example 9

(S)-1-(4-Chloro-phenyl)-2-[6-(1-hydroxy-1-methyl-propyl)-pyridin-3-yl]-7-isopropoxy-6-methoxy-1,4-dihydro-2H-isoquinolin-3-one

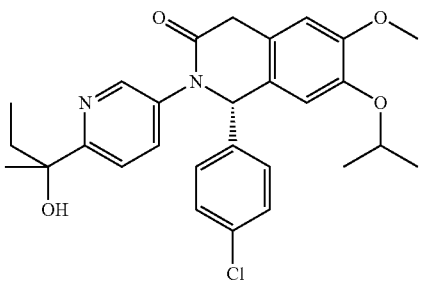 [SMILES: CCC(C)(O)c1ccc(N2C(=O)Cc3cc(OC)c(OC(C)C)cc3[C@@H]2c2ccc(Cl)cc2)cn1]

Example 9 was obtained analogously to example 1 except in step 1.1, 1-(5-bromopyridin-2-yl)ethanone was used instead of 4-iodoacetophenone and that ethylmagnesium bromide was used instead of (3-methoxyphenyl)magnesium.

HPLC: $^A t_{Ret}$=1.22 min; LC-MS: m/z 495.2 [M+H]$^+$

1H-NMR (600 MHz, DMSO-d$_6$): δ 8.3 (s, 1H), 7.59 (m, 2H), 7.37 (s, 4H), 7.02 (d, 1H), 6.88 (s, 1H), 6.17 (s, 1H), 5.03 (s, 1H), 4.44 (quint, 1H), 3.95 (d, 1H), 3.73 (s, 3H), 3.65 (d, 1H), 2.5 (s, 4H), 1.72 (dhept, 2H), 1.37 (d, 3H), 1.23 (d, 3H), 1.19 (d, 3H)

Example 10

(S)-1-(4-Chloro-phenyl)-2-[5-(1-hydroxy-1-methyl-propyl)-pyridin-2-yl]-7-isopropoxy-6-methoxy-1,4-dihydro-2H-isoquinolin-3-one

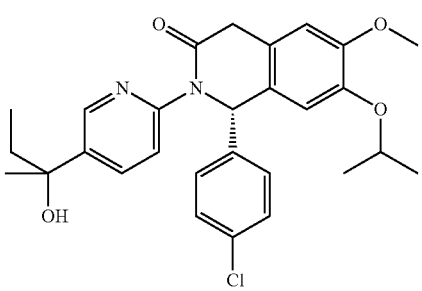

Example 10 was obtained analogously to example 1 except in step 1.1, 5-acetyl-2-bromo-pyridine was used instead of 4-iodoacetophenone and that ethylmagnesium bromide was used instead of (3-methoxyphenyl)magnesium bromide.

HPLC: $^A t_{Ret}$=1.30 min; LC-MS: m/z 495.2 [M+H]$^+$

1H-NMR (600 MHz, DMSO-d$_6$): δ 8.43 (d, 1H), 7.77 (m, 2H), 7.36 (d, 1H), 7.31 (dd, 4H), 6.89 (s, 1H), 6.82 (d, 1H), 5.02 (s, 1H), 4.57 (quint, 1H), 3.73 (s, 3H), 3.62 (m, 2H), 1.69 (m, 2H), 1.41 (s, 3H), 1.25 (d, 6H), 0.68 (t, 3H)

Example 11

(S)-1-(4-Chloro-phenyl)-2-[4-(1-hydroxy-1-methyl-ethyl)-phenyl]-7-isopropoxy-6-methoxy-1,4-dihydro-2H-isoquinolin-3-one

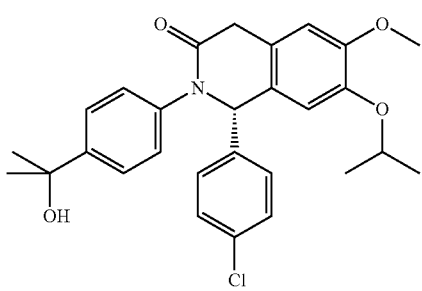 [SMILES: COc1cc2c(cc1OC(C)C)[C@H](c1ccc(Cl)cc1)N(c1ccc(C(C)(C)O)cc1)C(=O)C2]

Example 11 was obtained analogously to example 1 except in step 1.1, methylmagnesium bromide was used instead of (3-methoxyphenyl)magnesium bromide.

HPLC: $^{A}t_{Ret}$=1.11 min; LC-MS: m/z 480.1 [M+H]$^{+}$

1H-NMR (600 MHz, DMSO-d$_6$): δ 7.47-7.33 (m, 6H), 7.14-7.06 (m, 3H), 7.10 (s, 1H), 7.08 (s, 1H), 6.85 (s, 1H), 6.08 (s, 1H), 5.01 (s, 1H), 4.46 (quint, 1H), 3.88 (d, 1H), 3.72 (s, 3H), 3.59 (d, 2H), 1.39 (s, 6H), 1.24 (d, 3H), 1.20 (d, 3H)

Example 12

(S)-1-(4-Chloro-phenyl)-2-[5-(1-hydroxy-1-pyridin-4-yl-ethyl)-pyridin-2-yl]-7-isopropoxy-6-methoxy-1,4-dihydro-2H-isoquinolin-3-one

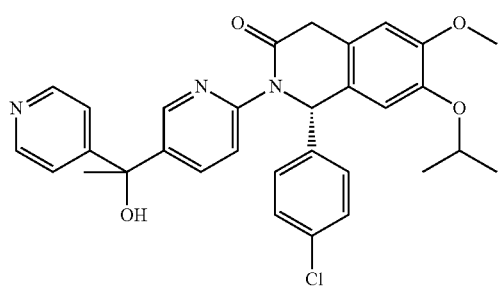 [SMILES: COc1cc2c(cc1OC(C)C)[C@H](c1ccc(Cl)cc1)N(c1ccc(C(C)(O)c3ccncc3)cn1)C(=O)C2]

Example 12 was obtained analogously to example 1 except that a different side chain was used in the cross coupling (example 12.1)

HPLC: $^{A}t_{Ret}$=0.91 min; LC-MS: m/z 544.1 [M+H]$^{+}$

1H-NMR (600 MHz, DMSO-d$_6$): δ 8.5 (br s, 2H), 7.9-7.75 (m, 3H), 7.45 (d, 2H), 7.35-7.25 (m, 5H), 6.9 (s, 1H), 6.8 (s, 1H), 6.15 (d, 1H), 4.45 (quint, 1H), 3.74 (s, 3H), 3.60 (d, 1H), 1.9 (s, 3H), 1.2 (s, 6H)

Intermediate 12.1

1-(6-Bromo-pyridin-3-yl)-1-pyridin-4-yl-ethanol

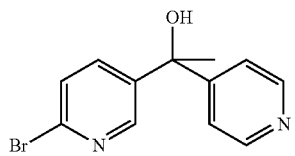 [SMILES: CC(O)(c1ccncc1)c1ccc(Br)nc1]

A solution of 5-acetyl-2-bromopyridine (Aldrich) (1.2 g, 5.82 mmol) and 3-iodopyridine (EGA-Chemie) (1.193 g, 5.82 mmol) in THF (10 ml) was immersed in a dry ice-acetone bath. n-BuLi (1.6M) in hexane (4.00 ml, 6.40 mmol) was added slowly by a syringe at −70° C. (exothermic reaction!). The reaction was allowed to warm up slowly to room temperature and was stirred over night. The reaction mixture was cooled to −20° C. and quenched with H$_2$O before dilution with ethyl acetate. The organic phase was separated and washed with brine. The organic phase was dried over Na$_2$SO$_4$, filtered and concentrated in vacuo and dried to obtain title compound as off-white solid.

HPLC: $^{A}t_{Ret}$=0.44 min; $^{F}t_{Ret}$=5.744 min; LC-MS: m/z 279.0 [M+H]$^{+}$

Example 13

(S)-1-(4-Chloro-phenyl)-2-{4-[1-hydroxy-1-(1-methyl-1H-imidazol-4-yl)-ethyl]-phenyl}-7-isopropoxy-6-methoxy-1,4-dihydro-2H-isoquinolin-3-one

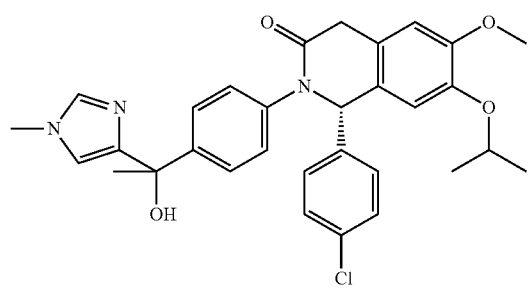 [SMILES: COc1cc2c(cc1OC(C)C)[C@H](c1ccc(Cl)cc1)N(c1ccc(C(C)(O)c3cn(C)cn3)cc1)C(=O)C2]

Example 13 was obtained analogously to example 12 except 1-(4-iodophenyl)-1-(1-methyl-1H-imidazol-4-yl) ethanol was used instead of 1-(6-bromopyridin-3-yl)-1-(pyridin-4-yl)ethanol.

HPLC: $^{A}t_{Ret}$=0.87 min; LC-MS: m/z 546.2 [M+H]$^{+}$

1H-NMR (600 MHz, DMSO-d$_6$): δ 7.5-7.3 (m, 7H), 7.1-7.0 (m, 3H), 6.85 (s, 1H), 6.05 (s, 1H), 4.45 (quint, 1H), 3.86 (d, 1H), 3.74 (s, 3H), 3.60 (d, 1H), 1.7 (s, 3H), 1.25 (d, 3H), 1.2 (d, 3H)

Example 14

(S)-1-(4-Chloro-phenyl)-2-{4-[1-hydroxy-1-(1-methyl-1H-pyrazol-3-yl)-ethyl]-phenyl}-7-isopropoxy-6-methoxy-1,4-dihydro-2H-isoquinolin-3-one

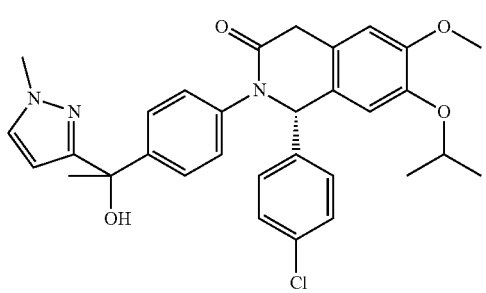 [SMILES: COc1cc2c(cc1OC(C)C)[C@H](c1ccc(Cl)cc1)N(c1ccc(C(C)(O)c3ccn(C)n3)cc1)C(=O)C2]

Example 14 was obtained analogously to example 12 except 1-(4-iodophenyl)-1-(1-methyl-1H-pyrazol-3-yl)ethanol was used instead of 1-(6-bromopyridin-3-yl)-1-(pyridin-4-yl)ethanol.

HPLC: $^A t_{Ret}$=1.08 min; LC-MS: m/z 546.2 [M+H]$^+$

1H-NMR (600 MHz, DMSO-d$_6$): δ 7.5 (s, 5H), 7.4-7.3 (m, 1H), 7.1-7.05 (m, 3H), 6.82 (s, 1H), 6.10 (s, 2H), 5.60 (s, 1H), 4.45 (quint, 1H), 3.86 (d, 1H), 3.75 (s, 3H), 3.70 (s, 3H), 3.60 (d, 1H), 1.7 (s, 3H), 1.25 (d, 3H), 1.20 (d, 3H)

Example 15

(S)-1-(4-Chloro-phenyl)-2-[5-(1-hydroxy-1-pyridin-3-yl-ethyl)-pyridin-2-yl]-7-isopropoxy-6-methoxy-1,4-dihydro-2H-isoquinolin-3-one

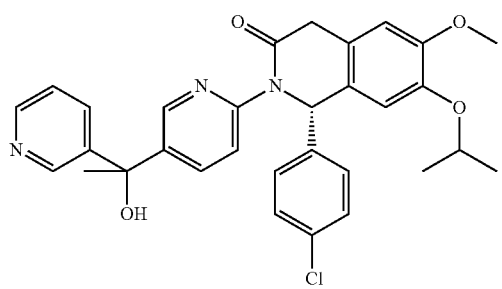 [SMILES: COc1cc2c(cc1OC(C)C)[C@H](c1ccc(Cl)cc1)N(c1ccc(C(C)(O)c3cccnc3)cn1)C(=O)C2]

Example 15 was obtained analogously to example 12 except in step 12.1, 2-iodopyridine was used instead of 3-iodopyridine.

HPLC: $^A t_{Ret}$=0.94 min; LC-MS: m/z 544.2 [M+H]$^+$

1H-NMR (600 MHz, DMSO-d$_6$): δ 8.7 (s, 1H), 8.5 (s, 1H), 8.4 (d, 1H), 7.9-7.75 (m, 3H), 7.45-7.25 (m, 6H), 6.9 (s, 1H), 6.8 (s, 1H), 4.55 (quint, 1H), 3.7 (s, 3H), 3.6 (s, 2H), 1.90 (s, 3H), 1.20 (s, 6H)

Example 16

(S)-1-(4-Chloro-phenyl)-2-[4-(1-hydroxy-1-pyridin-3-yl-ethyl)-phenyl]-7-isopropoxy-6-methoxy-1,4-dihydro-2H-isoquinolin-3-one

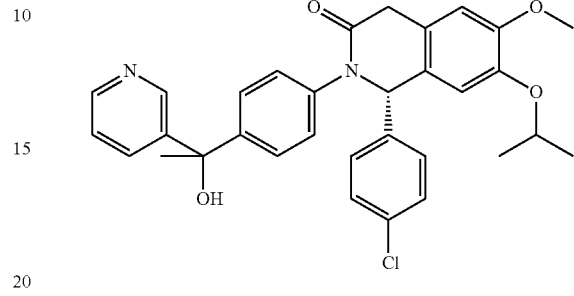

Example 16 was obtained analogously to example 1 except that a different side chain was used in the cross coupling (step 16.1)

HPLC: $^A t_{Ret}$=1.03 min; LC-MS: m/z 543.3 [M+H]$^+$

1H-NMR (600 MHz, DMSO-d$_6$): δ 8.62 (s, 1H), 8.38 (d, 1H), 7.77 (d, 1H), 7.41 (d, 2H), 7.35 (s, 4H), 7.29 (m, 1H), 7.10 (t, 3H), 6.84 (s, 1H), 6.07 (s, 1H), 5.94 (s, 1H), 4.45 (quint, 1H), 3.84 (d, 1H), 3.71 (s, 3H), 3.58 (d, 1H), 3.55 (s, 3H), 1.84 (s, 3H), 1.23 (d, 3H), 1.19 (d, 3H)

Intermediate 16.1

1-(4-Iodo-phenyl)-1-pyridin-3-yl-ethanol

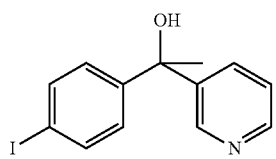 [SMILES: CC(O)(c1ccc(I)cc1)c1cccnc1]

To a solution of 3-iodopyridine (0.3 g, 1.463 mmol) in THF (4 ml) was added ethylmagnesium bromide in diethylether (3M) (0.976 ml, 2.93 mmol). The mixture was stirred at room temperature overnight. GC-MS after overnight showed no starting material and the reaction mixture was cooled in an ice-bath. 4-Iodoacetophenone (0.468 g, 1.902 mmol) was added. The ice-bath was removed after 15 minutes and the reaction was stirred at room temperature for 5 hrs. The reaction mixture was quenched with aqueous saturated NH$_4$Cl solution before dilution with ethyl acetate. The organic phase was separated and washed with brine. The organic phase was dried over Na$_2$SO$_4$, filtered and concentrated in vacuo to obtain the crude product which was purified by preparative HPLC (reversed phase). Fractions containing product were pooled and worked up (addition of NaHCO3, removal of acetonitrile followed by extraction with DCM) to obtain the title compound as yellowish oil.

HPLC: $^A t_{Ret}$=0.82 min; LC-MS: m/z 326.0 [M+H]$^+$

Example 17

(S)-1-(4-Chloro-phenyl)-2-[4-(1-hydroxy-1-pyridin-4-yl-ethyl)-phenyl]-7-isopropoxy-6-methoxy-1,4-dihydro-2H-isoquinolin-3-one

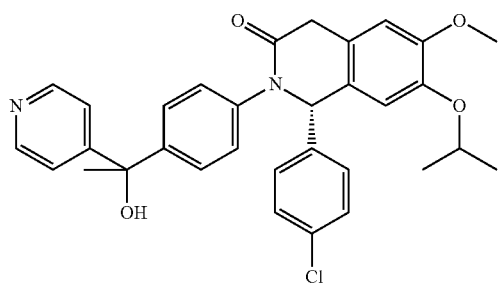 [SMILES: COc1cc2c(cc1OC(C)C)[C@H](c1ccc(Cl)cc1)N(c1ccc(C(C)(O)c3ccncc3)cc1)C(=O)C2]

Example 17 was obtained analogously to example 16 except in step 16.1, 4-iodopyridine (Apollo Scientific) was used instead of 3-iodopyridine.

HPLC: $^A t_{Ret}$=1.35 min; LC-MS: m/z 543.3 [M+H]$^+$

1H-NMR (600 MHz, DMSO-d$_6$): δ 8.47 (d, 2H), 7.5-7.35 (m, 4H), 7.2-7.1 (m, 3H), 6.86 (s, 1H), 6.10 (s, 1H), 5.95 (s, 1H), 4.5-4.4 (m, 1H), 3.86 (d, 1H), 3.74 (s, 3H), 3.60 (d, 1H), 1.8 (s, 3H), 1.25 (d, 3H), 1.20 (d, 3H)

Example 18

(S)-1-(4-Chloro-phenyl)-2-[4-(1-hydroxy-1-pyridin-2-yl-ethyl)-phenyl]-7-isopropoxy-6-methoxy-1,4-dihydro-2H-isoquinolin-3-one

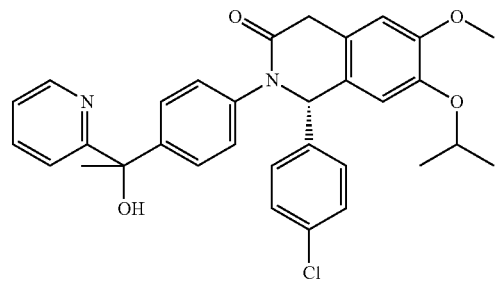 [SMILES: COc1cc2c(cc1OC(C)C)[C@H](c1ccc(Cl)cc1)N(c1ccc(C(C)(O)c3ccccn3)cc1)C(=O)C2]

Example 18 was obtained analogously to example 16 except in step 16.1. 2-iodopyridine (ABCR) was used instead of 3-iodopyridine.

HPLC: $^A t_{Ret}$=1.61 min; LC-MS: m/z 543.2 [M+H]$^+$

1H-NMR (600 MHz, DMSO-d$_6$): δ 8.43 (br s, 1H), 7.75 (t, 1H), 7.65 (d, 1H), 7.45 (d, 2H), 7.35 (s, 4H), 7.2 (t, 1H), 7.1-7.05 (m, 3H), 6.82 (s, 1H), 6.1 (s, 1H), 5.9 (s, 1H), 4.45 (quint, 1H), 3.86 (d, 1H), 3.74 (s, 3H), 3.60 (d, 1H), 1.8 (s, 3H), 1.25 (d, 3H), 1.20 (d, 3H)

Example 19

(S)-1-(4-Chloro-phenyl)-2-{4-[1-(3,4-difluoro-phenyl)-1-hydroxy-ethyl]-phenyl}-7-isopropoxy-6-methoxy-1,4-dihydro-2H-isoquinolin-3-one

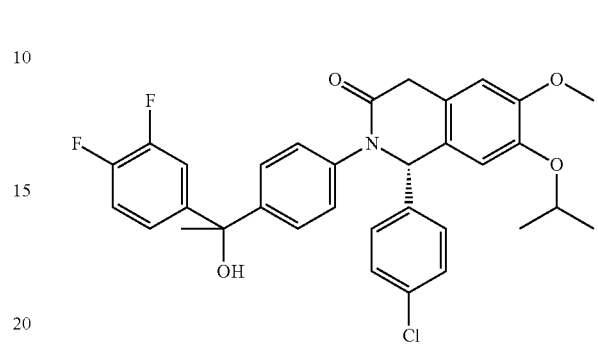

Example 19 was obtained analogously to example 16 except in step 16.1, 1,2-difluoro-4-iodobenzene (Aldrich) was used instead of 3-iodopyridine.

HPLC: $^A t_{Ret}$=2.20 min; LC-MS: m/z 579.2 [M+H]$^+$

1H-NMR (600 MHz, DMSO-d$_6$): δ 7.5-7.2 (m, 9H), 7.15-7.05 (m, 3H), 6.82 (s, 1H), 6.1 (s, 1H), 5.9 (s, 1H), 4.45 (quint, 1H), 3.86 (d, 1H), 3.74 (s, 3H), 3.60 (d, 1H), 1.8 (s, 3H), 1.25 (d, 3H), 1.20 (d, 3H)

Example 20

(S)-1-(4-Chloro-phenyl)-2-[2-fluoro-4-(1-hydroxy-1-pyridin-3-yl-ethyl)-phenyl]-7-isopropoxy-6-methoxy-1,4-dihydro-2H-isoquinolin-3-one

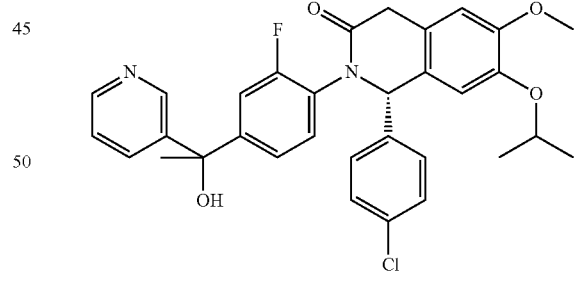

Example 20 was obtained analogously to example 16 except in step 16.1, 3-acetyl pyridine and 1-bromo-2-fluoro-4-iodobenzene were used instead of 4-iodoacetophenone and 4-iodopyridine.

HPLC: $^A t_{Ret}$=0.94 min; LC-MS: m/z 561.1 [M+H]$^+$

1H-NMR (600 MHz, DMSO-d$_6$): δ 8.64 (s, 1H), 8.40 (d, 1H), 7.80 (d, 1H), 7.37-7.28 (m, 5H), 7.24 (d, 1H), 6.93 (s, 1H), 6.85 (d, 1H), 6.09 (d, 1H), 5.97 (s, 1H), 4.4 (quint, 1H), 4.00 (d, 1H), 3.72 (s, 3H), 3.62 (d, 2H), 3.56 (s, 1H), 1.85 (s, 3H), 1.21 (d, 3H), 1.16 (d, 3H)

Example 21

N-[4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-phenyl]-acetamide

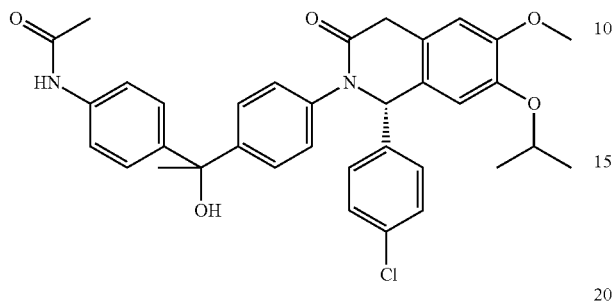

Example 21 was obtained analogously to example 1 except that a different side chain was used in the cross coupling (step 21.1)

HPLC: $^A t_{Ret}$=1.78 min; LC-MS: m/z 599.1 [M+H]$^+$

1H-NMR (600 MHz, DMSO-d$_6$): δ 7.44 (d, 2H), 7.35 (s, 4H), 7.30 (d, 2H), 7.09 (s, 1H), 7.06 (d, 1H), 6.83 (s, 1H), 6.06 (s, 1H), 5.64 (s, 1H), 4.44 (quint, 1H), 3.84 (d, 1H), 3.71 (s, 3H), 3.58 (d, 1H), 3.56 (s, 3H), 2.00 (s, 3H), 1.77 (s, 3H), 1.23 (d, 3H), 1.19 (d, 3H)

Intermediate 21.1

1N-{4-[1-Hydroxy-1-(4-iodo-phenyl)-ethyl]-phenyl}-acetamide

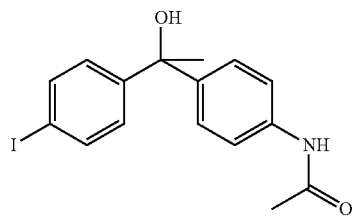 [SMILES: CC(=O)Nc1ccc(C(C)(O)c2ccc(I)cc2)cc1]

To a solution of 4-iodoacetanilide (0.2 g, 0.766 mmol) in THF (2 ml) was added isopropylmagnesiumchloride×LiCl (1.1M in THF) (1.045 ml, 1.149 mmol) via syringe. The sealed vial was stirred overnight at room temperature and a solution of 4-iodoacetophenone (0.226 g, 0.919 mmol) in THF (2.000 ml) was added slowly. The reaction was stirred for 5 hrs at r.t. The reaction mixture was quenched with aqueous saturated NH$_4$Cl solution before dilution with ethyl acetate. The organic phase was separated and washed with brine. The organic phase was dried over Na$_2$SO$_4$, filtered and concentrated in vacuo to obtain the crude material which was purified by automated column chromatography (normal phase, n-heptane (isom. mixture)/ethyl acetate, cartridge 12 g) to obtain the title compound as colorless oil.

HPLC: $^A t_{Ret}$=1.44 min; LC-MS: m/z 382.0 [M+H]$^+$

Example 22

(S)-1-(4-Chloro-phenyl)-2-{4-[1-(3,5-dimethoxy-phenyl)-1-hydroxy-ethyl]-phenyl}-7-isopropoxy-6-methoxy-1,4-dihydro-2H-isoquinolin-3-one

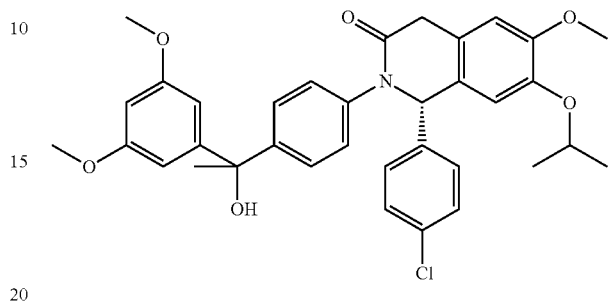

Example 22 was obtained analogously to example 21 except in step 21.1, 1-bromo-3,5-dimethoxybenzene was used instead of 4-iodoacetanilide and the Grignard exchange reaction was heated to 60° C. over night.

HPLC: $^A t_{Ret}$=1.24 min; LC-MS: m/z 602.3 [M+H]$^+$

1H-NMR (600 MHz, DMSO-d$_6$): δ 7.39 (d, 2H), 7.35 (s, 4H), 7.08 (s, 2H), 7.06 (s, 2H), 6.84 (s, 1H), 6.53 (s, 2H), 6.31 (s, 1H), 6.07 (s, 1H), 5.69 (s, 1H), 4.44 (quint, 1H), 3.86 (d, 1H), 3.72 (s, 3H), 3.68 (s, 6H), 1.73 (s, 3H), 1.23 (d, 3H), 1.19 (d, 3H)

Example 23

(S)-1-(4-Chloro-phenyl)-2-{4-[1-hydroxy-1-(6-methoxy-pyridin-3-yl)-ethyl]-phenyl}-7-isopropoxy-6-methoxy-1,4-dihydro-2H-isoquinolin-3-one

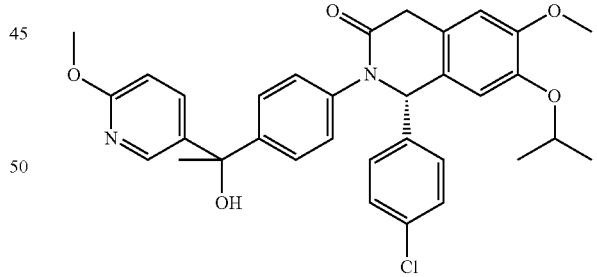

Example 23 was obtained analogously to example 21 except in step 21.1, 5-bromo-2-methoxypyridine was used instead of 4-iodoacetanilide and the Grignard exchange reaction was heated to 60° C. over night.

HPLC: $^A t_{Ret}$=1.20 min; LC-MS: m/z 573.1 [M+H]$^+$

1H-NMR (600 MHz, DMSO-d$_6$): δ 8.18 (s, 1H), 7.64 (d, 1H), 7.38 (d, 2H), 7.35 (s, 4H), 7.35 (d, 2H), 7.10 (d, 2H), 7.09 (s, 1H), 6.84 (s, 1H), 6.71 (d, 1H), 6.07 (s, 1H), 5.81 (s, 1H), 4.44 (quint, 1H), 3.85 (d, 1H), 3.79 (s, 3H), 3.71 (s, 3H), 3.58 (s, 1H), 1.80 (s, 3H), 1.23 (d, 3H), 1.19 (d, 3H)

Example 24

N-[4-(1-{5-[(S)-1-(4-Chloro-phenyl)-7-isopropoxy-6-methoxy-3-oxo-3,4-dihydro-1H-isoquinolin-2-yl]-pyridin-2-yl}-1-hydroxy-ethyl)-phenyl]-acetamide

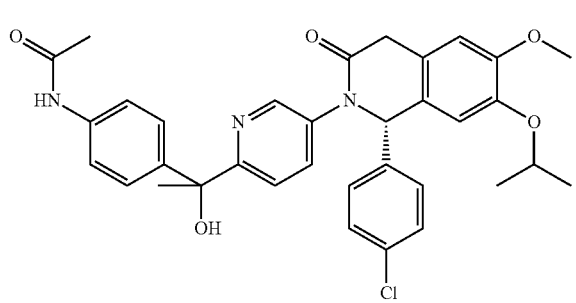 [SMILES: COc1cc2c(cc1OC(C)C)[C@H](c1ccc(Cl)cc1)N(c1ccc(C(C)(O)c3ccc(NC(C)=O)cc3)nc1)C(=O)C2]

Example 24 was obtained analogously to example 21 except in step 21.1, 1-(5-bromopyridin-2-yl)ethanone was used instead of iodoacetophenone.

HPLC: $^A t_{Ret}$=1.13 min; LC-MS: m/z 600.1 [M+H]$^+$

1H-NMR (600 MHz, DMSO-d$_6$): δ 9.85 (s, 1H), 8.28 (s, 1H), 7.58 (m, 2H), 7.42 (d, 1H), 7.35 (s, 4H), 7.33 (d, 1H), 7.01 (s, 1H), 6.85 (s, 1H), 6.14 (s, 1H), 5.86 (s, 1H), 4.44 (quint, 1H), 3.92 (d, 1H), 3.72 (s, 3H), 3.63 (d, 1H), 1.99 (s, 3H), 1.80 (s, 3H), 1.23 (d, 3H), 1.19 (d, 3H)

Example 25

N-[4-(1-{6-[(S)-1-(4-Chloro-phenyl)-7-isopropoxy-6-methoxy-3-oxo-3,4-dihydro-1H-isoquinolin-2-yl]-pyridin-3-yl}-1-hydroxy-ethyl)-phenyl]-acetamide

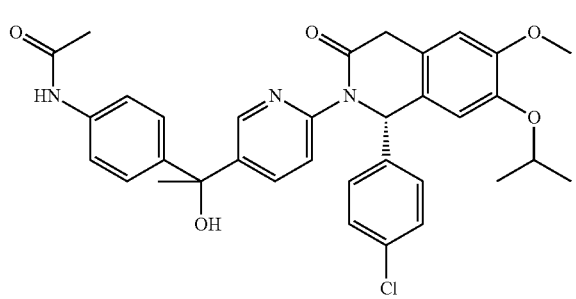 [SMILES: COc1cc2c(cc1OC(C)C)[C@H](c1ccc(Cl)cc1)N(c1ccc(C(C)(O)c3ccc(NC(C)=O)cc3)cn1)C(=O)C2]

Example 25 was obtained analogously to example 21 except in step 21.1, 5-acetyl-2-bromo-pyridine was used instead of iodoacetophenone.

HPLC: $^A t_{Ret}$=1.18 min; LC-MS: m/z 600.1 [M+H]$^+$

1H-NMR (600 MHz, DMSO-d$_6$): δ 9.89 (s, 1H), 8.42 (s, 1H), 7.75 (m, 2H), 7.47 (d, 2H), 7.34 (m, 5H), 7.26 (d, 2H), 6.84 (d, 2H), 5.84 (s, 1H), 4.56 (quint, 1H), 3.72 (s, 3H), 3.59 (s, 2H), 2.0 (s, 3H), 2.00 (dhept, 2H), 1.82 (s, 3H), 1.82 (d, 3H), 1.24 (m, 6H)

Example 26

N-[4-((S)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-phenyl]-acetamide

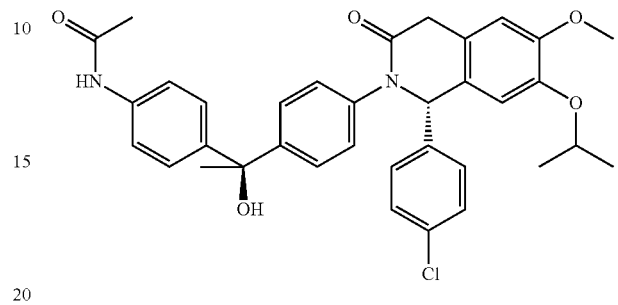

Example 26 was obtained by preparative chiral separation of example 21.

Column; Chiralpak IC 20 um, 76.5×375 mm; mobile phase: n-Heptane/EtOH/MeOH 60:20:20; flow: 80 ml/min; detection: 287 nm (UV) afforded:

HPLC: $^A t_{Ret}$=1.07 min; LC-MS: m/z 599.2 [M+H]$^+$

1H-NMR (600 MHz, DMSO-d$_6$): δ 9.86 (s, 1H), 7.45 (d, 2H), 7.36 (m, 5H), 7.30 (d, 2H), 7.09 (s, 1H), 7.07 (d, 2H), 6.84 (s, 1H), 6.06 (s, 1H), 5.65 (s, 1H), 4.45 (quint, 1H), 3.85 (d, 1H), 3.72 (s, 3H), 3.58 (d, 1H), 1.77 (s, 3H), 1.23 (d, 3H), 1.20 (d, 3H)

Example 27

N-[4-((R)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-phenyl]-acetamide

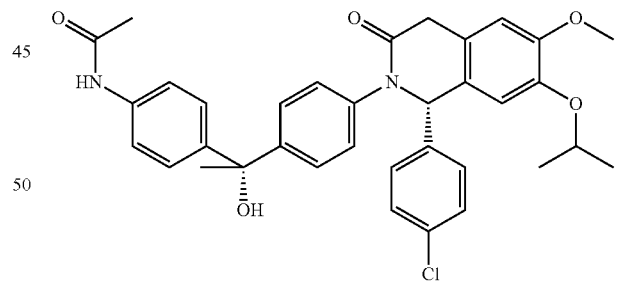

Example 27 was obtained by preparative chiral separation of example 21.

Column; Chiralpak IC 20 um, 76.5×375 mm; mobile phase: n-Heptane/EtOH/MeOH 60:20:20; flow: 80 ml/min; detection: 287 nm (UV) afforded:

HPLC: $^A t_{Ret}$=1.07 min; LC-MS: m/z 599.2 [M+H]$^+$

1H-NMR (600 MHz, DMSO-d$_6$): δ 9.86 (s, 1H), 7.45 (s, 2H), 7.36 (s, 6H), 7.31 (d, 2H), 7.12-7.04 (m, 3H), 6.84 (s, 1H), 6.07 (s, 1H), 5.65 (s, 1H), 4.45 (quint, 1H), 3.85 (d, 1H), 3.72 (s, 3H), 3.58 (d, 1H), 2.00 (s, 3H), 1.77 (s, 3H), 1.23 (d, 3H), 1.19 (d, 3H)

Example 28

N-[4-(1-{4-[(S)-1-(4-Chloro-phenyl)-7-isopropoxy-6-methoxy-3-oxo-3,4-dihydro-1H-isoquinolin-2-yl]-2-fluoro-phenyl}-1-hydroxy-ethyl)-phenyl]-acetamide

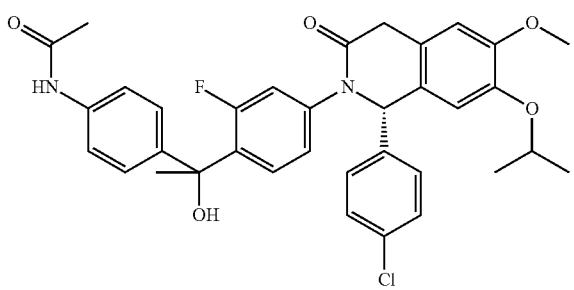 [SMILES: COc1cc2c(cc1OC(C)C)[C@H](c1ccc(Cl)cc1)N(c1ccc(C(C)(O)c3ccc(NC(C)=O)cc3)c(F)c1)C(=O)C2]

Example 28 was obtained analogously to example 21 except in step 21.1, 4-bromo-2-fluoroacetophenone was used instead of iodoacetophenone.

HPLC: $^A t_{Ret}$=1.09 min; LC-MS: m/z 617.1 [M+H]$^+$

1H-NMR (600 MHz, DMSO-d$_6$): δ 7.65 (t, 1H), 7.43 (d, 2H), 7.34 (s, 3H), 7.20 (d, 2H), 7.07 (s, 1H), 7.02 (dt, 1H), 6.96-6.89 (m, 1H), 6.83 (s, 1H), 6.15 (s, 1H), 5.72 (s, 1H), 4.45 (quint, 1H), 3.82 (d, 1H), 3.70 (s, 3H), 3.59 (d, 1H), 3.27 (s, 3H), 1.98 (s, 3H), 1.79 (s, 3H), 1.23 (d, 3H), 1.19 (d, 3H)

Example 29

N-(2-{4-[(S)-1-(4-Chloro-phenyl)-7-isopropoxy-6-methoxy-3-oxo-3,4-dihydro-1H-isoquinolin-2-yl]-phenyl}-2-hydroxy-propyl)-acetamide

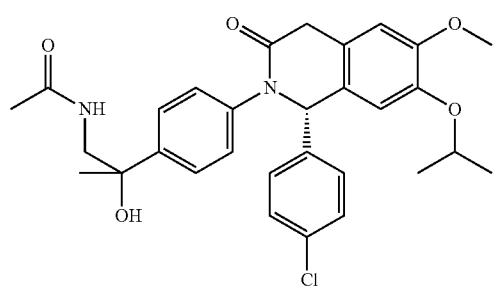 [SMILES: COc1cc2c(cc1OC(C)C)[C@H](c1ccc(Cl)cc1)N(c1ccc(C(C)(O)CNC(C)=O)cc1)C(=O)C2]

Example 29 was obtained analogously to example 1 except that a different side chain was used in the cross coupling (example 29.1)

HPLC: $^A t_{Ret}$=1.00 min; LC-MS: m/z 537.2 [M+H]$^+$

1H-NMR (600 MHz, DMSO-d$_6$): δ 7.77-7.71 (m, 1H), 7.47-7.34 (m, 7H), 7.15-7.10 (m, 3H), 6.85 (s, 1H), 6.09 (s, 1H), 5.28 (d, 1H), 4.47 (quint, 1H), 3.86 (d, 1H), 3.73 (s, 3H), 3.60 (d, 1H), 3.21-3.14 (m, 1H), 1.79 (s, 3H), 1.33 (s, 3H), 1.23 (d, 3H), 1.19 (d, 3H)

Intermediate 29.1

N-[2-(4-Bromo-phenyl)-2-hydroxy-propyl]-acetamide

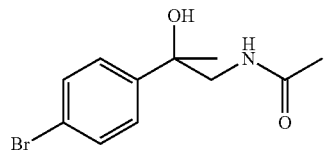

A solution of 1-bromo-4-iodobenzene (1.843 g, 6.51 mmol) in THF (10 ml) was immersed in a dry ice-acetone bath. Ethylmagnesiumbromid (3M) in diethylether (2.90 ml, 8.69 mmol) was added very slowly by a syringe at −41° C. to −39° C. (exothermic reaction, grey precipitation!) and the reaction was kept at −40° C. for 1 hr. A solution of 1-acetamido-acetone (0.5 g, 4.34 mmol) in THF (4 ml) was added slowly below −60° C. The reaction was allowed to warm up to room temperature. The reaction mixture was quenched with aqueous saturated NH$_4$Cl solution before dilution with ethyl acetate. The organic phase was separated and washed with brine. The organic phase was dried over Na$_2$SO$_4$, filtered and concentrated in vacuo to obtain the crude material which was purified by preparative. HPLC (reversed phase). Fractions containing the product were pooled and worked up (addition of NaHCO$_3$, removal of acetonitrile followed by extraction with DCM) to obtain title compound as a yellowish solid (13% yield).

HPLC: $^A t_{Ret}$=0.73 min; LC-MS: m/z 272.1 [M+H]$^+$

Example 30

(S)-1-(4-Chloro-phenyl)-2-{4-[1-hydroxy-1-(tetrahydro-pyran-4-yl)-ethyl]-phenyl}-7-isopropoxy-6-methoxy-1,4-dihydro-2H-isoquinolin-3-one

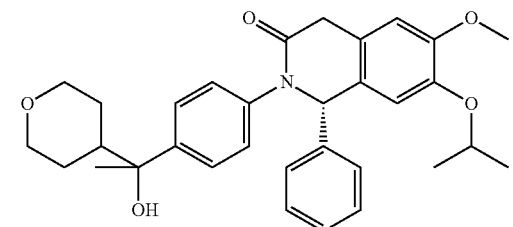

Example 30 was obtained analogously to example 29 except in step 29.1, 1-(tetrahydro-2H-pyran-4-yl)ethanone was used instead of 1-acetamido-acetone.

HPLC: $^A t_{Ret}$=1.11 min; LC-MS: m/z 550.2 [M+H]$^+$

1H-NMR (600 MHz, DMSO-d$_6$): δ 7.36 (d, 4H), 7.35 (s, 2H), 7.13-7.08 (m, 3H), 6.85 (s, 1H), 6.10 (d, 1H), 4.85 (s, 1H), 7.49-4.43 (m, 1H), 3.89-3.82 (m, 2H), 3.78-3.74 (m, 1H), 3.73 (s, 3H), 3.60 (d, 1H), 3.14 (dt, 2H), 1.70-1.64 (m, 1H), 1.47 (d, 1H), 1.38 (s, 3H), 1.3-1.26 (m, 1H), 1.24 (d, 3H), 1.20 (d, 3H), 1.10 (s, 1H)

Example 31

(S)-2-{4-[1-(1-Acetyl-piperidin-4-yl)-1-hydroxy-ethyl]-phenyl}-1-(4-chloro-phenyl)-7-isopropoxy-6-methoxy-1,4-dihydro-2H-isoquinolin-3-one

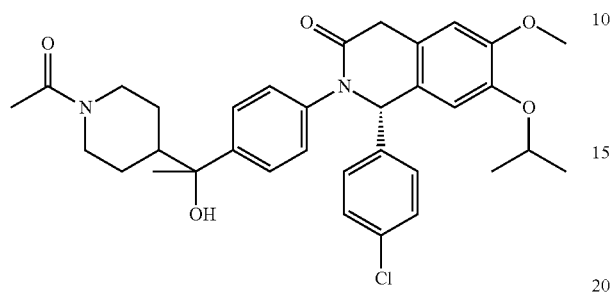

Example 31 was obtained analogously to example 29 except in step 29.1, 1-(4-acetylpiperidino)ethan-1-one was used instead of 1-acetamido-acetone.

HPLC: $^A t_{Ret}$=1.05 min; LC-MS: m/z 591.2 [M+H]$^+$

1H-NMR (600 MHz, DMSO-d$_6$): δ 7.4-7.32 (m, 6H), 7.13-7.1 (m, 3H), 6.87 (s, 1H), 4.8 (s, 1H), 4.45 (quint, 1H), 3.85 (d, 1H), 3.72 (s, 3H), 3.65 (d, 1H), 2.8 (dd, 1H), 2.3 (dd, 1H), 1.9 (d, 3H), 1.8-1.6 (m, 2H), 1.4 (s, 3H), 1.23 (d, 3H), 1.19 (d, 3H), 1.2-0.9 (m, 1H)

Example 32

(S)-1-(4-Chloro-phenyl)-2-{4-[(S)-1-hydroxy-1-(tetrahydro-pyran-4-yl)-ethyl]-phenyl}-7-isopropoxy-6-methoxy-1,4-dihydro-2H-isoquinolin-3-one

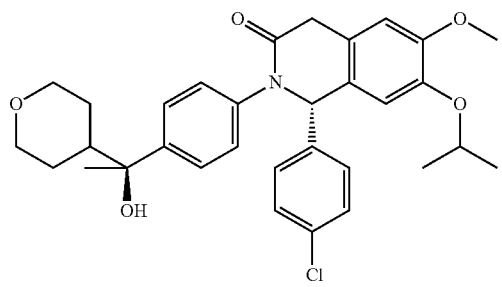 [SMILES: COc1cc2c(cc1OC(C)C)[C@H](c1ccc(Cl)cc1)N(c1ccc([C@@](C)(O)C3CCOCC3)cc1)C(=O)C2]

Example 32 was obtained by preparative chiral separation of example 30.

Column; Chiralpak OD-H, 30×250 mm; mobile phase: CO$_2$/2-propanol 70:30; flow rate: 100 g/min; detection: 220 nm (UV); peak 1 (4.65 min)

HPLC: $^A t_{Ret}$=1.15 min; LC-MS: m/z 550.2 [M+H]$^+$

1H-NMR (600 MHz, DMSO-d$_6$): δ 7.40-7.33 (m, 6H), 7.15-7.09 (m, 3H), 6.86 (s, 1H), 6.11 (s, 1H), 4.86 (s, 1H), 4.47 (quint, 1H), 4.47 (quint, 1H), 3.89-3.82 (m, 2H), 3.80-3.75 (m, 1H), 3.73 (s, 1H), 3.61 (d, 1H), 3.16 (dt, 2H), 2.00 (s, 1H), 1.68 (tt, 1H), 1.48 (br d, 1H), 1.39 (s, 3H), 1.33-1.07 (m, 9H)

Example 33

(S)-1-(4-Chloro-phenyl)-2-{4-[(R)-1-hydroxy-1-(tetrahydro-pyran-4-yl)-ethyl]-phenyl}-7-isopropoxy-6-methoxy-1,4-dihydro-2H-isoquinolin-3-one

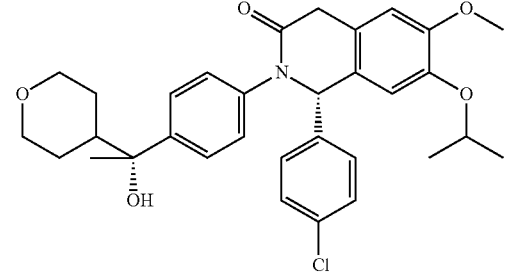 [SMILES: COc1cc2c(cc1OC(C)C)[C@H](c1ccc(Cl)cc1)N(c1ccc([C@](C)(O)C3CCOCC3)cc1)C(=O)C2]

Example 33 was obtained by chiral separation of example 30.

Column; Chiralpak OD-H, 30×250 mm; mobile phase: CO$_2$/2-propanol 70:30; flow rate: 100 g/min; detection: 220 nm (UV); peak 1 (6.44 min)

HPLC: $^A t_{Ret}$=1.16 min; LC-MS: m/z 550.2 [M+H]$^+$

1H-NMR (600 MHz, DMSO-d$_6$): δ 7.40-7.33 (m, 6H), 7.15-7.09 (m, 3H), 6.86 (s, 1H), 6.11 (s, 1H), 4.86 (s, 1H), 4.47 (quint, 1H), 4.47 (quint, 1H), 3.89-3.82 (m, 2H), 3.80-3.75 (m, 1H), 3.73 (s, 1H), 3.61 (d, 1H), 3.16 (dt, 2H), 2.00 (s, 1H), 1.68 (tt, 1H), 1.48 (br d, 1H), 1.39 (s, 3H), 1.33-1.07 (m, 9H)

Example 34

(S)-1-(4-Chloro-phenyl)-2-{4-[1-hydroxy-1-(1-methyl-piperidin-4-yl)-ethyl]-phenyl}-7-isopropoxy-6-methoxy-1,4-dihydro-2H-isoquinolin-3-one

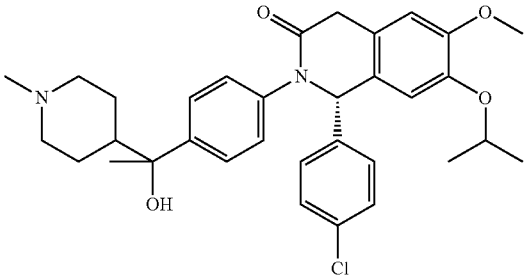 [SMILES: COc1cc2c(cc1OC(C)C)[C@H](c1ccc(Cl)cc1)N(c1ccc(C(C)(O)C3CCN(C)CC3)cc1)C(=O)C2]

Example 34 was obtained analogously to example 29 except in step 29.1, 1-(1-methylpiperidine-4-yl)ethan-1-one was used instead of 1-acetamido-acetone.

HPLC: $^A t_{Ret}$=0.83 min; LC-MS: m/z 563.3 [M+H]$^+$

1H-NMR (600 MHz, DMSO-d$_6$): δ 7.4-7.31 (m, 6H), 7.15-7.06 (m, 3H), 6.84 (s, 1H), 6.11-6.07 (m, 1H), 4.80 (s, 1H), 5.48-4.42 (m, 1H), 3.83 (d, 1H), 3.77 (s, 1H), 3.72 (s, 3H), 3.59 (d, 1H), 2.75 (dd, 2H), 2.09 (s, 2H), 1.79-1.65 (m, 2H), 1.64-1.39 (m, 3H), 1.37 (s, 3H), 1.23 (d, 1H), 1.19 (d, 3H)

Example 35

(S)-1-(4-Chloro-phenyl)-2-{3-fluoro-4-[1-hydroxy-1-(tetrahydro-pyran-4-yl)-ethyl]-phenyl}-7-isopropoxy-6-methoxy-1,4-dihydro-2H-isoquinolin-3-one

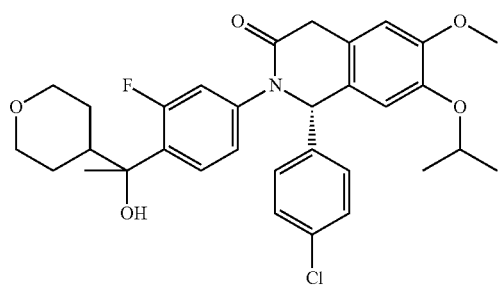 [SMILES: COc1cc2c(cc1OC(C)C)[C@H](c1ccc(Cl)cc1)N(c1ccc(C(C)(O)C3CCOCC3)c(F)c1)C(=O)C2]

Example 35 was obtained analogously to example 29 except in step 29.1, 4-bromo-2-fluoro-1-iodobenzene and 1-(tetrahydro-2H-pyran-4-yl)ethanone were used instead of 1-bromo-4-iodobenzene and 1-acetamido-acetone.

HPLC: $^A t_{Ret}$=1.27 min; LC-MS: m/z 568.1 [M+H]$^+$

1H-NMR (600 MHz, DMSO-d$_6$): δ 7.5 (t, 1H), 7.44 (d, 4H), 7.07 (d, 1H), 7.05-6.94 (m, 2H), 6.84 (s, 1H), 6.16 (d, 1H), 5.04 (s, 1H), 4.43 (quint, 1H), 3.90-3.69 (m, 6H), 3.60 (d, 1H), 3.14 (dt, 2H), 1.85 (br t, 1H), 1.60-1.38 (m, 5H), 1.35-1.25 (m, 1H), 1.22 (d, 3H), 1.15 (d, 3H), 0.81 (d, 1H)

Example 36

(S)-1-(4-Chloro-phenyl)-2-{4-[1-hydroxy-1-(tetrahydro-pyran-4-yl)-ethyl]-2-methoxy-phenyl}-7-isopropoxy-6-methoxy-1,4-dihydro-2H-isoquinolin-3-one

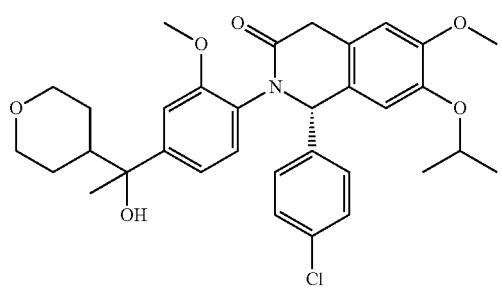 [SMILES: COc1cc2c(cc1OC(C)C)[C@H](c1ccc(Cl)cc1)N(c1ccc(C(C)(O)C3CCOCC3)cc1OC)C(=O)C2]

Example 36 was obtained analogously to example 29 except in step 29.1, 1-bromo-4-iodo-2-methoxybenzene and 1-(tetrahydro-2H-pyran-4-yl)ethanone were used instead of 1-bromo-4-iodobenzene and 1-acetamido-acetone.

HPLC: $^A t_{Ret}$=1.23 min; LC-MS: m/z 580.2 [M+H]$^+$

1H-NMR (600 MHz, DMSO-d$_6$): δ 7.3 (br s, 4H), 7.08 (br s, 1H), 6.92 (br s, 1H), 6.82 (s, 2H), 5.72 (br s, 1H), 4.84 (d, 1H), 4.41 (br s, 1H), 3.95-3.46 (m, 12H), 3.14 (dt, 2H), 1.72-1.61 (m, 1H), 1.50-1.00 (m, 13H)

Example 37

(S)-1-(4-Chloro-phenyl)-2-{5-[1-hydroxy-1-(tetrahydro-pyran-4-yl)-ethyl]-pyridin-2-yl}-7-isopropoxy-6-methoxy-1,4-dihydro-2H-isoquinolin-3-one

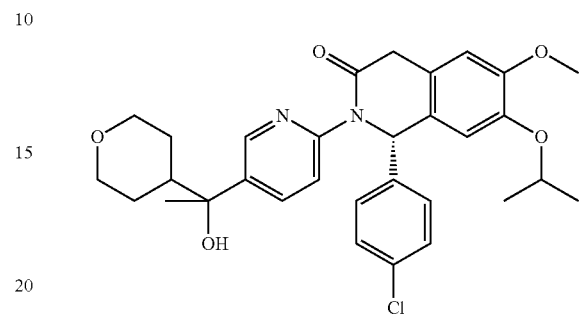

Example 37 was obtained analogously to example 29 except in step 29.1, 2-bromo-5-iodopyridine and 1-(tetrahydro-2H-pyran-4-yl)ethanone were used instead of 1-bromo-4-iodobenzene and 1-acetamido-acetone.

HPLC: $^A t_{Ret}$=1.13 min; LC-MS: m/z 551.2 [M+H]$^+$

1H-NMR (600 MHz, DMSO-d$_6$): δ 8.40 (d, 1H), 7.83-7.73 (m, 2H), 7.36 (d, 1H), 7.33 (d, 2H), 7.27 (d, 2H), 6.89 (s, 1H), 6.82 (d, 1H), 5.06 (d, 1H), 4.57 (quint, 1H), 3.81 (dd, 1H), 3.73 (s, 3H), 3.62 (s, 2H), 3.16 (dt, 2H), 1.71 (t, 2H), 1.50 (d, 1H), 1.42 (s, 3H), 1.31-1.11 (m, 4H), 1.25 (d, 6H)

Example 38

(S)-1-(4-Chloro-phenyl)-2-{3-fluoro-4-[(R)-1-hydroxy-1-(tetrahydro-pyran-4-yl)-ethyl]-phenyl}-7-isopropoxy-6-methoxy-1,4-dihydro-2H-isoquinolin-3-one

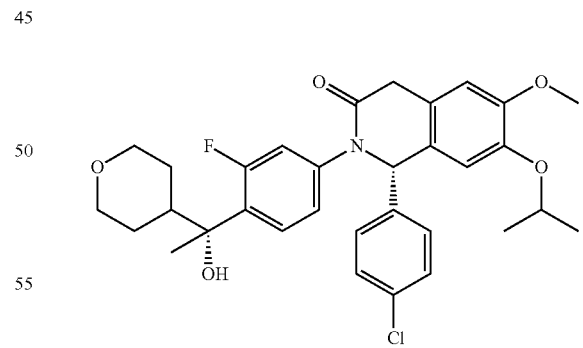

Example 38 was obtained by preparative chiral separation of example 35.

Column; Chiralpak AD-H, 4.6×250 mm; mobile phase: n-heptane/2-propanol 85:15;

flow rate: 1.25 ml/min; detection: 220 nm (UV); peak 1 (14.536 min).

HPLC: $^A t_{Ret}$=1.17 min; LC-MS: m/z 568.3 [M+H]$^+$

Example 39

(S)-1-(4-Chloro-phenyl)-2-{3-fluoro-4-[(S)-1-hydroxy-1-(tetrahydro-pyran-4-yl)-ethyl]-phenyl}-7-isopropoxy-6-methoxy-1,4-dihydro-2H-isoquinolin-3-one

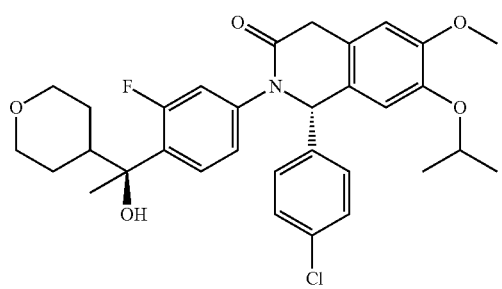 [SMILES: COc1cc2c(cc1OC(C)C)[C@H](c1ccc(Cl)cc1)N(c1ccc([C@@](C)(O)C3CCOCC3)c(F)c1)C(=O)C2]

Example 39 was obtained by preparative chiral separation of example 35.

Column; Chiralpak AD-H, 4.6×250 mm; mobile phase: n-heptane/2-propanol 85:15;

flow rate: 1.25 ml/min; detection: 220 nm (UV); peak 2 (20.376 min).

HPLC: $^A t_{Ret}$=1.17 min; LC-MS: m/z 568.3 [M+H]$^+$

Example 40

(S)-1-(4-Chloro-phenyl)-2-{4-[hydroxy-(tetrahydro-pyran-4-yl)-methyl]-phenyl}-7-isopropoxy-6-methoxy-1,4-dihydro-2H-isoquinolin-3-one

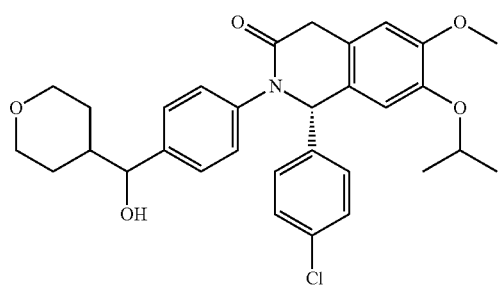 [SMILES: COc1cc2c(cc1OC(C)C)[C@H](c1ccc(Cl)cc1)N(c1ccc(C(O)C3CCOCC3)cc1)C(=O)C2]

Example 40 was obtained analogously to example 29 except in step 29.1, 4-formyl tetrahydropyran was used instead of 1-acetamido-acetone.

HPLC: $^A t_{Ret}$=1.09 min; LC-MS: m/z 536.3 [M+H]$^+$

1H-NMR (600 MHz, DMSO-d$_6$): δ 7.35 (s, 4H), 7.24 (d, 2H), 7.11 (s, 2H), 7.08 (s, 1H), 6.84 (s, 1H), 6.09 (s, 1H), 4.45 (quint, 1H), 3.21 (s, 1H), 3.90-3.74 (m, 4H), 3.73 (s, 3H), 3.21-3.11 (m, 3H), 1.67-1.60 (m, 2H), 3.15 (dt, 2H), 1.23 (d, 1H), 1.19 (d, 3H), 1.08-1.04 (m, 1H)

Example 41

(S)-1-(4-Chloro-phenyl)-2-[4-(1,3-dihydroxy-1-methyl-propyl)-phenyl]-7-isopropoxy-6-methoxy-1,4-dihydro-2H-isoquinolin-3-one

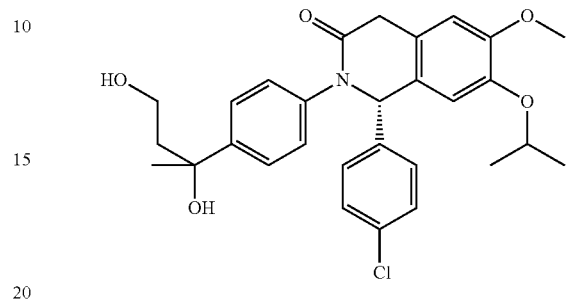

Example 41 was obtained analogously to example 29 except in step 29.1, 4-(tert-butyldimethylsilyloxy)butan-2-one, which was prepared by TBDMS protection of 4-hydroxybutan-2-one, was used instead of 1-acetamido-acetone.

The TBDMS group is cleaved in the Grignard reaction.

HPLC: $^A t_{Ret}$=1.00 min; LC-MS: m/z 510.1 [M+H]$^+$

1H-NMR (600 MHz, DMSO-d$_6$): δ 7.45-7.35 (m, 6H), 7.2-7.1 (m, 2H), 6.85 (s, 1H), 6.1 (s, 1H), 5.05 (s, 1H), 4.45 (quint, 1H), 4.4-4.3 (m, 1H), 3.83 (d, 1H), 3.74 (s, 3H), 3.45-3.3 (m, 2H), 1.8 (s, 2H), 1.45 (s, 3H), 1.23 (d, 1H), 1.19 (d, 3H)

Example 42

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid tert-butyl ester

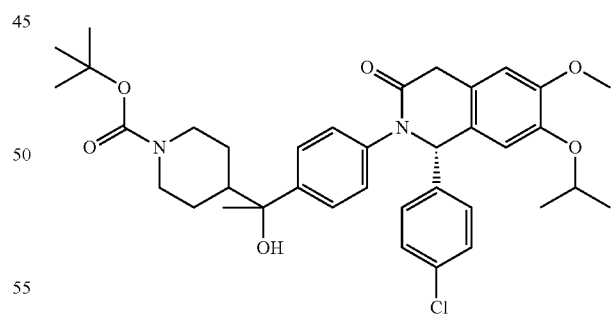

Example 42 was obtained analogously to example 29 except in step 29.1, tert-butyl 4-acetylpiperidine-1-carboxylate was used instead of 1-acetamido-acetone.

HPLC: $^A t_{Ret}$=1.30 min; LC-MS: m/z 649.3 [M+H]$^+$

1H-NMR (600 MHz, DMSO-d$_6$): δ 7.35-7.29 (m, 6H), 7.10-7.05 (m, 3H), 6.83 (s, 1H), 6.07 (s, 1H), 4.83 (d, 1H), 4.45 (quint, 1H), 3.99-3.79 (m, 3H), 3.71 (s, 3H), 3.58 (d, 1H), 1.64-1.52 (m, 3H), 1.36 (s, 3H), 1.33 (s, 9H), 1.23 (d, 1H), 1.19 (d, 3H), 1.08-0.92 (m, 2H)

Example 43

(S)-1-(4-Chloro-phenyl)-2-[4-(1-hydroxy-1-piperidin-4-yl-ethyl)-phenyl]-7-isopropoxy-6-methoxy-1,4-dihydro-2H-isoquinolin-3-one

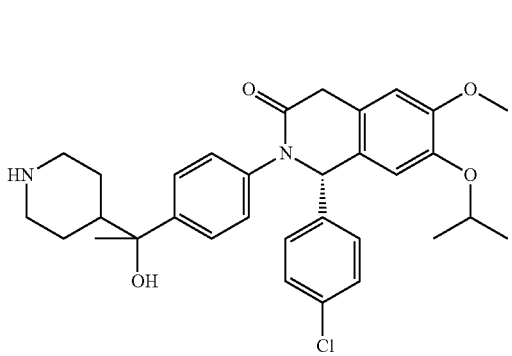

Example 43 was obtained from example 42 by using HCl (4M) in 1,4-dioxane. The reaction was stirred 2 hrs at r.t. The reaction mixture was diluted with ethyl acetate and washed with aqueous NaHCO$_3$ solution and brine. The organic phase was dried over Na$_2$SO$_4$, filtered and concentrated in vacuo to obtain the crude product which was purified by preparative HPLC (reversed phase). Fractions containing the product were pooled and worked up (addition of NaHCO$_3$, removal of acetonitrile followed by extraction with DCM) to obtain the title compound as slightly yellowish solid.

HPLC: $^At_{Ret}$=0.94 min; LC-MS: m/z 549.3 [M+H]$^+$

1H-NMR (600 MHz, DMSO-d$_6$): δ 7.40-7.32 (m, 4H), 7.26-7.10 (m, 5H), 6.86 (s, 1H), 6.13 (d, 1H), 4.49-4.43 (m, 1H), 3.83 (d, 1H), 3.73 (s, 3H), 3.62 (d, 1H), 2.99 (s, 3H), 2.87 (dd, 2H), 2.28 (dt, 2H), 1.59 (t, 1H), 1.48 (t, 1H), 1.42 (s, 3H), 1.23 (d, 1H), 1.19 (d, 3H), 1.13-0.92 (m, 2H)

Example 44

(S)-1-(4-Chloro-phenyl)-2-{4-[1,2-dihydroxy-1-(4-methoxy-phenyl)-ethyl]-phenyl}-7-isopropoxy-6-methoxy-1,4-dihydro-2H-isoquinolin-3-one

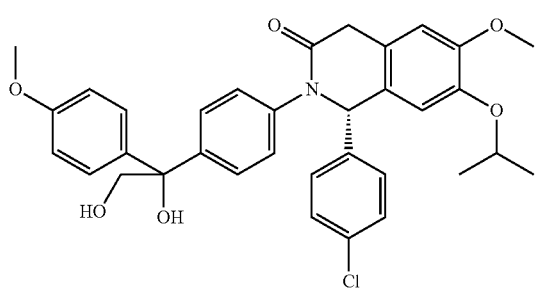 [SMILES: COc1ccc(C(O)(CO)c2ccc(N3C(=O)Cc4cc(OC)c(OC(C)C)cc4[C@@H]3c3ccc(Cl)cc3)cc2)cc1]

Example 44 was obtained analogously to example 1 except that a different side chain was used in the cross coupling (intermediate 44.1)

HPLC: $^At_{Ret}$=1.13 min; LC-MS: m/z 588.2 [M+H]$^+$

1H-NMR (600 MHz, DMSO-d$_6$): δ 7.40-7.33 (m, 6H), 7.30 (d, 2H), 7.12 (s, 1H), 7.08 (d, 2H), 6.84 (s, 1H), 6.82 (d, 2H), 6.08 (s, 1H), 5.44 (d, 1H), 4.85-4.82 (m, 1H), 4.45 (quint, 1H), 3.93-3.82 (m, 3H), 3.72 (s, 3H), 3.70 (s, 3H), 3.57 (d, 3H), 1.23 (d, 1H), 1.19 (d, 3H)

Intermediate 44.1

1-(4-Iodo-phenyl)-1-(4-methoxy-phenyl)ethane-1,2-diol

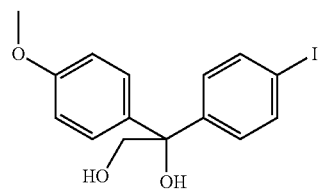 [SMILES: COc1ccc(C(O)(CO)c2ccc(I)cc2)cc1]

Example 44.1 was obtained by dihydroxylation: the AD-mix-alpha (1.008 g, 0.720 mmol) in tert. BuOH (20 ml)/Water (20.00 ml) was immersed in an ice-bath. After 5 minutes 1-iodo-4-(1-(4-methoxyphenyl)vinyl)benzene (example 44.2) (0.22 g, 0.654 mmol) was added as solid. The reaction mixture was heated at 45° C. overnight. The organic solvent was removed under reduced pressure and the remaining aqueous phase was extracted three times with dichloromethane. The organic phases were pooled, dried over sodium sulfate, filtered and concentrated in vacuo to obtain the title compound as slightly yellow solid.

HPLC: $^At_{Ret}$=1.01 min; LC-MS: m/z 353 [M–H$_2$O+H]$^+$

Intermediate 44.2

1-iodo-4-(1-(4-methoxyphenyl)vinyl)benzene

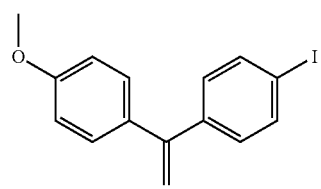 [SMILES: C=C(c1ccc(I)cc1)c1ccc(OC)cc1]

The side chain used in example 5 (1-(4-iodophenyl)-1-(4-methoxyphenyl)ethanol) (1.25 g, 2.86 mmol) was treated with acetic anhydride (13.49 ml, 143 mmol) and HCl conc (1.042 ml, 34.3 mmol) and the reaction mixture was stirred at room temperature overnight. The reaction mixture was filtered. The precipitate was washed well with n-heptane then dried in vacuo to obtain the title compound as white solid.

HPLC: $^At_{Ret}$=1.46 min; LC-MS: m/z 337.0 [M+H]$^+$

Example 45

(S)-1-(4-Chloro-phenyl)-2-{4-[1-(4,4-difluoro-cyclohexyl)-1-hydroxy-ethyl]-phenyl}-7-isopropoxy-6-methoxy-1,4-dihydro-2H-isoquinolin-3-one

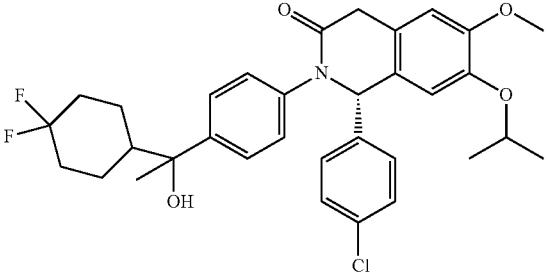 [SMILES: COc1cc2c(cc1OC(C)C)[C@H](c1ccc(Cl)cc1)N(c1ccc(C(C)(O)C3CCC(F)(F)CC3)cc1)C(=O)C2]

Example 45 was obtained analogously to example 29 except in step 29.1, 1-(4,4-difluorocyclohexyl)ethanone was used instead of 1-acetamido-acetone.

HPLC: $^A t_{Ret}$=1.25 min; LC-MS: m/z 584.2 [M+H]$^+$

1H-NMR (600 MHz, DMSO-d$_6$): δ 7.35 (d, 6H), 7.13-7.08 (m, 3H), 6.85 (s, 1H), 6.10 (s, 1H), 4.92 (s, 1H), 4.48-4.1 (m, 1H), 3.88-3.81 (m, 1H), 3.72 (s, 3H), 3.60 (d, 1H), 1.94 (d, 2H), 1.77-1.55 (m, 4H), 1.39 (s, 3H), 2.13 (d, 3H), 1.19 (d, 3H)

Example 46

(S)-1-(4-Chloro-phenyl)-2-{4-[(R)-1-(4,4-difluoro-cyclohexyl)-1-hydroxy-ethyl]-phenyl}-7-isopropoxy-6-methoxy-1,4-dihydro-2H-isoquinolin-3-one

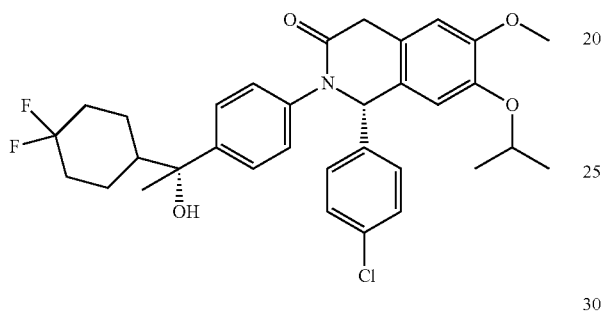

Example 46 was obtained by preparative chiral separation of example 45.

Column; Chiralpak IC, 30×250 mm; mobile phase: CO$_2$/ethanol/2-propanol 60:40:0.4;

flow rate: 100 g/min; detection: 215 nm (UV); peak 1 (4.66 min).

HPLC: $^A t_{Ret}$=1.25 min; LC-MS: m/z 584.3 [M+H]$^+$

1H-NMR (600 MHz, DMSO-d$_6$): δ 7.40-7.33 (m, 6H), 7.14-7.08 (m, 3H), 6.86 (s, 1H), 6.11 (s, 1H), 4.94 (d, 1H), 4.47 (quint, 1H), 3.86 (d, 1H), 3.74 (s, 3H), 3.61 (d, 1H), 1.95 (br d, 2H), 1.78-1.56 (m, 4H), 1.41 (s, 3H), 1.40-1.36 (m, 1H), 1.25 (d, 3H), 1.21 (d, 3H)

Example 47

(S)-1-(4-Chloro-phenyl)-2-{4-[(S)-1-(4,4-difluoro-cyclohexyl)-1-hydroxy-ethyl]-phenyl}-7-isopropoxy-6-methoxy-1,4-dihydro-2H-isoquinolin-3-one

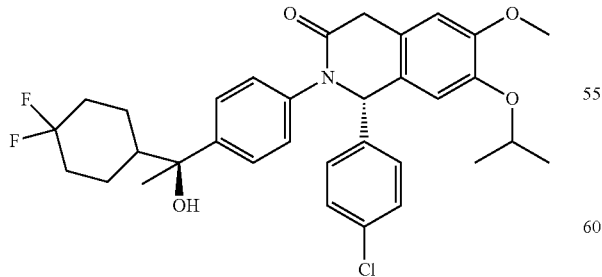

Example 47 was obtained by preparative chiral separation of example 45.

Column; Chiralpak IC, 30×250 mm; mobile phase: CO$_2$/ethanol/2-propanol 60:40:0.4;

flow rate: 100 g/min; detection: 215 nm (UV); peak 2 (6.72 min).

HPLC: $^A t_{Ret}$=1.25 min; LC-MS: m/z 584.3 [M+H]$^+$

1H-NMR (600 MHz, DMSO-d$_6$): δ 7.40-7.33 (m, 6H), 7.14-7.08 (m, 3H), 6.86 (s, 1H), 6.11 (s, 1H), 4.94 (d, 1H), 4.47 (quint, 1H), 3.86 (d, 1H), 3.74 (s, 3H), 3.61 (d, 1H), 1.95 (br d, 2H), 1.78-1.56 (m, 4H), 1.41 (s, 3H), 1.40-1.36 (m, 1H), 1.25 (d, 3H), 1.21 (d, 3H)

Example 48

(S)-1-(4-Chloro-phenyl)-2-{4-[1-hydroxy-1-(tetrahydro-furan-3-yl)-ethyl]-phenyl}-7-isopropoxy-6-methoxy-1,4-dihydro-2H-isoquinolin-3-one

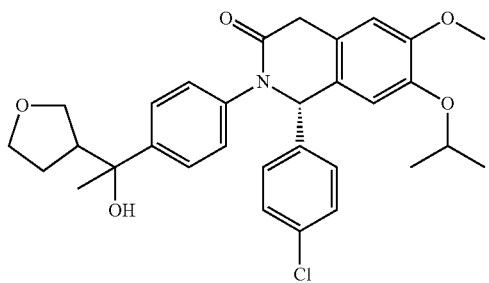 [SMILES: COc1cc2c(cc1OC(C)C)[C@H](c1ccc(Cl)cc1)N(c1ccc(C(C)(O)C3CCOC3)cc1)C(=O)C2]

Example 48 was obtained analogously to example 29 except in step 29.1, 1-(tetrahydrofuran-3-yl)ethanone was used instead of 1-acetamido-acetone.

HPLC: $^A t_{Ret}$=1.11 min; LC-MS: m/z 536.2 [M+H]$^+$

Example 49

(S)-1-(4-Chloro-phenyl)-2-{4-[1-hydroxy-1-(2-oxo-piperidin-4-yl)-ethyl]-phenyl}-7-isopropoxy-6-methoxy-1,4-dihydro-2H-isoquinolin-3-one

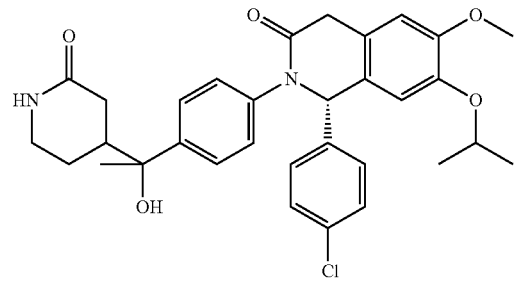 [SMILES: COc1cc2c(cc1OC(C)C)[C@H](c1ccc(Cl)cc1)N(c1ccc(C(C)(O)C3CCNC(=O)C3)cc1)C(=O)C2]

Example 49 was obtained analogously to example 29 except in step 29.1, 4-acetylpiperidin-2-one was used instead of 1-acetamido-acetone.

HPLC: $^A t_{Ret}$=0.98 min; LC-MS: m/z 563.2 [M+H]$^+$

Intermediate 49.1

4-Acetylpiperidin-2-one

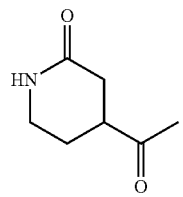

A solution of N-methoxy-N-methyl-2-oxopiperidine-4-carboxamide (2.72 g, 9.79 mmol) in THF (30 ml) was immersed in an ice-bath. MeMgBr (3M) in Et$_2$O (4.57 ml, 13.70 mmol) was added slowly and the remaining white suspension was stirred for 1 h in an ice-bath and over night at room temperature. The reaction mixture was quenched carefully with aqueous saturated NaHCO$_3$ and extracted with DCM. The organic layers were washed with brine, combined, dried over Na$_2$SO$_4$, filtered and concentrated in vacuo to obtain the title compound as yellow-brown oil. The crude product was directly used in the next step.

Intermediate 49.2

N-methoxy-N-methyl-2-oxopiperidine-4-carboxamide

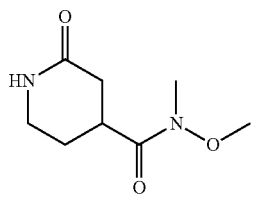

To a stirred solution of 2-oxopiperidine-4-carboxylic acid (CAS #24537-50-6) (1.4 g, 9.78 mmol) in DCM (20 ml) was added portion wise CDI (1.665 g, 10.27 mmol). The suspension was stirred at room temperature for 5 hrs and N,O-dimethylhydroxylamine (1.002 g, 10.27 mmol) was added to the suspension and the reaction mixture was stirred overnight at room temperature. HCl (4M) in 1,4-dioxane (2.445 ml, 9.78 mmol) was added to the cloudy brown-orange solution and the reaction was stirred for 30 min (pH 7). The white precipitate was filtered off and the filtrate was washed with aqueous NaHCO$_3$ solution. The organic phase was dried over Na$_2$SO$_4$, filtered and concentrated in vacuo to obtain the title compound as brown liquid.

HPLC: $^A t_{Ret}$=0.45 min; LC-MS: m/z 187.1 [M+H]$^+$

Example 50

(S)-1-(4-Chloro-phenyl)-2-[4-(1-hydroxy-cyclopentyl)-phenyl]-7-isopropoxy-6-methoxy-1,4-dihydro-2H-isoquinolin-3-one

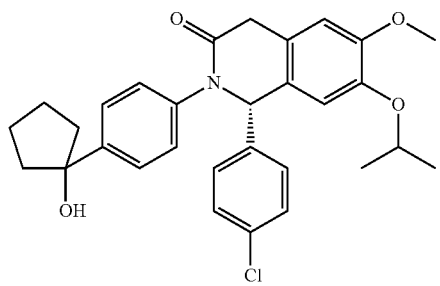 [SMILES: COc1cc2c(cc1OC(C)C)[C@H](c1ccc(Cl)cc1)N(c1ccc(C3(O)CCCC3)cc1)C(=O)C2]

Example 50 was obtained analogously to example 29 except in step 29.1, cyclopentanone was used instead of 1-acetamido-acetone.

HPLC: $^A t_{Ret}$=1.21 min; LC-MS: m/z 506.0 [M+H]$^+$

Example 51

(S)-1-(4-Chloro-phenyl)-2-[4-(1-hydroxy-cyclobutyl)-phenyl]-7-isopropoxy-6-methoxy-1,4-dihydro-2H-isoquinolin-3-one

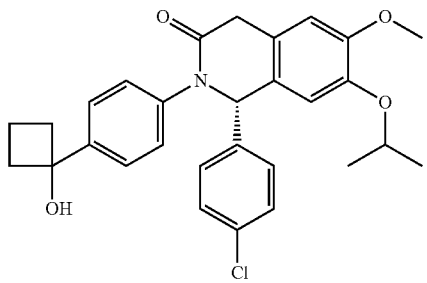 [SMILES: COc1cc2c(cc1OC(C)C)[C@H](c1ccc(Cl)cc1)N(c1ccc(C3(O)CCC3)cc1)C(=O)C2]

Example 51 was obtained analogously to example 29 except in step 29.1, cyclobutanone was used instead of 1-acetamido-acetone.

HPLC: $^A t_{Ret}$=1.18 min; LC-MS: m/z 492.0 [M+H]$^+$

Example 52

(S)-2-{4-[1-(1-Acetyl-piperidin-4-yl)-1-hydroxy-ethyl]-phenyl}-7-((R)-sec-butoxy)-1-(4-chloro-phenyl)-6-methoxy-1,4-dihydro-2H-isoquinolin-3-one

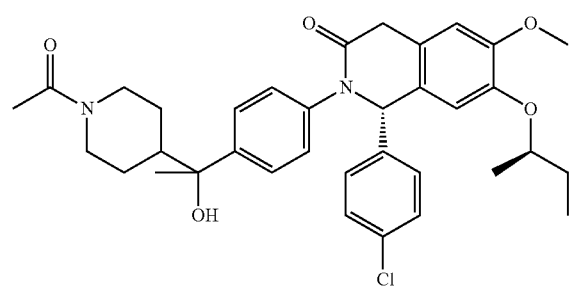 [SMILES: CC[C@@H](C)Oc1cc2c(cc1OC)CC(=O)N(c1ccc(C(C)(O)C3CCN(C(C)=O)CC3)cc1)[C@H]2c1ccc(Cl)cc1]

Example 52 was obtained analogously to example 29 except in step 29.1, 1-(4-acetylpiperidino)ethan-1-one was used instead of 1-acetamido-acetone. In the cross coupling a modified core (intermediate 52.1) was used.

HPLC: $^A t_{Ret}$=1.12 min; LC-MS: m/z 605.3 [M+H]$^+$

Intermediate 52.1

(S)-7-((R)-sec-Butoxy)-1-(4-chloro-phenyl)-6-methoxy-1,4-dihydro-2H-isoquinolin-3-one

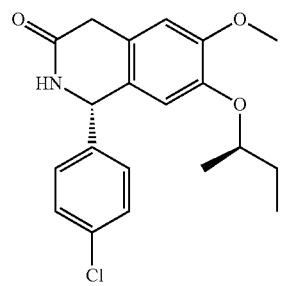 [SMILES: CC[C@@H](C)Oc1cc2c(cc1OC)CC(=O)N[C@H]2c1ccc(Cl)cc1]

To the solution of intermediate 52.2 (1.30 g, 4.19 mmol) in THF (42 mL) was added subsequently (S)-butan-2-ol (0.466 g, 6.29 mmol), di-tert-butylazodicarboxylate (1.93 g, 8.39 mmol) and triphenylphosphine (polymer bound 3 mmol/g resin) (2.79 mg, 8.39 mmol) at 0° C. The mixture was stirred for 75 min at RT. The reaction was filtered, washed with ethyl acetate and the filtrate was concentrated. The residue was extracted with ethyl acetate (3×) and 1M aqueous NaHCO$_3$ (1×). The organic phases were washed with brine and dried over Na$_2$SO$_4$, filtered and evaporated to dryness. Purification of the residue by normal phase column chromatography, eluting with DCM-MeOH (98:2→95:5), gave the title compound after crystallization (TBME) as white crystals (628 mg, 1.728 mmol, 41%)

HPLC: $^D t_{Ret}$=1.06 min; LC-MS: m/z 360.1 [M+H]$^+$;

1H-NMR (400 MHz, DMSO-d$_6$): δ 0.82 (t, 3H), 1.13 (d, 3H), 1.46 (m, 1H), 1.52 (m, 1H), 3.30-3.35 (d, 1H), 3.46-3.51 (d, 1H), 3.69 (s, 3H), 4.16 (m, 1H), 5.52 (m, 1H), 6.76 (s, 1H), 6.80 (s, 1H), 7.32 (q, 4H), 8.48 (d, 1H).

Intermediate 52.2

(S)-1-(4-Chloro-phenyl)-7-hydroxy-6-methoxy-1,4-dihydro-2H-isoquinolin-3-one

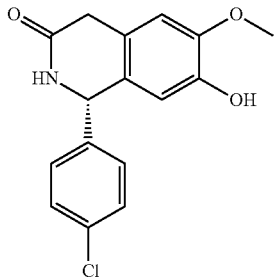

A mixture of intermediate 1.2 (5.0 g, 14.46 mmol) and ortho-phosphoric acid 85% (48.7 mL, 723 mmol) was stirred for 1.5 h at 100° C. The reaction mixture was cooled to RT, poured (carefully) on 1M aqueous NaHCO$_3$ (500 mL), pH 7.0, and extracted with EtOAc (3×) The organic phases were washed with brine and dried over Na$_2$SO$_4$, filtered and evaporated to dryness. Purification of the residue by normal phase column chromatography, eluting with DCM, gave the title compound as yellow foam (4.40 g, 14.20 mmol, 98%).

HPLC: $^D t_{Ret}$=0.78 min; LC-MS: m/z 304.2 [M+H]$^+$;

1H-NMR (400 MHz, DMSO-d$_6$): δ 3.27-3.34 (d, 1H), 3.44-3.49 (d, 1H), 3.71 (s, 3H), 5.46 (br, 1H), 6.53 (s, 1H), 6.72 (s, 1H), 7.32 (q, 4H), 8.41 (s, 1H), 8.85 (s, 1H).

Example 53

(S)-2-{4-[(S)-1-(1-Acetyl-piperidin-4-yl)-1-hydroxyethyl]-phenyl}-1-(4-chloro-phenyl)-7-isopropoxy-6-methoxy-1,4-dihydro-2H-isoquinolin-3-one

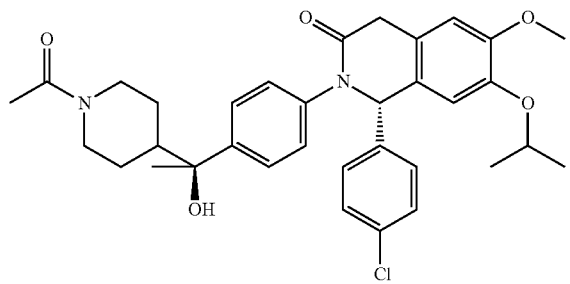 [SMILES: COc1cc2c(cc1OC(C)C)[C@H](c1ccc(Cl)cc1)N(c1ccc([C@@](C)(O)C3CCN(C(C)=O)CC3)cc1)C(=O)C2]

Example 53 was obtained by chiral separation of example 31.

Column; Chiralpak OD-H, 30×250 mm; mobile phase: CO$_2$/2-propanol/2-propylamine 65:35:0.35; flow rate: 80 ml/min; detection: 288 nm (UV); peak 1 (4.01 min).

HPLC: $^A t_{Ret}$=1.08 min; LC-MS: m/z 591.2 [M+H]$^+$

1H-NMR (600 MHz, DMSO-d$_6$): δ 7.40-7.32 (m, 6H), 7.14-7.08 (m, 3H), 6.86 (s, 1H), 6.10 (s, 1H), 4.94-4.82 (d, 1H), 4.45 (quint, 1H), 4.37 (dd, 1H), 3.85 (d, 1H), 3.60 (d, 1H), 2.83 (dt, 1H), 2.29 (dt, 1H), 1.93 (d, 3H), 1.71-1.57 (m, 2H), 1.39 (s, 3H), 2.13 (d, 3H), 1.19 (d, 3H), 1.15-0.92 (m, 2H)

Example 54

(S)-2-{4-[(R)-1-(1-Acetyl-piperidin-4-yl)-1-hydroxy-ethyl]-phenyl}-1-(4-chloro-phenyl)-7-isopropoxy-6-methoxy-1,4-dihydro-2H-isoquinolin-3-one

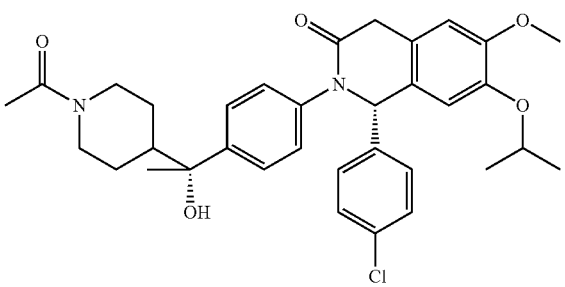

Example 54 was obtained by chiral separation of example 31.

Column; Chiralpak OD-H, 30×250 mm; mobile phase: CO$_2$/2-propanol/2-propylamine 65:35:0.35; flow rate: 80 ml/min; detection: 288 nm (UV); peak 2 (5.39 min).

HPLC: $^A t_{Ret}$=1.08 min; LC-MS: m/z 591.2 [M+H]$^+$

1H-NMR (600 MHz, DMSO-d$_6$): δ 7.40-7.32 (m, 6H), 7.14-7.08 (m, 3H), 6.86 (s, 1H), 6.10 (s, 1H), 4.94-4.82 (d, 1H), 4.45 (quint, 1H), 4.37 (dd, 1H), 3.85 (d, 1H), 3.60 (d, 1H), 2.83 (dt, 1H), 2.29 (dt, 1H), 1.93 (d, 3H), 1.71-1.57 (m, 2H), 1.39 (s, 3H), 2.13 (d, 3H), 1.19 (d, 3H), 1.15-0.92 (m, 2H)

Example 55

3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid tert-butyl ester

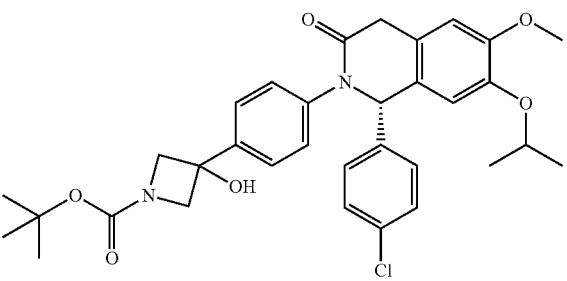 [SMILES: COc1cc2c(cc1OC(C)C)[C@H](c1ccc(Cl)cc1)N(c1ccc(C3(O)CN(C(=O)OC(C)(C)C)C3)cc1)C(=O)C2]

Example 55 was obtained analogously to example 29 except in step 29.1, 1-Boc-3-azetidinone was used instead of 1-acetamido-acetone.

HPLC: $^At_{Ret}$=1.21 min; LC-MS: m/z 593.3 [M+H]$^+$

1H-NMR (600 MHz, DMSO-d$_6$): δ 7.45 (d, 2H), 7.36 (s, 4H), 7.2 (d, 2H), 7.1 (s, 1H), 6.85 (s, 1H), 6.35 (s, 1H), 6.1 (s, 1H), 4.45 (quint, 1H), 4.1-3.9 (m, 4H), 3.86 (d, 1H), 3.74 (s, 3H), 3.60 (d, 1H), 1.4 (s, 9H), 1.23 (d, 3H), 1.19 (d, 3H)

Example 56

(S)-1-(4-Chloro-phenyl)-2-[4-(3-hydroxy-azetidin-3-yl)-phenyl]-7-isopropoxy-6-methoxy-1,4-dihydro-2H-isoquinolin-3-one

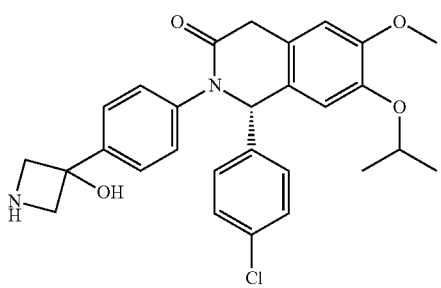 [SMILES: COc1cc2c(cc1OC(C)C)[C@H](c1ccc(Cl)cc1)N(c1ccc(C3(O)CNC3)cc1)C(=O)C2]

Example 56 was obtained from example 55. A solution of 3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid tert-butyl ester (70 mg, 0.118 mmol) in DCM (1 ml) was immersed in an ice-bath followed by addition of TFA (0.045 ml, 0.590 mmol). The yellow reaction solution turned brown and was stirred for 30 minutes. The reaction mixture was treated with ice/saturated aq. sodium hydrogencarbonate solution and extracted with DCM. The organic phase was separated, dried over sodium sulfate, filtered and concentrated in vacuo to obtain the title compound as yellowish solid.

HPLC: $^At_{Ret}$=0.97 min; $^Ft_{Ret}$=8.432 min; LC-MS: m/z 493.3 [M+H]$^+$

1H-NMR (600 MHz, DMSO-d$_6$): δ 7.6 (d, 2H), 7.4-7.35 (m, 4H), 7.17 (d, 2H), 7.1 (s, 1H), 6.85 (s, 1H), 6.1 (s, 1H), 6.0 (s, 1H), 4.45 (quint, 1H), 3.86 (d, 1H), 3.8 (d, 1H), 3.74 (s, 3H), 3.65-3.55 (m, 2H), 1.24 (d, 3H), 1.20 (d, 3H)

Example 57

(S)-2-[4-(1-Acetyl-3-hydroxy-azetidin-3-yl)-phenyl]-1-(4-chloro-phenyl)-7-isopropoxy-6-methoxy-1,4-dihydro-2H-isoquinolin-3-one

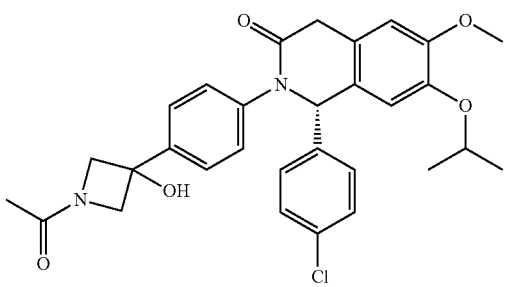 [SMILES: COc1cc2c(cc1OC(C)C)[C@H](c1ccc(Cl)cc1)N(c1ccc(C3(O)CN(C(C)=O)C3)cc1)C(=O)C2]

A solution of (S)-1-(4-chloro-phenyl)-2-[4-(3-hydroxy-azetidin-3-yl)-phenyl]-7-isopropoxy-6-methoxy-1,4-dihydro-2H-isoquinolin-3-one (example 56) (40 mg, 0.081 mmol) in DCM (2 ml) was immersed in an ice-bath. DIPEA (Fluka) (0.043 ml, 0.243 mmol) was added, followed by acetyl chloride (Aldrich) (7.50 µl, 0.105 mmol). Afterwards the reaction was stirred in the ice-bath for 30 min. The reaction mixture was taken up in aqueous NaHCO$_3$ solution. The organic phase was extracted two times with DCM. The organic layers were pooled, dried over Na$_2$SO$_4$, filtered and concentrated in vacuo to obtain the crude product which was purified by preparative TLC (DCM/MeOH 9:1; Rf range from 0.08 to 0.15 was scratched from the plate). The silicagel was taken up in 20 ml DCM/MeOH 1:1. The silicagel was filtered off and the filtrate was evaporated in vacuo to obtain the title compound as yellowish solid.

HPLC: $^At_{Ret}$=0.98 min; $^Ft_{Ret}$=9.150 min; LC-MS: m/z 535.3 [M+H]$^+$

Example 58

3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid methyl ester

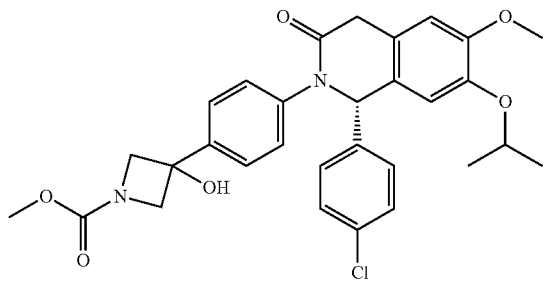

A solution of (S)-1-(4-chloro-phenyl)-2-[4-(3-hydroxy-azetidin-3-yl)-phenyl]-7-isopropoxy-6-methoxy-1,4-dihydro-2H-isoquinolin-3-one (example 56) (40 mg, 0.081 mmol) in DCM (2 ml) was immersed in an ice-bath. DIPEA (Fluka) (0.043 ml, 0.243 mmol) was added, followed by methyl chloroformate (Fluka) (8.17 µl, 0.105 mmol). Afterwards the reaction was stirred in an ice-bath for 30 min. The reaction mixture was taken up in aqueous NaHCO$_3$ solution. The organic phase was extracted two times with DCM. The organic layers were pooled, dried over Na$_2$SO$_4$, filtered and concentrated in vacuo to obtain the crude product which was purified by preparative. TLC (DCM/MeOH 9:1; Rf range from 0.31 to 0.46 was scratched from the plate). The silicagel was taken up in 20 ml DCM/MeOH 1:1. The silicagel was filtered off. The filtrate was evaporated in vacuo to obtain the title compound as white solid.

HPLC: $^At_{Ret}$=1.06 min; $^Ft_{Ret}$=9.388 min; LC-MS: m/z 551.3 [M+H]$^+$

Example 59

3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid dimethylamide

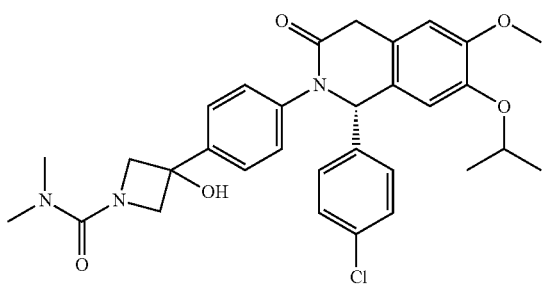

Example 59 was obtained analogously to example 58 except that dimethylcarbanoyl chlorid (Fluka) was used instead of methyl chloroformate.

HPLC: $^A t_{Ret}$=1.02 min; LC-MS: m/z 564.3 [M+H]$^+$

Example 60

3-{4-[(S)-1-(4-Chloro-phenyl)-7-isopropoxy-6-methoxy-3-oxo-3,4-dihydro-1H-isoquinolin-2-yl]-phenyl}-3-hydroxy-azetidine-1-carboxylic acid methylamide

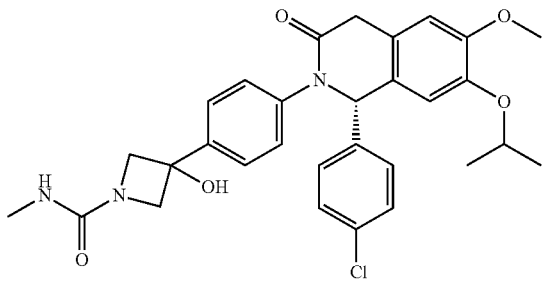

Example 60 was obtained analogously to example 58 except that THF and iscocyanatomethane were used instead of DCM and methyl chloroformate.

HPLC: $^A t_{Ret}$=0.96 min; LC-MS: m/z 550.4 [M+H]$^+$

Example 61

(S)-1-(4-Chloro-phenyl)-2-[4-(1-cyclopropanecarbonyl-3-hydroxy-azetidin-3-yl)-phenyl]-7-isopropoxy-6-methoxy-1,4-dihydro-2H-isoquinolin-3-one

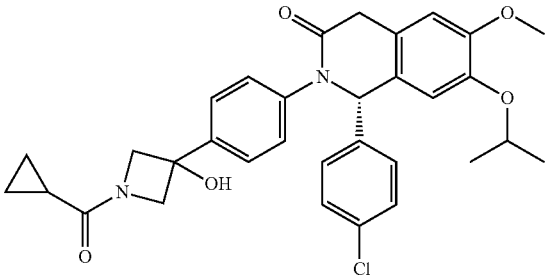 [SMILES: COc1cc2c(cc1OC(C)C)[C@H](c1ccc(Cl)cc1)N(c1ccc(C3(O)CN(C(=O)C4CC4)C3)cc1)C(=O)C2]

Example 61 was obtained analogously to example 58 except that cyclopropanecarbonyl chloride (Fluka) was used instead of methyl chloroformate.

HPLC: $^A t_{Ret}$=1.04 min; LC-MS: m/z 561.3 [M+H]$^+$

Example 62

(S)-1-(4-Chloro-phenyl)-2-[4-(3-hydroxy-1-methanesulfonyl-azetidin-3-yl)-phenyl]-7-isopropoxy-6-methoxy-1,4-dihydro-2H-isoquinolin-3-one

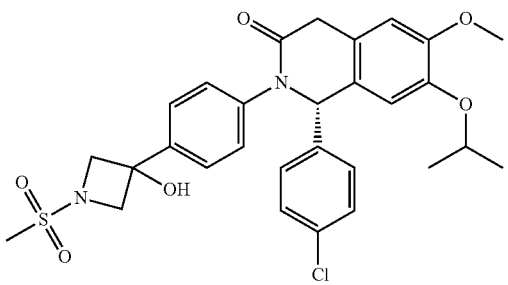 [SMILES: COc1cc2c(cc1OC(C)C)[C@H](c1ccc(Cl)cc1)N(c1ccc(C3(O)CN(S(C)(=O)=O)C3)cc1)C(=O)C2]

Example 62 was obtained analogously to example 58 except that methanesulfonyl chloride (Fluka) was used instead of methyl chloroformate.

HPLC: $^A t_{Ret}$=1.05 min; LC-MS: m/z 571.3 [M+H]$^+$

Example 63

(S)-1-(4-Chloro-phenyl)-2-[4-(1-cyclohexyl-1-hydroxy-ethyl)-phenyl]-7-isopropoxy-6-methoxy-1,4-dihydro-2H-isoquinolin-3-one

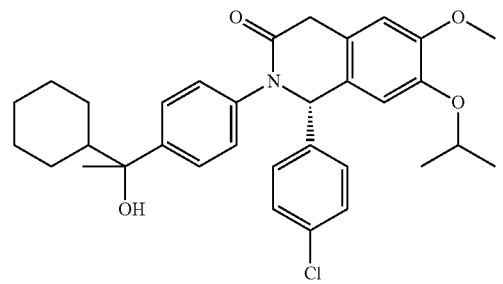 [SMILES: COc1cc2c(cc1OC(C)C)[C@H](c1ccc(Cl)cc1)N(c1ccc(C(C)(O)C3CCCCC3)cc1)C(=O)C2]

Example 63 was obtained analogously to example 1 except that a different side chain was used in the cross coupling (step 63.1)

HPLC: $^A t_{Ret}$=1.35 min; LC-MS: m/z 548.5 [M+H]$^+$

Intermediate 63.1

1-(4-bromophenyl)-1-cyclohexylethanol

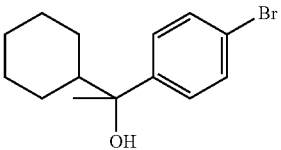 [SMILES: CC(O)(c1ccc(Br)cc1)C1CCCCC1]

A solution of (4-bromophenyl)(cyclohexyl)methanone (step 63.2) (3.1 g, 11.60 mmol) in THF (30 ml) was immersed in an ice-bath, followed by dropwise addition of MeMgBr (3M) in diethylether (7.74 ml, 23.21 mmol). The yellow reaction solution was stirred in the ice-bath for 1.5 hrs. The reaction mixture was quenched carefully with saturated aqueous NH$_4$Cl solution and taken up in ethyl acetate. The organic phase was separated and washed with brine. The organic phase was dried over Na$_2$SO$_4$, filtered and concentrated in vacuo to obtain the title compound as yellow oil.

HPLC: $^A t_{Ret}$=1.32 min; LC-MS: m/z 265.3 [M−H$_2$O+H]$^+$

Intermediate 63.2

(4-Bromophenyl)(cyclohexyl)methanone

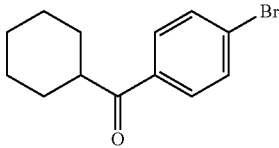 [SMILES: O=C(c1ccc(Br)cc1)C1CCCCC1]

To a solution of (4-bromophenyl)(cyclohexyl)methanol (3.45 g, 12.82 mmol) in DCM (100 ml) was added manganese dioxide (11.14 g, 128 mmol) at room temperature. The reaction mixture was stirred overnight at room temperature. The reaction mixture was diluted with ethyl acetate and the organic phase was washed with aqueous NaHCO$_3$ solution and brine. The organic phase was dried over Na$_2$SO$_4$, filtered and concentrated in vacuo to obtain the title compound as slightly orange solid.

HPLC: $^At_{Ret}$=1.35 min; $^Ft_{Ret}$=10.708 min

Intermediate 63.3

(4-Bromophenyl)(cyclohexyl)methanol

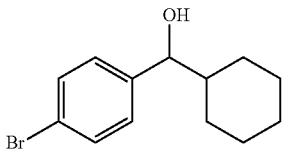 [SMILES: OC(c1ccc(Br)cc1)C1CCCCC1]

A solution of 4-bromobenzaldehyde (4.5 g, 24.32 mmol) in THF (40 ml) was immersed in an ice/methanol bath, followed by the dropwise addition of cyclohexylmagnesium chloride (2M) in diethylether (18.24 ml, 36.5 mmol) at −1° C. to +2° C. The reaction was allowed to warm up to room temperature and the reaction was stopped after 1 hr. The reaction mixture was quenched with saturated aqueous NH$_4$Cl solution before dilution with ethyl acetate. The organic phase was separated and washed with brine. The organic phase was dried over Na$_2$SO$_4$, filtered and concentrated in vacuo to obtain the crude product which was purified by flash chromatography (normal phase, n-heptane (isom. mixture)/ethyl acetate 4:1) to obtain the title compound as yellow oil.

HPLC: $^At_{Ret}$=1.25 min; LC-MS: m/z 251.3 [M−H$_2$O+H]$^+$

Example 64

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-azetidine-1-carboxylic acid tert-butyl ester

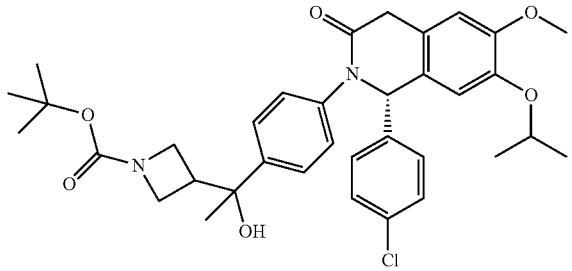 [SMILES: COc1cc2c(cc1OC(C)C)[C@H](c1ccc(Cl)cc1)N(c1ccc(C(C)(O)C3CN(C(=O)OC(C)(C)C)C3)cc1)C(=O)C2]

Example 64 was obtained analogously to example 29 except in step 29.1, 3-acetyl-azetidine-1-carboxylic acid tert-butyl ester was used instead of 1-acetamido-acetone.

HPLC: $^At_{Ret}$=1.24 min; LC-MS: m/z 621.3 [M+H]$^+$

1H-NMR (600 MHz, DMSO-d$_6$): δ 7.4 (d, 2H), 7.38 (s, 4H), 7.15-7.10 (m, 2H), 6.85 (s, 1H), 6.12 (s, 1H), 5.3 (s, 1H), 4.45 (quint, 1H), 4.0-3.85 (m, 1H), 3.86 (d, 1H), 3.74 (s, 3H), 3.60 (d, 1H), 2.9 (br s, 6H), 1.40-1.2 (m, 18H)

Intermediate 64.1

3-Acetyl-azetidine-1-carboxylic acid tert-butyl ester

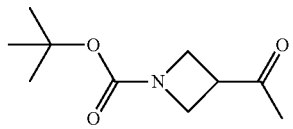

3-Acetyl-azetidine-1-carboxylic acid tert-butyl ester was prepared from commercial available 1-(tert-butoxycarbonyl)azetidine-3-carboxylic acid (Aldrich) in two steps as described in step 49.2 and step 49.1

HPLC: $^At_{Ret}$=0.79 min; $^Ft_{Ret}$=7.56 min

Example 65

(S)-2-[4-(1-Azetidin-3-yl-1-hydroxy-ethyl)-phenyl]-1-(4-chloro-phenyl)-7-isopropoxy-6-methoxy-1,4-dihydro-2H-isoquinolin-3-one

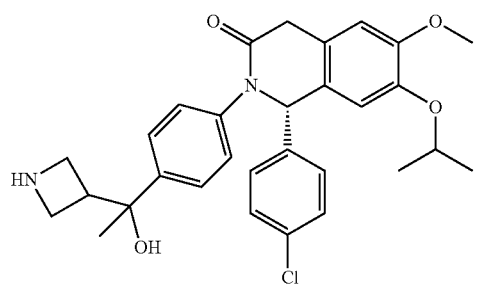 [SMILES: COc1cc2c(cc1OC(C)C)[C@H](c1ccc(Cl)cc1)N(c1ccc(C(C)(O)C3CNC3)cc1)C(=O)C2]

Example 65 was obtained from example 64 analogously to example 56.

HPLC: $^At_{Ret}$=0.88 min; LC-MS: m/z 521.3 [M+H]$^+$

1H-NMR (600 MHz, DMSO-d$_6$): δ 7.4 (d, 2H), 7.38 (s, 4H), 6.85 (s, 2H), 6.1 (d, 2H), 4.45 (quint, 1H), 3.86 (d, 1H), 3.74 (s, 3H), 3.6 (d, 1H), 3.1 (br s, 2H), 1.4-1.2 (m, 9H)

Example 66

(S)-2-{4-[1-(1-Acetyl-azetidin-3-yl)-1-hydroxy-ethyl]-phenyl}-1-(4-chloro-phenyl)-7-isopropoxy-6-methoxy-1,4-dihydro-2H-isoquinolin-3-one

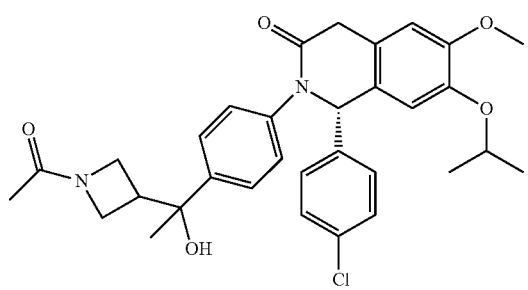 [SMILES: COc1cc2c(cc1OC(C)C)[C@H](c1ccc(Cl)cc1)N(c1ccc(C(C)(O)C3CN(C(C)=O)C3)cc1)C(=O)C2]

Example 66 was prepared from example 65 analogously to example 57.

HPLC: $^A t_{Ret}$=1.01 min; LC-MS: m/z 563.3 [M+H]$^+$

1H-NMR (600 MHz, DMSO-d$_6$): δ 7.42-7.37 (m, 6H), 7.15-7.10 (m, 3H), 6.85 (s, 1H), 6.10 (s, 1H), 4.45 (quint, 1H), 4.15-3.4 (m, 9H), 3.0-2.85 (m, 1H), 1.7 (d, 2H), 1.4-1.3 (m, 2H), 1.25 (d, 3H), 1.19 (d, 3H)

Example 67

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-azetidine-1-carboxylic acid methylamide

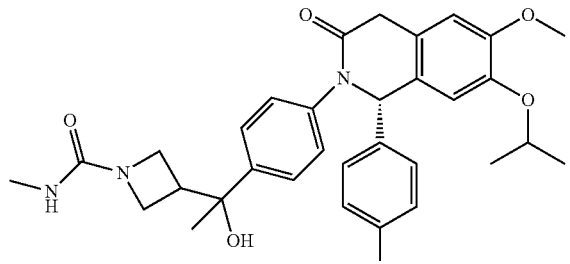

Example 67 was obtained analogously to example 58 except that THF and iscocyanatomethane were used instead of DCM and methyl chloroformate.

HPLC: $^A t_{Ret}$=1.00 min; LC-MS: m/z 578.3 [M+H]$^+$

1H-NMR (600 MHz, DMSO-d$_6$): δ 7.42-7.37 (m, 6H), 7.15-7.10 (m, 3H), 6.85 (s, 1H), 6.12-6.10 (m, 2H), 5.3 (s, 1H), 4.45 (quint, 1H), 3.9-3.5 (m, 9H), 3.95-3.80 (m, 1H), 2.5 (s, 3H), 1.30-1.15 (m, 9H)

Example 68

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-azetidine-1-carboxylic acid dimethylamide

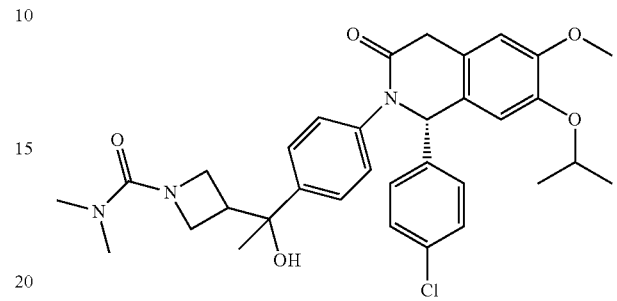

Example 68 was obtained analogously to example 58 except that dimethylcarbanoyl chlorid (Fluka) was used instead of methyl chloroformate.

HPLC: $^A t_{Ret}$=1.06 min; LC-MS: m/z 592.3 [M+H]$^+$

Example 69

(S)-1-(4-Chloro-phenyl)-2-(4-{1-hydroxy-1-[1-(3,3,3-trifluoro-propyl)-azetidin-3-yl]-ethyl}-phenyl)-7-isopropoxy-6-methoxy-1,4-dihydro-2H-isoquinolin-3-one

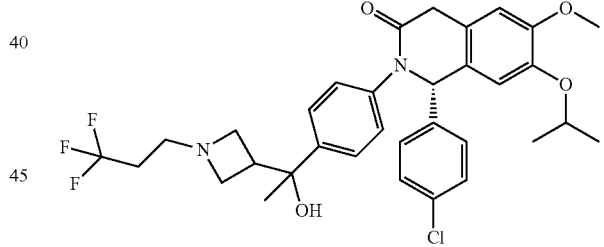

Example 69 was obtained from example 65.

To a solution of example 65 (40 mg, 0.077 mmol) in DCM (2 ml) was added 3,3,3-trifluoropropanal (11.18 mg, 0.100 mmol) and AcOH (8.79 µl, 0.154 mmol), followed by NaBH(OAc)$_3$ (20.34 mg, 0.096 mmol) at room temperature. The reaction was stirred for 2.5 hrs at room temperature. The reaction mixture was taken up in aqueous NaHCO$_3$ solution. The organic phase was extracted two times with DCM. The organic layers were pooled, dried over Na$_2$SO$_4$, filtered and concentrated in vacuo to obtain the crude material, which was purified by preparative TLC (solvent DCM/MeOH 9:1; Rf range from 0.32 to 0.42 was scratched from the plate). The silicagel was taken up in 20 ml DCM/MeOH 1:1 and filtered off. The filtrate was evaporated in vacuo to obtain the title compound as yellowish solid.

HPLC: $^A t_{Ret}$=0.95 min; $^F t_{Ret}$=9.033 min; LC-MS: m/z 617.4 [M+H]$^+$

1H-NMR (600 MHz, DMSO-d$_6$): δ 7.40-7.33 (m, 6H), 7.15-7.07 (m, 3H), 6.86 (s, 1H), 6.11 (d, 1H), 5.1 (s, 1H), 4.45 (quint, 1H), 3.87 (d, 1H), 3.74 (s, 3H), 3.61 (d, 1H), 3.35-2.7 (m, 5H), 2.25-2.15 (m, 2H), 1.30-1.15 (m, 9H)

Example 70

(S)-1-(4-Chloro-phenyl)-2-{4-[1-hydroxy-1-(1-methyl-azetidin-3-yl)-ethyl]-phenyl}-7-isopropoxy-6-methoxy-1,4-dihydro-2H-isoquinolin-3-one

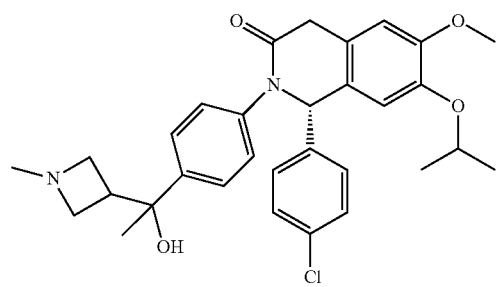 [SMILES: COc1cc2c(cc1OC(C)C)[C@H](c1ccc(Cl)cc1)N(c1ccc(C(C)(O)C3CN(C)C3)cc1)C(=O)C2]

Example 70 was obtained analogously to example 69 except that formaldehyde was used instead of 3,3,3-trifluoropropanal.

HPLC: $^A$t$_{Ret}$=0.89 min; LC-MS: m/z 535.4 [M+H]$^+$

Example 71

(S)-1-(4-Chloro-phenyl)-2-{4-[1-(1-ethyl-azetidin-3-yl)-1-hydroxy-ethyl]-phenyl}-7-isopropoxy-6-methoxy-1,4-dihydro-2H-isoquinolin-3-one

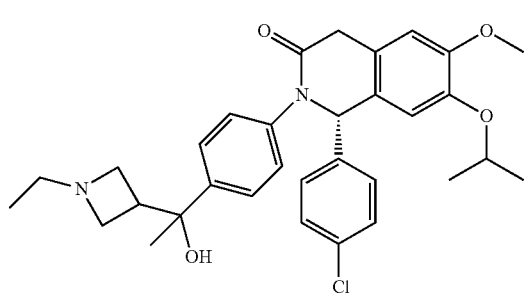 [SMILES: CCN1CC(C(C)(O)c2ccc(N3C(=O)Cc4cc(OC)c(OC(C)C)cc4[C@@H]3c3ccc(Cl)cc3)cc2)C1]

Example 71 was obtained analogously to example 69 except that acetaldehyde was used instead of 3,3,3-trifluoropropanal.

HPLC: $^A$t$_{Ret}$=0.90 min; LC-MS: m/z 549.2 [M+H]$^+$

Example 72

(S)-1-(4-Chloro-phenyl)-2-{4-[1-hydroxy-1-(1-isopropyl-azetidin-3-yl)-ethyl]-phenyl}-7-isopropoxy-6-methoxy-1,4-dihydro-2H-isoquinolin-3-one

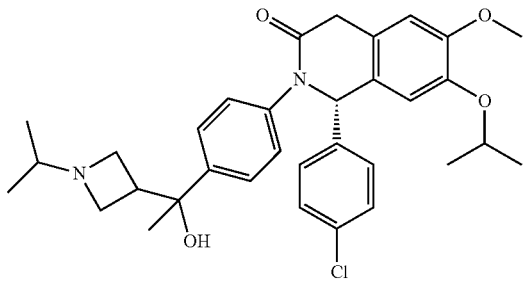 [SMILES: COc1cc2c(cc1OC(C)C)[C@H](c1ccc(Cl)cc1)N(c1ccc(C(C)(O)C3CN(C(C)C)C3)cc1)C(=O)C2]

Example 72 was obtained analogously to example 69 except that acetone was used instead of 3,3,3-trifluoropropanal.

HPLC: $^A$t$_{Ret}$=0.93 min; LC-MS: m/z 563.4 [M+H]$^+$

Example 73

(S)-1-(4-Chloro-phenyl)-2-{4-[1-hydroxy-1-(1-methanesulfonyl-azetidin-3-yl)-ethyl]-phenyl}-7-isopropoxy-6-methoxy-1,4-dihydro-2H-isoquinolin-3-one

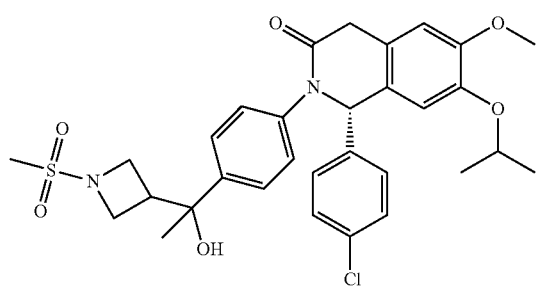 [SMILES: COc1cc2c(cc1OC(C)C)[C@H](c1ccc(Cl)cc1)N(c1ccc(C(C)(O)C3CN(S(C)(=O)=O)C3)cc1)C(=O)C2]

Example 73 was obtained analogously to example 58 except that methanesulfonyl chloride (Fluka) was used instead of methyl chloroformate.

HPLC: $^A$t$_{Ret}$=1.08 min; LC-MS: m/z 599.4 [M+H]$^+$

Example 74

(S)-1-(4-Chloro-phenyl)-2-(4-{1-hydroxy-1-[1-(2,2,2-trifluoro-ethyl)-azetidin-3-yl]-ethyl}-phenyl)-7-isopropoxy-6-methoxy-1,4-dihydro-2H-isoquinolin-3-one

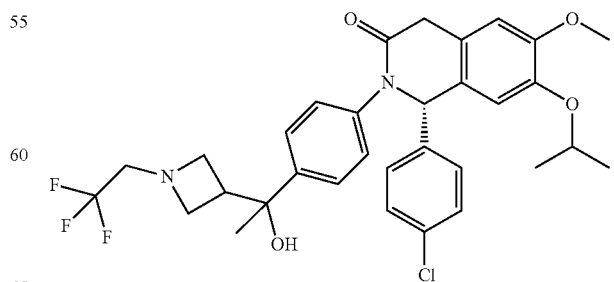

Example 74 was obtained from example 65.

To a solution of example 65 (40 mg, 0.077 mmol) in acetone (2 ml) was added NEt$_3$ (Fluka) (0.054 ml, 0.384 mmol) followed by 2,2,2-trifluorethyltrifluoromethane sulfonate (ABCR) (0.013 ml, 0.092 mmol). The reaction was heated at 65° C. for 12 hrs. The reaction mixture was taken up in aqueous NaHCO$_3$ solution. The organic phase was extracted two times with DCM. The organic layers were pooled, dried over Na$_2$SO$_4$, filtered and concentrated in vacuo to obtain the crude material which was purified by preparative TLC (solvent DCM/MeOH 9:1; Rf range from 0.23 to 0.30 was scratched from the plate). The silicagel was taken up in 20 ml DCM/MeOH 1:1 and filtered off. The filtrate was evaporated in vacuo to obtain the title compound as yellowish solid HPLC: $^A t_{Ret}$=1.11 min; $^F t_{Ret}$=8.940 min; LC-MS: m/z 603.4 [M+H]$^+$ 1H-NMR (600 MHz, DMSO-d$_6$): δ 7.40-7.35 (m, 6H), 7.13-7.08 (m, 3H), 6.86 (s, 1H), 6.11 (d, 1H), 5.15 (s, 1H), 4.45 (quint, 1H), 3.86 (d, 1H), 3.74 (s, 3H), 3.60 (d, 1H), 3.4-3.0 (m, 6H), 2.9-2.8 (m, 1H), 1.3 (s, 3H), 1.25 (d, 3H), 1.19 (d, 3H)

Example 75

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid amide

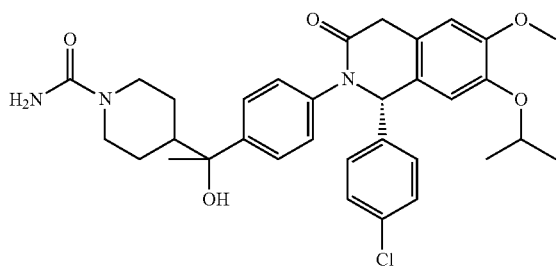 [SMILES: COc1cc2c(cc1OC(C)C)[C@H](c1ccc(Cl)cc1)N(c1ccc(C(C)(O)C3CCN(C(N)=O)CC3)cc1)C(=O)C2]

Example 75 is prepared from intermediate 75.1 which is equal to example 43. An alternative synthetic route is outlined below (steps 75.1-75.6).

A solution of intermediate 75.1 (also example 43) (30 mg, 0.055 mmol) in pyridine (0.5 ml) was immersed in an ice-bath followed by the addition of trimethylsilyl isocyanate (9.83 mg, 0.082 mmol). The reaction was allowed to warm up to room temperature and stirred overnight. The reaction mixture was taken up in aqueous NaHCO$_3$ solution. The organic phase was extracted twice with DCM. The organic layers were pooled, dried over Na$_2$SO$_4$, filtered and concentrated in vacuo to obtain the crude material which was purified by prep. TLC (DCM/MeOH 12:1). The product was scratched from the plate and the silicagel was taken up in 20 ml DCM/MeOH 1:1. The silicagel was filtered off. The filtrate was evaporated in vacuo and the residue was dissolved in 1,4-dioxane and freeze dried overnight to obtain the title compound as white solid.

HPLC: $^A t_{Ret}$=1.00 min; $^F t_{Ret}$=9.326 min; LC-MS: m/z 592.9 [M+H]$^+$

1H-NMR (600 MHz, DMSO-d$_6$): δ 7.39-7.33 (m, 6H), 7.12 (d, 1H), 6.86 (s, 1H), 6.11 (d, 1H), 5.81 (s, 1h), 4.85 (s, 1H), 4.49-4.43 (m, 1H), 3.95 (d, 1H), 3.90-3.82 (m, 1H), 3.73 (s, 3H), 2.47-2.37 (m, 2H), 1.63-1.52 (m, 2H), 1.38 (s, 3H), 1.23 (d, 1H), 1.19 (d, 3H), 1.11-0.97 (m, 2H)

Intermediate 75.1

(S)-1-(4-Chloro-phenyl)-2-[4-(1-hydroxy-1-piperidin-4-yl-ethyl)-phenyl]-7-isopropoxy-6-methoxy-1,4-dihydro-2H-isoquinolin-3-one

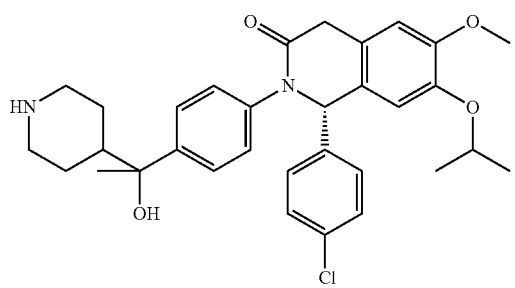

A solution of intermediate 75.2 (1.90 g, 2.78 mmol) in ethanol (100 ml) was degassed 5× with argon, then chlorobenzene (0.566 ml, 5.56 mmol), HCl 1.25M in EtOH (2.447 ml, 3.06 mmol) and Pd/C 5% (0.296 g, 2.78 mmol) were added, followed by a balloon of hydrogen. The reaction mixture was stirred at room temperature for 2.5 hrs, then the catalyst was filtered off and the filtrate was evaporated to dryness. The residue was diluted with ethyl acetate and the organic phase was washed with aqueous NaHCO$_3$ solution and brine. The organic phase was dried over Na$_2$SO$_4$, filtered and concentrated in vacuo to obtain the title compound as yellowish solid.

HPLC: $^A t_{Ret}$=0.94 min; LC-MS: m/z 549.4 [M+H]$^+$
RP-HPLC 100% (t=8.735 min.)

Intermediate 75.2

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid benzyl ester

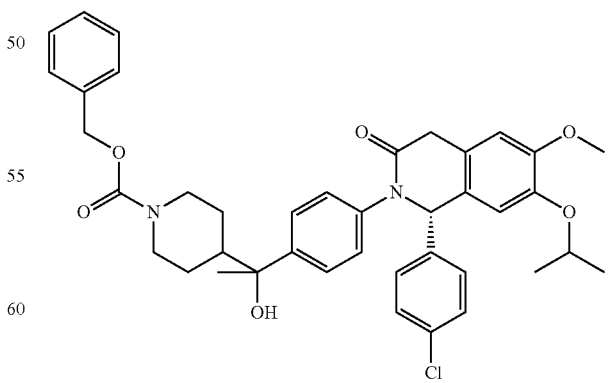

Intermediate 75.2 was obtained analogously to example 1 except that intermediate 75.3 was used instead of 1-(4-iodophenyl)-1-(3-methoxyphenyl)ethanol (step 1.1).

HPLC: $^{A}t_{Ret}$=1.29 min; $^{F}t_{Ret}$=10.586 min; LC-MS: m/z 683.4 [M+H]$^{+}$ Intermediate 75.3

4-[1-(4-Bromo-phenyl)-1-hydroxy-ethyl]-piperidine-1-carboxylic acid benzyl ester

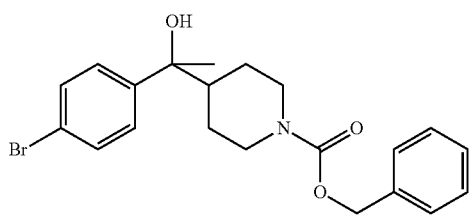 [SMILES: CC(O)(c1ccc(Br)cc1)C1CCN(C(=O)OCc2ccccc2)CC1]

A solution of intermediate 75.4 (5.0 g, 12.43 mmol) in THF (100 ml) was immersed in an ice-methanol-bath. MeMgBr 3M in diethylether (8.29 ml, 24.86 mmol) was added dropwise and the yellow reaction solution was stirred in the cooling-bath. After 1.5 hrs the reaction was finished and the reaction mixture was carefully quenched with saturated aqueous NH$_4$Cl solution. Ethyl acetate was added and the organic phase was separated and washed with brine. The organic phase was dried over Na$_2$SO$_4$, filtered and concentrated in vacuo to obtain the crude material which was purified by automated column chromatography (normal phase, n-heptane (isom. mixture)/ethyl acetate) to obtain the title compound as colorless oil.

HPLC: $^{A}t_{Ret}$=1.23 min; $^{F}t_{Ret}$=10.120 min; LC-MS: m/z 418.2 [M+H]$^{+}$ Intermediate 75.4

4-(4-Bromo-benzoyl)-piperidine-1-carboxylic acid benzyl ester

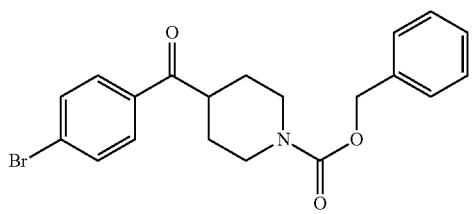 [SMILES: O=C(c1ccc(Br)cc1)C1CCN(C(=O)OCc2ccccc2)CC1]

To a solution of intermediate 75.5 (8.27 g, 20.46 mmol) in dichloromethane (250 ml) was added MnO$_2$ (17.78 g, 205 mmol) at room temperature and again after 2 hrs additional MnO$_2$ (7.11 g, 82 mmol) was added. After overall 4 hrs, the reaction was complete and the mixture was filtered off. The remaining filtrate was concentrated to obtain the crude product which was purified by automated column chromatography (normal phase, n-heptane (isom. mixture)/ethyl acetate) to obtain the title compound as slightly colored oil.

HPLC: $^{A}t_{Ret}$=1.27 min; LC-MS: m/z 402.2 [M+H]$^{+}$

Intermediate 75.5

4-[(4-Bromo-phenyl)-hydroxy-methyl]-piperidine-1-carboxylic acid benzyl ester

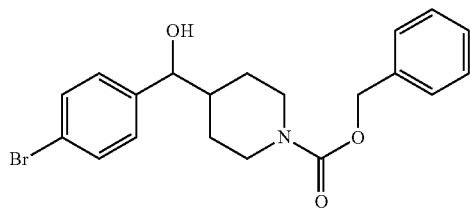 [SMILES: O=C(OCc1ccccc1)N1CCC(C(O)c2ccc(Br)cc2)CC1]

A solution of 1-bromo-4-iodobenzene (17.16 g, 60.7 mmol) in THF (130 ml) was immersed in a dry ice-methanol bath. EtMgBr 3M in diethylether (27.0 ml, 81 mmol) was added slowly via syringe at −44° C. to −40° C. (exothermic reaction, grey precipitation!). The reaction mixture was allowed to warm up to −10° C. and after 2 hrs 1-bromo-4-iodobenzene was gone. Then a solution of benzyl 4-formylpiperidine-1-carboxylate (10 g, 40.4 mmol) in THF (30 ml) was added slowly below −65° C. The reaction was allowed to warm up to room temperature and stirred for 14 hrs. The reaction mixture was quenched with saturated aqueous ammonia chloride solution and diluted with ethyl acetate. The organic phase was separated and washed with brine. The organic phase was dried over Na$_2$SO$_4$, filtered and concentrated in vacuo to obtain the crude material which was purified by automated column chromatography (normal phase, ethyl acetate/n-heptane) to obtain the title compound as colorless oil.

HPLC: $^{A}t_{Ret}$=1.18 min; $^{F}t_{Ret}$=9.881 min; LC-MS: m/z 404.1 [M+H]$^{+}$ Example 76

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid methyl ester

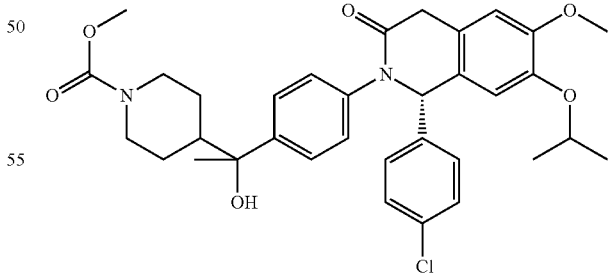

Example 76 was obtained analogously to example 58 except that methyl chloroformate and (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one were used.

HPLC: $^{A}t_{Ret}$=1.16 min; LC-MS: m/z 608.2 [M+H]$^{+}$

1H-NMR (600 MHz, DMSO-d$_6$): δ 7.40-7.32 (m, 6H), 7.14-7.08 (m, 3H), 6.86 (s, 1H), 6.10 (d, 1H), 4.88 (s, 1H), 4.49-4.43 (m, 1H), 4.07-3.88 (s, 1H), 3.85 (dd, 1H), 3.73 (s, 3H), 3.60 (d, 1H), 1.67-1.59 (m, 2H), 1.38 (s, 3H), 1.23 (d, 1H), 1.19 (d, 3H), 1.13-1.00 (m, 2H)

1H-NMR (600 MHz, DMSO-d$_6$): δ 7.40-7.33 (m, 6H), 7.15-7.10 (m, 3H), 6.87 (s, 1H), 6.11 (d, 1H), 4.47 (quintd, 1H), 3.87 (d, 1H), 3.73 (s, 3H), 3.61 (d, 1H), 1.40 (s, 3H), 1.25 (d, 3H), 1.22 (d, 3H)

Example 77

(S)-1-(4-Chloro-phenyl)-2-(4-{1-hydroxy-1-[1-(2,2,2-trifluoro-ethyl)-piperidin-4-yl]-ethyl}-phenyl)-7-isopropoxy-6-methoxy-1,4-dihydro-2H-isoquinolin-3-one

Example 79

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid methylamide

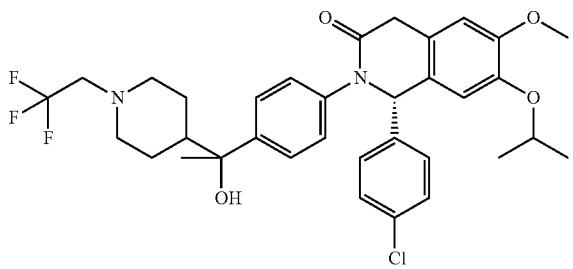 [SMILES: COc1cc2c(cc1OC(C)C)[C@H](c1ccc(Cl)cc1)N(c1ccc(C(C)(O)C3CCN(CC(F)(F)F)CC3)cc1)C(=O)C2]

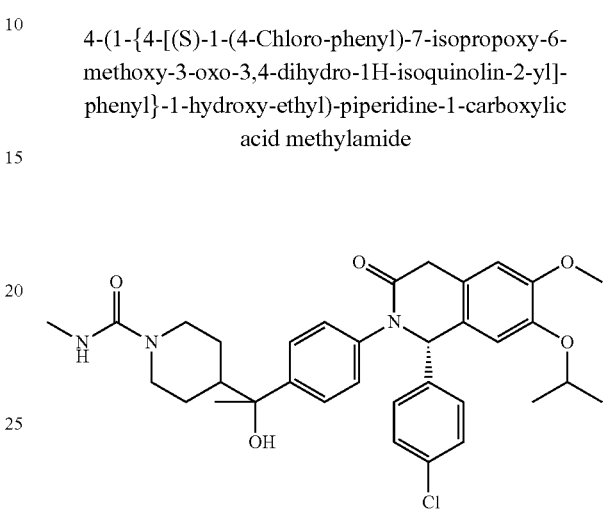

Example 77 was obtained analogously to example 74 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^A$t$_{Ret}$=1.26 min; LC-MS: m/z 631.4 [M+H]$^+$

1H-NMR (600 MHz, DMSO-d$_6$): δ 7.39-7.33 (m, 6H), 7.14-7.08 (m, 3H), 6.86 (s, 1H), 6.11 (d, 1H), 4.84 (d, 1H), 4.47 (quintd, 1H), 3.86 (dd, 1H), 3.74 (s, 3H), 3.61 (d, 1H), 3.05 (q, 2H), 2.88 (dd, 2H), 2.15 (dt, 2H), 1.55 (d, 1H), 1.25 (d, 3H), 1.21 (d, 3H)

Example 79 was obtained analogously to example 67 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^A$t$_{Ret}$=1.03 min; LC-MS: m/z 606.4 [M+H]$^+$

Example 80

S)-1-(4-Chloro-phenyl)-2-{4-[1-(1-cyclopropanecarbonyl-piperidin-4-yl)-1-hydroxy-ethyl]-phenyl}-7-isopropoxy-6-methoxy-1,4-dihydro-2H-isoquinolin-3-one

Example 78

(S)-1-(4-Chloro-phenyl)-2-{4-[1-hydroxy-1-(1-isopropyl-piperidin-4-yl)-ethyl]-phenyl}-7-isopropoxy-6-methoxy-1,4-dihydro-2H-isoquinolin-3-one

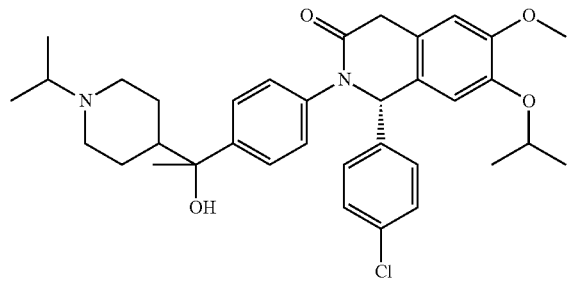 [SMILES: COc1cc2c(cc1OC(C)C)[C@H](c1ccc(Cl)cc1)N(c1ccc(C(C)(O)C3CCN(C(C)C)CC3)cc1)C(=O)C2]

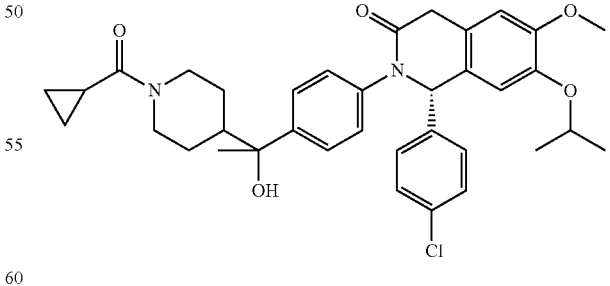

Example 78 was obtained analogously to example 72 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^A$t$_{Ret}$=0.94 min; LC-MS: m/z 591.4 [M+H]$^+$

Example 80 was obtained analogously to example 61 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^A$t$_{Ret}$=1.12 min; LC-MS: m/z 617.4 [M+H]$^+$

Example 81

(S)-1-(4-Chloro-phenyl)-2-{4-[1-hydroxy-1-(1-methanesulfonyl-piperidin-4-yl)-ethyl]-phenyl}-7-isopropoxy-6-methoxy-1,4-dihydro-2H-isoquinolin-3-one

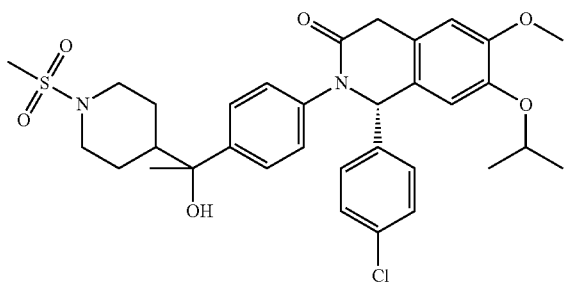

Example 81 was obtained analogously to example 73 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^{A}t_{Ret}$=1.10 min; LC-MS: m/z 627.3 [M+H]$^{+}$

Example 82

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid dimethylamide

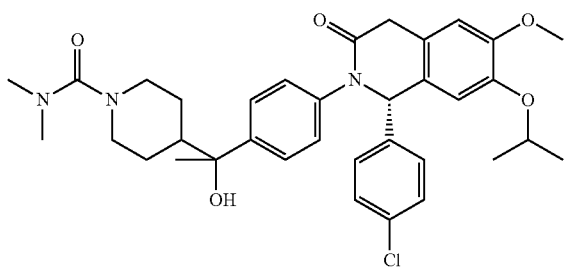 [SMILES: CNC(=O)N1CCC(C(C)(O)c2ccc(N3C(=O)Cc4cc(OC)c(OC(C)C)cc4[C@@H]3c3ccc(Cl)cc3)cc2)CC1]

Example 82 was obtained analogously to example 68 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^{A}t_{Ret}$=1.11 min; LC-MS: m/z 620.3 [M+H]$^{+}$

Example 83

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid isopropyl ester

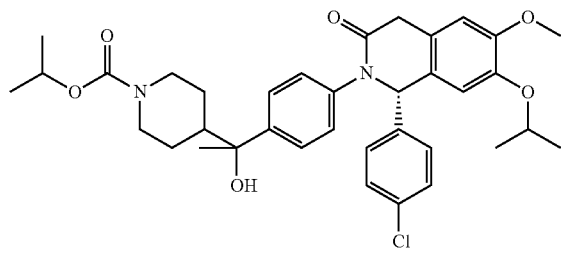 [SMILES: COc1cc2c(cc1OC(C)C)[C@H](c1ccc(Cl)cc1)N(c1ccc(C(C)(O)C3CCN(C(=O)OC(C)C)CC3)cc1)C(=O)C2]

Example 83 was obtained analogously to example 58 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one and isopropyl chloroformate (1M in toluene) were used.

HPLC: $^{A}t_{Ret}$=1.24 min; LC-MS: m/z 635.3 [M+H]$^{+}$

Example 84

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid isopropylamide

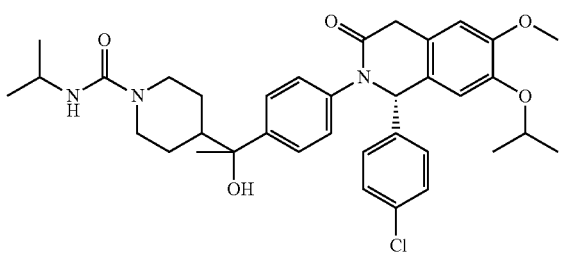 [SMILES: COc1cc2c(cc1OC(C)C)[C@H](c1ccc(Cl)cc1)N(c1ccc(C(C)(O)C3CCN(C(=O)NC(C)C)CC3)cc1)C(=O)C2]

Example 84 was obtained analogously to example 67 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one and isopropylisocyanate were used.

HPLC: $^{A}t_{Ret}$=1.11 min; LC-MS: m/z 634.4 [M+H]$^{+}$

Example 85

(S)-1-(4-Chloro-phenyl)-2-{4-[1-(1-ethyl-piperidin-4-yl)-1-hydroxy-ethyl]-phenyl}-7-isopropoxy-6-methoxy-1,4-dihydro-2H-isoquinolin-3-one

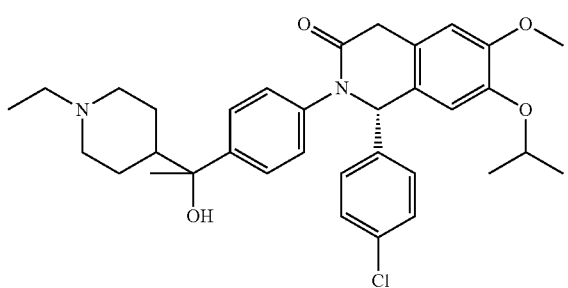 [SMILES: CCN1CCC(C(C)(O)c2ccc(N3C(=O)Cc4cc(OC)c(OC(C)C)cc4[C@@H]3c3ccc(Cl)cc3)cc2)CC1]

Example 85 was obtained analogously to example 71 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^{A}t_{Ret}$=0.91 min; LC-MS: m/z 577.4 [M+H]$^{+}$

1H-NMR (600 MHz, DMSO-d$_6$): δ 7.40-7.34 (m, 6H), 7.15-7.06 (m, 3H), 6.86 (s, 1H), 6.11 (d, 1H), 4.79 (s, 1H), 4.47 (m, 1H), 3.86 (d, 1H), 3.74 (s, 3H), 3.61 (d, 1H), 2.83 (br dd, 2H), 2.20 (q, 2H), 1.64 (dt, 2H), 1.54 (d, 1H), 1.43-1.36 (m, 4H), 1.25 (d, 3H), 1.21 (d, 3H), 0.93 (t, 3H)

Example 86

S)-1-(4-Chloro-phenyl)-2-(4-{1-hydroxy-1-[1-(3,3,3-trifluoro-propyl)-piperidin-4-yl]-ethyl}-phenyl)-7-isopropoxy-6-methoxy-1,4-dihydro-2H-isoquinolin-3-one

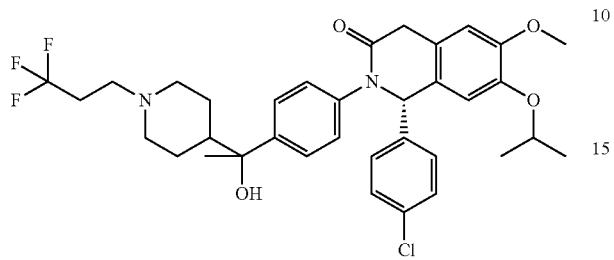

Example 86 was obtained analogously to example 69 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one was used.

HPLC: $^{A}t_{Ret}$=0.97 min; LC-MS: m/z 645.3 [M+H]$^{+}$

1H-NMR (600 MHz, DMSO-d$_6$): δ 7.40-7.31 (m, 6H), 7.16-7.07 (m, 3H), 6.86 (s, 1H), 6.11 (d, 1H), 4.82 (s, 1H), 4.51-4.44 (m, 1H), 3.86 (d, 1H), 3.74 (s, 3H), 3.61 (d, 1H), 2.84 (br dd, 2H), 2.41 (br s, 4H), 1.75 (br dt, 2H), 1.56 (br d, 1H), 1.44-1.37 (m, 4H), 1.25 (d, 3H), 1.21 (d, 3H)

Example 87

(S)-1-(4-Chloro-phenyl)-2-(4-{1-[1-(2,2-difluoro-acetyl)-piperidin-4-yl]-1-hydroxy-ethyl}-phenyl)-7-isopropoxy-6-methoxy-1,4-dihydro-2H-isoquinolin-3-one

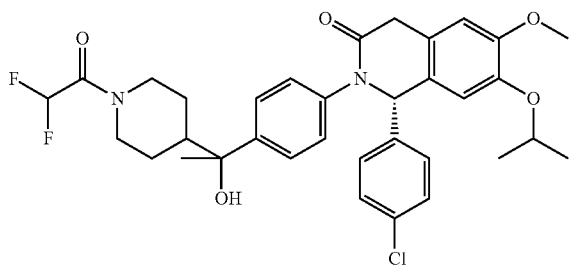 [SMILES: COc1cc2c(cc1OC(C)C)[C@H](c1ccc(Cl)cc1)N(c1ccc(C(C)(O)C3CCN(C(=O)C(F)F)CC3)cc1)C(=O)C2]

The microwave vial was charged with a solution of intermediate 75.1 (47 mg, 0.086 mmol) in DMSO (0.3 ml), then dibromodifluoromethane (0.017 ml, 0.171 mmol) followed by tetrakis(dimethylamino)ethylene (0.044 ml, 0.188 mmol) were added at room temperature. The reaction was stopped after 5 hrs and the crude reaction mixture was diluted with methanol and purified by preparative RP-HPLC. The fraction containing the product was collected and worked up (addition of NaHCO$_3$, removal of acetonitrile followed by extraction with DCM). The residue was dissolved in 1,4-dioxane and freeze dried overnight to obtain the title compound as yellowish solid.

HPLC: $^{A}t_{Ret}$=1.12 min; LC-MS: m/z 627.4 [M+H]$^{+}$

Example 88

3-[4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidin-1-yl]-3-oxo-propionitrile

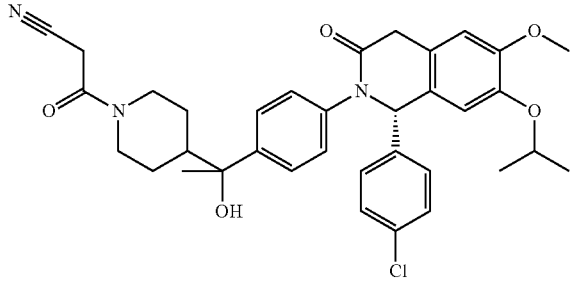 [SMILES: COc1cc2c(cc1OC(C)C)[C@H](c1ccc(Cl)cc1)N(c1ccc(C(C)(O)C3CCN(C(=O)CC#N)CC3)cc1)C(=O)C2]

Intermediate 75.1 (35 mg, 0.064 mmol), 2-cyanoacetic acid (6.51 mg, 0.076 mmol), triethylamine (0.013 ml, 0.096 mmol), 1-hydroxy-7-azabenzotriazole (13.01 mg, 0.096 mmol) and EDC·HCl (18.33 mg, 0.096 mmol) were mixed in DMF (1 ml). The reaction mixture was stirred overnight at room temperature. The reaction was filtered by a microfilter and the remaining filtrate was purified by prep. RP-HPLC (reversed phase). The corresponding fraction was worked up (addition of NaHCO$_3$, removal of acetonitrile followed by extraction with DCM) and the residue was dissolved in 1,4-dioxane and freeze dried to obtain the title compound as white solid.

HPLC: $^{A}t_{Ret}$=1.06 min; $^{F}t_{Ret}$=9.363 min; LC-MS: m/z 616.4 [M+H]$^{+}$ 1H-NMR (600 MHz, DMSO-d$_6$): δ 7.40-7.33 (m, 6H), 7.14-7.10 (m, 3H), 6.86 (s, 1H), 6.11 (d, 1H), 4.94 (s, 1H), 4.46 (quint, 1H), 4.33 (br dd, 1H), 4.07-3.91 (m, 2H), 3.90-3.93 (m, 3H), 3.74 (s, 3H), 3.61 (d, 1H), 2.86 (dt, 1H), 1.75-1.62 (m, 2H), 1.39 (s, 3H), 1.27-0.99 (m, 4H), 1.25 (d, 3H), 1.21 (d, 3H)

Example 89

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde

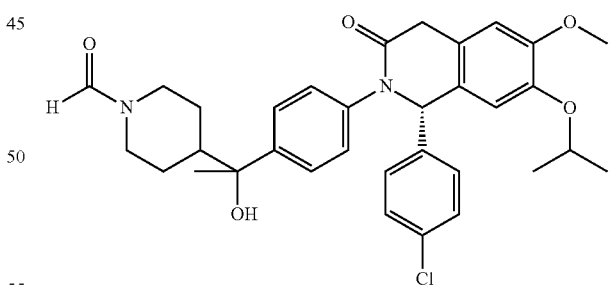

A solution of intermediate 75.1 (28 mg, 0.051 mmol) in ethyl formate (830 µL, 10.20 mmol) was stirred at room temperature for 48 hrs. Ethyl formate was removed under reduced pressure to obtain a yellow oil which was purified by prep. RP-HPLC (reversed phase). The corresponding fractions were pooled and worked up (addition of NaHCO$_3$, removal of acetonitrile followed by extraction with DCM). The residue was dissolved in 1,4-dioxane and freeze dried to obtain the title compound as white solid.

HPLC: $^{A}t_{Ret}$=1.04 min; $^{F}t_{Ret}$=9.498 min; LC-MS: m/z 577.4 [M+H]$^{+}$ 1H-NMR (600 MHz, DMSO-d$_6$): δ 7.91 (d, 1H), 7.40-7.34 (m, 6H), 7.14-7.10 (m, 3H), 6.87 (s, 1H), 6.11 (d, 1H), 4.93 (s, 1H), 4.46 (m, 1H), 4.17 (br dd, 1), 3.86 (d, 1H), 3.74 (s, 3H), 3.70-3.59 (m, 2H), 2.87 (dt, 1H), 2.47-2.33 (m, 1H), 1.78-1.63 (m, 2H), 1.40 (s, 3H), 1.37-1.28 (m, 2H), 1.25 (dd, 3H), 1.21 (q, 3H), 1.13-0.90 (m, 2H)

Example 90

4-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbonyl fluoride

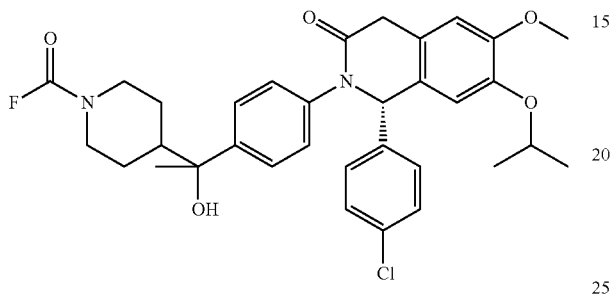

A solution of intermediate 75.1 (115 mg, 0.209 mmol) in THF (15 ml) was immersed in an ice-methanol-bath. Then DIPEA (0.366 ml, 2.094 mmol) was added and an unknown amount of carbonic chloride fluoride gas was introduced into the reaction solution. Reaction control after 30 minutes stirring in the cooling bath showed completion of the reaction. The reaction mixture was quenched carefully by addition of aqueous NaHCO$_3$ solution. Ethyl acetate was added and the phases were separated. The organic phase was washed with brine, dried over Na$_2$SO$_4$, filtered and concentrated in vacuo to obtain the crude material which was purified by prep. RP-HPLC (reversed phase). The corresponding fractions were pooled and worked up (addition of NaHCO$_3$, removal of acetonitrile followed by extraction with DCM). The residue was dissolved in 1,4-dioxane and freeze dried to obtain the title compound as yellowish solid.

HPLC: $^At_{Ret}$=1.16 min; LC-MS: m/z 595.3 [M+H]$^+$

1H-NMR (600 MHz, DMSO-d$_6$): δ 7.40-7.33 (m, 6H), 7.14-7.09 (m, 3H), 6.87 (s, 1H), 4.93 (s, 1H), 4.45 (quint, 1H), 3.9-3.75 (m, 3H), 3.74 (s, 3H), 3.61 (d, 1H), 2.9-2.7 (m, 2H), 1.75-1.65 (m, 2H), 1.39 (s, 3H), 1.37-1.15 (m, 4H), 1.25 (d, 3H), 1.21 (d, 3H)

Example 91

Acetic acid 2-[4-(1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-piperidin-1-yl]-2-oxo-ethyl ester

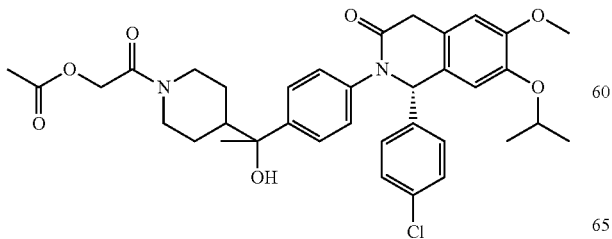

Example 91 was obtained analogously to example 57 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one and acetoxyacetyl chloride were used.

HPLC: $^At_{Ret}$=1.06 min; LC-MS: m/z 649.5 [M+H]$^+$

1H-NMR (600 MHz, DMSO-d$_6$): δ 7.40-7.33 (m, 6H), 7.14-7.09 (m, 3H), 6.87 (s, 1H), 6.11 (s, 1H), 4.93 (s, 1H), 4.71 (m, 1H), 4.30 (br dd, 1H), 3.86 (d, 3H), 3.74 (s, 3H), 3.61 (d, 1H), 2.83 (dt, 1H), 2.45-2.31 (m, 1H), 2.06 (s, 3H), 1.75-1.61 (m, 2H), 1.39 (s, 3H), 1.25 (d, 3H), 1.21 (d, 3H), 1.19-0.95 (m, 2H)

Example 92

(S)-1-(4-Chloro-phenyl)-2-(4-{1-hydroxy-1-[1-(2-hydroxy-acetyl)-piperidin-4-yl]-ethyl}-phenyl)-7-isopropoxy-6-methoxy-1,4-dihydro-2H-isoquinolin-3-one

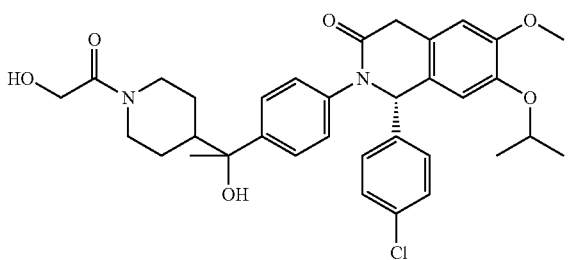 [SMILES: COc1cc2c(cc1OC(C)C)[C@H](c1ccc(Cl)cc1)N(c1ccc(C(C)(O)C3CCN(C(=O)CO)CC3)cc1)C(=O)C2]

Example 92 was obtained from example 91. Example 91 (30 mg, 0.046 mmol) was dissolved in methanol (5 ml), potassium carbonate (12.77 mg, 0.092 mmol) was added and the mixture was warmed to 40° C. for 45 minutes. The reaction was complete and methanol was removed under reduced pressure. The crude product was purified by preparative TLCs (DCM/MeOH 10:1, then DCM/MeOH 85:15) to obtain the title compound as white solid HPLC: $^At_{Ret}$=1.02 min; $^Ft_{Ret}$=9.265 min; LC-MS: m/z 607.4 [M+H]$^+$ 1H-NMR (600 MHz, DMSO-d$_6$): δ 7.4-7.33 (m, 6H), 7.14-7.09 (m, 3H), 6.87 (s, 1H), 6.10 (d, 1H), 4.91 (s, 1H), 4.5-4.38 (m, 3H), 3.86 (d, 1H), 3.74 (s, 3H), 3.61 (d, 1H), 2.85-2.71 (m, 1H), 2.47-2.35 (m, 1H), 1.75-1.58 (m, 1H), 1.39 (s, 3H), 1.25 (d, 3H), 1.21 (d, 3H)

Example 93

(S)-1-(4-Chloro-phenyl)-2-(4-{1-hydroxy-1-[1-(2-hydroxy-ethyl)-piperidin-4-yl]-ethyl}-phenyl)-7-isopropoxy-6-methoxy-1,4-dihydro-2H-isoquinolin-3-one

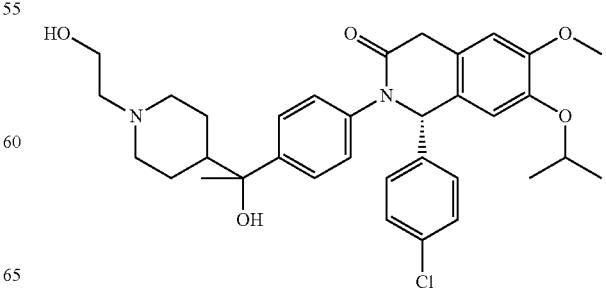

A microwave vial was charged with a solution of intermediate 75.1 (31 mg, 0.056 mmol) in DMF (1 ml). Then potassium carbonate (23.41 mg, 0.169 mmol) followed by 2-bromoethanol (5.98 μl, 0.085 mmol) were added, the vial was sealed and the reaction mixture was stirred for 16 hrs at room temperature. The reaction mixture was filtered through a syringe filter and the filtrate was purified by prep. RP-HPLC (reversed phase). The corresponding fractions were pooled and worked up (addition of NaHCO$_3$, removal of acetonitrile followed by extraction with DCM). The residue was dissolved in 1,4-dioxane and freeze dried overnight to obtain the title compound as white solid.

HPLC: $^A$t$_{Ret}$=0.88 min; $^F$t$_{Ret}$=8.756 min; LC-MS: m/z 593.4 [M+H]$^+$ Example 94

(S)-1-(4-Chloro-phenyl)-2-{4-[(S)-1-hydroxy-1-(1-methyl-piperidin-4-yl)-ethyl]-phenyl}-7-isopropoxy-6-methoxy-1,4-dihydro-2H-isoquinolin-3-one

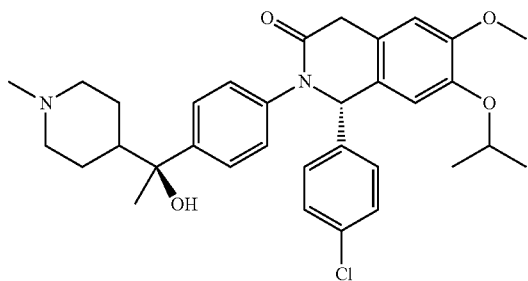

Example 94 was obtained by chiral separation of example 34.

Column; Chiralcel OD-H, 20×250 mm; mobile phase: n-heptane/ethanol/methanol 80:15:5+0.1% TFA; flow rate: 12 ml/min; detection: 220 nm (UV); peak 1 (11.0 min).

HPLC: $^A$t$_{Ret}$=0.92 min; LC-MS: m/z 563.3 [M+H]$^+$

Example 95

(S)-1-(4-Chloro-phenyl)-2-{4-[(R)-1-hydroxy-1-(1-methyl-piperidin-4-yl)-ethyl]-phenyl}-7-isopropoxy-6-methoxy-1,4-dihydro-2H-isoquinolin-3-one

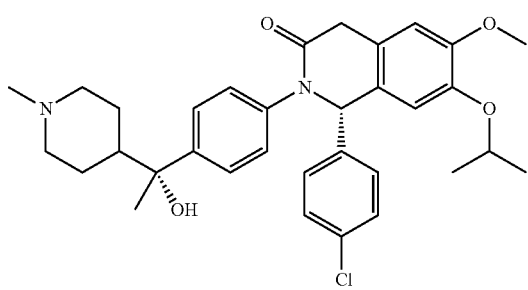 [SMILES: COc1cc2c(cc1OC(C)C)[C@H](c1ccc(Cl)cc1)N(c1ccc([C@](C)(O)C3CCN(C)CC3)cc1)C(=O)C2]

Example 95 was obtained by chiral separation of example 34.

Column; Chiralcel OD-H, 20×250 mm; mobile phase: n-heptane/ethanol/methanol 80:15:5+0.1% TFA; flow rate: 12 ml/min; detection: 220 nm (UV); peak 1 (22.0 min).

HPLC: $^A$t$_{Ret}$=0.92 min; LC-MS: m/z 563.3 [M+H]$^+$

Example 96

(S)-1-(4-Chloro-phenyl)-2-{4-[1-hydroxy-1-(1-oxetan-3-yl-piperidin-4-yl)-ethyl]-phenyl}-7-isopropoxy-6-methoxy-1,4-dihydro-2H-isoquinolin-3-one

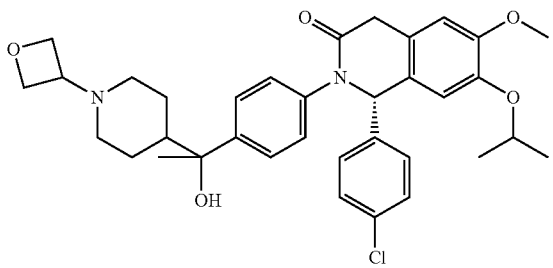 [SMILES: COc1cc2c(cc1OC(C)C)[C@H](c1ccc(Cl)cc1)N(c1ccc(C(C)(O)C3CCN(C4COC4)CC3)cc1)C(=O)C2]

Example 96 was obtained analogously to example 72 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one and oxetan-3-one were used.

HPLC: $^A$t$_{Ret}$=0.89 min; LC-MS: m/z 605.5 [M+H]$^+$

1H-NMR (600 MHz, DMSO-d$_6$): δ 7.4-7.33 (m, 6H), 7.14-7.09 (m, 3H), 6.87 (s, 1H), 6.10 (d, 1H), 4.84 (s, 1H), 4.5-4.44 (m, 3H), 4.37-4.33 (m, 2H), 3.86 (d, 1H), 3.74 (s, 3H), 3.61 (d, 1H), 3.24 (quint, 1H), 2.65 (br dd, 2H), 1.61-1.50 (m, 3H), 1.40 (s, 3H), 1.31-1.14 (m, 4H), 1.25 (d, 3H), 1.21 (d, 3H)

Example 97

(S)-1-(4-Chloro-phenyl)-2-{4-[1-(1-cyclobutyl-piperidin-4-yl)-1-hydroxy-ethyl]-phenyl}-7-isopropoxy-6-methoxy-1,4-dihydro-2H-isoquinolin-3-one

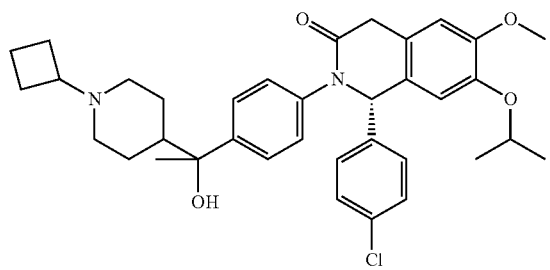 [SMILES: COc1cc2c(cc1OC(C)C)[C@H](c1ccc(Cl)cc1)N(c1ccc(C(C)(O)C3CCN(C4CCC4)CC3)cc1)C(=O)C2]

Example 97 was obtained analogously to example 72 except that (S)-1-(4-chloro-phenyl)-2-[4-(1-hydroxy-1-piperidin-4-yl-ethyl)-phenyl]-7-isopropoxy-6-methoxy-1,4-dihydro-2H-isoquinolin-3-one and cyclobutanone were used.

HPLC: $^A$t$_{Ret}$=0.94 min; LC-MS: m/z 603.4 [M+H]$^+$

Example 98

(S)-1-(4-Chloro-phenyl)-2-(4-{1-hydroxy-1-[1-(tetrahydro-pyran-4-yl)-azetidin-3-yl]-ethyl}-phenyl)-7-isopropoxy-6-methoxy-1,4-dihydro-2H-isoquinolin-3-one

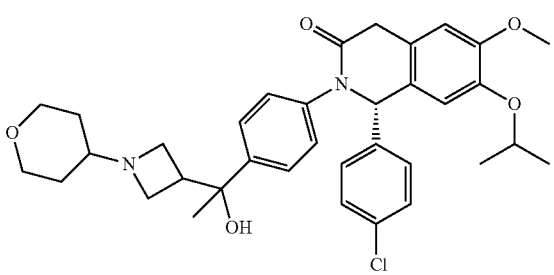 [SMILES: COc1cc2c(cc1OC(C)C)[C@H](c1ccc(Cl)cc1)N(c1ccc(C(C)(O)C3CN(C4CCOCC4)C3)cc1)C(=O)C2]

Example 98 was obtained analogously to example 69 except that tetrahydro-4H-pyran-4-one (Maybridge) was used instead of 3,3,3-trifluoropropanal.

HPLC: $^A$t$_{Ret}$=0.91 min; LC-MS: m/z 605.5 [M+H]$^+$

Example 99

(S)-1-(4-Chloro-phenyl)-2-{4-[1-(1-cyclohexyl-azetidin-3-yl)-1-hydroxy-ethyl]-phenyl}-7-isopropoxy-6-methoxy-1,4-dihydro-2H-isoquinolin-3-one

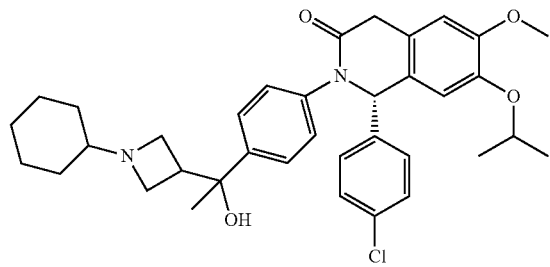 [SMILES: COc1cc2c(cc1OC(C)C)[C@H](c1ccc(Cl)cc1)N(c1ccc(C(C)(O)C3CN(C4CCCCC4)C3)cc1)C(=O)C2]

Example 99 was obtained analogously to example 69 except that cyclohexanone was used instead of 3,3,3-trifluoropropanal.

HPLC: $^A t_{Ret}$=0.99 min; LC-MS: m/z 603.4 [M+H]$^+$

Example 100

(S)-1-(4-Chloro-phenyl)-2-(4-{1-[1-(1-ethyl-piperidin-4-yl)-azetidin-3-yl]-1-hydroxy-ethyl}-phenyl)-7-isopropoxy-6-methoxy-1,4-dihydro-2H-isoquinolin-3-one

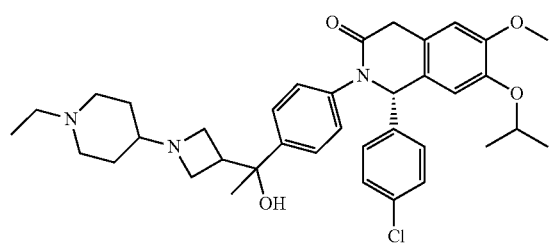 [SMILES: CCN1CCC(N2CC(C(C)(O)c3ccc(N4C(=O)Cc5cc(OC)c(OC(C)C)cc5[C@@H]4c4ccc(Cl)cc4)cc3)C2)CC1]

Example 100 was obtained analogously to example 69 except that 1-ethylpiperidine-4-one was used instead of 3,3,3-trifluoropropanal.

HPLC: $^A t_{Ret}$=0.78 min; LC-MS: m/z 632.5 [M+H]$^+$

Example 101

(S)-1-(4-Chloro-phenyl)-2-(4-{1-hydroxy-1-[1-(1-methyl-piperidin-4-yl)-azetidin-3-yl]-ethyl}-phenyl)-7-isopropoxy-6-methoxy-1,4-dihydro-2H-isoquinolin-3-one

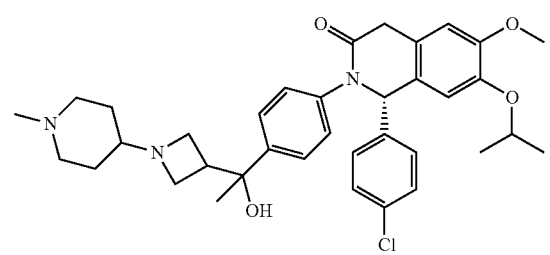 [SMILES: COc1cc2c(cc1OC(C)C)[C@H](c1ccc(Cl)cc1)N(c1ccc(C(C)(O)C3CN(C4CCN(C)CC4)C3)cc1)C(=O)C2]

Example 101 was obtained analogously to example 69 except that 1-methylpiperidine-4-one was used instead of 3,3,3-trifluoropropanal.

HPLC: $^A t_{Ret}$=0.76 min; LC-MS: m/z 618.5 [M+H]$^+$

Example 102

(S)-1-(4-Chloro-phenyl)-2-(4-{1-hydroxy-1-[1-(2-hydroxy-acetyl)-azetidin-3-yl]-ethyl}-phenyl)-7-isopropoxy-6-methoxy-1,4-dihydro-2H-isoquinolin-3-one

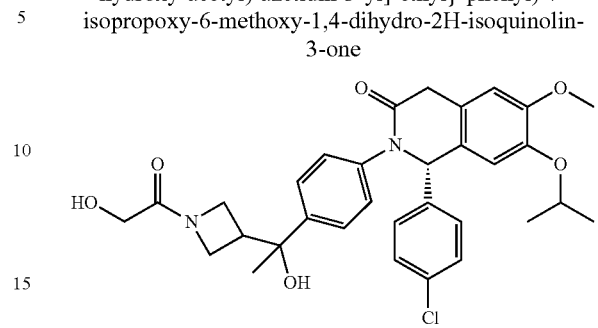

Example 102 was obtained analogously to example 92 and 91 except that (S)-2-[4-(1-azetidin-3-yl-1-hydroxy-ethyl)-phenyl]-1-(4-chloro-phenyl)-7-isopropoxy-6-methoxy-1,4-dihydro-2H-isoquinolin-3-one was used.

HPLC: $^A t_{Ret}$=0.97 min; LC-MS: m/z 579.4 [M+H]$^+$

Example 103

(S)-1-(4-Chloro-phenyl)-2-{4-[1-hydroxy-1-(1-oxetan-3-yl-azetidin-3-yl)-ethyl]-phenyl}-7-isopropoxy-6-methoxy-1,4-dihydro-2H-isoquinolin-3-one

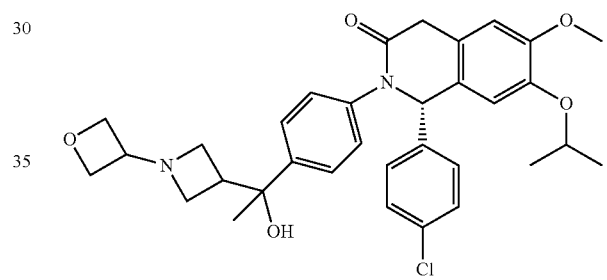

Example 103 was obtained analogously to example 69 except that oxetan-3-one was used instead of 3,3,3-trifluoropropanal.

HPLC: $^A t_{Ret}$=0.89 min; $^F t_{Ret}$=8.765 min LC-MS: m/z 577.3 [M+H]$^+$

Example 104

(S)-2-{4-[1-(8-Acetyl-8-aza-bicyclo[3.2.1]oct-3-yl)-1-hydroxy-ethyl]-phenyl}-1-(4-chloro-phenyl)-7-isopropoxy-6-methoxy-1,4-dihydro-2H-isoquinolin-3-one

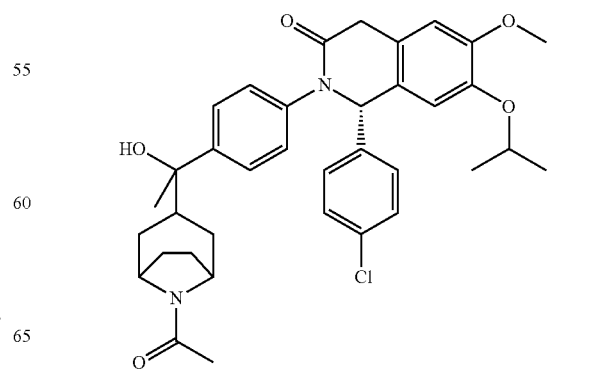

Example 104 was obtained analogously to example 57 except that (S)-2-{4-[1-(8-aza-bicyclo[3.2.1]oct-3-yl)-1-hydroxy-ethyl]-phenyl}-1-(4-chloro-phenyl)-7-isopropoxy-6-methoxy-1,4-dihydro-2H-isoquinolin-3-one (intermediate 104.1) was used.

HPLC: $^{A}t_{Ret}$=1.09 min; $^{F}t_{Ret}$=9.922 min; LC-MS: m/z 617.5 [M+H]$^{+}$

Intermediate 104.1

(S)-2-{4-[1-(8-Aza-bicyclo[3.2.1]oct-3-yl)-1-hydroxy-ethyl]-phenyl}-1-(4-chloro-phenyl)-7-isopropoxy-6-methoxy-1,4-dihydro-2H-isoquinolin-3-one

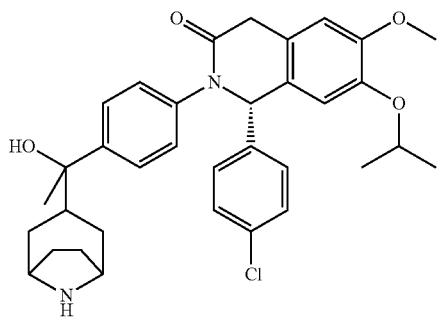 [SMILES: COc1cc2c(cc1OC(C)C)[C@H](c1ccc(Cl)cc1)N(c1ccc(C(C)(O)C3CC4CCC(C3)N4)cc1)C(=O)C2]

Intermediate 104.1 was obtained analogously to intermediate 75.1 except that 3-(1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carboxylic acid benzyl ester (intermediate 104.2) was used.

HPLC: $^{A}t_{Ret}$=0.92 min; $^{F}t_{Ret}$=8.880 min; LC-MS: m/z 575.4 [M+H]$^{+}$

Intermediate 104.2

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carboxylic acid benzyl ester

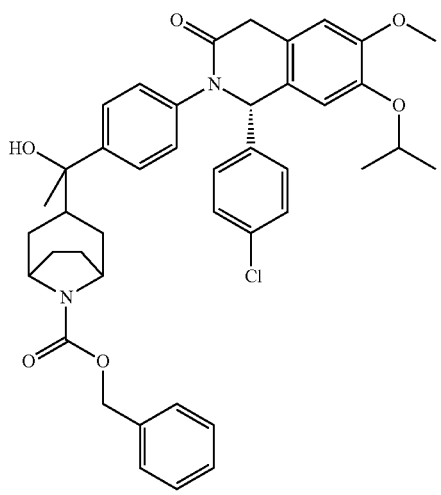 [SMILES: COc1cc2c(cc1OC(C)C)[C@H](c1ccc(Cl)cc1)N(c1ccc(C(C)(O)C3CC4CCC(C3)N4C(=O)OCc3ccccc3)cc1)C(=O)C2]

Intermediate 104.2 was obtained analogously to example 1 except that intermediate 104.3 was used instead of 1-(4-iodophenyl)-1-(3-methoxyphenyl)ethanol (step 1.1).

HPLC: $^{A}t_{Ret}$=1.33 min; $^{F}t_{Ret}$=10.847 min; LC-MS: m/z 709.4 [M+H]$^{+}$

Intermediate 104.3

3-[1-(4-Bromo-phenyl)-1-hydroxy-ethyl]-8-aza-bicyclo[3.2.1]octane-8-carboxylic acid benzyl ester

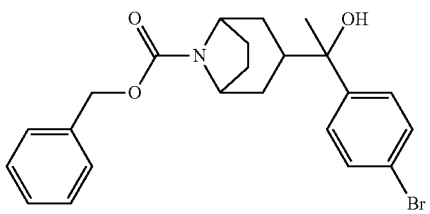

Intermediate 104.3 was obtained analogously to intermediate 75.3 except that intermediate 104.4 was used instead of 4-(4-bromo-benzoyl)-piperidine-1-carboxylic acid benzyl ester.

HPLC: $^{A}t_{Ret}$=1.29 min; $^{F}t_{Ret}$=10.410 min; LC-MS: m/z 444.2 [M+H]$^{+}$

Intermediate 104.4

3-(4-Bromo-benzoyl)-8-aza-bicyclo[3.2.1]octane-8-carboxylic acid benzyl ester

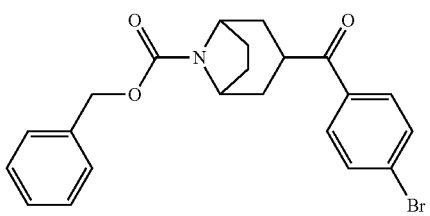

Intermediate 104.4 was obtained analogously to intermediate 75.4 except that intermediate 104.5 was used instead of 4-[(4-bromo-phenyl)-hydroxy-methyl]-piperidine-1-carboxylic acid benzyl ester.

HPLC: $^{A}t_{Ret}$=1.30 min; $^{F}t_{Ret}$=10.447 min; LC-MS: m/z 428.3 [M+H]$^{+}$

Intermediate 104.5

3-[(4-Bromo-phenyl)-hydroxy-methyl]-8-aza-bicyclo[3.2.1]octane-8-carboxylic acid benzyl ester

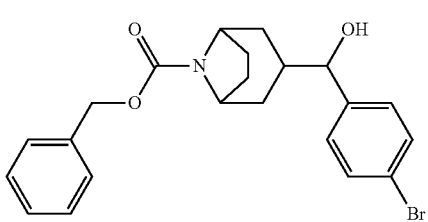 [SMILES: CC(O)(c1ccc(Br)cc1)C1CC2CCC(C1)N2C(=O)OCc1ccccc1]

Intermediate 104.5 was obtained analogously to intermediate 75.5 except that intermediate 104.6 was used instead of benzyl 4-formylpiperidine-1-carboxylate.

HPLC: $^{A}t_{Ret}$=1.23 min; LC-MS: m/z 430.2 [M+H]$^{+}$

Intermediate 104.6

3-Formyl-8-aza-bicyclo[3.2.1]octane-8-carboxylic acid benzyl ester

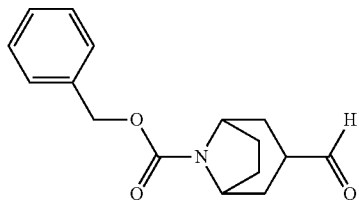 [SMILES: O=CC1CC2CCC(C1)N2C(=O)OCc1ccccc1]

Intermediate 104.6 was synthesized starting from tropinone (8-methyl-8-azabicyclo[3.2.1]octan-3-one, CAS #532-24-1) according literature procedure: Zhongbo Fei et al., *J. Org. Chem.* 2008, 73, 9016-9021 and patent WO2007/115821

Example 105

(S)-1-(4-Chloro-phenyl)-2-{4-[1-hydroxy-1-(8-methyl-8-aza-bicyclo[3.2.1]oct-3-yl)-ethyl]-phenyl}-7-isopropoxy-6-methoxy-1,4-dihydro-2H-isoquinolin-3-one

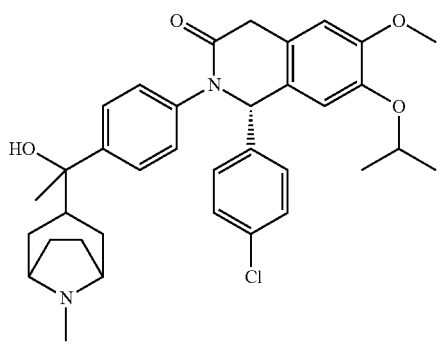 [SMILES: COc1cc2c(cc1OC(C)C)[C@H](c1ccc(Cl)cc1)N(c1ccc(C(C)(O)C3CC4CCC(C3)N4C)cc1)C(=O)C2]

Example 105 was obtained analogously to example 70 except that intermediate 104.1 and formaldehyde were used.
HPLC: $^A t_{Ret}$=0.92 min; $^F t_{Ret}$=9.086 min; LC-MS: m/z 589.4 [M+H]$^+$ Example 106

(S)-1-(4-Chloro-phenyl)-2-(4-{1-hydroxy-1-[8-(2,2,2-trifluoro-ethyl)-8-aza-bicyclo[3.2.1]oct-3-yl]-ethyl}-phenyl)-7-isopropoxy-6-methoxy-1,4-dihydro-2H-isoquinolin-3-one

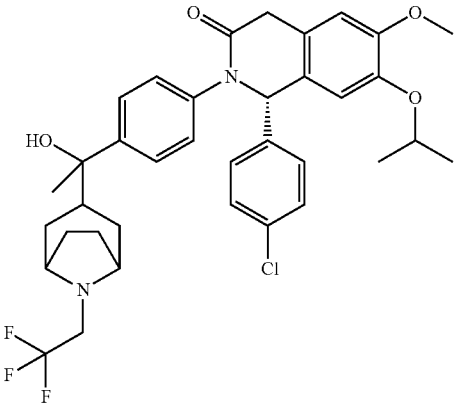 [SMILES: COc1cc2c(cc1OC(C)C)[C@H](c1ccc(Cl)cc1)N(c1ccc(C(C)(O)C3CC4CCC(C3)N4CC(F)(F)F)cc1)C(=O)C2]

Example 106 was obtained analogously to example 77 except that intermediate 104.1 was used.
HPLC: $^A t_{Ret}$=1.25 min; $^F t_{Ret}$=9.113 min; LC-MS: m/z 657.5 [M+H]$^+$ Example 107

(S)-1-(4-Chloro-phenyl)-2-{4-[1-hydroxy-1-(8-methanesulfonyl-8-aza-bicyclo[3.2.1]oct-3-yl)-ethyl]-phenyl}-7-isopropoxy-6-methoxy-1,4-dihydro-2H-isoquinolin-3-one

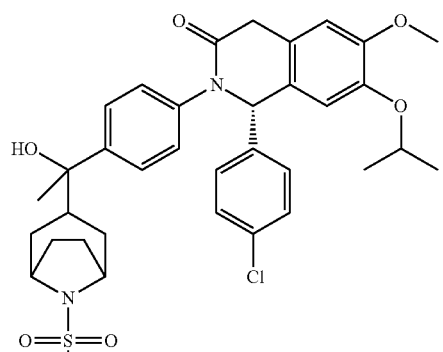

Example 107 was obtained analogously to example 81 except that intermediate 104.1 was used.
HPLC: $^A t_{Ret}$=1.13 min; $^F t_{Ret}$=9.68 min; LC-MS: m/z 653.5 [M+H]$^+$ Example 108

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carboxylic acid dimethylamide

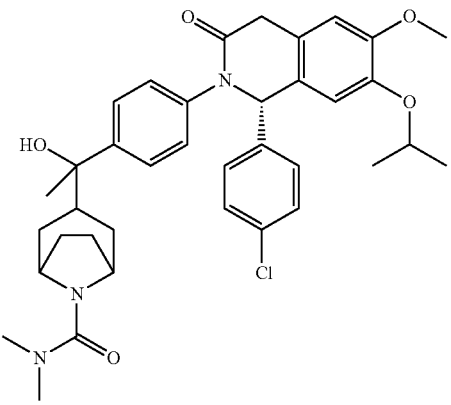 [SMILES: COc1cc2c(cc1OC(C)C)[C@H](c1ccc(Cl)cc1)N(c1ccc(C(C)(O)C3CC4CCC(C3)N4C(=O)N(C)C)cc1)C(=O)C2]

Example 108 was obtained analogously to example 82 except that intermediate 104.1 was used.
HPLC: $^A t_{Ret}$=1.15 min; $^F t_{Ret}$=10.09 min; LC-MS: m/z 646.5 [M+H]$^+$

Example 109

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carboxylic acid methylamide

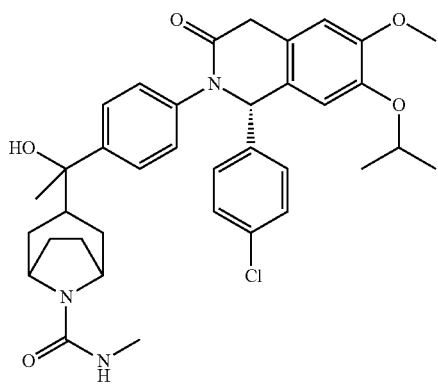 [SMILES: CNC(=O)N1C2CCC1CC(C(C)(O)c1ccc(N3C(=O)Cc4cc(OC)c(OC(C)C)cc4[C@@H]3c3ccc(Cl)cc3)cc1)C2]

Example 109 was obtained analogously to example 79 except that intermediate 104.1 was used.

HPLC: $^A t_{Ret}$=1.07 min; $^F t_{Ret}$=9.785 min; LC-MS: m/z 632.4 [M+H]$^+$

Example 110

(S)-1-(4-Chloro-phenyl)-2-{4-[1-hydroxy-1-(8-isopropyl-8-aza-bicyclo[3.2.1]oct-3-yl)-ethyl]-phenyl}-7-isopropoxy-6-methoxy-1,4-dihydro-2H-isoquinolin-3-one

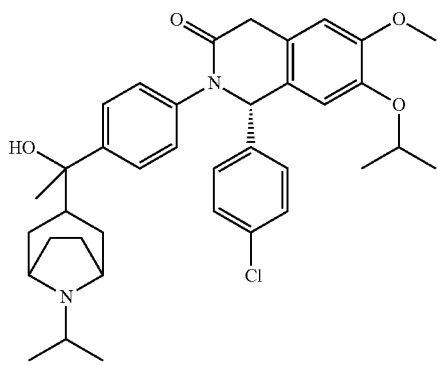 [SMILES: COc1cc2c(cc1OC(C)C)[C@H](c1ccc(Cl)cc1)N(c1ccc(C(C)(O)C3CC4CCC(C3)N4C(C)C)cc1)C(=O)C2]

Example 110 was obtained analogously to example 78 except that intermediate 104.1 was used.

HPLC: $^A t_{Ret}$=0.96 min; $^F t_{Ret}$=9.204 min; LC-MS: m/z 617.4 [M+H]$^+$

Example 111

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-8-aza-bicyclo[3.2.1]octane-8-carbaldehyde

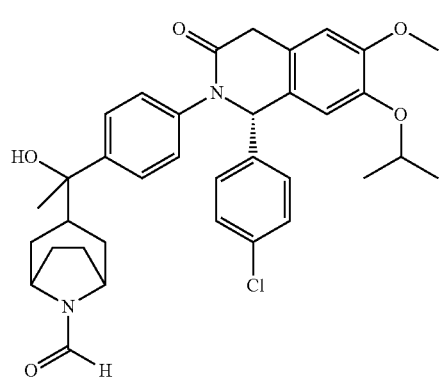 [SMILES: COc1cc2c(cc1OC(C)C)[C@H](c1ccc(Cl)cc1)N(c1ccc(C(C)(O)C3CC4CCC(C3)N4C=O)cc1)C(=O)C2]

Example 111 was obtained analogously to example 89 except that intermediate 104.1 was used.

HPLC: $^A t_{Ret}$=1.07 min; $^F t_{Ret}$=9.754 min; LC-MS: m/z 603.4 [M+H]$^+$

Example 112

(S)-1-(4-Chloro-phenyl)-2-{4-[1-(8-ethyl-8-aza-bicyclo[3.2.1]oct-3-yl)-1-hydroxy-ethyl]-phenyl}-7-isopropoxy-6-methoxy-1,4-dihydro-2H-isoquinolin-3-one

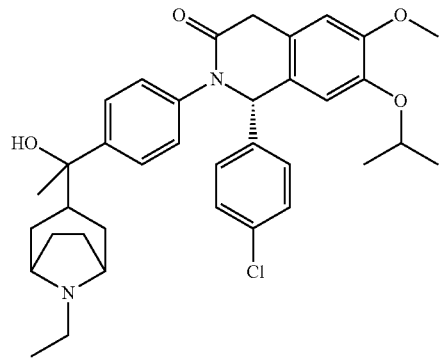 [SMILES: CCN1C2CCC1CC(C(C)(O)c1ccc(N3C(=O)Cc4cc(OC)c(OC(C)C)cc4[C@@H]3c3ccc(Cl)cc3)cc1)C2]

Example 112 was obtained analogously to example 85 except that intermediate 104.1 was used.

HPLC: $^A t_{Ret}$=0.94 min; $^F t_{Ret}$=9.176 min; LC-MS: m/z 603.5 [M+H]$^+$

Example 113

(S)-1-(4-Chloro-phenyl)-2-(4-{1-hydroxy-1-[8-(2-hydroxy-ethyl)-8-aza-bicyclo[3.2.1]oct-3-yl]-ethyl}-phenyl)-7-isopropoxy-6-methoxy-1,4-dihydro-2H-isoquinolin-3-one

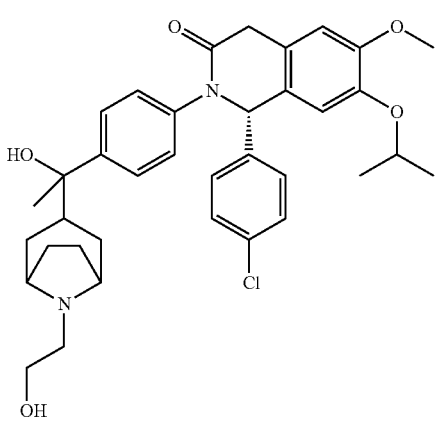 [SMILES: COc1cc2c(cc1OC(C)C)[C@H](c1ccc(Cl)cc1)N(c1ccc(C(C)(O)C3CC4CCC(C3)N4CCO)cc1)C(=O)C2]

Example 113 was obtained analogously to example 93 except that intermediate 104.1 was used.

HPLC: $^A t_{Ret}$=0.90 min; $^F t_{Ret}$=8.94 min; LC-MS: m/z 619.5 [M+H]$^+$

Example 114

(S)-1-(4-Chloro-phenyl)-2-(4-{1-hydroxy-1-[8-(2-hydroxy-acetyl)-8-aza-bicyclo[3.2.1]oct-3-yl]-ethyl}-phenyl)-7-isopropoxy-6-methoxy-1,4-dihydro-2H-isoquinolin-3-one

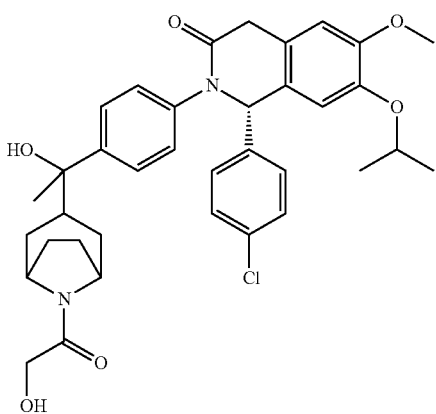 [SMILES: COc1cc2c(cc1OC(C)C)[C@H](c1ccc(Cl)cc1)N(c1ccc(C(C)(O)C3CC4CCC(C3)N4C(=O)CO)cc1)C(=O)C2]

Example 114 was obtained analogously to example 92 and 91 except that intermediate 104.1 was used.

HPLC: $^A t_{Ret}$=1.05 min; $^F t_{Ret}$=9.49 min; LC-MS: m/z 633.5 [M+H]$^+$

Example 115

(S)-1-(4-Chloro-phenyl)-2-{4-[1-hydroxy-1-(8-oxetan-3-yl-8-aza-bicyclo[3.2.1]oct-3-yl)-ethyl]-phenyl}-7-isopropoxy-6-methoxy-1,4-dihydro-2H-isoquinolin-3-one

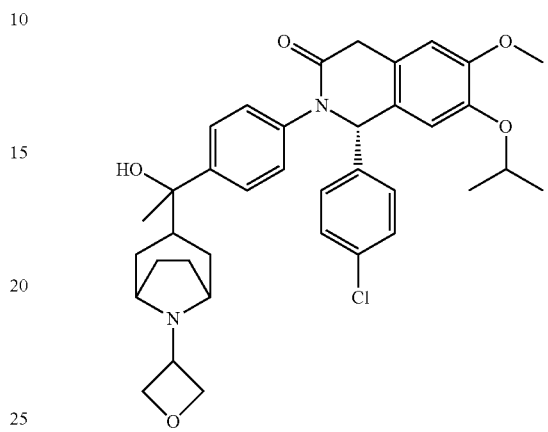

Example 115 was obtained analogously to example 96 except that intermediate 104.1 was used.

HPLC: $^A t_{Ret}$=0.92 min; $^F t_{Ret}$=8.97 min; LC-MS: m/z 631.3 [M+H]$^+$

Example 116

(S)-2-{4-[1-(9-Aza-bicyclo[3.3.1]non-3-yl)-1-hydroxy-ethyl]-phenyl}-1-(4-chloro-phenyl)-7-isopropoxy-6-methoxy-1,4-dihydro-2H-isoquinolin-3-one

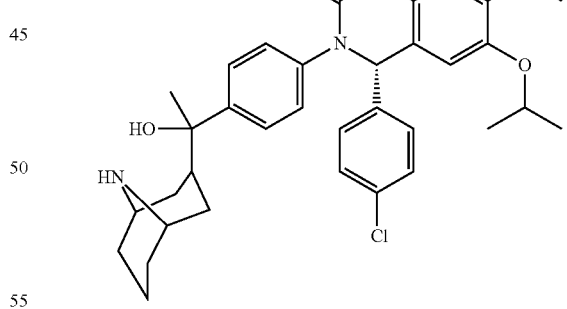

Example 116 is obtained analogously to intermediate 104.1 except that the synthesis was started with pseude-pelletierine (9-methyl-9-aza-bicyclo[3.3.1]nonan-3-one; CAS #552-70-5) instead of tropinone (8-methyl-8-azabicyclo[3.2.1]octan-3-one) following the chemistry which is outlined in intermediates 104.6 to 104.1 and described in the synthesis of example 75.

HPLC: $^A t_{Ret}$=0.94 min; $^F t_{Ret}$=8.993 min; LC-MS: m/z 589.4 [M+H]$^+$

Example 117

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-9-aza-bicyclo[3.3.1]nonane-9-carbaldehyde

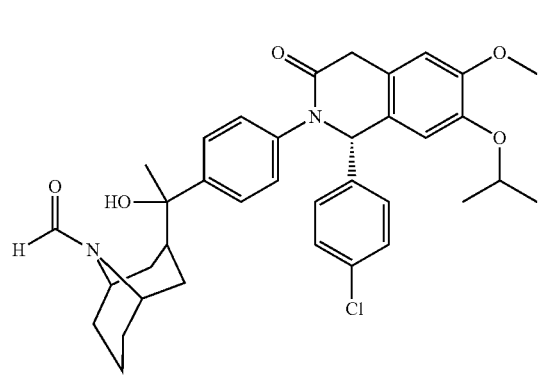 [SMILES: COc1cc2c(cc1OC(C)C)[C@H](c1ccc(Cl)cc1)N(c1ccc(C(C)(O)C3CC4CCCC(C3)N4C=O)cc1)C(=O)C2]

Example 117 was obtained analogously to example 89 except that example 116 was used.

HPLC: $^A t_{Ret}$=1.14 min; $^F t_{Ret}$=9.920 min; LC-MS: m/z 617.3 [M+H]$^+$

Example 118

(S)-1-(4-Chloro-phenyl)-2-(4-{1-hydroxy-1-[9-(2,2,2-trifluoro-ethyl)-9-aza-bicyclo[3.3.1]non-3-yl]-ethyl}-phenyl)-7-isopropoxy-6-methoxy-1,4-dihydro-2H-isoquinolin-3-one

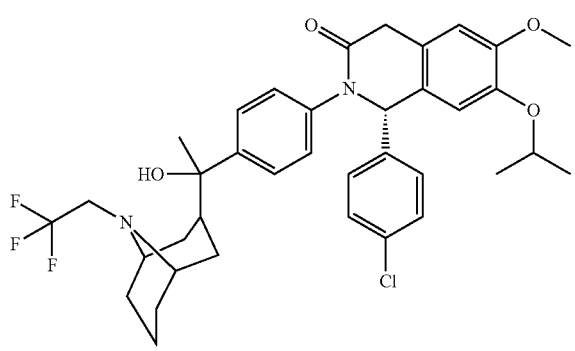 [SMILES: COc1cc2c(cc1OC(C)C)[C@H](c1ccc(Cl)cc1)N(c1ccc(C(C)(O)C3CC4CCCC(C3)N4CC(F)(F)F)cc1)C(=O)C2]

Example 118 was obtained analogously to example 77 except that example 116 was used.

HPLC: $^A t_{Ret}$=1.42 min; $^F t_{Ret}$=9.224 min; LC-MS: m/z 671.4 [M+H]$^+$

Example 119

3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-9-aza-bicyclo[3.3.1]nonane-9-carboxylic acid methylamide

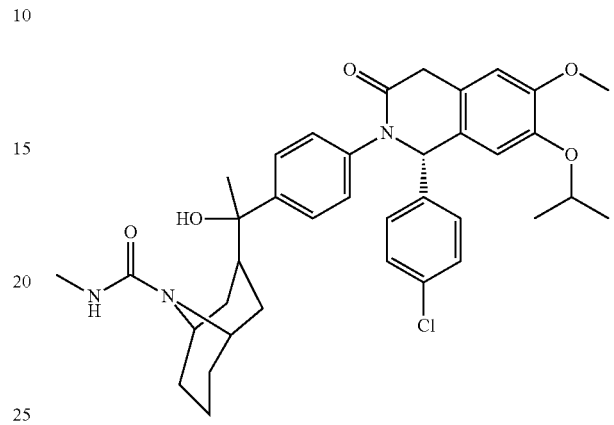

Example 119 was obtained analogously to example 79 except that example 116 was used.

HPLC: $^A t_{Ret}$=1.13 min; $^F t_{Ret}$=9.886 min; LC-MS: m/z 646.4 [M+H]$^+$

Example 120

(S)-1-(4-Chloro-phenyl)-2-{4-[1-hydroxy-1-(9-oxetan-3-yl-9-aza-bicyclo[3.3.1]non-3-yl)-ethyl]-phenyl}-7-isopropoxy-6-methoxy-1,4-dihydro-2H-isoquinolin-3-one

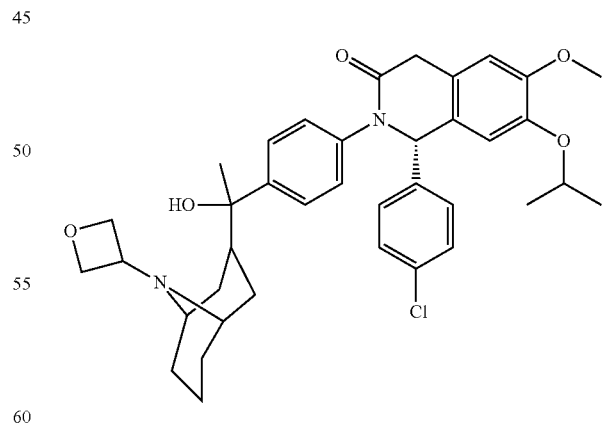

Example 120 was obtained analogously to example 96 except that example 116 was used.

HPLC: $^A t_{Ret}$=0.94 min; $^F t_{Ret}$=9.07 min; LC-MS: m/z 645.3 [M+H]$^+$

Example 121

Acetic acid 2-[3-(1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-9-aza-bicyclo[3.3.1]non-9-yl]-2-oxo-ethyl ester

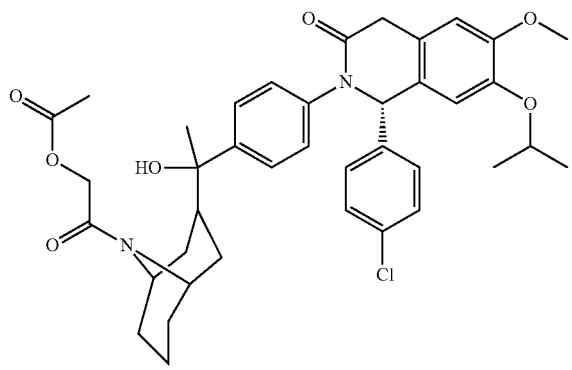 [SMILES: COc1cc2c(cc1OC(C)C)[C@H](c1ccc(Cl)cc1)N(c1ccc(C(C)(O)C3CC4CCCC(C3)N4C(=O)COC(C)=O)cc1)C(=O)C2]

Example 121 was obtained analogously to example 91 except that example 116 was used.

HPLC: $^A t_{Ret}$=1.15 min; $^F t_{Ret}$=9.82 min; LC-MS: m/z 689.3 [M+H]$^+$

Example 122

(S)-1-(4-Chloro-phenyl)-2-{4-[1-(9-ethyl-9-aza-bicyclo[3.3.1]non-3-yl)-1-hydroxy-ethyl]-phenyl}-7-isopropoxy-6-methoxy-1,4-dihydro-2H-isoquinolin-3-one

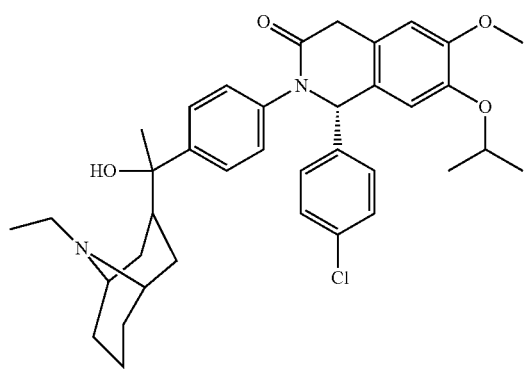 [SMILES: CCN1C2CCCC1CC(C(C)(O)c1ccc(N3C(=O)Cc4cc(OC)c(OC(C)C)cc4[C@@H]3c3ccc(Cl)cc3)cc1)C2]

Example 122 was obtained analogously to example 85 except that example 116 was used.

HPLC: $^A t_{Ret}$=0.96 min; $^F t_{Ret}$=9.21 min; LC-MS: m/z 617.3 [M+H]$^+$

Example 123

(S)-1-(4-Chloro-phenyl)-2-(4-{1-hydroxy-1-[9-(2-hydroxy-acetyl)-9-aza-bicyclo[3.3.1]non-3-yl]-ethyl}-phenyl)-7-isopropoxy-6-methoxy-1,4-dihydro-2H-isoquinolin-3-one

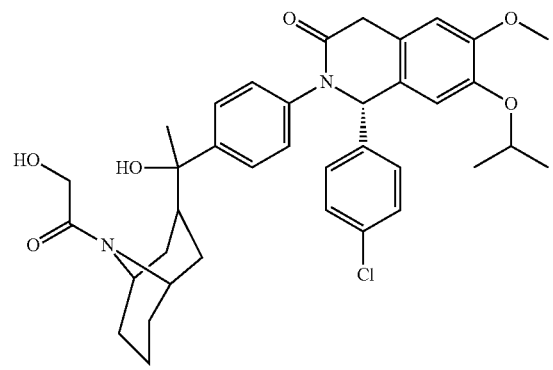 [SMILES: COc1cc2c(cc1OC(C)C)[C@H](c1ccc(Cl)cc1)N(c1ccc(C(C)(O)C3CC4CCCC(C3)N4C(=O)CO)cc1)C(=O)C2]

Example 123 was obtained from example 121 analogously to example 92.

HPLC: $^A t_{Ret}$=1.10 min; $^F t_{Ret}$=9.72 min; LC-MS: m/z 647.4 [M+H]$^+$

Example 124

4-((R)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde

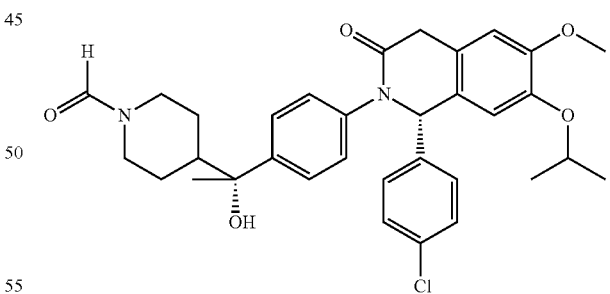

Example 124 was obtained by preparative chiral separation of example 89.

Column; Chiralpak AD, 50×500 mm; mobile phase: heptane/ethanol/70:30; flow rate: 70 ml/min; detection: 210 nm (UV); peak 1 (9.267 min).

HPLC: $^A t_{Ret}$=1.03 min; $^F t_{Ret}$=9.472 min; LC-MS: m/z 577.5 [M+H]$^+$

Example 125

4-((S)-1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde

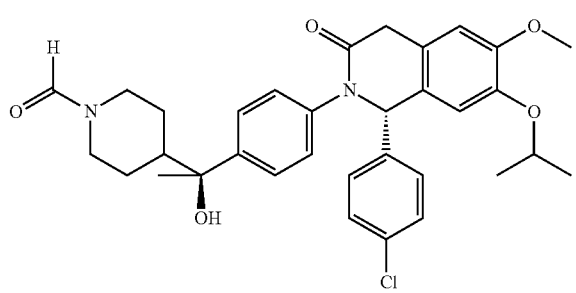 [SMILES: COc1cc2c(cc1OC(C)C)[C@H](c1ccc(Cl)cc1)N(c1ccc([C@@](C)(O)C3CCN(C=O)CC3)cc1)C(=O)C2]

Example 125 was obtained by preparative chiral separation of example 89.

Column; Chiralpak AD, 50×500 mm; mobile phase: heptane/ethanol/70:30; flow rate: 70 ml/min; detection: 210 nm (UV); peak 2 (17.570 min).

HPLC: $^A t_{Ret}$=1.03 min; $^F t_{Ret}$=9.458 min; LC-MS: m/z 577.4 [M+H]$^+$

Example 126

(S)-1-(4-Chloro-phenyl)-2-{4-[(R)-1-hydroxy-1-(1-oxetan-3-yl-piperidin-4-yl)-ethyl]-phenyl}-7-isopropoxy-6-methoxy-1,4-dihydro-2H-isoquinolin-3-one

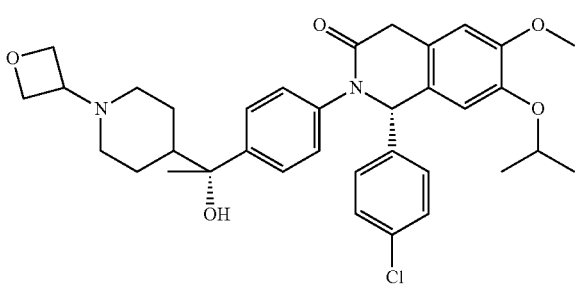

Example 126 was obtained by preparative chiral separation of example 96.

Column; Chiralpak AD-H, 30×250 mm; mobile phase: CO$_2$/ethanol+1% isopropylamine 70:30; flow rate: 100 ml/min; detection: 220 nm (UV); peak 1 (3.33 min).

HPLC: $^A t_{Ret}$=0.89 min; $^F t_{Ret}$=8.776 min; LC-MS: m/z 605.3 [M+H]$^+$

Example 127

(S)-1-(4-Chloro-phenyl)-2-{4-[(S)-1-hydroxy-1-(1-oxetan-3-yl-piperidin-4-yl)-ethyl]-phenyl}-7-isopropoxy-6-methoxy-1,4-dihydro-2H-isoquinolin-3-one

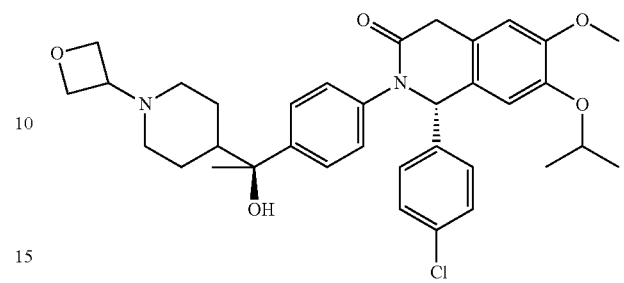

Example 127 was obtained by preparative chiral separation of example 96.

Column; Chiralpak AD-H, 30×250 mm; mobile phase: CO$_2$/ethanol+1% isopropylamine 70:30; flow rate: 100 ml/min; detection: 220 nm (UV); peak 2 (4.41 min).

HPLC: $^A t_{Ret}$=0.89 min; $^F t_{Ret}$=8.736 min; LC-MS: m/z 605.3 [M+H]$^+$

Example 128

Acetic acid 2-[4-((S)-1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-piperidin-1-yl]-2-oxo-ethyl ester

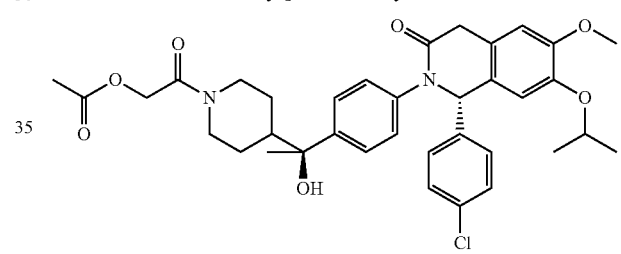

Example 128 was obtained by preparative chiral separation of example 91.

Column: Chiralpak ADi, 50×330 mm; mobile phase: ethylacetate/ethanol 92:8; flow rate: 60 ml/min; detection: 254 nm (UV); peak 1 (7.064 min).

HPLC: $^A t_{Ret}$=1.06 min; $^F t_{Ret}$=9.438 min; LC-MS: m/z 579.4 [M+H]$^+$

Example 129

Acetic acid 2-[4-((R)-1-{4-[(S)-1-(4-chloro-phenyl)-7-isopropoxy-6-methoxy-3-oxo-3,4-dihydro-1H-isoquinolin-2-yl]-phenyl}-1-hydroxy-ethyl)-piperidin-1-yl]-2-oxo-ethyl ester

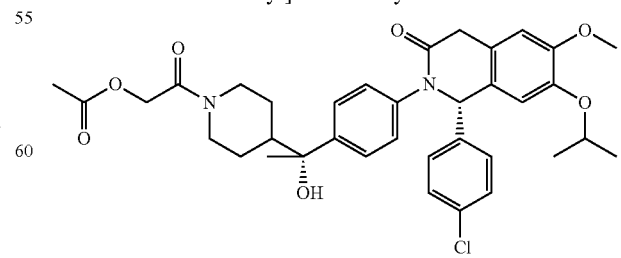

Example 129 was obtained by preparative chiral separation of example 91.

Column: Chiralpak ADi, 50×330 mm; mobile phase: ethylacetate/ethanol 92:8; flow rate: 60 ml/min; detection: 254 nm (UV); peak 2 (9.723 min).

HPLC: $^A t_{Ret}$=1.06 min; $^F t_{Ret}$=9.402 min; LC-MS: m/z 649.3 [M+H]$^+$

Example 130

(S)-1-(4-Chloro-phenyl)-2-(4-{1-[1-((R)-2,3-dihydroxy-propyl)-piperidin-4-yl]-1-hydroxy-ethyl}-phenyl)-7-isopropoxy-6-methoxy-1,4-dihydro-2H-isoquinolin-3-one

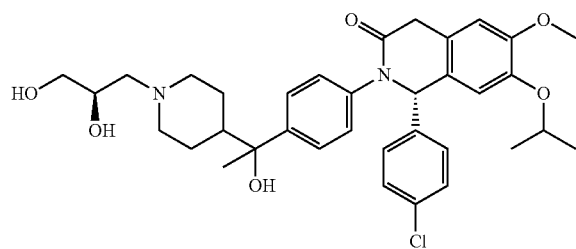 [SMILES: COc1cc2c(cc1OC(C)C)[C@H](c1ccc(Cl)cc1)N(c1ccc(C(C)(O)C3CCN(C[C@@H](O)CO)CC3)cc1)C(=O)C2]

To a solution of intermediate 75.1 (75 mg, 0.137 mmol) in ethanol (1 ml) was added potassium carbonate (37.8 mg, 0.273 mmol) followed by (R)-tert-butyldimethyl(oxiran-2-ylmethoxy)silane (38.6 mg, 0.205 mmol) at room temperature. The vial was sealed and kept in the microwave for 6 minutes at 120° C. The reaction mixture was diluted with ethyl acetate and the organic phase was washed with water and brine. The organic phase was dried over Na$_2$SO$_4$, filtered and concentrated in vacuo to obtain a yellowish oil.

To a solution of the crude intermediate in THF (3 ml) was added HCl 1M (0.732 ml, 0.732 mmol) and the reaction mixture was stirred at room temperature for 1.5 hrs. The reaction mixture was taken up in ethyl acetate and the organic phase was washed with aqueous NaHCO$_3$ solution and brine. The organic phase was dried over Na$_2$SO$_4$, filtered and concentrated in vacuo to obtain the crude product which was purified by preparative RP-HPLC (reversed phase). The fraction containing the product was worked up (addition of NaHCO$_3$, removal of acetonitrile followed by extraction with DCM) and the residue was dissolved in 1,4-dioxane and freeze dried overnight to obtain the title compound as white solid.

HPLC: $^A t_{Ret}$=0.88 min; $^F t_{Ret}$=8.474 min; LC-MS: m/z 623.5 [M+H]$^+$

Example 131

(S)-1-(4-Chloro-phenyl)-2-(4-{(S)-1-hydroxy-1-[1-(2-hydroxy-ethyl)-piperidin-4-yl]-ethyl}-phenyl)-7-isopropoxy-6-methoxy-1,4-dihydro-2H-isoquinolin-3-one

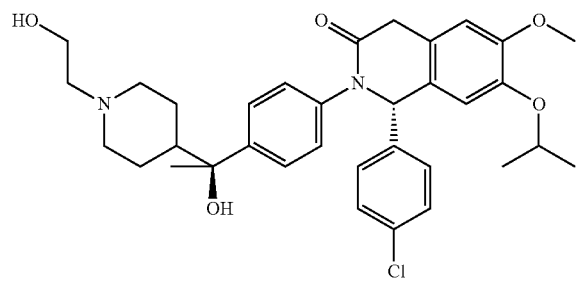 [SMILES: COc1cc2c(cc1OC(C)C)[C@H](c1ccc(Cl)cc1)N(c1ccc([C@@](C)(O)C3CCN(CCO)CC3)cc1)C(=O)C2]

Example 131 was obtained by preparative chiral separation of example 93.

Column: Chiralpak AS-H, 30×250 mm; mobile phase: CO$_2$/2-propanol+1% isopropylamine 60:40; flow rate: 100 ml/min; detection: 220 nm (UV); peak 1 (3.75 min).

HPLC: $^A t_{Ret}$=0.89 min; $^F t_{Ret}$=8.744 min; LC-MS: m/z 593.4 [M+H]$^+$

Example 132

(S)-1-(4-Chloro-phenyl)-2-(4-{(R)-1-hydroxy-1-[1-(2-hydroxy-ethyl)-piperidin-4-yl]-ethyl}-phenyl)-7-isopropoxy-6-methoxy-1,4-dihydro-2H-isoquinolin-3-one

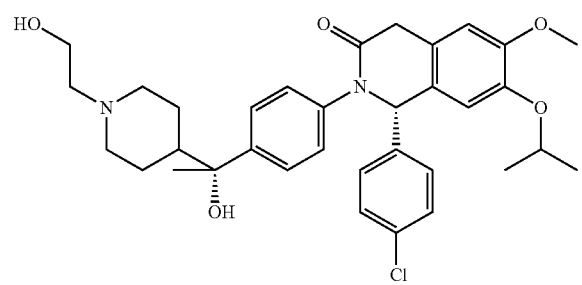 [SMILES: COc1cc2c(cc1OC(C)C)[C@H](c1ccc(Cl)cc1)N(c1ccc([C@](C)(O)C3CCN(CCO)CC3)cc1)C(=O)C2]

Example 132 was obtained by preparative chiral separation of example 93.

Column: Chiralpak AS-H, 30×250 mm; mobile phase: CO$_2$/2-propanol+1% isopropylamine 60:40; flow rate: 100 ml/min; detection: 220 nm (UV); peak 2 (5.17 min).

HPLC: $^A t_{Ret}$=0.89 min; $^F t_{Ret}$=8.668 min; LC-MS: m/z 593.4 [M+H]$^+$

Example 133

(S)-1-(4-Chloro-phenyl)-2-(4-{(S)-1-hydroxy-1-[1-(2-hydroxy-acetyl)-piperidin-4-yl]-ethyl}-phenyl)-7-isopropoxy-6-methoxy-1,4-dihydro-2H-isoquinolin-3-one

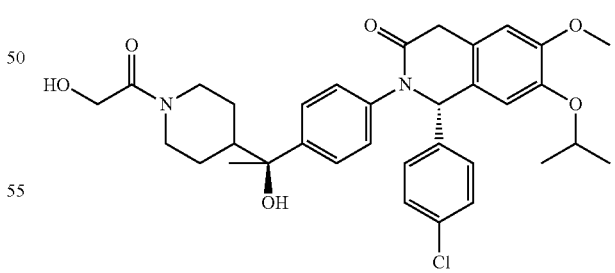

Example 133 was obtained by preparative chiral separation of example 92.

Column: Chiralcel OD-H, 30×250 mm; mobile phase: CO$_2$/2-propanol+1% isopropylamine 65:35; flow rate: 140 g/min; detection: 225 nm (UV); peak 1 (4.65 min).

HPLC: $^A t_{Ret}$=1.01 min; $^F t_{Ret}$=9.247 min; LC-MS: m/z 607.3 [M+H]$^+$

Example 134

(S)-1-(4-Chloro-phenyl)-2-(4-{(R)-1-hydroxy-1-[1-(2-hydroxy-acetyl)-piperidin-4-yl]-ethyl}-phenyl)-7-isopropoxy-6-methoxy-1,4-dihydro-2H-isoquinolin-3-one

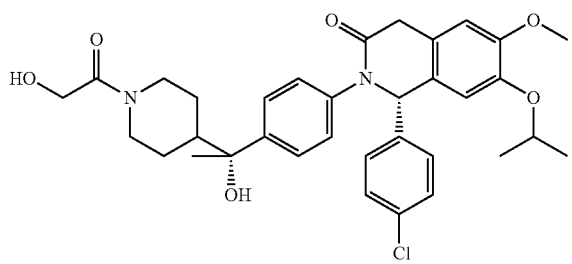

Example 134 was obtained by preparative chiral separation of example 92.

Column: Chiralcel OD-H, 30×250 mm; mobile phase: CO$_2$/2-propanol+1% isopropylamine 65:35; flow rate: 140 g/min; detection: 225 nm (UV); peak 2 (6.05 min).

HPLC: $^A t_{Ret}$=1.01 min; $^F t_{Ret}$=9.201 min; LC-MS: m/z 607.3 [M+H]$^+$

Example 135

(S)-1-(4-Chloro-phenyl)-2-{4-[1-hydroxy-1-(7-oxa-bicyclo[2.2.1]hept-1-yl)-ethyl]-phenyl}-7-isopropoxy-6-methoxy-1,4-dihydro-2H-isoquinolin-3-one

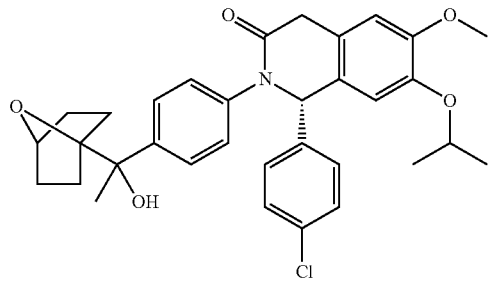 [SMILES: COc1cc2c(cc1OC(C)C)[C@H](c1ccc(Cl)cc1)N(c1ccc(C(C)(O)C34CCC(CC3)O4)cc1)C(=O)C2]

The title compound (263 mg, 0.468 mmol, 41%) was obtained as a slightly yellow foam from intermediate 135.1 (400 mg, 1.15 mmol) analogously to example 1.

HPLC: $^C t_{Ret}$=5.96 min; LC-MS: m/z 562.3 [M+H]$^+$ $^A t_{Ret}$=1.24 min.

Intermediate 135.1

1-(4-Bromo-phenyl)-1-(7-oxa-bicyclo[2.2.1]hept-1-yl)ethanol

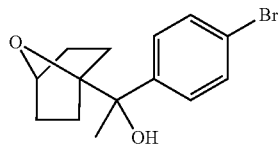 [SMILES: CC(O)(c1ccc(Br)cc1)C12CCC(CC1)O2]

The title intermediate (1.12 g, 3.73 mmol) was obtained as a white solid from intermediate 135.2 analogously to intermediates 145.9, 145.10, 145.11.

HPLC: $^C t_{Ret}$=5.23 min; $^A t_{Ret}$=1.14 min;

1H-NMR (400 MHz, DMSO-d$_6$): δ 1.21-1.29 (m, 2H), 1.39-1.57 (m, 5H), 1.52 (s, 3H), 4.40 (t, 1H), 5.13 (s, 1H), 7.44 (s, 4H)

Intermediate 135.2

7-Oxa-bicyclo[2.2.1]heptane-1-carbaldehyde

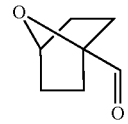

To a stirred solution of intermediate 135.3 (2.20 g, 16.31 mmol) in DCM (163 ml) was added pyridinium chlorochromate (6.73 g, 30.6 mmol). The suspension was stirred for 2.5 h at 40° C. The reaction mixture was filtered over Celite, washed with TBME-diethyl ether 1:1. The filtrate was concentrated in vacuo and the residue was taken up in TBME and filtered again over Celite. The filtrate was concentrated and the residue afforded the crude title compound as a beige oil (2.0 g, 15.0 mmol). This material was used for the next step without further purifications.

Intermediate 135.3

(7-Oxa-bicyclo[2.2.1]hept-1-yl)methanol

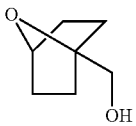

To a stirred solution of intermediate 135.4 (7.70 g, 38.5 mmol) in MeOH (193 ml) was added sodium methoxyde (5.4M in MeOH) (14.2 ml, 7.69 mmol). Stirring was continued for 2.5 h at RT. The reaction mixture was quenched with 1M NH$_4$Cl (900 ml) and extracted with DCM (2×). The organic phases were dried over Na$_2$SO$_4$, filtered and evaporated to dryness. Purification of the residue by "Kugelrohr" distillation (0.5 mbar/65° C.), gave the title compound as a colorless liquid (4.65 g, 34.5 mmol, 90%).

1H-NMR (600 MHz, DMSO-d$_6$): δ 1.38-1.75 (m, 8H), 3.63 (d, 2H), 4.43 (t, 1H), 4.75 (t, 1H)

Intermediate 135.4

Acetic acid 7-oxa-bicyclo[2.2.1]hept-1-ylmethyl ester

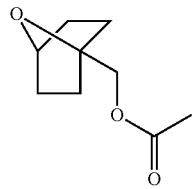

To a stirred solution of intermediate 135.5 (10.0 g, 39.9 mmol) in DMF (400 ml) was added tetramethylammonium acetate (11.81 g, 80 mmol). The reaction mixture was stirred for 19 h at 60° C. The reaction mixture was filtered, at RT, over Celite and washed with EtOAc. The filtrate was washed subsequently with 1M sodium thiosulphate (1×), water (4×) and brine. The organic phases were dried over Na$_2$SO$_4$, filtered and evaporated to dryness. The residue afforded the crude title compound as orange liquid (7.70 g, 38.5 mmol). This material was used for the next step without further purifications.

Intermediate 135.5

1-(iodomethyl)-7-oxabicyclo[2.2.1]heptane

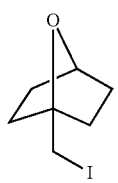

A solution of intermediate 135.6 (2.4 g, 21.4 mmol) and N-iodosuccinimide (8.8 g, 37.6 mmol) in dry acetonitrile (100 ml) was stirred at RT in the dark overnight. The resulting mixture was poured into water and extracted with ether. The extract was washed successively with sat. aq. $Na_2S_2O_4$, sat. aq. $NaHCO_3$ and brine, then dried with $Na_2SO_4$. After concentration at 200 mbar and 30° C., the residue was purified by silica gel chromatography (EtOAc/Hexane: 0-20% gradient) to afford the title compound.

1H-NMR (400 MHz, $CDCl_3$): δ 4.66-4.62 (m, 1H), 3.55 (s, 2H), 1.97-1.60 (m, 8H).

Intermediate 135.6

4-Methylenecyclohexanol

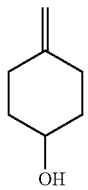

To a solution of intermediate 135.7 (2.8 g, 25.45 mmol) in MeOH (100 ml) was added $NaBH_4$ (1.93 g, 50.9 mmol) at 0° C. The reaction was stirred at room temperature for 2 h, and quenched with sat. aq. $NH_4Cl$. The reaction was extracted with DCM, the collected organic extracts were dried ($Na_2SO_4$), concentrated at 200 mbar and 30° C. to afford the title compound which was used without further purification.

Intermediate 135.7

4-methylenecyclohexanone

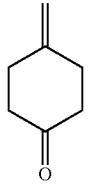

To a solution of intermediate 135.8 (5.12 g, 33.2 mmol) in acetone (15 ml) and water (15 ml) was added oxalic acid dihydride (8.33 g, 66.1 mol), the reaction was stirred at room temperature for 3 h. Solid $NaHCO_3$ was added slowly to the reaction, the solid was filtered and washed thoroughly with diethylether. The combined organic extracts were concentrated at 200 mbar and 30° C. to afford the title compound which was used without further purification.

1H-NMR (400 MHz, $CDCl_3$): δ 4.88 (s, 2H), 2.52 (t, 4H), 2.43 (t, 4H).

Intermediate 135.8

8-methylene-1,4-dioxaspiro[4.5]decane

A solution of n-BuLi (2.5 M in hexanes, 30 ml, 75 mmol) was slowly added to a suspension of methyltriphenylphosphonium bromide (28.07 g, 79 mmol) in THF (150 ml) at −10° C. After stirring for 1 h, 1,4-dioxaspiro[4.5]decan-8-one (8.01 g, 51.3 mmol) was added. The reaction was warmed to room temperature and stirred for 4 h. The reaction was quenched with sat. aq. $NH_4Cl$ and extracted by diethyl ether. The combined organic extracts were dried ($Na_2SO_4$), concentrated at 200 mbar and 30° C. The residue was diluted with DCM and hexanes (1:1), and the solid was filtered. The organic extracts were concentrated at 200 mbar and 30° C., followed by silica gel chromatography (EtOAc/hexanes: 0-10%-20% gradient) to afford the title compound.

1H-NMR (400 MHz, $CDCl_3$): δ 4.69 (s, 2H), 3.99 (s, 4H), 2.30 (t, 4H), 1.72 (t, 4H).

Example 136

(S)-1-(4-Chloro-phenyl)-2-{4-[(R)-1-hydroxy-1-(7-oxa-bicyclo[2.2.1]hept-1-yl)-ethyl]-phenyl}-7-isopropoxy-6-methoxy-1,4-dihydro-2H-isoquinolin-3-one

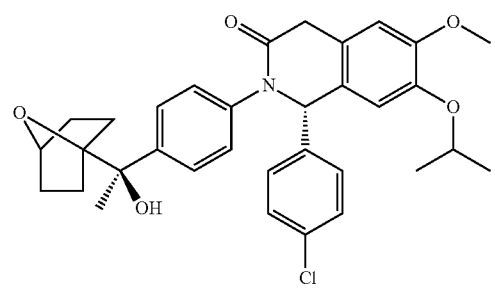 [SMILES: COc1cc2c(cc1OC(C)C)[C@H](c1ccc(Cl)cc1)N(c1ccc([C@@](C)(O)C34CCC(CC3)O4)cc1)C(=O)C2]

Example 137

(S)-1-(4-Chloro-phenyl)-2-{4-[(S)-1-hydroxy-1-(7-oxa-bicyclo[2.2.1]hept-1-yl)-ethyl]-phenyl}-7-isopropoxy-6-methoxy-1,4-dihydro-2H-isoquinolin-3-one

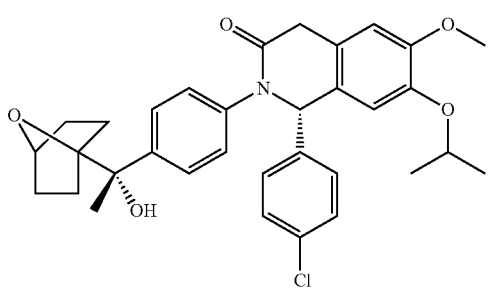 [SMILES: COc1cc2c(cc1OC(C)C)[C@H](c1ccc(Cl)cc1)N(c1ccc([C@](C)(O)C34CCC(CC3)O4)cc1)C(=O)C2]

Preparative chiral separation of example 135 (241 mg, 0.424 mmol): Column; Chiralpak IC 20 um, 76.5×375 mm; mobile phase: n-Heptane/EtOH/MeOH 60:20:20; flow: 80 ml/min; detection: 287 nm (UV) afforded:

Example 136 first eluting peak ($R_t$=66 min) (108 mg, 0.190 mmol, 45%):

HPLC: $^C t_{Ret}$=5.91; LC-MS: m/z 562.2 [M+H]$^+$ $^A t_{Ret.}$=1.25 min

Example 137 second eluting peak ($R_t$=106 min) (115 mg, 0.200 mmol, 47%):

HPLC: $^C t_{Ret}$=5.91; LC-MS: m/z 562.2 [M+H]$^+$ $^A t_{Ret.}$=1.25 min

Example 138

(S)-2-[4-(1-Bicyclo[2.2.1]hept-1-yl-1-hydroxy-ethyl)-phenyl]-1-(4-chloro-phenyl)-7-isopropoxy-6-methoxy-1,4-dihydro-2H-isoquinolin-3-one

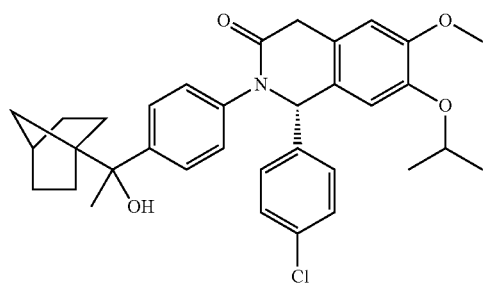 [SMILES: COc1cc2c(cc1OC(C)C)[C@H](c1ccc(Cl)cc1)N(c1ccc(C(C)(O)C34CCC(CC3)C4)cc1)C(=O)C2]

The title compound (273 mg, 0.483 mmol, 40%) was obtained as a slightly yellow foam from intermediate 138.1 (358 mg, 1.20 mmol) analogously to example 1.

HPLC: $^C t_{Ret}$=6.81 min; LC-MS: m/z 560.3 [M+H]$^+$ $^A t_{Ret.}$=1.41 min.

Intermediate 138.1

1-Bicyclo[2.2.1]hept-1-yl-1-(4-bromo-phenyl)-ethanol

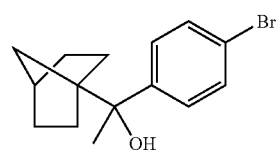 [SMILES: CC(O)(c1ccc(Br)cc1)C12CCC(CC1)C2]

The title intermediate (0.93 g, 3.12 mmol) was obtained as a colorless oil from bicyclo[2.2.1]heptane-1-carbaldehyde [CAS #2094-67-9] analogously to intermediates 145.9, 145.10, 145.11.

HPLC: $^C t_{Ret}$=6.48 min; $^A t_{Ret.}$=1.36 min; 1H-NMR (400 MHz, DMSO-$d_6$): δ 0.82-1.66 (m, 10H), 1.48 (s, 3H), 2.04 (m, 1H), 4.84 (s, 1H), 7.38 (dd, 4H)

Example 139

(S)-2-[4-((S)-1-Bicyclo[2.2.1]hept-1-yl-1-hydroxy-ethyl)-phenyl]-1-(4-chloro-phenyl)-7-isopropoxy-6-methoxy-1,4-dihydro-2H-isoquinolin-3-one

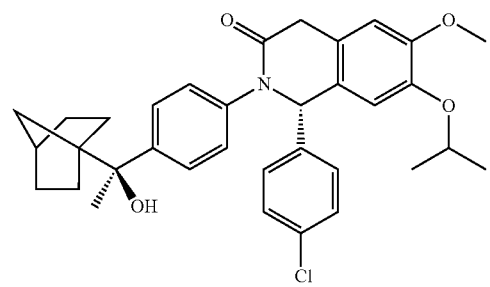 [SMILES: COc1cc2c(cc1OC(C)C)[C@H](c1ccc(Cl)cc1)N(c1ccc([C@@](C)(O)C34CCC(CC3)C4)cc1)C(=O)C2]

Example 140

(S)-2-[4-((R)-1-Bicyclo[2.2.1]hept-1-yl-1-hydroxy-ethyl)-phenyl]-1-(4-chloro-phenyl)-7-isopropoxy-6-methoxy-1,4-dihydro-2H-isoquinolin-3-one

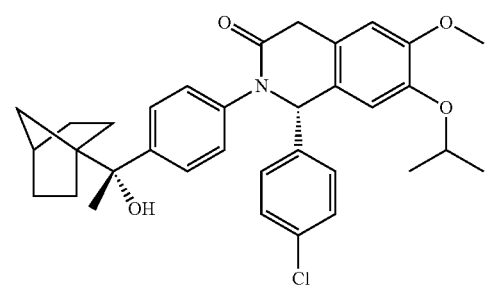 [SMILES: COc1cc2c(cc1OC(C)C)[C@H](c1ccc(Cl)cc1)N(c1ccc([C@](C)(O)C34CCC(CC3)C4)cc1)C(=O)C2]

Preparative chiral separation of example 138 (237 mg, 0.419 mmol): Column; Chiralpak ODH 5 um, 30×250 mm; mobile phase: iPrOH/EtOH 30:70, afforded:

Example 139 first eluting peak (R$_t$=5.0 min) (100 mg, 0.177 mmol, 42%):
HPLC: $^C$t$_{Ret}$=6.74; LC-MS: m/z 560.3 [M+H]$^+$ $^A$t$_{Ret}$=1.42 min Example 140 second eluting peak (R$_t$=8.0 min) (95 mg, 0.168 mmol, 40%):
HPLC: $^C$t$_{Ret}$=6.74; LC-MS: m/z 560.3 [M+H]$^+$ $^A$t$_{Ret}$=1.42 min Example 141

(S)-2-[4-(1-Adamantan-1-yl-1-hydroxy-ethyl)-phenyl]-1-(4-chloro-phenyl)-7-isopropoxy-6-methoxy-1,4-dihydro-2H-isoquinolin-3-one

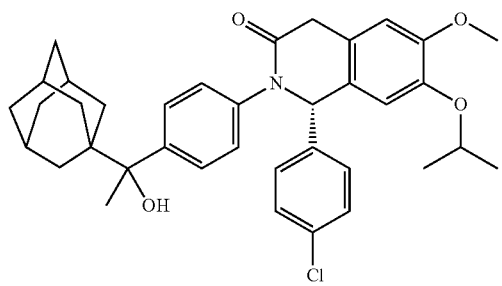 [SMILES: COc1cc2c(cc1OC(C)C)[C@H](c1ccc(Cl)cc1)N(c1ccc(C(C)(O)C34CC5CC(CC(C5)C3)C4)cc1)C(=O)C2]

The title compound (309 mg, 0.510 mmol, 45%) was obtained as a slightly orange foam from intermediate 141.1 (388 mg, 1.145 mmol) analogously to example 1.
HPLC: $^C$t$_{Ret}$=7.48 min; LC-MS: m/z 600.3 [M+H]$^+$ $^A$t$_{Ret}$=1.54 min.

Intermediate 141.1

1-Adamantan-1-yl-1-(4-bromo-phenyl)ethanol

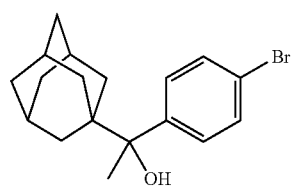 [SMILES: CC(O)(c1ccc(Br)cc1)C12CC3CC(CC(C3)C1)C2]

The title intermediate (0.96 g, 2.83 mmol) was obtained as a colourless oil from adamantane-1-carbaldehyde [CAS #2094-74-8] analogously to intermediates 145.9, 145.10, 145.11.

HPLC: $^C$t$_{Ret}$=7.33 min; 1H-NMR (400 MHz, DMSO-d$_6$): δ 1.38 (s, 3H), 1.41-1.56 (m, 12H), 1.86 (bs, 3H), 4.68 (s, 1H), 7.34 (dd, 4H)

Example 142

(S)-2-[4-((S)-1-Adamantan-1-yl-1-hydroxy-ethyl)-phenyl]-1-(4-chloro-phenyl)-7-isopropoxy-6-methoxy-1,4-dihydro-2H-isoquinolin-3-one

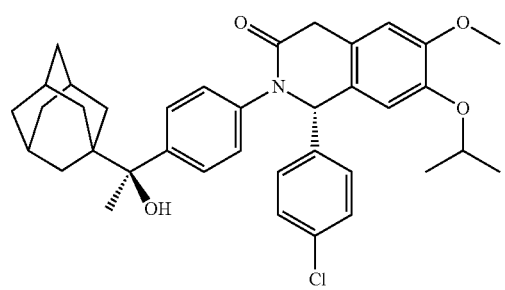 [SMILES: COc1cc2c(cc1OC(C)C)[C@H](c1ccc(Cl)cc1)N(c1ccc([C@@](C)(O)C34CC5CC(CC(C5)C3)C4)cc1)C(=O)C2]

Example 143

(S)-2-[4-((R)-1-Adamantan-1-yl-1-hydroxy-ethyl)-phenyl]-1-(4-chloro-phenyl)-7-isopropoxy-6-methoxy-1,4-dihydro-2H-isoquinolin-3-one

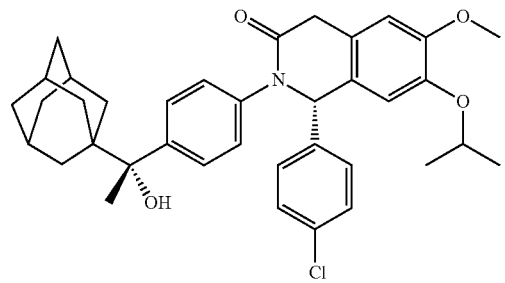 [SMILES: COc1cc2c(cc1OC(C)C)[C@H](c1ccc(Cl)cc1)N(c1ccc([C@](C)(O)C34CC5CC(CC(C5)C3)C4)cc1)C(=O)C2]

Preparative chiral separation of example 141 (283 mg, 0.472 mmol): Column; Chiralpak IC 20 um, 76.5×375 mm; mobile phase: n-Heptane/EtOH/MeOH 60:20:20; flow: 80 ml/min; detection: 287 nm (UV) afforded:

Example 142 first eluting peak (R$_t$=50 min) (125 mg, 0.208 mmol, 44%):
LC-MS: m/z 600.3 [M+H]$^+$ $^A$t$_{Ret}$=1.53 min Example 143 second eluting peak (R$_t$=86 min) (133 mg, 0.222 mmol, 47%):
LC-MS: m/z 600.3 [M+H]$^+$ $^A$t$_{Ret}$=1.53 min

Example 144

(S)-2-[4-(1-Adamantan-2-yl-1-hydroxy-ethyl)-phenyl]-1-(4-chloro-phenyl)-7-isopropoxy-6-methoxy-1,4-dihydro-2H-isoquinolin-3-one

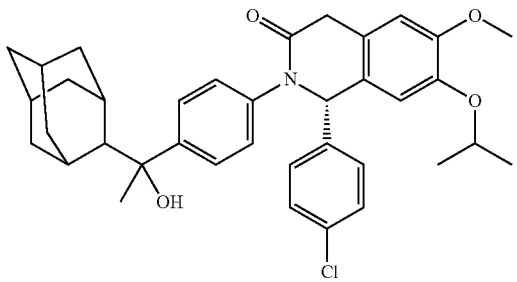 [SMILES: COc1cc2c(cc1OC(C)C)[C@H](c1ccc(Cl)cc1)N(c1ccc(C(C)(O)C3C4CC5CC(C4)CC3C5)cc1)C(=O)C2]

The title compound (234 mg, 0.390 mmol, 34%) was obtained as a slightly yellow foam from intermediate 144.1 (388 mg, 1.157 mmol) analogously to example 1.

HPLC: $^B t_{Ret}$=7.92 min; LC-MS: m/z 600.4 [M+H]$^+$ $^A t_{Ret}$=1.51 min.

Intermediate 144.1

1-Adamantan-2-yl-1-(4-bromo-phenyl)ethanol

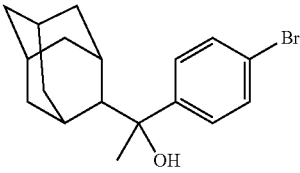 [SMILES: CC(O)(c1ccc(Br)cc1)C1C2CC3CC(C2)CC1C3]

To a stirred solution of intermediate 144.2 (1.24 g, 3.88 mmol) in THF (30 ml) was added methylmagnesium bromide (1.4M in THF-toluene 1:3) (6.10 ml, 8.55 mmol) during 5 min at 0° C. Stirring was continued for 2 h at RT and then quenched with 1M NH$_4$Cl. The mixture was extracted with EtOAc (2×). The organic phases were washed with brine and dried over Na$_2$SO$_4$, filtered and evaporated to dryness. Purification of the residue by normal phase column chromatography, eluting with EtOAc-hexane, gave the title compound as a colorless oil (0.924 g, 2.73 mmol, 70%): HPLC: $^B t_{Ret}$=7.92 min; 1H-NMR (400 MHz, DMSO-d$_6$): δ 1.22-1.77 (m, 12H), 1.46 (s, 3H), 2.22 (bs, 1H), 2.36 (d, 1H), 2.54 (d, 1H), 4.78 (s, 1H), 7.40 (dd, 4H)

Intermediate 144.2

Adamantan-2-yl-(4-bromo-phenyl)-methanone

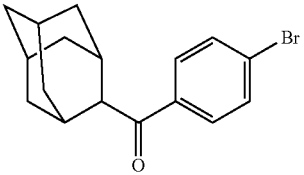 [SMILES: O=C(c1ccc(Br)cc1)C1C2CC3CC(C2)CC1C3]

To a stirred solution of intermediate 144.3 (1.40 g, 4.36 mmol) in acetone (50 ml) was added Jones reagent (1.88 g, 8.72 mmol) during 5 min at RT. Stirring was continued for 1.5 h at RT. The reaction mixture was extracted between 2M NaOH and EtOAc (2×). The organic phases were washed with brine and dried over Na$_2$SO$_4$, filtered and evaporated to dryness. Purification of the residue by normal phase column chromatography, eluting with EtOAc-hexane, gave the crude title compound as a white solid (1.24 g, 3.69 mmol, 85%): HPLC: $^B t_{Ret}$=7.92 min

Intermediate 144.3

Adamantan-2-yl-(4-bromo-phenyl)-methanol

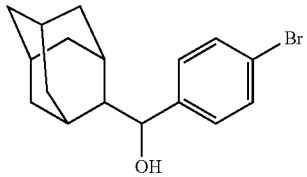 [SMILES: OC(c1ccc(Br)cc1)C1C2CC3CC(C2)CC1C3]

Reaction Vessel 1:

To a solution of 1-bromo-4-iodobenzene (2.83 g, 10.0 mmol) in diethyl ether (30 ml) (under argon atmosphere) was added isopropylmagnesium chloride (2M in diethyl ether) (6.25 ml, 12.5 mol) during 5 min at −25° C. The solution was stirred for 3 h at 0° C. to get the "Grignard-Solution"

Reaction vessel 2:

To a stirred solution of spiro[oxirane-2,2'-tricyclo[3.3.1.1³,⁷]decane] [CAS 24759-97-5] (1.66 g, 10.0 mmol) in diethyl ether (50 ml) (under argon atmosphere) was added the "Grignard-Solution" during 5 min at −70° C. The reaction mixture was stirred for additional 2 h at −42° C. and 14 h at RT. The reaction mixture was cooled to 0° C. and then quenched with 1M HCl (200 ml). The mixture was extracted with TBME (2×200 ml). The organic phases were washed with 1M NaHCO$_3$ and dried over Na$_2$SO$_4$, filtered and evaporated to dryness. Purification of the residue by normal phase column chromatography, eluting with EtOAc-hexane 1:10, gave the title compound as a white foam (1.59 g, 4.90 mmol, 49%): HPLC: $^C t_{Ret}$=6.67 min; $^A t_{Ret}$=1.42 min; 1H-NMR (600 MHz, DMSO-d$_6$): δ 1.36-2.04 (m, 14H), 2.31 (bs, 1H), 4.66 (m, 1H), 5.17 (d, 1H), 7.39 (dd, 4H)

Example 145

(S)-1-(4-Chloro-phenyl)-2-{4-[1-hydroxy-1-(tetrahydro-pyran-4-yl)-ethyl]-phenyl}-7-isopropoxy-6-(2-methoxy-ethoxy)-1,4-dihydro-2H-isoquinolin-3-one

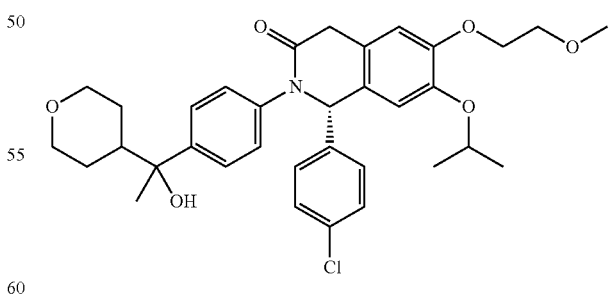

The title compound (80 mg, 0.132 mmol, 44%) was obtained as a slightly yellow foam from intermediate 145.1 (116 mg, 0.298 mmol) and intermediate 145.9 (85 mg, 0.298 mmol), analogously to example 1.

HPLC: $^B t_{Ret}$=5.68 min; LC-MS: m/z 594.3 [M+H]$^+$ $^A t_{Ret}$=1.13 min.

Intermediate 145.1

(S)-1-(4-Chloro-phenyl)-7-isopropoxy-6-(2-methoxy-ethoxy)-1,4-dihydro-2H-isoquinolin-3-one

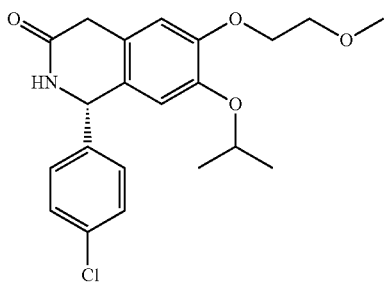 [SMILES: COCCOc1cc2c(cc1OC(C)C)[C@H](c1ccc(Cl)cc1)NC(=O)C2]

To a stirred solution of intermediate 145.2 (200 mg, 0.60 mmol) in DMF (2 ml) was added K$_2$CO$_3$ (167 mg, 1.20 mmol) and 1-bromo-2-methoxy-ethane (0.068 ml, 0.723 mmol). The suspension was stirred for 2 h at 100° C. The cooled reaction mixture was concentrated and the residue was extracted between EtOAc (2×) and water (3×). The organic phases were washed with brine and dried over Na$_2$SO$_4$, filtered and evaporated. Purification of the residue by normal phase column chromatography, eluting with EtOAc-hexane, gave the title compound as a white solid (138 mg, 0.35 mmol, 58%): HPLC: $^B$t$_{Ret}$=5.08 min; LC-MS: m/z 390.2 [M+H]$^+$ $^A$t$_{Ret}$=1.00 min

Intermediate 145.2

(S)-1-(4-Chloro-phenyl)-6-hydroxy-7-isopropoxy-1,4-dihydro-2H-isoquinolin-3-one

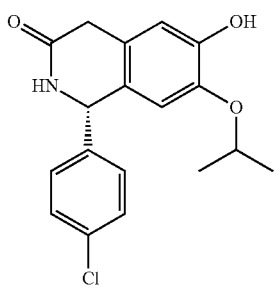 [SMILES: CC(C)Oc1cc2c(cc1O)CC(=O)N[C@H]2c1ccc(Cl)cc1]

To a stirred solution of intermediate 145.3 (4.80 g, 10.5 mmol) in THF-MeOH 1:1 (660 ml) was added pTsOH×H$_2$O (2.40 g, 12.6 mmol). The reaction mixture was stirred for 7 h at 50° C. To the cooled reaction mixture was added 1M NaHCO$_3$ (100 ml) and THF-MeOH was removed in vacuo. The residue was extracted with DCM (4×). The organic phases were washed with brine and dried over Na$_2$SO$_4$, filtered and evaporated. Purification of the residue by normal phase column chromatography, eluting with DCM-MeOH 95:5, gave the title compound as a slightly yellow foam (2.85 g, 8.37 mmol, 80%): HPLC: $^C$t$_{Ret}$=4.71 min; LC-MS: m/z 332.2 [M+H]$^+$ $^A$t$_{Ret}$=0.92 min; 1H-NMR (600 MHz, DMSO-d$_6$): δ 1.19 (q, 6H), 3.36 (dd, 2H), 4.41 (m, 1H), 5.50 (s, 1H), 6.60 (s, 1H), 6.82 (s, 1H), 7.34 (dd, 4H), 8.50 (s, 1H), 8.91 (s, 1H)

Intermediate 145.3

(S)-1-(4-Chloro-phenyl)-7-isopropoxy-6-(4-methoxy-benzyloxy)-1,4-dihydro-2H-isoquinolin-3-one

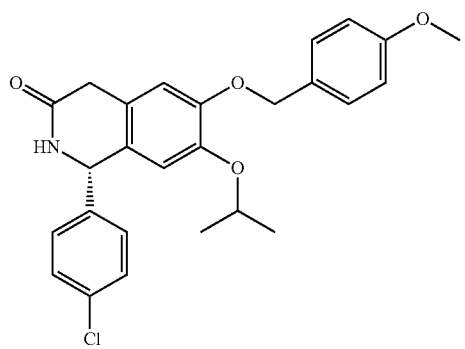 [SMILES: COc1ccc(COc2cc3c(cc2OC(C)C)C(c2ccc(Cl)cc2)NC(=O)C3)cc1]

Intermediate 145.4

(R)-1-(4-Chloro-phenyl)-7-isopropoxy-6-(4-methoxy-benzyloxy)-1,4-dihydro-2H-isoquinolin-3-one

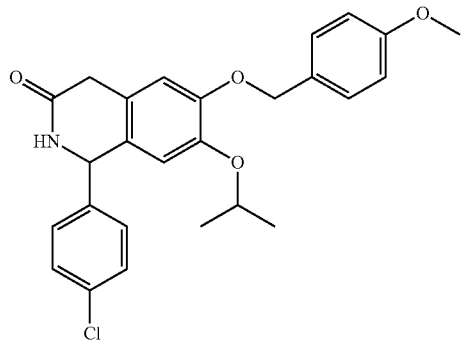 [SMILES: COc1ccc(COc2cc3c(cc2OC(C)C)C(c2ccc(Cl)cc2)NC(=O)C3)cc1]

Preparative chiral separation of intermediate 145.5 (10.10 g, 22.35 mmol): Column; Chiralpak AS 20 um, 50×500 mm; mobile phase: EtOH/MeOH 50:50; Flow: 80 ml/min Detection: 281 nm (UV) afforded:

Intermediate 145.3 first eluting peak (R$_t$=6.9 min-23.4 min) (4.80 g, 10.5 mmol, 47%):

HPLC: $^C$t$_{Ret}$=5.87 min; LC-MS: m/z 452.3 [M+H]$^+$ $^A$t$_{Ret}$=1.22 min

Intermediate 145.4 second eluting peak (R$_t$=59.6 min-193.9 min) (4.95 g, 10.85 mmol, 48%): HPLC: $^C$t$_{Ret}$=5.87 min; LC-MS: m/z 452.3 [M+H]$^+$ $^A$t$_{Ret}$=1.22 min Intermediate 145.5

1-(4-Chloro-phenyl)-7-isopropoxy-6-(4-methoxy-benzyloxy)-1,4-dihydro-2H-isoquinolin-3-one

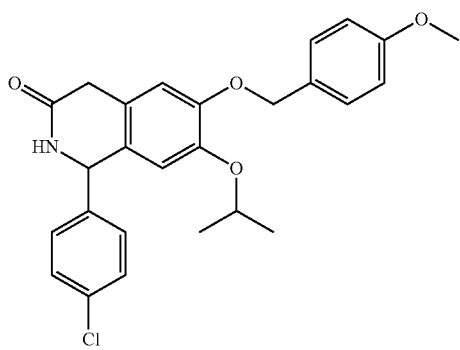

To a stirred solution of intermediate 145.6 (22.0 g, 61.0 mmol) in DMF (200 ml) was added K$_2$CO$_3$ (25.3 g, 183 mmol) and 1-chloromethyl-4-methoxy-benzene (9.10 ml, 67.1 mmol). The suspension was stirred for 1 h at 100° C. The cooled reaction mixture was concentrated and the residue was extracted between EtOAc (2×) and water (3×). The organic phases were washed with brine and dried over Na$_2$SO$_4$, filtered and evaporated. The residue was crystallized from TBME to give the title compound as a white solid (20.7 g, 44.9 mmol, 74%): HPLC: $^C$t$_{Ret}$=5.87 min; LC-MS: m/z 452.3 [M+H]$^+$ $^A$t$_{Ret.}$=1.22 min Intermediate 145.6

1-(4-Chloro-phenyl)-6-hydroxy-7-isopropoxy-1,4-dihydro-2H-isoquinolin-3-one

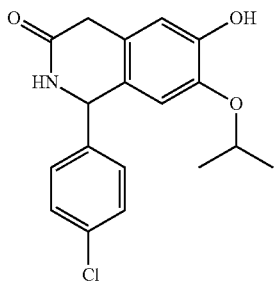

To a stirred mixture of intermediate 145.7 (20.0 g, 57.8 mmol) in DMF (400 ml) was subsequently added sodium hydride (4.30 g, 179 mmol) at 0° C. After stirring 15 min at RT, butane-1-thiol (13.7 mL, 127 mmol) was added dropwise at 13-16° C. and the resulting reaction mixture immediately heated (oil bath; 170° C.) to 135° C. and stirring was continued for 10 min. The reaction mixture was cooled an extracted between DCM (4×) and 1M NaHCO$_3$. The organic phases were washed with brine and dried over Na$_2$SO$_4$, filtered and evaporated, to afford the crude title compound which was used without further purification. HPLC:$^B$t$_{Ret}$=4.71 min; LC-MS: m/z 332.2 [M+H]$^+$ $^A$t$_{Ret.}$=0.95 min Intermediate 145.7

1-(4-Chloro-phenyl)-7-isopropoxy-6-methoxy-1,4-dihydro-2H-isoquinolin-3-one

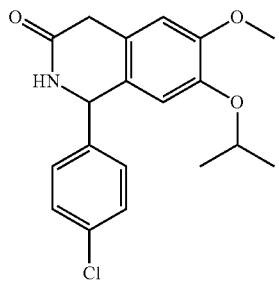 [SMILES: COc1cc2c(cc1OC(C)C)C(c1ccc(Cl)cc1)NC(=O)C2]

To a solution of intermediate 145.8 (150 g, 329 mmol) in DMF (650 mL) was successively added cesium carbonate (125 g, 658 mmol) and 2-iodopropane (100 mL, 988 mmol), then the reaction mixture was heated at 55° C. for 3 h. The reaction mixture was slowly poured into the stirred 2 L of iced water. Resulting mixture was extracted with 3 L of EtOAc two times, then washed with 1 L of water 2 times and 0.5 L of brine. Concentration in vacuo gave crude solid, which was stirred in 100 mL of EtOAc at RT, then filtration and dry up gave the title intermediate (97.2 g, 281 mmol, 85%). HPLC: $^E$t$_{Ret}$=4.99 min; LC-MS: m/z 346.2 [M+H]$^+$; 1H-NMR (400 MHz, DMSO-d$_6$): δ 1.16 (dd, J=18.94, 6.05 Hz, 6H), 3.28-3.54 (m, 2H), 3.70 (s, 3H), 4.32-4.47 (m, 1H), 5.53 (d, J=3.90 Hz, 1H), 6.77 (s, 1H), 6.83 (s, 1H), 7.28 (d, 2H), 7.36 (d, 2H), 8.49 (d, J=3.90 Hz, 1H).

Intermediate 145.8

1-(4-Chloro-phenyl)-7-hydroxy-6-methoxy-1,4-dihydro-2H-isoquinolin-3-one

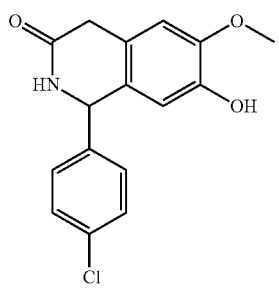 [SMILES: COc1cc2c(cc1O)C(c1ccc(Cl)cc1)NC(=O)C2]

To a suspension of 4-hydroxy-3-methoxyphenylacetonitrile (150 g, 0.919 mol) in phosphoric acid 85% (877 mL, 15.000 mol) was added 4-chlorobenzaldehyde (168 g, 1.195 mol), then the reaction mixture was heated at 120° C. for 2 h. After cooling to 90° C., the reaction mixture was slowly poured into the stirred 4 L of iced water. Resulting suspension was stirred at RT for 2 h, then filtered and washed with 500 ml of water 4 times. Crude and wet material was stirred in acetonitrile (1 L) at RT for 1 h, then filtration and dry up gave the title intermediate (163.6 g, 0.539 mol, 58.6%). HPLC: $^E$t$_{Ret}$=4.20 min; LC-MS: m/z 304.0 [M+H]$^+$; 1H-NMR (400 MHz, DMSO-d$_6$): δ 3.25-3.53 (m, 2H), 3.72 (s, 3H), 5.47 (d, J=3.12 Hz, 1H), 6.53 (s, 1H), 6.72 (s, 1H), 7.24 (d, 2H), 7.37 (d, 2H), 8.42 (d, J=3.51 Hz, 1H), 8.86 (br. s., 1H).

Intermediate 145.9

1-(4-Bromo-phenyl)-1-(tetrahydro-pyran-4-yl)-ethanol

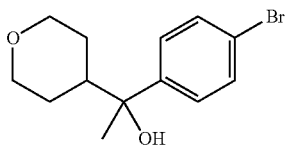 [SMILES: CC(O)(c1ccc(Br)cc1)C1CCOCC1]

To a stirred solution of intermediate 145.10 (2.69 g, 10 mmol) in THF (27 ml) was added methylmagnesium bromide (1.4M in THF-toluene 1:3) (14.28 ml, 20 mmol) during 5 min at 8-10° C. Stirring was continued for 1 h at 10° C. and then carefully quenched with 1M NH$_4$Cl. The mixture was extracted with EtOAc (2×). The organic phases were washed with brine and dried over Na$_2$SO$_4$, filtered and evaporated to dryness. The residue was crystallized from diisopropyl ether to give the title compound as a white solid (2.50 g, 8.77 mmol, 88%): HPLC: $^C t_{Ret}$=4.78 min; 1H-NMR (400 MHz, DMSO-d$_6$): δ 1.70 (d, 1H), 1.15-1.32 (m, 2H), 1.47 (d, 1H), 1.37 (s, 3H), 1.62 (m, 1H), 3.06-3.20 (m, 2H), 3.72-3.85 (m, 2H), 4.90 (s, 1H), 7.39 (dd, 4H)

Intermediate 145.10

(4-Bromo-phenyl)-(tetrahydro-pyran-4-yl)-methanone

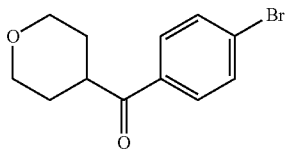 [SMILES: O=C(c1ccc(Br)cc1)C1CCOCC1]

To a stirred solution of intermediate 145.11 (26.58 g, 98 mmol) in DCM (1.5 L) was added MnO$_2$ (85 g, 0.98 mol) at RT. Stirring was continued for 2 h at RT, then additional MnO$_2$ (42.6 g, 0.49 mol) was added and stirring was continued for 15 h at RT. The reaction mixture was filtered and the filtrate was concentrated in vacuo. The residue was crystallized from diisopropyl ether to give the title compound as a white solid (25.64 g, 95 mmol, 97%): HPLC: $^C t_{Ret}$=4.99 min; 1H-NMR (400 MHz, DMSO-d$_6$): δ 1.49-1.68 (m, 4H), 3.46 (m, 2H), 3.64 (m, 1H), 3.86 (m, 2H), 7.82 (dd, 4H)

Intermediate 145.11

(4-Bromo-phenyl)-(tetrahydro-pyran-4-yl)-methanol

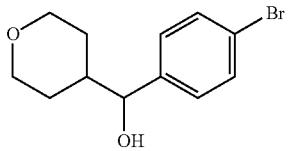 [SMILES: OC(c1ccc(Br)cc1)C1CCOCC1]

To a solution of 1-bromo-4-iodobenzene (31.1 g, 110 mmol) in THF (300 ml) (under argon atmosphere) was added isopropylmagnesium chloride (2M in THF) (60 ml, 120 mol) during 10 min at −25° C. The solution was stirred for 1 h at −20° C. and then warmed up to 0° C. and tetrahydro-pyran-4-carbaldehyde (10.98 ml, 100 mmol) was added dropwise over 10 min at 0-7° C. The reaction mixture was quenched with 1M NH$_4$Cl (500 ml) and extracted with EtOAc (2×). The organic phases were washed with water and brine, dried over Na$_2$SO$_4$, filtered and evaporated to dryness. The residue was crystallized from DCM-diisopropyl ether (1:2) to give the title compound as a white solid (24.32 g, 90 mmol, 90%): HPLC: $^C t_{Ret}$=4.43 min; 1H-NMR (400 MHz, DMSO-d$_6$): δ 1.07 (d, 1H), 1.21 (m, 2H), 1.62 (m, 2H), 3.15 (m, 2H), 3.78 (m, 2H), 4.23 (m, 1H), 5.26 (d, 1H), 7.35 (dd, 4H)

Example 146

(S)-1-(4-Chloro-phenyl)-2-{4-[1-hydroxy-1-(tetrahydro-pyran-4-yl)-ethyl]-phenyl}-7-isopropoxy-6-(pyridin-2-ylmethoxy)-1,4-dihydro-2H-isoquinolin-3-one

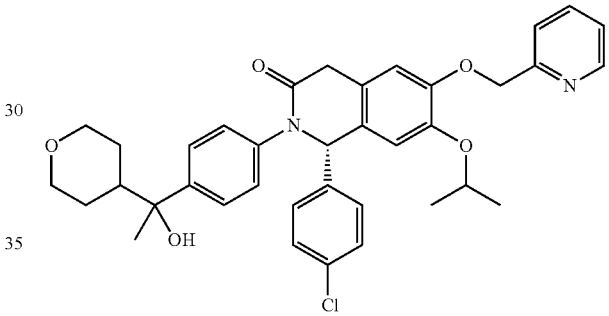

The title compound (60 mg, 0.096 mmol, 40%) was obtained as a slightly yellow foam from intermediate 146.1 (100 mg, 0.236 mmol) and intermediate 145.9 (81 mg, 0.284 mmol), analogously to example 1.

HPLC: $^B t_{Ret}$=5.58 min; LC-MS: m/z 627.3 [M+H]$^+$ $^A t_{Ret.}$=1.15 min.

Intermediate 146.1

(S)-1-(4-Chloro-phenyl)-7-isopropoxy-6-(pyridin-2-ylmethoxy)-1,4-dihydro-2H-isoquinolin-3-one

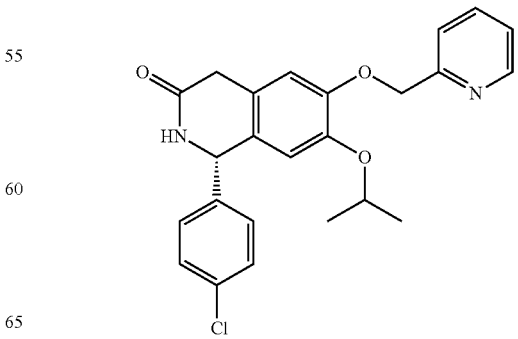

To a stirred solution of intermediate 145.2 (200 mg, 0.603 mmol) in THF (8.0 ml) was added subsequently, pyridin-2-yl-methanol (0.070 ml, 0.723 mmol), di-tert-butylazodicarboxylate (278 mg, 1.206 mmol), triphenylphosphine polymer bound (316 mg, 1.206 mmol) and stirred for 19 h at RT. The reaction mixture was filtered and the filtrate extracted between EtOAc (2×) and 1M NaHCO$_3$. The organic phases were washed with brine and dried over Na$_2$SO$_4$, filtered and evaporated. The residue was crystallized from EtOAc to give the title compound as a white solid (123 mg, 0.288 mmol, 48%): HPLC: $^B$t$_{Ret}$=4.98 min; LC-MS: m/z 423.2 [M+H]$^+$ $^A$t$_{Ret.}$=1.02 min Example 147

(S)-1-(4-Chloro-phenyl)-2-{4-[1-hydroxy-1-(tetrahydro-pyran-4-yl)-ethyl]-phenyl}-7-isopropoxy-6-(oxetan-3-ylmethoxy)-1,4-dihydro-2H-isoquinolin-3-one

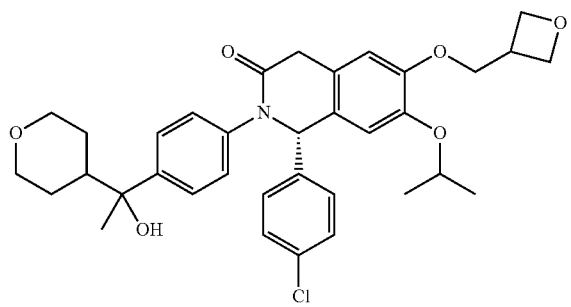 [SMILES: CC(C)Oc1cc2c(cc1OCC1COC1)CC(=O)N(c1ccc(C(C)(O)C3CCOCC3)cc1)[C@H]2c1ccc(Cl)cc1]

The title compound (66 mg, 0.109 mmol, 44%) was obtained as a slightly yellow foam from intermediate 147.1 (100 mg, 0.249 mmol) and intermediate 145.9 (85 mg, 0.299 mmol), analogously to example 1
HPLC: $^B$t$_{Ret}$=5.67 min; LC-MS: m/z 606.3 [M+H]$^+$ $^A$t$_{Ret.}$=1.11 min.

Intermediate 147.1

(S)-1-(4-Chloro-phenyl)-7-isopropoxy-6-(oxetan-3-ylmethoxy)-1,4-dihydro-2H-isoquinolin-3-one

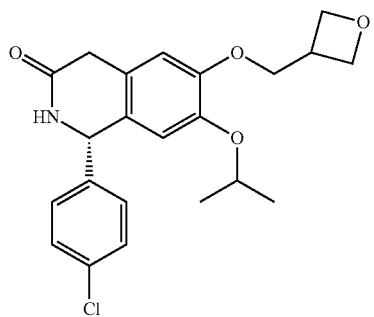 [SMILES: CC(C)Oc1cc2c(cc1OCC1COC1)CC(=O)N[C@H]2c1ccc(Cl)cc1]

The title Intermediate (132 mg, 0.328 mmol, 55%) was obtained as a white solid from intermediate 147.2 (200 mg, 0.603 mmol) and oxetan-3-yl-methanol (53.1 mg, 0.603 mmol), analogously to intermediate 146.1.

HPLC: $^B$t$_{Ret}$=5.07 min; LC-MS: m/z 402.2 [M+H]$^+$ $^A$t$_{Ret.}$=0.99 min Example 148

2-((S)-1-(4-Chloro-phenyl)-2-{4-[1-hydroxy-1-(tetrahydro-pyran-4-yl)-ethyl]-phenyl}-7-isopropoxy-3-oxo-1,2,3,4-tetrahydro-isoquinolin-6-yloxy)-N-methyl-acetamide

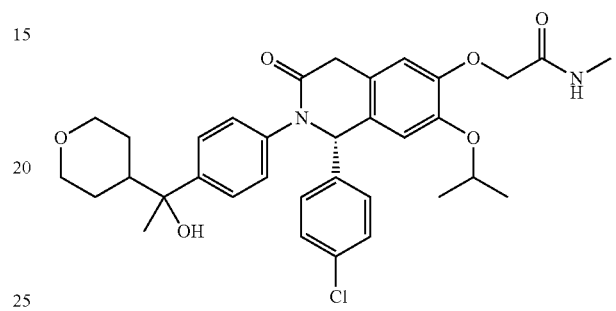

The title compound (64 mg, 0.103 mmol, 60%) was obtained as a slightly yellow foam from intermediate 148.1 (70 mg, 0.174 mmol) and intermediate 145.9 (55 mg, 0.191 mmol), analogously to example 1.
HPLC: $^B$t$_{Ret}$=5.09 min; LC-MS: m/z 607.3 [M+H]$^+$ $^A$t$_{Ret.}$=1.01 min.

Intermediate 148.1

2-[(S)-1-(4-Chloro-phenyl)-7-isopropoxy-3-oxo-1,2,3,4-tetrahydro-isoquinolin-6-yloxy]-N-methyl-acetamide

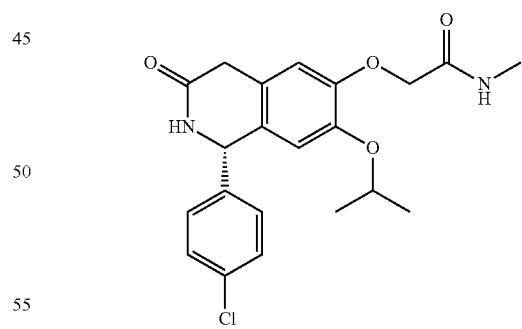

The solution of intermediate 148.2 (100 mg, 0.248 mmol) in methyl amine (2M in MeOH) (2.0 ml) was stirred for 2 h at 50° C. The cooled reaction mixture was extracted between EtOAc (2×) and 1M NaHCO$_3$. The organic phases were washed with brine and dried over Na$_2$SO$_4$, filtered and evaporated. The residue was crystallized from TBME to give the title compound as a white solid (72 mg, 0.179 mmol, 72%): HPLC: $^B$t$_{Ret}$=4.64 min;
LC-MS: m/z 403.2 [M+H]$^+$ $^A$t$_{Ret.}$=0.88 min Intermediate 148.2

[(S)-1-(4-Chloro-phenyl)-7-isopropoxy-3-oxo-1,2,3,4-tetrahydro-isoquinolin-6-yloxy]-acetic acid methyl ester

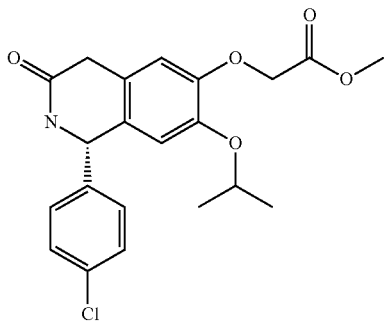 [SMILES: COC(=O)COc1cc2c(cc1OC(C)C)[C@H](c1ccc(Cl)cc1)NC(=O)C2]

To a stirred solution of intermediate 145.2 (200 mg, 0.60 mmol) in DMF (5 ml) was added $K_2CO_3$ (167 mg, 1.20 mmol) and bromo-acetic acid methyl ester (0.067 ml, 0.723 mmol). The suspension was stirred for 2 h at 50° C. The cooled reaction mixture was concentrated and the residue was extracted between EtOAc (2×) and 1M $NaHCO_3$. The organic phases were washed with brine and dried over $Na_2SO_4$, filtered and evaporated, to afford the crude title compound as white solid (227 mg, 0.556 mmol, 92%) which was used without further purification. HPLC: $^B t_{Ret}$=5.07 min; LC-MS: m/z 404.2 [M+H]$^+$ $^A t_{Ret.}$=0.99 min Example 149

2-((S)-1-(4-Chloro-phenyl)-2-{4-[1-hydroxy-1-(tetrahydro-pyran-4-yl)-ethyl]-phenyl}-7-isopropoxy-3-oxo-1,2,3,4-tetrahydro-isoquinolin-6-yloxy)-N,N-dimethyl-acetamide

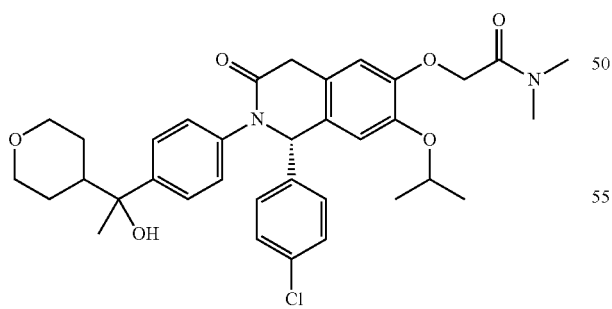

The title compound (64 mg, 0.101 mmol, 60%) was obtained as a slightly yellow foam from intermediate 149.1 (70 mg, 0.168 mmol) and intermediate 145.9 (62 mg, 0.218 mmol), analogously to example 1. HPLC: $^B t_{Ret}$=5.19 min; LC-MS: m/z 621.4 [M+H]$^+$ $^A t_{Ret.}$=1.03 min.

Intermediate 149.1

2-[(S)-1-(4-Chloro-phenyl)-7-isopropoxy-3-oxo-1,2,3,4-tetrahydro-isoquinolin-6-yloxy]-N,N-dimethyl-acetamide

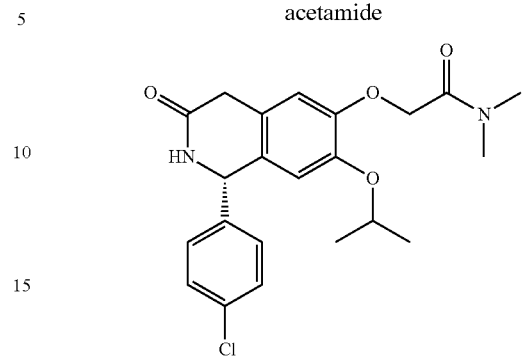

The title intermediate (79 mg, 0.189 mmol, 77%) was obtained as a white solid from intermediate 148.2 (100 mg, 0.248 mmol) and dimethyl amine (2M in MeOH), analogously intermediate 148.1. HPLC: $^B t_{Ret}$=4.66 min; LC-MS: m/z 417.2 [M+H]$^+$ $^A t_{Ret.}$=0.90 min.

Example 150

(S)-1-(4-Chloro-phenyl)-2-{4-[1-(1,1-dioxo-hexahydro-1-thiopyran-4-yl)-1-hydroxy-ethyl]-phenyl}-7-isopropoxy-6-d$^3$-methoxy-1,4-dihydro-2H-isoquinolin-3-one

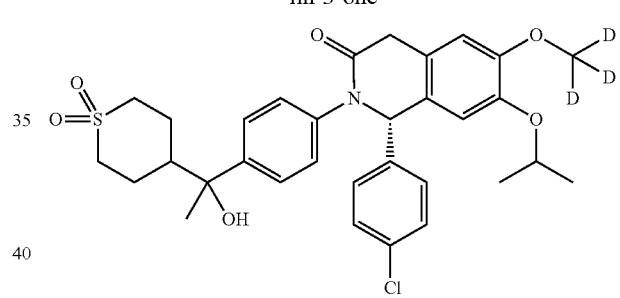

The title compound (162 mg, 0.266 mmol, 46%) was obtained as a slightly beige foam from intermediate 150.1 (200 mg, 0.568 mmol) and intermediate 166.1 (210 mg, 0.624 mmol), analogously to Example 1.
HPLC: $^C t_{Ret}$=5.18 min; LC-MS: m/z 601.4 [M+H]$^+$ $^A t_{Ret.}$=1.06 min.

Intermediate 150.1

(S)-1-(4-Chloro-phenyl)-7-isopropoxy-6-d$^3$-methoxy-1,4-dihydro-2H-isoquinolin-3-one

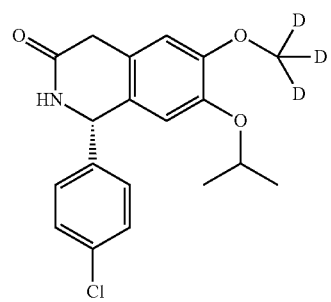 [SMILES: [2H]C([2H])([2H])Oc1cc2c(cc1OC(C)C)[C@H](c1ccc(Cl)cc1)NC(=O)C2]

Intermediate 150.2

(R)-1-(4-Chloro-phenyl)-7-isopropoxy-6-d³-methoxy-1,4-dihydro-2H-isoquinolin-3-one

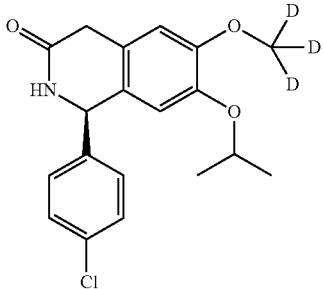 [SMILES: [2H]C([2H])([2H])Oc1cc2c(cc1OC(C)C)[C@@H](c1ccc(Cl)cc1)NC(=O)C2]

Preparative chiral separation of intermediate 150.3 (3.40 g, 9.26 mmol): Instrumentation: Thar SFC200; Column; Chiralpak OD-H, 50×250 mm; mobile phase: $CO_2$-MeOH 50:50; flow: 100 g/min; detection: 215 nm (UV) afforded:

Intermediate 150.1 first eluting peak ($R_t$=4.83-5.13 min) (1.23 g, 3.49 mmol, 37%):
HPLC: $^{C}t_{Ret}$=5.06 min; 1H-NMR (400 MHz, DMSO-$d_6$): δ 1.16 (q, 6H), 3.40 (dd, 2H), 4.39 (m, 1H), 5.53 (d, 1H), 6.76 (s, 1H), 6.82 (s, 1H), 7.32 (dd, 4H), 8.48 (d, 1H)

Intermediate 150.2 second eluting peak ($R_t$=5.24-5.63 min) (1.23 g, 3.49 mmol, 37%): HPLC: $^{C}t_{Ret}$=5.06 min;

Intermediate 150.3

1-(4-Chloro-phenyl)-7-isopropoxy-6-d³-methoxy-1,4-dihydro-2H-isoquinolin-3-one

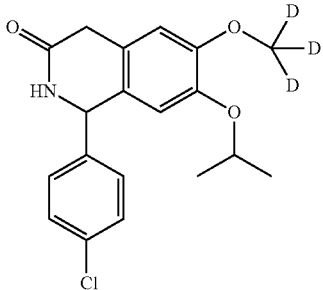 [SMILES: [2H]C([2H])([2H])Oc1cc2c(cc1OC(C)C)C(c1ccc(Cl)cc1)NC(=O)C2]

To a solution of intermediate 145.6 (1.50 g, 4.52 mmol) in DMF (4.0 ml) was added potassium carbonate (1.25 g, 9.04 mmol) and iodomethane-d3 (1.41 ml, 22.6 mmol). The suspension was stirred for 2 h at 60° C. The reaction mixture was extracted between EtOAc (3×) and 1M aqueous $NaHCO_3$ (1×). The organic phases were washed with brine and dried over $Na_2SO_4$, filtered and evaporated to dryness. Purification of the residue by normal phase column chromatography, eluting with EtOAc-hexane, gave the title compound after crystallization (DCM-hexane) as a white solid (1.10 g, 3.09 mmol, 68%): HPLC: $^{B}t_{Ret}$=5.02 min; LC-MS: m/z 349.3 [M+H]⁺. $^{A}t_{Ret}$=1.03 min.

Example 151

4-(1-{4-[(S)-1-(4-Chloro-phenyl)-7-isopropoxy-6-d³-methoxy-3-oxo-3,4-dihydro-1H-isoquinolin-2-yl]-phenyl}-1-hydroxy-ethyl)-piperidine-1-carbaldehyde

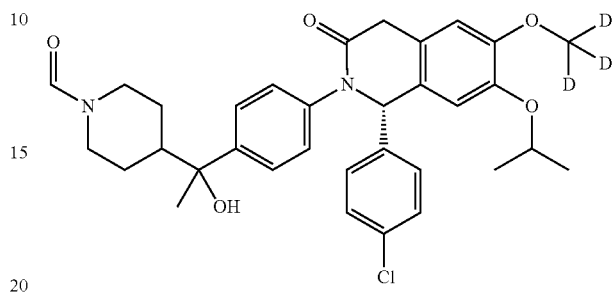

The stirred solution of intermediate 151.1 (130 mg, 0.233 mmol) in ethyl formate (3.83 ml) was stirred for 17 h at 50° C. The reaction mixture was concentrated in vacuo and the residue was purified by reverse phase prep-HPLC (Waters system). To the combined fractions was added 1M $NaHCO_3$ and then acetonitrile was removed in vacuo. The residue was extracted between EtOAc (2×) and 1M aqueous $NaHCO_3$ (1×). The organic phases were washed with brine and dried over $Na_2SO_4$, filtered and evaporated to dryness, to afford the title compound as a slightly yellow foam (83 mg, 0.142 mmol, 61%): HPLC: $^{B}t_{Ret}$=5.26 min; LC-MS: m/z 580.3 [M+H]⁺. $^{A}t_{Ret}$=1.06 min.

Intermediate 151.1

(S)-1-(4-Chloro-phenyl)-2-[4-(1-hydroxy-1-piperidin-4-yl-ethyl)-phenyl]-7-isopropoxy-6-d³-methoxy-1,4-dihydro-2H-isoquinolin-3-one

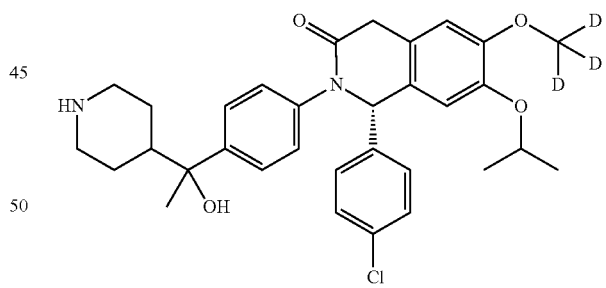

To a stirred solution of intermediate 151.2 (220 mg, 0.317 mol) in EtOH (12.5 ml) was added subsequently chlorobenzene (0.065 ml, 0.635 mmol), HCl (1.25 M in EtOH) (0.279 ml, 0.349 mmol) and hydrogenated under 1 atmosphere of hydrogen for 45 min in the presence of Pd/C 10% (Aldrich 330108) (34 mg). The reaction mixture was then filtered and the solvent evaporated under reduced pressure. Purification of the residue by normal phase column chromatography, eluting with DCM-MeOH-aq. $NH_4OH$ 30% 200:10:1, gave the title compound as a slightly yellow foam (132 mg, 0.237 mmol, 75%):
HPLC: $^{C}t_{Ret}$=4.69 min; LC-MS: m/z 552.4 [M+H]⁺ $^{A}t_{Ret}$=0.89 min

Intermediate 151.2

4-(1-{4-[(S)-1-(4-Chloro-phenyl)-7-isopropoxy-6-d³-methoxy-3-oxo-3,4-dihydro-1H-isoquinolin-2-yl]-phenyl}-1-hydroxy-ethyl)-piperidine-1-carboxylic acid benzyl ester

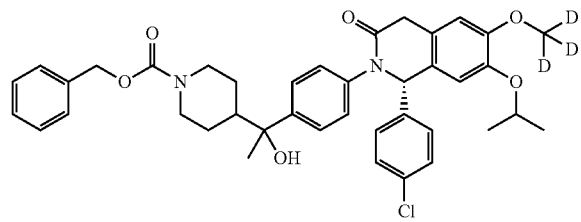 [SMILES: [2H]C([2H])([2H])Oc1cc2c(cc1OC(C)C)[C@H](c1ccc(Cl)cc1)N(c1ccc(C(C)(O)C3CCN(C(=O)OCc4ccccc4)CC3)cc1)C(=O)C2]

The title intermediate (226 mg, 0.326 mmol, 34%) was obtained as a slightly beige foam from intermediate 150.1 (340 mg, 0.0.965 mmol) and intermediate 75.3 (458 mg, 1.061 mmol), analogously to example 1.

HPLC: $^B t_{Ret}$=6.30 min; LC-MS: m/z 687.3 [M+H]⁺ $^A t_{Ret.}$=1.34 min.

Example 152

(S)-1-(4-Chloro-phenyl)-2-{4-[(R)-1-(1,1-dioxo-hexahydro-1-thiopyran-4-yl)-1-hydroxy-ethyl]-phenyl}-7-isopropoxy-6-d³-methoxy-1,4-dihydro-2H-isoquinolin-3-one

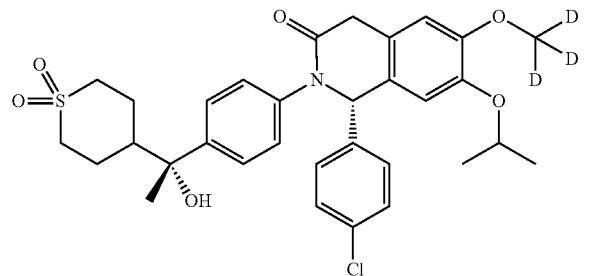 [SMILES: [2H]C([2H])([2H])Oc1cc2c(cc1OC(C)C)[C@H](c1ccc(Cl)cc1)N(c1ccc([C@](C)(O)C3CCS(=O)(=O)CC3)cc1)C(=O)C2]

Example 153

(S)-1-(4-Chloro-phenyl)-2-{4-[(S)-1-(1,1-dioxo-hexahydro-1-thiopyran-4-yl)-1-hydroxy-ethyl]-phenyl}-7-isopropoxy-6-d³-methoxy-1,4-dihydro-2H-isoquinolin-3-one

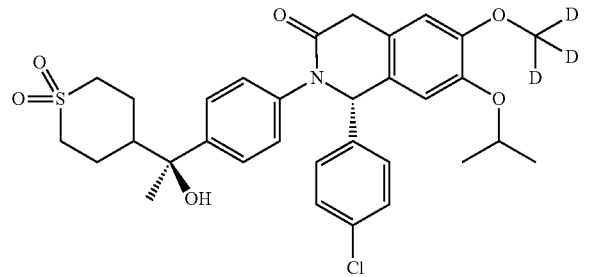 [SMILES: [2H]C([2H])([2H])Oc1cc2c(cc1OC(C)C)[C@H](c1ccc(Cl)cc1)N(c1ccc([C@@](C)(O)C3CCS(=O)(=O)CC3)cc1)C(=O)C2]

Preparative chiral separation of example 150 (67 mg, 0.110 mmol): Column; Chiralpak AD-H 5 um, 250×20 mm; mobile phase: n-Heptane/EtOH/MeOH 70:15:15; flow: 12 ml/min; detection: 210 nm (UV) afforded:

Example 152 first eluting peak (R$_t$=11.6 min) (26 mg, 0.043 mmol, 39%):
HPLC: $^C t_{Ret}$=5.18 min; LC-MS: m/z 601.4 [M+H]⁺ $^A t_{Ret.}$=1.06 min

Example 153 second eluting peak (R$_t$=15.2 min) (25 mg, 0.041 mmol, 37%):
HPLC: $^C t_{Ret}$=5.18 min; LC-MS: m/z 601.4 [M+H]⁺ $^A t_{Ret.}$=1.06 min

Example 154

4-((R)-1-{4-[(S)-1-(4-Chloro-phenyl)-7-isopropoxy-6-d³-methoxy-3-oxo-3,4-dihydro-1H-isoquinolin-2-yl]-phenyl}-1-hydroxy-ethyl)-piperidine-1-carbaldehyde

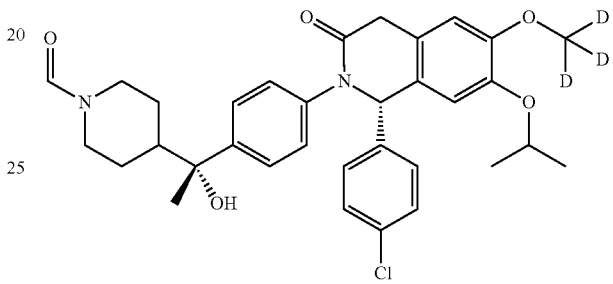

Example 155

4-((S)-1-{4-[(S)-1-(4-Chloro-phenyl)-7-isopropoxy-6-d³-methoxy-3-oxo-3,4-dihydro-1H-isoquinolin-2-yl]-phenyl}-1-hydroxy-ethyl)-piperidine-1-carbaldehyde

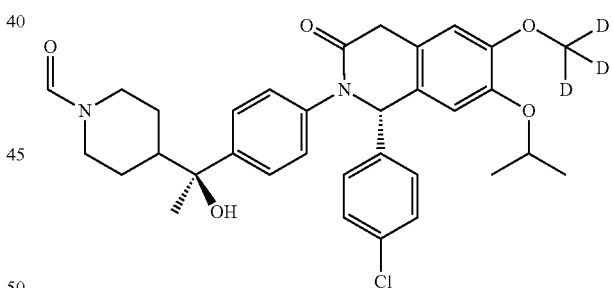

Preparative chiral separation of example 151 (72 mg, 0.110 mmol): Column; Chiralpak AD-H 5 um, 250×20 mm; mobile phase: n-Heptane/EtOH 60:40; flow: 12 ml/min; detection: 210 nm (UV) afforded:

Example 154 first eluting peak (R$_t$=6.1 min) (25 mg, 0.039 mmol, 39%):
HPLC: $^C t_{Ret}$=5.26 min; LC-MS: m/z 580.3 [M+H]⁺. $^A t_{Ret.}$=1.06 min.

Example 155 second eluting peak (R$_t$=9.4 min) (27 mg, 0.042 mmol, 37%):
HPLC: $^C t_{Ret}$=5.26 min; LC-MS: m/z 580.3 [M+H]⁺. $^A t_{Ret.}$=1.06 min.

Example 156

(S)-1-(4-Chloro-phenyl)-2-{4-[1-hydroxy-1-(3-oxa-7-aza-bicyclo[3.3.1]non-9-yl)-ethyl]-phenyl}-7-isopropoxy-6-methoxy-1,4-dihydro-2H-isoquinolin-3-one

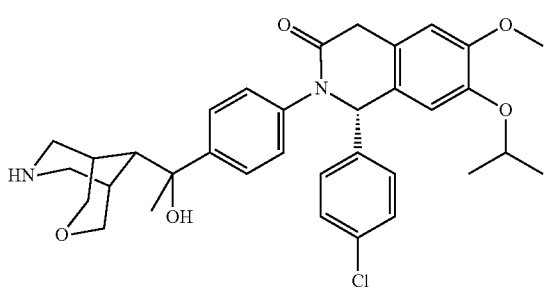 [SMILES: COc1cc2c(cc1OC(C)C)[C@H](c1ccc(Cl)cc1)N(c1ccc(C(C)(O)C3C4CNCC3COC4)cc1)C(=O)C2]

The title compound (347 mg, 0.0.581 mmol, 91%) was obtained as a slightly yellow foam from example 156.1 (470 mg, 0.642 mmol), analogously to example 151.1; HPLC: $^C t_{Ret}$=4.77 min; LC-MS: m/z 591.4 [M+H]$^+$ $^A t_{Ret}$=0.92 min.

Intermediate 156.1

9-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-3-oxa-7-aza-bicyclo[3.3.1]nonane-7-carboxylic acid benzyl ester

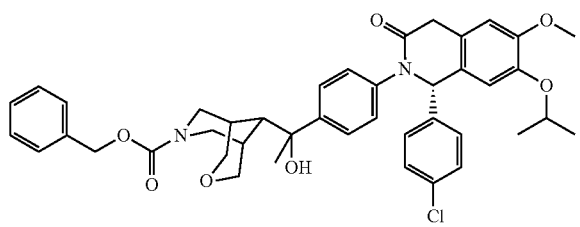 [SMILES: COc1cc2c(cc1OC(C)C)[C@H](c1ccc(Cl)cc1)N(c1ccc(C(C)(O)C3C4COCC3CN(C(=O)OCc3ccccc3)C4)cc1)C(=O)C2]

The title intermediate (476 mg, 0.0.650 mmol, 44%) was obtained as a slightly yellow foam from intermediate 156.2 (725 mg, 1.58 mmol) analogously to example 1.

HPLC: $^C t_{Ret}$=6.16 min; LC-MS: m/z 725.4 [M+H]$^+$ $^A t_{Ret}$=1.32 min.

Intermediate 156.2

9-[1-(4-Bromo-phenyl)-1-hydroxy-ethyl]-3-oxa-7-aza-bicyclo[3.3.1]nonane-7-carboxylic acid benzyl ester

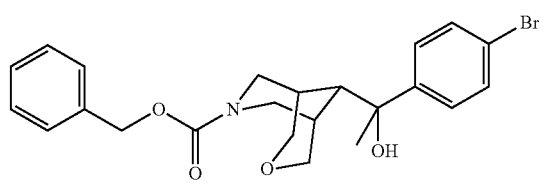 [SMILES: CC(O)(c1ccc(Br)cc1)C1C2COCC1CN(C(=O)OCc1ccccc1)C2]

The title intermediate (0.990 g, 2.13 mmol) was obtained as a white foam from intermediate 156.3 analogously to intermediates 145.9, 145.10, 145.11.

HPLC: $^C t_{Ret}$=5.82 min; LC-MS: m/z 460.2 [M+H]$^+$ $^A t_{Ret}$=1.25 min.

Intermediate 156.3

(THP axial) 9-Formyl-3-oxa-7-aza-bicyclo[3.3.1]nonane-7-carboxylic acid benzyl ester

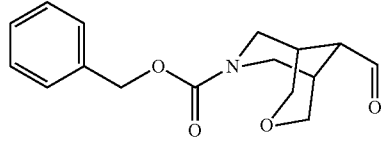 [SMILES: O=CC1C2COCC1CN(C(=O)OCc1ccccc1)C2]

Intermediate 156.4

(THP equatorial) 9-Formyl-3-oxa-7-aza-bicyclo[3.3.1]nonane-7-carboxylic acid benzyl ester

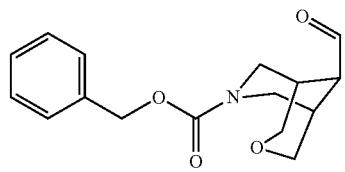 [SMILES: O=CC1C2COCC1CN(C(=O)OCc1ccccc1)C2]

To a stirred solution of intermediate 321.5 (5.40 g, 17.6 mol) in acetone (60.5 ml) was added water (10.1 ml) and 1M HCl (4.41 ml, 4.41 mmol). The reaction mixture was stirred for 17 h at 50° C. and then acetone was evaporated. The residue was carefully basified with 1M NaHCO$_3$ and extracted with EtOAc (2×). The organic phases were washed with brine, dried over Na$_2$SO$_4$, filtered and evaporated to dryness to get the crude aldehyde (the NMR showed a mixture of equatorial and axial configuration). The aldehydes were separated by normal phase column chromatography, eluting with heptane-EtOAc 1:3, to give the title intermediates:

Intermediate 156.3 white solid (1.96 g, 6.71 mmol, 39%): TLC (heptane-EtOAc 1:2) Rf=0.26; 1H-NMR (600 MHz, DMSO-d$_6$): δ 2.23-2.27 (d, 2H), 2.67 (s, 1H), 3.16 (dd, 2H), 3.56-3.63 (m, 4H), 4.23 (q, 2H), 5.06 (m, 2H), 7.33-7.37 (m, 5H), 9.76 (s, 1H) (the conformation was confirmed by ROESY NMR)

Intermediate 156.4 colorless oil (1.70 g, 5.82 mmol, 34%): TLC (heptane-EtOAc 1:2) Rf=0.18; 1H-NMR (600 MHz, DMSO-d$_6$): δ 2.20-2.23 (d, 2H), 2.77 (s, 1H), 3.15 (dd, 2H), 3.62 (d, 2H), 3.89-4.01 (m, 4H), 5.04 (m, 2H), 7.28-7.36 (m, 5H), 9.71 s, 1H) (the conformation was confirmed by ROESY NMR)

Intermediate 156.5

9-Methoxymethylene-3-oxa-7-aza-bicyclo[3.3.1]nonane-7-carboxylic acid benzyl ester

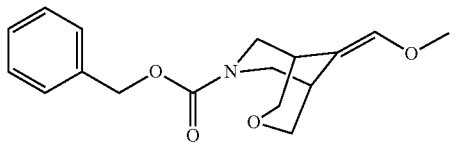 [SMILES: COC=C1C2COCC1CN(C(=O)OCc1ccccc1)C2]

The title intermediate (5.50 g, 17.95 mmol, 90%) was obtained as a beige oil from intermediate 156.6 (5.56 g, 20 mmol) analogously to example 158.3. HPLC: $^C t_{Ret}$=4.86 min; LC-MS: m/z 304.3 [M+H]$^+$ $^A t_{Ret.}$=1.04 min.

Intermediate 156.6

9-Oxo-3-oxa-7-aza-bicyclo[3.3.1]nonane-7-carboxylic acid benzyl ester

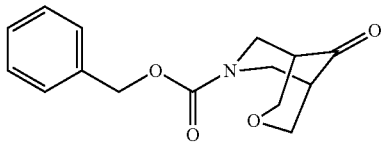 [SMILES: O=C1C2COCC1CN(C(=O)OCc1ccccc1)C2]

To a stirred mixture of 3-oxa-7-aza-bicyclo[3.3.1]nonan-9-one hydrochloride [CAS #1228600-54-1] (4.80 g, 27 mmol), EtOAc (105 ml) and saturated aqueous Na$_2$CO$_3$ (105 ml) was added benzyl chloroformate (4.60 ml, 32.4 ml) at 0° C. The reaction mixture was stirred for 1 h at 0° C. and then extracted with EtOAc (2×). The organic phases were washed with brine, dried over Na$_2$SO$_4$, filtered and evaporated to dryness. Purification of the residue by normal phase column chromatography, eluting with heptane-EtOAc 1:1, gave the title compound as a colorless oil (5.75 g, 20.68 mmol, 77%): 1H-NMR (400 MHz, DMSO-d$_6$): δ 2.31-2.35 (d, 2H), 2.34 dd, 2H), 3.78 (d, 2H), 4.19 (t, 2H), 4.55 (q, 2H), 5.11 (m, 2H), 7.28-7.38 (m, 5H).

Example 157

9-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-3-oxa-7-aza-bicyclo[3.3.1]nonane-7-carbaldehyde

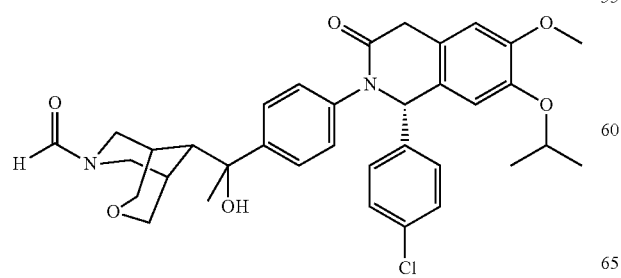

The title compound (135 mg, 0.216 mmol, 72%) was obtained as a slightly yellow foam from example 156 (179 mg, 0.300 mmol), analogously to example 151.
HPLC: $^C t_{Ret}$=5.26 min; LC-MS: m/z 619.4 [M+H]$^+$ $^A t_{Ret.}$=1.06 min.

Example 158

(S)-1-(4-Chloro-phenyl)-2-{4-[1-hydroxy-1-(8-oxabicyclo[3.2.1]oct-3-yl)-ethyl]-phenyl}-7-isopropoxy-6-methoxy-1,4-dihydro-2H-isoquinolin-3-one

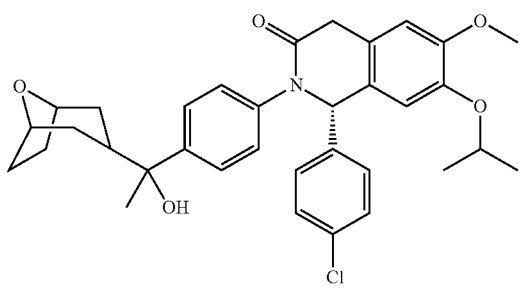 [SMILES: COc1cc2c(cc1OC(C)C)[C@H](c1ccc(Cl)cc1)N(c1ccc(C(C)(O)C3CC4CCC(C3)O4)cc1)C(=O)C2]

The title compound (91 mg, 0.158 mmol, 16%) was obtained as a slightly yellow foam from intermediate 158.1 (300 mg, 0.964 mmol) analogously to example 1.
HPLC: $^D t_{Ret}$=5.48 min; LC-MS: m/z 576.3 [M+H]$^+$ $^A t_{Ret.}$=1.16 min.

Intermediate 158.1

1-(4-Bromo-phenyl)-1-(8-oxa-bicyclo[3.2.1]oct-3-yl)ethanol

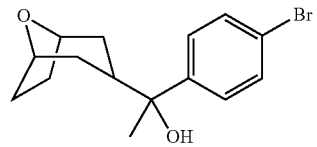 [SMILES: CC(O)(c1ccc(Br)cc1)C1CC2CCC(C1)O2]

The title intermediate (0.750 g, 2.41 mmol) was obtained as a white solid from intermediate 158.2 analogously to intermediates 145.9, 145.10, 145.11.
HPLC: $^D t_{Ret}$=5.11 min; $^A t_{Ret.}$=1.04 min; 1H-NMR (400 MHz, DMSO-d$_6$): δ 0.76 (m, 1H), 1.32 (s, 3H), 1.36 (m, 2H), 1.48 (m, 2H), 1.67 (m, 3H), 1.93 (m, 1H), 4.14 (m, 1H), 4.26 (m, 1H), 4.82 (s, 1H), 7.38 (dd, 4H)

Intermediate 158.2

8-Oxa-bicyclo[3.2.1]octane-3-carbaldehyde

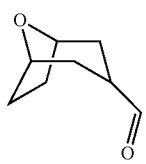

To a stirred solution of intermediate 158.3 (1.71 g, 11.09 mol) in acetonitrile (13.5 ml) was added 2M HCl (11.09 ml, 22.18 mmol). Stirring was continued for 1.5 h at RT and then carefully basified with 1M NaHCO₃. The mixture was extracted with diethyl ether (4×). The organic phases were dried over Na₂SO₄, filtered and evaporated to dryness to get the crude aldehyde (the NMR showed a mixture of equatorial and axial configuration) witch was dissolved in THF (19 ml) and MeOH (19 ml). To the stirred solution was added DBU (0.092 ml, 0.610 mmol) and stirring was continued for 1 h. The reaction mixture was neutralized with 1M HCl, saturated with NaCl and extracted with EtOAc (6×). The organic phases were dried over Na₂SO₄, filtered and evaporated to dryness. Purification of the residue by normal phase column chromatography, eluting with a gradient of heptane-EtOAc 80:20 to 0:100, gave the title compound as a colorless oil (1.22 g, 8.70 mmol, 78%): 1H-NMR (600 MHz, DMSO-d₆): δ 1.56-2.05 (m, 8H), 2.65 (m, 1H), 4.48 (m, 2H), 9.55 (s, 1H) (equatorial conformation was confirmed by ROESY NMR).

Intermediate 158.3

3-Methoxymethylene-8-oxa-bicyclo[3.2.1]octane

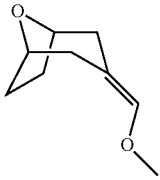

A solution of sodium bis(trimethylsilyl)amide 1M in THF (24.48 ml, 24.48 mmol) was added drop wise to a suspension of (methoxymethyl)triphenylphosphonium chloride (8.39 g, 24.48 mmol) in THF (98 ml) at −40° C. Stirring was continued for 0.5 h at −40° C. and then the solution of 8-oxa-bicyclo[3.2.1]octan-3-one [CAS #77745-32-5] (1.93 g, 15.3 mmol) in THF (20 ml) was added at −40° C. The suspension was allowed to warm to RT and stirring was continued for 6 h. The reaction mixture was quenched with a saturated solution of NH₄Cl and extracted with EtOAc (2×). The combined organic phases were washed with brine, dried over Na₂SO₄, filtered and evaporated to dryness. The crude product was purified by silica gel column chromatography (eluting with a gradient of heptane-EtOAc 97:3 to 0:100) yielding the title compound as a slightly yellow oil (1.71 g, 11.09 mmol, 72%): 1H-NMR (400 MHz, CDCl₃): δ 1.58-2.43 (m, 8H), 3.54 (s, 3H), 4.41 (m, 2H), 5.85 (s, 1H)

Example 159

(S)-1-(4-Chloro-phenyl)-2-{4-[(S)-1-hydroxy-1-(8-oxabicyclo[3.2.1]oct-3-yl)-ethyl]-phenyl}-7-isopropoxy-6-methoxy-1,4-dihydro-2H-isoquinolin-3-one

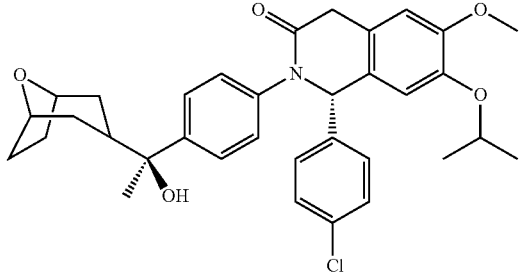 [SMILES: COc1cc2c(cc1OC(C)C)[C@H](c1ccc(Cl)cc1)N(c1ccc([C@@](C)(O)C3CC4CCC(C3)O4)cc1)C(=O)C2]

Example 160

(S)-1-(4-Chloro-phenyl)-2-{4-[(R)-1-hydroxy-1-(8-oxa-bicyclo[3.2.1]oct-3-yl)-ethyl]-phenyl}-7-isopropoxy-6-methoxy-1,4-dihydro-2H isoquinolin-3-one

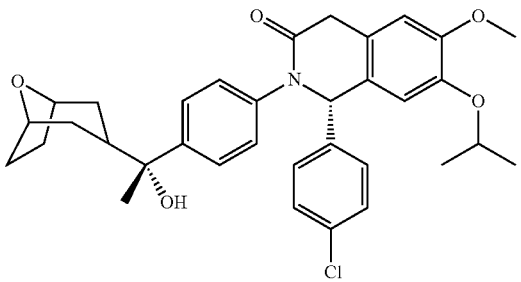 [SMILES: COc1cc2c(cc1OC(C)C)[C@H](c1ccc(Cl)cc1)N(c1ccc([C@](C)(O)C3CC4CCC(C3)O4)cc1)C(=O)C2]

Preparative chiral separation of example 158 (130 mg, 0.212 mmol): Column; Chiralpak OD 20 um, 50×500 mm; mobile phase: n-heptane/propan-2-ol 85:15; Flow: 70 ml/min Detection: 210 nm (UV) afforded:

Example 159 first eluting peak (R$_f$=19 min) (46 mg, 0.080 mmol, 37%):
HPLC: $^D t_{Ret}$=5.48 min; LC-MS: m/z 576.3 [M+H]⁺ $^A t_{Ret.}$=1.16 min.

Example 160 second eluting peak (R$_f$=28 min) (42 mg, 0.073 mmol, 34%):
HPLC: $^D t_{Ret}$=5.48 min; LC-MS: m/z 576.3 [M+H]⁺ $^A t_{Ret.}$=1.16 min.

Example 161

(S)-1-(4-Chloro-phenyl)-2-{4-[1-hydroxy-1-(9-oxa-bicyclo[3.3.1]non-3-yl)-ethyl]-phenyl}-7-isopropoxy-6-methoxy-1,4-dihydro-2H-isoquinolin-3-one

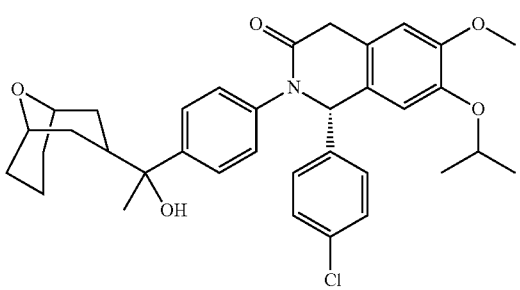 [SMILES: COc1cc2c(cc1OC(C)C)[C@H](c1ccc(Cl)cc1)N(c1ccc(C(C)(O)C3CC4CCCC(C3)O4)cc1)C(=O)C2]

The title compound (19 mg, 0.031 mmol, 16%) was obtained as a slightly yellow foam from intermediate 161.1 (92 mg, 0.283 mmol) analogously to example 1.

HPLC: $^D t_{Ret}$=5.64 min; LC-MS: m/z 590.4 [M+H]⁺ $^A t_{Ret.}$=1.21 min.

Intermediate 161.1

1-(4-Bromo-phenyl)-1-(9-oxa-bicyclo[3.3.1]non-3-yl)-ethanol

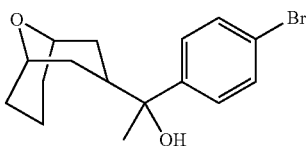 [SMILES: CC(O)(c1ccc(Br)cc1)C1CC2CCCC(C1)O2]

The title intermediate (95 mg, 0.307 mmol) was obtained as a colorless oil starting from 9-oxa-bicyclo[3.3.1]nonan-3-one (Tetrahedron Letters (1964), (25-26), 1705-6) [CAS #10469-63-3] analogously to intermediates 145.9, 145.10, 145.11, 158.2, 158.3; HPLC:
$^{D}t_{Ret}$=5.36 min; 1H-NMR (400 MHz, DMSO-d$_6$): δ 0.86 (m, 2H), 1.35 (s, 3H), 1.45-1.97 (m, 9H), 3.76 (t, 1H), 3.90 (t, 1H), 4.84 (s, 1H), 7.40 (dd, 4H).

Example 162

S)-1-(4-Chloro-phenyl)-2-{4-[1-hydroxy-1-(2,2,6,6-tetramethyl-tetrahydro-pyran-4-yl)-ethyl]-phenyl}-7-isopropoxy-6-methoxy-1,4-dihydro-2H-isoquinolin-3-one

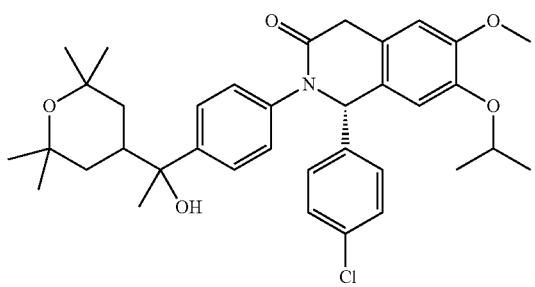 [SMILES: COc1cc2c(cc1OC(C)C)[C@H](c1ccc(Cl)cc1)N(c1ccc(C(C)(O)C3CC(C)(C)OC(C)(C)C3)cc1)C(=O)C2]

The title compound (78 mg, 0.129 mmol, 14%) was obtained as a white foam from intermediate 162.1 (309 mg, 0.905 mmol) analogously to example 1.
HPLC: $^{D}t_{Ret}$=5.76 min; LC-MS: m/z 606.5 [M+H]$^+$ $^{A}t_{Ret.}$=1.30 min

Intermediate 162.1

1-(4-Bromo-phenyl)-1-(2,2,6,6-tetramethyl-tetrahydro-pyran-4-yl)-ethanol

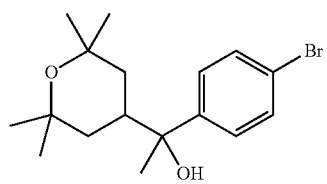 [SMILES: CC1(C)CC(C(C)(O)c2ccc(Br)cc2)CC(C)(C)O1]

The title intermediate (95 mg, 0.307 mmol) was obtained as a colorless oil starting from 2,2,6,6-tetramethyl-tetrahydro-pyran-4-one [CAS #1197-66-6] analogously to intermediates 145.9, 145.10, 145.11, 158.2, 158.3; HPLC:$^{D}t_{Ret}$=5.50 min; 1H-NMR (400 MHz, DMSO-d$_6$): δ 0.81-1.22 (m, 3H), 0.97 (s, 3H), 1.04 (s, 3H), 1.05 (s, 3H), 1.14 (s, 3H), 1.38 (s, 3H), 2.54 (m, 1H), 2.04 (m, 1H), 4.88 (s, 1H), 7.40 (dd, 4H).

Example 163

(S)-1-(4-Chloro-phenyl)-2-{4-[(S)-1-hydroxy-1-(2,2,6,6-tetramethyl-tetrahydro-pyran-4-yl)-ethyl]-phenyl}-7-isopropoxy-6-methoxy-1,4-dihydro-2H-isoquinolin-3-one

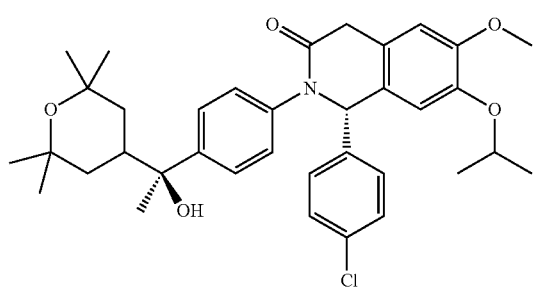 [SMILES: COc1cc2c(cc1OC(C)C)[C@H](c1ccc(Cl)cc1)N(c1ccc([C@@](C)(O)C3CC(C)(C)OC(C)(C)C3)cc1)C(=O)C2]

Example 164

(S)-1-(4-Chloro-phenyl)-2-{4-[(R)-1-hydroxy-1-(2,2,6,6-tetramethyl-tetrahydro-pyran-4-yl)-ethyl]-phenyl}-7-isopropoxy-6-methoxy-1,4-dihydro-2H-isoquinolin-3-one

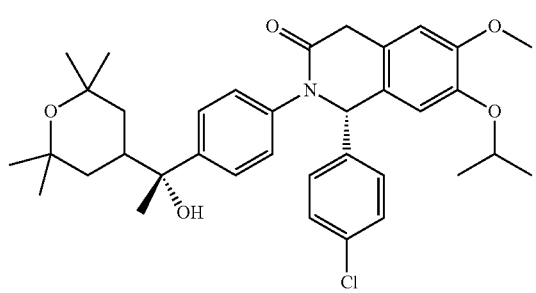 [SMILES: COc1cc2c(cc1OC(C)C)[C@H](c1ccc(Cl)cc1)N(c1ccc([C@](C)(O)C3CC(C)(C)OC(C)(C)C3)cc1)C(=O)C2]

Preparative chiral separation of example 162 (50 mg, 0.082 mmol): Column; Chiralpak OD 5 um, 20×250 mm; mobile phase: n-heptane/propan-2-ol 60:40; Flow: 50 ml/min
Detection: 220 nm (UV) afforded:

Example 163 first eluting peak ($R_t$=5.1 min) (20 mg, 0.032 mmol, 39%):
HPLC: $^{D}t_{Ret}$=5.76 min; LC-MS: m/z 606.5 [M+H]$^+$ $^{A}t_{Ret.}$=1.30 min

Example 164 second eluting peak ($R_t$=8.0 min) (18 mg, 0.028 mmol, 34%):
HPLC: $^{D}t_{Ret}$=5.76 min; LC-MS: m/z 606.5 [M+H]$^+$ $^{A}t_{Ret.}$=1.30 min

Example 165

1-(4-Chloro-phenyl)-6-difluoromethoxy-2-{4-[1-hydroxy-1-(tetrahydro-pyran-4-yl)-ethyl]-phenyl}-7-isopropoxy-1,4-dihydro-2H-isoquinolin-3-one

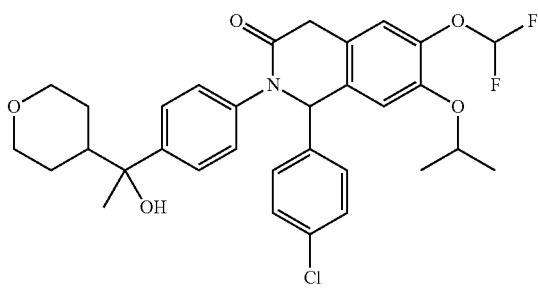 [SMILES: CC(C)Oc1cc2c(cc1OC(F)F)CC(=O)N(c1ccc(C(C)(O)C3CCOCC3)cc1)C2c1ccc(Cl)cc1]

To a stirred solution of intermediate 165.1 (35 mg, 0.055 mmol) in THF (1.0 ml) was added chlorotrimethylsilane (0.0071 ml, 0.055 mmol) at 2° C. Stirring was continued for 0.5 h at 2° C. and then methylmagnesium bromide (1.4M in THF-toluene 1:3) (0.083 ml, 0.116 mmol) during 2 min at 2° C. Stirring was continued for 2 h at 2° C. and then carefully quenched with 1M NH$_4$Cl. The mixture was extracted with EtOAc (2×). The organic phases were washed with brine and dried over Na$_2$SO$_4$, filtered and evaporated to dryness. Purification of the residue by normal phase column chromatography, eluting with DCM-MeOH 95:5, gave the title compound as a beige foam (6.0 mg, 0.010 mmol, 18%): HPLC: $^E t_{Ret}$=7.55 min; LC-MS: m/z 586.3 [M+H]$^+$ $^A t_{Ret.}$=1.24 min

Intermediate 165.1

1-(4-Chloro-phenyl)-6-difluoromethoxy-7-isopropoxy-2-[4-(tetrahydro-pyran-4-carbonyl)-phenyl]-1,4-dihydro-2H-isoquinolin-3-one

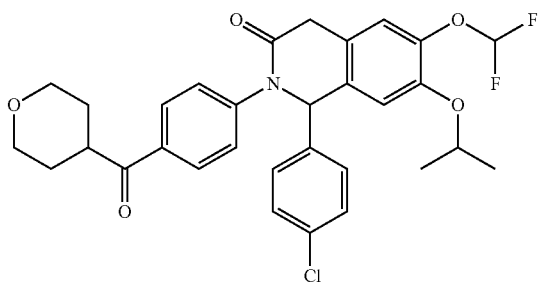 [SMILES: CC(C)Oc1cc2c(cc1OC(F)F)CC(=O)N(c1ccc(C(=O)C3CCOCC3)cc1)C2c1ccc(Cl)cc1]

To a solution of intermediate 165.2 (0.280 g, 0.538 mmol) in DMF (5.8 ml) was added cesium carbonate (0.351 g, 1.077 mmol) and methyl chlorofluoroacetate (0.115 g, 1.077 mmol). The suspension was stirred for 19 h at 120° C. The reaction mixture was extracted between EtOAc (2×) and water (1×). The organic phases were washed with water (2×) and dried over Na$_2$SO$_4$, filtered and evaporated to dryness. The residue was purified by silica gel column chromatography (eluting with a gradient of heptane-EtOAc 50:50 to 30:70) yielding the title compound as a slightly yellow foam (0.036 g, 0.064 mmol, 6.0%): HPLC: $^E t_{Ret}$=7.83 min; LC-MS: m/z 570.2 [M+H]$^+$ $^A t_{Ret.}$=1.29 min

Intermediate 165.2

1-(4-Chloro-phenyl)-6-hydroxy-7-isopropoxy-2-[4-(tetrahydro-pyran-4-carbonyl)-phenyl]-1,4-dihydro-2H-isoquinolin-3-one

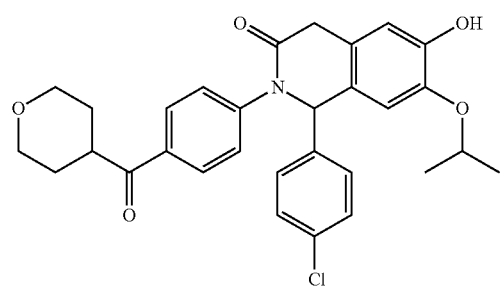 [SMILES: CC(C)Oc1cc2c(cc1O)CC(=O)N(c1ccc(C(=O)C3CCOCC3)cc1)C2c1ccc(Cl)cc1]

To a stirred solution of intermediate 165.3 (1.31 g, 2.046 mmol) in THF-MeOH 1:1 (80 ml) was added pTsOH×H$_2$O (0.506 g, 2.66 mmol). The reaction mixture was stirred for 18 h at 50° C. To the cooled reaction mixture was added 1M NaHCO$_3$ (80 ml) and extracted with EtOAc (2×). The organic phases were dried over Na$_2$SO$_4$, filtered and evaporated. Purification of the residue by normal phase column chromatography, eluting with DCM-MeOH 97:3, gave the title compound as a slightly yellow foam (1.06 g, 2.038 mmol, 99%): HPLC: $^E t_{Ret}$=7.05 min; LC-MS: m/z 520.3 [M+H]$^+$ $^A t_{Ret.}$=1.13 min

Intermediate 165.3

1-(4-Chloro-phenyl)-7-isopropoxy-6-(4-methoxy-benzyloxy)-2-[4-(tetrahydro-pyran-4-carbonyl)-phenyl]-1,4-dihydro-2H-isoquinolin-3-one

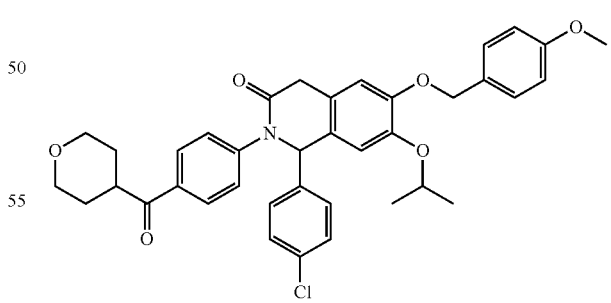

The title intermediate (1.315 g, 2.054 mmol, 46%) was obtained as a yellow foam from intermediate 145.5 (2.00 g, 4.43 mmol) and intermediate 145.10 (1.43 g, 5.31 mmol) analogously to example 1.

HPLC: $^E t_{Ret}$=8.18 min; LC-MS: m/z 640.3 [M+H]$^+$ $^A t_{Ret.}$=1.33 min.

Example 166

(S)-1-(4-Chloro-phenyl)-2-{4-[1-(1,1-dioxo-hexahydro-1-thiopyran-4-yl)-1-hydroxy-ethyl]-phenyl}-7-isopropoxy-6-methoxy-1,4-dihydro-2H-isoquinolin-3-one

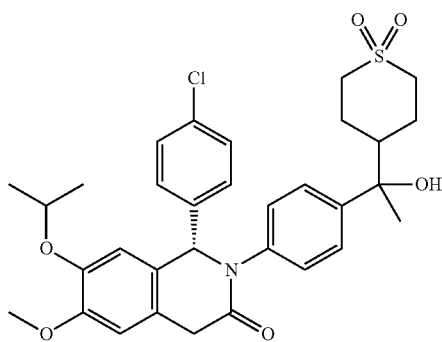 [SMILES: COc1cc2c(cc1OC(C)C)[C@H](c1ccc(Cl)cc1)N(c1ccc(C(C)(O)C3CCS(=O)(=O)CC3)cc1)C(=O)C2]

A dry 20 ml microwave vial was charged with K₃PO₄ (503 mg, 2.371 mmol), (S)-1-(4-chlorophenyl)-7-isopropoxy-6-methoxy-1,2-dihydroisoquinolin-3(4H)-one (410 mg, 1.186 mmol), 1-(4-bromo-phenyl)-1-(1,1-dioxo-hexahydro-1-thiopyran-4-yl)-ethanol (474 mg, 1.423 mmol) and dioxane (6.7 ml). The reaction mixture was degassed with argon, then trans-1,2-diaminocyclohexane (27.1 mg, 0.029 ml, 0.237 mmol) and copper(I)iodide (45.2 mg, 0.273 mmol) were added. The vial was sealed and heated for 6 hrs to 97° C. in an oil bath. Further trans-1,2-diaminocyclohexane (27.1 mg, 0.029 ml, 0.237 mmol) and copper(I)iodide (45.2 mg, 0.273 mmol) were added and the reaction was continued to stir at 97° C. for 24 hrs. The reaction mixture was filtered through a pad of hyflo, the residue was washed with dioxane and the filtrate was concentrated to dryness. The crude product was purified by reversed phase prep-HPLC (gradient elution, MeCN/water+0.1% TFA). Fractions containing pure material were combined, concentrated and the resulting aqueous mixture was neutralized with a saturated solution of NaHCO₃, followed by extraction with DCM. The organic layer was dried over Na₂SO₄, filtered and evaporated to dryness to yield the title example (301 mg, 0.503 mmol, 42%) as a colourless resin.

HPLC: $^{B}t_{Ret}$=6.77;

HPLC/MS: $^{A}t_{Ret}$=1.05 min: LC-MS: m/z 615.3 [M+NH₃]⁺.

1H-NMR (600 MHz, DMSO-d₆): δ 1.20 (d, J=6.05 Hz, 3H), 1.24 (d, J=6.05 Hz, 3H), 1.40 (s, 3H), 1.55-1.76 (m, 3H), 1.79-1.87 (m, 1H), 1.97-2.04 (m, 1H), 2.89-3.07 (m, 4H), 3.60 (d, J=19.58 Hz, 1H), 3.72 (s, 3H), 3.84 (dd, J=19.58, 3.63 Hz, 1H), 4.45 (dq, J=9.11, 6.05 Hz, 1H), 5.10 (s, 1H), 6.10 (d, J=6.46 Hz, 1H), 6.85 (s, 1H), 7.10-7.15 (m, 3H), 7.31-7.39 (m, 6H).

Intermediate 166.1

1-(4-Bromo-phenyl)-1-(1,1-dioxo-hexahydro-1-thiopyran-4-yl)-ethanol

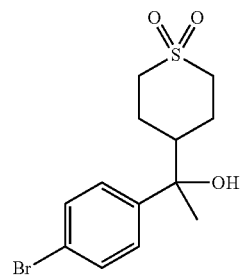 [SMILES: CC(O)(c1ccc(Br)cc1)C1CCS(=O)(=O)CC1]

To a solution of 1-bromo-4-iodobenzene (2.84 g, 10.04 mmol) in THF (16 ml) at −45° C. to −39° C. was added ethylmagnesium bromide 3M in Et₂O (4.46 ml, 13.39 mmol). The reaction mixture was warmed to −10° C. and stirred for 2 hrs. The suspension was then cooled to −70° C. and a solution of 1-(1,1-dioxo-hexahydro-1-thiopyran-4-yl)-ethanone (1.18 g, 6.70 mmol) in THF (16 ml) was added. After stirring for 10 min at the given temperature the reaction mixture was allowed to warm to RT and stirred for 16 hrs. The yellow suspension was cooled with an ice bath and quenched with an aqueous solution of saturated NH₄Cl (20 ml), diluted with ethyl acetate and extracted with ethyl acetate. The organic phases were combined, washed with brine, dried over Na₂SO₄, filtered and concentrated in vacuo. The crude product was purified by silica gel column chromatography (eluting with a gradient of DCM:EtOH=100:0 to 96:04) yielding the title intermediate (976 mg, 2.93 mmol, 44%) as a colourless foam.

HPLC: $^{B}t_{Ret}$=5.88; HPLC/MS: $^{A}t_{Ret}$=0.84 min: LC-MS: m/z 352.2 [M+NH₄]⁺. MW=334

1H-NMR (600 MHz, DMSO-d₆): δ 1.42 (s, 3H), 1.53-1.73 (m, 3H), 1.83 (t, J=11.91 Hz, 1H), 2.03 (d, J=13.93 Hz, 1H), 2.87-2.93 (m, 1H), 2.95-3.08 (m, 3H) 5.19 (s, 1H), 7.35 (d, J=8.48 Hz, 2H), 7.50 (d, J=8.48 Hz, 2H).

Example 167

(S)-1-(4-Chloro-phenyl)-2-{4-[(R)-1-(1,1-dioxo-hexahydro-1-thiopyran-4-yl)-1-hydroxy-ethyl]-phenyl}-7-isopropoxy-6-methoxy-1,4-dihydro-2H-isoquinolin-3-one

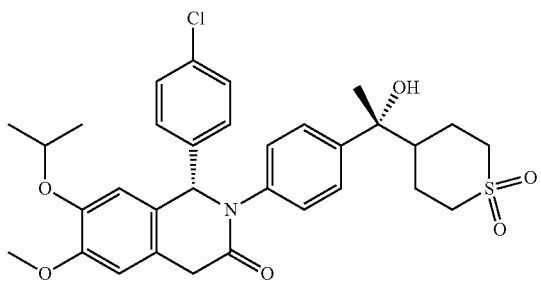 [SMILES: COc1cc2c(cc1OC(C)C)[C@H](c1ccc(Cl)cc1)N(c1ccc([C@](C)(O)C3CCS(=O)(=O)CC3)cc1)C(=O)C2]

and

Example 168

(S)-1-(4-Chloro-phenyl)-2-{4-[(S)-1-(1,1-dioxo-hexahydro-1-thiopyran-4-yl)-1-hydroxy-ethyl]-phenyl}-7-isopropoxy-6-methoxy-1,4-dihydro-2H-isoquinolin-3-one

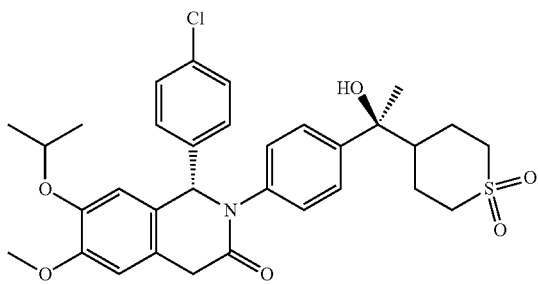 [SMILES: COc1cc2c(cc1OC(C)C)[C@H](c1ccc(Cl)cc1)N(c1ccc([C@@](C)(O)C3CCS(=O)(=O)CC3)cc1)C(=O)C2]

The title example 167 and example 168 were obtained by chiral separation of example 166 (185 mg, 0.309 mmol).

Column: ChiralPAK AD-H (5 um, 250×20 mm); mobile phase: n-heptane/EtOH 75/25+TFA; flow rate: 15 ml/min; detection UV: 210 nm Example 167: 7.86 min (62.6 mg, ee>99.0%)
Example 168: 10.69 min (57 mg, ee>99.0%)

Example 169

(S)-1-(4-Chloro-phenyl)-2-{4-[1-hydroxy-1-(1-oxo-hexahydro-1-thiopyran-4-yl)-ethyl]-phenyl}-7-isopropoxy-6-methoxy-1,4-dihydro-2H-isoquinolin-3-one

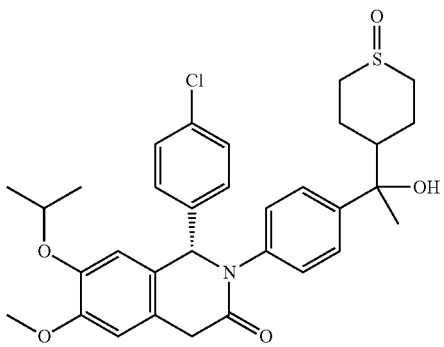 [SMILES: COc1cc2c(cc1OC(C)C)[C@H](c1ccc(Cl)cc1)N(c1ccc(C(C)(O)C3CCS(=O)CC3)cc1)C(=O)C2]

A dry microwave vial was charged with $K_3PO_4$ (307 mg, 1.446 mmol), (S)-1-(4-chlorophenyl)-7-isopropoxy-6-methoxy-1,2-dihydroisoquinolin-3(4H)-one (250 mg, 0.723 mmol), 1-(4-bromo-phenyl)-1-(1-oxo-hexahydro-1-thiopyran-4-yl)-ethanol (252 mg, 0.795 mmol) and dioxane (4 ml). The reaction mixture was degassed with argon, then trans-1,2-diaminocyclohexane (16.5 mg, 0.017 ml, 0.145 mmol) and copper(I)iodide (27.5 mg, 0.145 mmol) were added. The vial was sealed and heated for 6 hrs to 97° C. in an oil bath. Further trans-1,2-diaminocyclohexane (16.5 mg, 0.017 ml, 0.145 mmol) and copper(I)iodide (27.5 mg, 0.145 mmol) were added and the reaction was continued to stir at 97° C. for 24 hrs. The reaction mixture was filtered through a pad of hyflo, the residue was washed with dioxane and the filtrate concentrated to dryness. The crude product was purified by silica gel column chromatography (eluting with a gradient of DCM: DCM/EtOH (9/1)=95:05 to 20:80) yielding the title example (157 mg, 0.256 mmol, 35%) as a yellow foam.

HPLC: $^B t_{Ret}$=6.80; HPLC/MS: $^A t_{Ret}$=0.99 min: LC-MS: m/z 599.3 $[M+NH_3]^+$.

1H-NMR (600 MHz, DMSO-$d_6$): δ (1/1 diastereomeric mixture, single isomer at sulfoxide): 1.20 (d, J=5.85 Hz, 3H), 1.24 (d, J=5.85 Hz, 3H), 1.35-1.46 (m, 4H), 1.56-1.63 (m, 1H), 1.64-1.73 (m, 1H), 1.78-1.91 (m, 2H), 2.44-2.55 (m, 2H), 2.72-2.86 (m, 2H), 3.54-3.64 (m, 1H), 3.72 (s, 3H), 3.84 (dd, J=19.58, 3.03 Hz, 1H), 4.46 (td, J=6.00, 2.52 Hz, 1H), 4.99 (s, 1H), 6.11 (s, 0.5H), 6.12 (s, 0.5H), 6.85 (s, 1H), 7.08-7.16 (m, 3H), 7.32-7.39 (m, 6H).

Intermediate 169.1

1-(4-Bromo-phenyl)-1-(1-oxo-hexahydro-1-thiopyran-4-yl)-ethanol

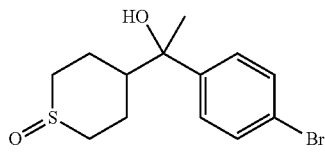 [SMILES: CC(O)(c1ccc(Br)cc1)C1CCS(=O)CC1]

To a solution of 1-bromo-4-iodobenzene (1.52 g, 5.36 mmol) in THF (8.5 ml) at −45° C. to −39° C. was added ethylmagnesium bromide 3M in $Et_2O$ (2.38 ml, 7.15 mmol). The reaction mixture was warmed to −10° C. and stirred for 2 hrs. As not all of the starting material was converted the suspension was cooled to −45° C. to −39° C. and further ethylmagnesium bromide 3M in $Et_2O$ (0.50 ml, 1.50 mmol) was added and stirring was continued for 1 hrs at −10° C. The reaction mixture was cooled to −70° C. and a solution of 1-(1-oxo-hexahydro-1-thiopyran-4-yl)-ethanone (573 mg, 3.58 mmol) in THF (3 ml) was added. After stirring for 10 min at the given temperature the reaction mixture was allowed to warm to RT and stirred for 16 hrs. The beige suspension was cooled with an ice bath and quenched with a solution of aqueous saturated $NH_4Cl$ (10 ml), diluted with ethyl acetate and extracted with ethyl acetate. The organic phases were combined, washed with brine, dried using $Na_2SO_4$, filtered and concentrated in vacuo. The crude product was purified by silica gel column chromatography (eluting with a gradient of DCM:DCM/EtOH (9/1)=100:0 to 60:40) yielding the title intermediate (253 mg, 0.797 mmol, 22%) as a colourless foam.

HPLC: $^B t_{Ret}$=5.73; HPLC/MS: $^A t_{Ret}$=0.75 min: LC-MS: m/z 319.1 $[M+H]^+$.

1H-NMR (600 MHz, DMSO-$d_6$): δ 1.36-1.46 (m, 4H), 1.59-1.74 (m, 2H), 1.76-1.90 (m, 2H), 2.45-2.57 (m, 2H), 2.66-2.87 (m, 2H), 5.08 (s, 1H), 7.36 (d, J=8.53 Hz, 2H), 7.50 (d, J=8.53 Hz, 2H).

Example 170

(S)-1-(4-Chloro-phenyl)-2-{4-[(R)-1-hydroxy-1-(1-oxo-hexahydro-thiopyran-4-yl)-ethyl]-phenyl}-7-isopropoxy-6-methoxy-1,4-dihydro-2H-isoquinolin-3-one

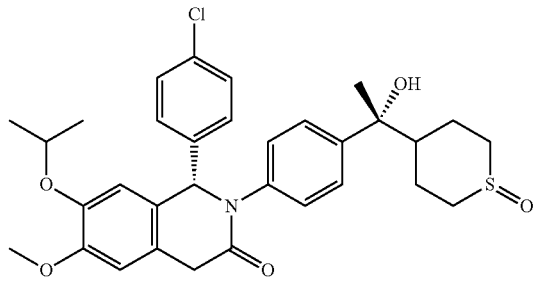 [SMILES: COc1cc2c(cc1OC(C)C)[C@H](c1ccc(Cl)cc1)N(c1ccc([C@](C)(O)C3CCS(=O)CC3)cc1)C(=O)C2]

and

Example 171

(S)-1-(4-Chloro-phenyl)-2-{4-[(S)-1-hydroxy-1-(1-oxo-hexahydro-1-thiopyran-4-yl)-ethyl]-phenyl}-7-isopropoxy-6-methoxy-1,4-dihydro-2H-isoquinolin-3-one

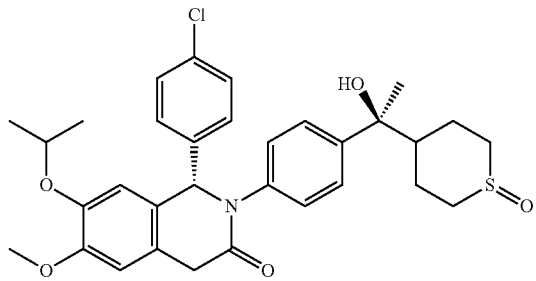 [SMILES: COc1cc2c(cc1OC(C)C)[C@H](c1ccc(Cl)cc1)N(c1ccc([C@@](C)(O)C3CCS(=O)CC3)cc1)C(=O)C2]

The title example 170 and example 171 were obtained by chiral separation of example 169 (121 mg, 0.208 mmol).

Column: ChiralpAK IC (5 um, 2×20 cm); mobile Phase: EtOH/MeOH 60/40; flow rate: 6 ml/min; detection UV: 220 nm Example 170: 13.52 min (30 mg, ee>99%)
Example 171: 12.02 min (29 mg, ee>99%)

Example 172

(S)-1-(4-Chloro-phenyl)-2-{4-[1-(8,8-dioxo-8-thia-bicyclo[3.2.1]oct-3-yl)-1-hydroxy-ethyl]-phenyl}-7-isopropoxy-6-methoxy-1,4-dihydro-2H-isoquinolin-3-one

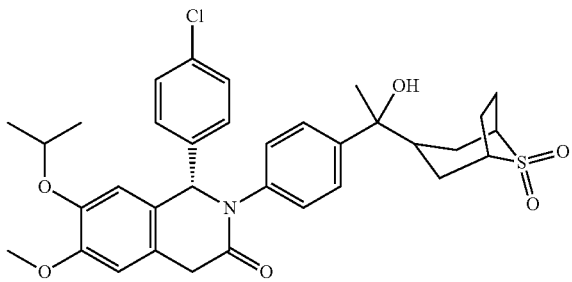 [SMILES: COc1cc2c(cc1OC(C)C)[C@H](c1ccc(Cl)cc1)N(c1ccc(C(C)(O)C3CC4CCC(C3)S4(=O)=O)cc1)C(=O)C2]

A dry microwave vial was charged with $K_3PO_4$ (896 mg, 4.220 mmol), (S)-1-(4-chlorophenyl)-7-isopropoxy-6-methoxy-1,2-dihydroisoquinolin-3(4H)-one (730 mg, 2.111 mmol), 1-(4-bromo-phenyl)-1-(8,8-dioxo-8-thia-bicyclo[3.2.1]oct-3-yl)-ethanol (910 mg, 2.530 mmol) and dioxane (6.5 ml). The reaction mixture was degassed with argon, then trans-1,2-diaminocyclohexane (241 mg, 0.254 ml, 2.111 mmol) and copper(I)iodide (402 mg, 2.111 mmol) were added. The vial was sealed and heated for 17 hrs to 97° C. in an oil bath. The reaction mixture was filtered through a pad of hyflo, the residue was washed with dioxane and the filtrate concentrated to dryness. The crude product was purified by silica gel column chromatography (eluting with a gradient of TBME:DCM/EtOH (9/1)=95:05 to 55:45) yielding the title example (786 mg, 1.259 mmol, 60%) as a yellow foam.

HPLC: $^B t_{Ret}$=7.01; HPLC/MS: $^A t_{Ret}$=1.09 min: LC-MS: m/z 641.3 [M+NH$_3$]$^+$.

1H-NMR (600 MHz, DMSO-d$_6$): δ 1.18-1.28 (m, 7H), 1.39 (d, J=1.51 Hz, 3H), 1.70-1.80 (m, 1H), 1.83-1.91 (m, 1H), 1.94-2.13 (m, 5H), 2.16-2.25 (m, 1H), 2.96 (m, J=4.70 Hz, 1H), 3.06-3.10 (m, 1H), 3.61 (dd, J=19.76, 3.01 Hz, 1H), 3.74 (s, 3H), 3.85 (dd, J=19.67, 11.20 Hz, 1H), 4.47 (dq, J=12.42, 6.21 Hz, 1H), 5.04 (d, J=2.07 Hz, 1H), 6.10 (s, 0.5H), 6.12 (s, 0.5H), 6.87 (s, 1H), 7.08-7.16 (m, 3H), 7.29-7.45 (m, 6H).

Intermediate 172.1

1-(4-Bromo-phenyl)-1-(8,8-dioxo-8-thia-bicyclo[3.2.1]oct-3-yl)-ethanol

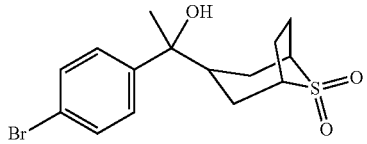 [SMILES: CC(O)(c1ccc(Br)cc1)C1CC2CCC(C1)S2(=O)=O]

To a solution of (4-bromo-phenyl)-(8,8-dioxo-8-thia-bicyclo[3.2.1]oct-3-yl)-methanone (885 mg, 2.58 mmol) in THF (7 ml) at −10° C. to −8° C. was added methylmagnesium bromide 1.4M in toluene/THF 3/1 (3.68 ml, 5.16 mmol). The reaction mixture was stirred for 30 min. The solution was cooled with an ice bath and quenched with a solution of aqueous saturated NH$_4$Cl and water 1/1 (7.5 ml), diluted and extracted with ethyl acetate. The organic phases were combined, washed with brine, dried using Na$_2$SO$_4$, filtered and concentrated in vacuo. The crude product (940 mg, 2.54 mmol, 97%) was used in the next step without further purification.

HPLC: $^B t_{Ret}$=6.30; HPLC/MS: $^A t_{Ret}$=0.92 min: LC-MS: m/z 376.1 [M+H]$^+$.

1H-NMR (600 MHz, DMSO-d$_6$): δ 1.17-1.24 (m, 1H), 1.38 (s, 3H), 1.69-1.79 (m, 1H), 1.82-1.90 (m, 1H), 1.92-2.10 (m, 5H), 2.11-2.21 (m, 1H), 2.87-2.94 (m, 1H), 3.01-3.08 (m, 1H), 5.08 (s, 1H), 7.36-7.41 (m, 2H), 7.45-7.49 (m, 2H).

Intermediate 172.2

(4-Bromo-phenyl)-(8,8-dioxo-8-thia-bicyclo[3.2.1]oct-3-yl)-methanone

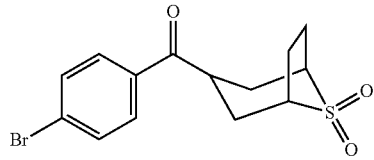 [SMILES: O=C(c1ccc(Br)cc1)C1CC2CCC(C1)S2(=O)=O]

A solution of 3-chloroperoxybenzoic acid (2.079 g, 7.23 mmol) in ethyl acetate (10 ml) was added dropwise to a solution of (4-bromo-phenyl)-(8-thia-bicyclo[3.2.1]oct-3-yl)-methanone in ethyl acetate (7 ml) at RT and the reaction mixture was continued to stir for 4 hrs. The suspension was filtered and the residue was washed with ethyl acetate and dried in vacuo to yield the title intermediate (892 mg, 2.57 mmol, 89%) as a colourless solid.

HPLC: $^B t_{Ret}$=6.49;

1H-NMR (600 MHz, DMSO-d$_6$): δ 2.02-2.08 (m, 2H), 2.13-2.20 (m, 2H), 2.23-2.35 (m, 4H), 3.22 (br. s., 2H), 3.84-3.92 (m, 1H), 7.77 (d, J=8.47 Hz, 2H), 7.98 (d, J=8.47 Hz, 2H).

Intermediate 172.3

(4-Bromo-phenyl)-(8-thia-bicyclo[3.2.1]oct-3-yl)methanone

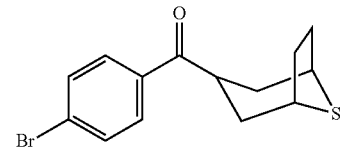 [SMILES: O=C(c1ccc(Br)cc1)C1CC2CCC(C1)S2]

To a solution of (4-bromo-phenyl)-(8-thia-bicyclo[3.2.1]oct-3-yl)-methanol (1.99 g, 6.35 mmol) in DCM (100 ml) was added a total of manganese dioxide (8.28 g, 95.2 mmol) at RT and the reaction mixture was stirred for 24 hrs. The suspension was filtered and the residue was washed with DCM, dried in vacuo to yield the title intermediate (1.87 g, 5.83 mmol, 92%) as a colourless solid.

HPLC: $^B t_{Ret}$=7.88; HPLC/MS: $^A t_{Ret}$=1.28 min: LC-MS: m/z 313.1 [M+H]$^+$.

1H-NMR (600 MHz, DMSO-d$_6$): δ 1.81-1.88 (m, 2H), 1.91-1.97 (m, 2H), 2.00-2.05 (m, 2H), 2.23-2.29 (m, 2H), 3.64 (br. s., 2H), 3.81-3.89 (m, 1H), 7.74 (d, J=8.47 Hz, 2H), 7.91 (d, J=8.47 Hz, 2H).

Intermediate 172.4

(4-Bromo-phenyl)-(8-thia-bicyclo[3.2.1]oct-3-yl)-methanol

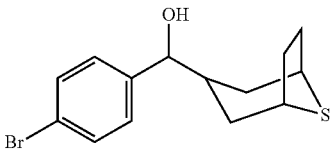 [SMILES: OC(c1ccc(Br)cc1)C1CC2CCC(C1)S2]

To a solution of 1-bromo-4-iodobenzene (1.49 g, 5.28 mmol) in THF (13.5 ml) at −30° C. to −25° C. was added isopropylmagnesium chloride 2M in THF (2.88 ml, 5.76 mmol). The reaction mixture was stirred at −30 to −20° C. for 2 hrs. The reaction mixture was allowed to warm to −3° C. and a solution of 8-thia-bicyclo[3.2.1]octane-3-carbaldehyde (750 mg, 4.80 mmol) in THF was added and the solution was stirred for 1 hr while cooled in an ice bath. The reaction mixture was quenched at 0° C. with a solution of aqueous saturated NH$_4$Cl and water 2/1 (15 ml), diluted with ethyl acetate and extracted with ethyl acetate. The organic phases were combined, washed with brine, dried using Na$_2$SO$_4$, filtered and concentrated in vacuo. The crude product was crystallized and washed with diisopropyl ether/hexanes and the remaining mother liquor was purified by silica gel column chromatography (eluting with a gradient of hexanes:ethyl acetate 100:0 to 85:15) yielding the title intermediate (1.02 g, 3.26 mmol, 68%) as a beige solid.

HPLC: $^B t_{Ret}$=7.42; HPLC/MS: $^A t_{Ret}$=1.18 min: LC-MS: m/z 357.1 [M−H+HCOOH]$^−$.

1H-NMR (600 MHz, DMSO-d$_6$): δ 1.34-1.42 (m, 1H), 1.47-1.56 (m, 2H), 1.75-1.93 (m, 6H), 3.46 (s, 1H), 3.51 (s, 1H), 4.20 (t, J=5.28 Hz, 1H), 5.20 (d, J=4.30 Hz, 1H), 7.21 (d, J=8.21 Hz, 2H), 7.46 (d, J=8.21 Hz, 2H).

Intermediate 172.5

8-Thia-bicyclo[3.2.1]octane-3-carbaldehyde

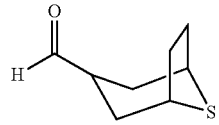

To a solution of (1R,2's,5S)-8-thiaspiro[bicyclo[3.2.1]octane-3,2'-oxirane] (3.069 g, 19.64 mmol) in THF (50 ml) at 0° C. was added borontrifluoride etherate (1.394 g, 1.25 ml, 9.82 mmol) drop wise and the reaction mixture was stirred at 0° C. for 3 hrs. The reaction mixture was quenched with a saturated aqueous solution of NaHCO$_3$, ethyl acetate was added and extracted with ethyl acetate. The organic phases were combined, washed with brine, dried using Na$_2$SO$_4$, filtered and concentrated in vacuo. The remaining oil was dissolved in THF/MeOH 1/1 (28 ml), DBU (0.150 g, 0.15 ml, 0.892 mmol) was added and the solution was stirred at RT for 1 hr. Ethyl acetate (150 ml) and a solution of 0.5 M HCl (50 ml) were added, the reaction mixture was extracted with ethyl acetate, combined organic phases were washed with a solution of NaHCO$_3$ (2%) and brine, dried using Na$_2$SO$_4$ and concentrated in vacuo. The crude product was purified by silica gel column chromatography (eluting with a gradient of hexanes:ethyl acetate 100:0 to 90:10) yielding the title intermediate (2.00 g, 12.80 mmol, 65%) as a colourless oil.

HPLC: $^{B}t_{Ret}$=5.66; HPLC/MS: $^{A}t_{Ret}$=0.82 min: LC-MS: m/z 157.1 [M+H]$^{+}$.

1H-NMR (400 MHz, DMSO-d$_6$): δ 1.60-1.73 (m, 2H), 1.87-2.08 (m, 6H), 2.65-2.80 (m, 1H), 3.62 (br. s., 2H), 9.46 (s, 1H).

Intermediate 172.6

(1R,2's,5S)-8-thiaspiro[bicyclo[3.2.1]octane-3,2'-oxirane]

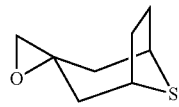

Trimethylsulfoxonium iodide (9.90 g, 45.0 mmol) was added to a solution of potassium tert-butoxide (5.32 g, 45.0 mmol) in THF (110 ml), heated to reflux and stirred for 3 hrs under an atmosphere of nitrogen. A solution of 8-thia-bicyclo[3.2.1]octan-3-one (4.27 g, 30.00 mmol) in THF (30 ml) was added in one portion and the mixture was continued to reflux for 2 hrs. The reaction mixture was cooled to RT, diluted with toluene and water. The water layer was separated and extracted with toluene. The combined organic phases were washed with water, brine, dried using Na$_2$SO$_4$, filtered and evaporated to dryness. The crude product was purified by silica gel column chromatography (eluting with a gradient of hexanes:ethyl acetate 100:0 to 90:10) yielding the title intermediate (3.099 g, 19.83 mmol, 66.1%) as a colourless oil.

HPLC: $^{B}t_{Ret}$=6.01; HPLC/MS: $^{A}t_{Ret}$=0.82 min: LC-MS: m/z 157.11 [M+H]$^{+}$.

1H-NMR (600 MHz, DMSO-d$_6$): δ 1.55 (dd, J=14.78, 4.05 Hz, 2H), 2.06-2.16 (m, 2H), 2.41 (s, 2H), 2.43-2.47 (m, 2H), 2.53 (d, J=14.49 Hz, 2H), 3.69 (br. s., 2H).

Example 173

(S)-1-(4-Chloro-phenyl)-2-{4-[(R)-1-(8,8-dioxo-8-thia-bicyclo[3.2.1]oct-3-yl)-1-hydroxy-ethyl]-phenyl}-7-isopropoxy-6-methoxy-1,4-dihydro-2H-isoquinolin-3-one

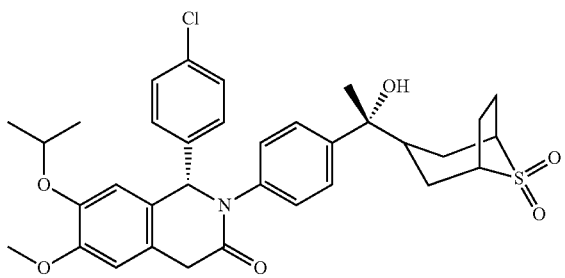 [SMILES: COc1cc2c(cc1OC(C)C)[C@H](c1ccc(Cl)cc1)N(c1ccc([C@](C)(O)C3CC4CCC(C3)S4(=O)=O)cc1)C(=O)C2]

and

Example 174

(S)-1-(4-Chloro-phenyl)-2-{4-[(S)-1-(8,8-dioxo-8-thia-bicyclo[3.2.1]oct-3-yl)-1-hydroxy-ethyl]-phenyl}-7-isopropoxy-6-methoxy-1,4-dihydro-2H-isoquinolin-3-one

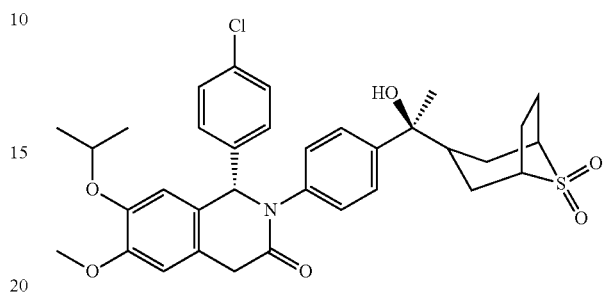

The title example 173 and example 174 were obtained by chiral separation of example 172 (400 mg, 0.208 mmol).

Column: ChiralpAK IC (20 um, 76.5×375 mm); mobile phase: n-Heptane/CH$_2$Cl$_2$/EtOH 30/60/10; flow rate: 70-200 ml/min; detection UV: 225 nm Example 173: 71.75 min (193 mg, ee>99%)
Example 174: 53.37 min (193 mg, ee>99%)

Example 175

(S)-1-(4-Chloro-phenyl)-2-{4-[1-(9,9-dioxo-9-thia-bicyclo[3.3.1]non-3-yl)-1-hydroxy-ethyl]-phenyl}-7-isopropoxy-6-methoxy-1,4-dihydro-2H-isoquinolin-3-one

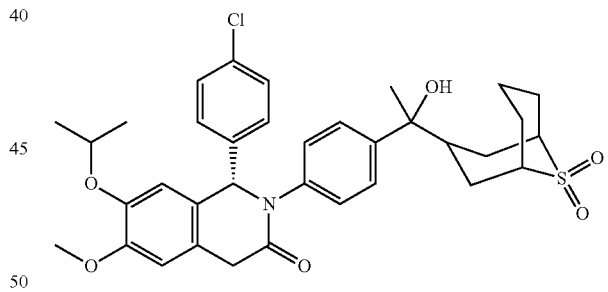

A dry microwave vial was charged with K$_3$PO$_4$ (356 mg, 1.677 mmol), (S)-1-(4-chlorophenyl)-7-isopropoxy-6-methoxy-1,2-dihydroisoquinolin-3(4H)-one (290 mg, 0.835 mmol), 1-(4-bromo-phenyl)-1-(9,9-dioxo-9-thia-bicyclo[3.3.1]non-3-yl)-ethanol (376 mg, 1.006 mmol) and dioxane (2.6 ml). The reaction mixture was degassed with argon, then trans-1,2-diaminocyclohexane (96 mg, 0.101 ml, 0.839 mmol) and copper(I)iodide (160 mg, 0.839 mmol) were added. The vial was sealed and heated for 17 hrs to 97° C. in an oil bath. The reaction mixture was diluted with dioxane, filtered through a pad of hyflo, the residue was washed with dioxane and the filtrate concentrated to dryness. The crude product was purified by reversed phase prep-HPLC (gradient elution, MeCN/water+0.1% TFA). Fractions containing pure material were combined, concentrated and the resulting aqueous mixture was neutralized with a saturated solution of NaHCO₃, followed by extraction with DCM. The organic layer was dried over Na₂SO₄, filtered and evaporated to dryness to yield the title example (222 mg, 0.348 mmol, 42%) as a colourless resin.

HPLC: $^B t_{Ret}$=7.13; HPLC/MS: $^A t_{Ret}$=1.16 min: LC-MS: m/z 655.3 [M+NH₃]⁺.

1H-NMR (600 MHz, DMSO-d₆): δ 1.18-1.28 (m, 6H), 1.31-1.55 (m, 4H), 1.83-2.61 (m, 10H), 2.86 (br. s., 1H), 2.99 (br. s., 1H), 3.62 (d, J=18.26 Hz, 1H), 3.74 (s, 3H), 3.81-3.89 (m, 1H), 4.47 (dq, J=12.38, 6.10 Hz, 1H), 5.03 (s, 1H), 6.11 (s, 0.5H), 6.13 (s, 0.5H), 6.87 (s, 1H), 7.07-7.17 (m, 3H), 7.30-7.45 (m, 6H).

Intermediate 175.1

1-(4-Bromo-phenyl)-1-(9,9-dioxo-9-thia-bicyclo[3.3.1]non-3-yl)-ethanol

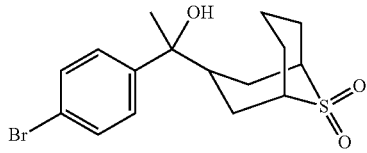 [SMILES: CC(O)(c1ccc(Br)cc1)C1CC2CCCC(C1)S2(=O)=O]

To a solution of (4-Bromo-phenyl)-(9,9-dioxo-9-thia-bicyclo[3.3.1]non-3-yl)-methanone (768 mg, 2.150 mmol) in THF (5.8 ml) at 8° C. to 10° C. was added methylmagnesium bromide 1.4M in toluene/THF 3/1 (3.07 ml, 4.30 mmol). The reaction mixture was stirred for 30 min. The solution was cooled with an ice bath and quenched with a solution of aqueous saturated NH₄Cl and water 1/1, diluted and extracted with ethyl acetate. The organic phases were combined, washed with brine, dried using Na₂SO₄, filtered and concentrated in vacuo. The crude solid product (778 mg, 2.084 mmol, 97%) was used in the next step without further purification.

HPLC: $^B t_{Ret}$=6.50; HPLC/MS: $^A t_{Ret}$=0.98 min: LC-MS: m/z 390.0 [M+NH₃]⁺.

1H-NMR (600 MHz, DMSO-d₆): δ 1.45 (s, 3H), 1.49-1.63 (m, 2H), 1.90-2.16 (m, 4H), 2.23-2.65 (m, 5H), 2.80 (br. s, 1H), 2.93 (br. s, 1H), 4.82 (s, 1H), 7.39-7.44 (m, 2H), 7.46-7.51 (m, 2H).

Intermediate 175.2

(4-Bromo-phenyl)-(9,9-dioxo-9-thia-bicyclo[3.3.1]non-3-yl)-methanone

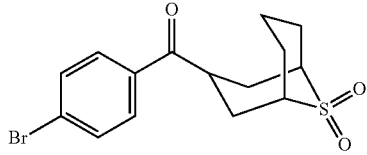 [SMILES: O=C(c1ccc(Br)cc1)C1CC2CCCC(C1)S2(=O)=O]

A solution of 3-Chloroperoxybenzoic acid (1.945 g, 6.76 mmol) in ethyl acetate (10 ml) was added dropwise to a solution of 4-bromo-phenyl)-(9-thia-bicyclo[3.3.1]non-3-yl)-methanone (880 mg, 2.71 mmol) in ethyl acetate (7 ml) at RT and the reaction mixture was continued to stir for 4 hrs. The suspension was filtered, the residue was washed with ethyl acetate and dried in vacuo to yield the title intermediate (770 mg, 2.026 mmol, 94%) as a colourless solid.

HPLC: $^B t_{Ret}$=6.65;

1H-NMR (600 MHz, DMSO-d₆): δ 1.61-1.70 (m, 1H), 2.17-2.29 (m, 4H), 2.33-2.55 (m, 5H), 3.11 (br. s., 2H), 4.23-4.32 (m, 1H), 7.78 (d, J=8.47 Hz, 2H), 7.94 (d, J=8.66 Hz, 2H).

Intermediate 175.3

(4-Bromo-phenyl)-(9-thia-bicyclo[3.3.1]non-3-yl)-methanone

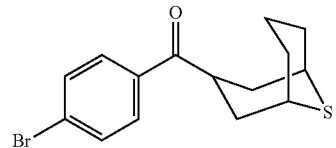 [SMILES: O=C(c1ccc(Br)cc1)C1CC2CCCC(C1)S2]

To a solution of (4-Bromo-phenyl)-(9-thia-bicyclo[3.3.1]non-3-yl)-methanol (1.10 g, 3.38 mmol) in DCM (53 ml) was added a total of manganese dioxide (4.88 g, 56.131 mmol) at RT and the reaction mixture was stirred for 24 hrs. The suspension was filtered through a pad of hyflo and the residue was washed with DCM, dried in vacuo to yield the title intermediate (880 mg, 2.57 mmol, 95%) as a beige solid.

HPLC: $^B t_{Ret}$=8.14; HPLC/MS: $^A t_{Ret}$=1.37 min: LC-MS: m/z 327.1 [M+H]⁺.

1H-NMR (600 MHz, DMSO-d₆): δ 1.70-1.81 (m, 1H), 1.98-2.15 (m, 8H), 2.19-2.34 (m, 1H), 3.00 (br. s., 2H), 4.27-4.38 (m, 1H), 7.71-7.76 (m, 2H), 7.85-7.90 (m, 2H).

Intermediate 175.4

(4-Bromo-phenyl)-(9-thia-bicyclo[3.3.1]non-3-yl)-methanol

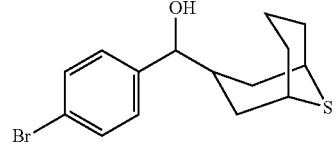 [SMILES: OC(c1ccc(Br)cc1)C1CC2CCCC(C1)S2]

To a solution of 1-bromo-4-iodobenzene (1.462 g, 5.17 mmol) in THF (13 ml) at −30° C. to −25° C. was added isopropylmagnesium chloride 2M in THF (2.82 ml, 5.64 mmol). The reaction mixture was stirred at −30 to −20° C. for 2 hrs, allowed to warm to −3° C. and 9-thia-bicyclo[3.3.1]nonane-3-carbaldehyde (800 mg, 4.70 mmol) was added, the syringe was rinsed with THF (1 ml) and the solution was stirred for 1.5 hrs while cooled in an ice bath. The reaction mixture was quenched at 0° C. with a solution of aqueous saturated NH₄Cl and water 2/1 (15 ml), diluted with ethyl acetate and extracted with ethyl acetate. The organic phases were combined, washed with brine, dried using Na₂SO₄, filtered and concentrated in vacuo. The crude product was purified by silica gel column chromatography (eluting with a gradient of hexanes:MTBE 98:02 to 70:30) yielding the title intermediate (1.11 g, 2.88 mmol, 61%) as a colourless resin.

HPLC: $^B t_{Ret}$=7.67; HPLC/MS: $^A t_{Ret}$=1.27 min: LC-MS: m/z 327.2 [M+H]⁺.

1H-NMR (600 MHz, DMSO-d$_6$): δ 1.53-1.59 (m, 1H), 1.61-1.68 (m, 1H), 1.75-1.89 (m, 4H), 1.94-2.09 (m, 4H), 2.43-2.52 (m, 1H), 2.89 (br. s., 1H), 2.95 (br. s., 1H), 4.15 (t, J=5.08 Hz, 1H), 5.30 (d, J=4.71 Hz, 1H), 7.28 (d, J=8.28 Hz, 2H), 7.51 (d, J=8.47 Hz, 2H).

Intermediate 175.5

9-Thia-bicyclo[3.3.1]nonane-3-carbaldehyde

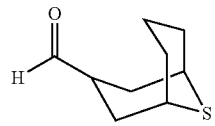

To a solution of 3-Methoxymethylene-9-thia-bicyclo[3.3.1]nonane (2.50 g, 13.56 mmol) in THF (35 ml) were added water (7 ml) and a 4M solution of HCl (6.78 ml, 27.10 mmol) and the reaction mixture was stirred for 16 hrs at 55° C. The reaction mixture was quenched with a saturated aqueous solution of NaHCO$_3$, ethyl acetate was added and extracted with ethyl acetate. The organic phases were combined, washed with brine, dried using Na$_2$SO$_4$, filtered and concentrated in vacuo. The remaining oil was dissolved in THF/MeOH 1/1 (60 ml), DBU (0.146 g, 0.14 ml, 0.957 mmol) was added and the solution was stirred at RT for 1 hr. Ethyl acetate (150 ml), the reaction mixture was neutralized using a solution of 0.5 M HCl and extracted with ethyl acetate. The combined organic phases were washed with brine, dried using Na$_2$SO$_4$ and concentrated in vacuo. The crude product was purified by silica gel column chromatography (eluting with a gradient of hexanes:ethyl acetate 100:0 to 75:25) yielding the title intermediate (2.21 g, 12.33 mmol, 64%) as a colourless oil.

HPLC: $^B$t$_{Ret}$=6.09; HPLC/MS: $^A$t$_{Ret}$=0.95 min: LC-MS: m/z 171.1 [M+H]$^+$.

1H-NMR (400 MHz, DMSO-d$_6$): δ 1.60-1.71 (m, 1H), 1.88-2.18 (m, 9H), 3.00-3.16 (m, 3H), 9.52 (d, J=0.63 Hz, 1H).

Intermediate 175.6

3-Methoxymethylene-9-thia-bicyclo[3.3.1]nonane

A solution of sodium bis(trimethylsilyl)amide 1M in THF (37.9 ml, 37.9 mmol) was added dropwise to a suspension of (methoxymethyl)triphenylphosphonium chloride (13.40 g, 37.9 mmol) in THF (60 ml) at −10° C., followed by the addition of 9-thia-bicyclo[3.3.1]nonan-3-one (3.95 g, 25.3 mmol) at −10° C. The suspension was allowed to warm to Rt and stirring was continued for 16 hrs.

The reaction mixture was cooled to 0° C. and quenched with a saturated solution of NH$_4$Cl and water, diluted with ethyl acetate and extracted with ethyl acetate. The combined organic phases were washed with brine, dried using Na$_2$SO$_4$, filtered and evaporated to dryness. The crude product was purified by silica gel column chromatography (eluting with a gradient of hexanes:DCM 100:0 to 75:25) yielding the title intermediate (3.50 g, 18.99 mmol, 75%) as a colourless oil.

HPLC: $^B$t$_{Ret}$=7.48;

1H-NMR (400 MHz, DMSO-d$_6$): δ 1.43 (ddt, J=14.03, 5.33, 2.83, 2.83 Hz, 1H), 1.84-2.06 (m, 4H), 2.27-2.46 (m, 3H), 2.66 (dd, J=14.47, 1.95 Hz, 1H), 2.89 (br. s., 2H), 2.92-2.99 (m, 1H), 3.48 (d, J=0.78 Hz, 3H), 5.84 (m, 1H).

Example 176

(S)-1-(4-Chloro-phenyl)-2-{4-[(R)-1-(9,9-dioxo-9-thia-bicyclo[3.3.1]non-3-yl)-1-hydroxy-ethyl]-phenyl}-7-isopropoxy-6-methoxy-1,4-dihydro-2H-isoquinolin-3-one

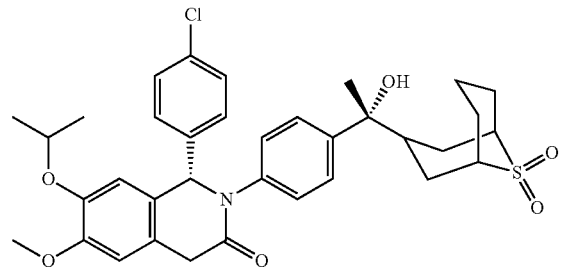 [SMILES: COc1cc2c(cc1OC(C)C)[C@H](c1ccc(Cl)cc1)N(c1ccc([C@](C)(O)C3CC4CCCC(C3)S4(=O)=O)cc1)C(=O)C2]

and

Example 177

(S)-1-(4-Chloro-phenyl)-2-{4-[(S)-1-(9,9-dioxo-9-thia-bicyclo[3.3.1]non-3-yl)-1-hydroxy-ethyl]-phenyl}-7-isopropoxy-6-methoxy-1,4-dihydro-2H-isoquinolin-3-one

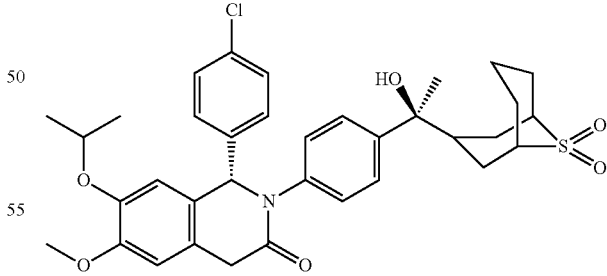

The title example 176 and example 177 were obtained by chiral separation of example 175 (193 mg, 0.302 mmol).

Column: Chiralcel AS-H (30×250 mm); mobile phase: scCO$_2$/EtOH/2-propylamine 62/38/0.38; flow rate: 80 ml/min; detection UV: 215 nm Example 176: 9.19 min (98 mg, ee=98.9%)

Example 177: 6.75 min (91 mg, ee>99.5%)

Example 178

(S)-1-(4-Chloro-phenyl)-2-{4-[1-hydroxy-1-(2-oxa-bicyclo[2.2.2]oct-4-yl)-ethyl]-phenyl}-7-isopropoxy-6-methoxy-1,4-dihydro-2H-isoquinolin-3-one

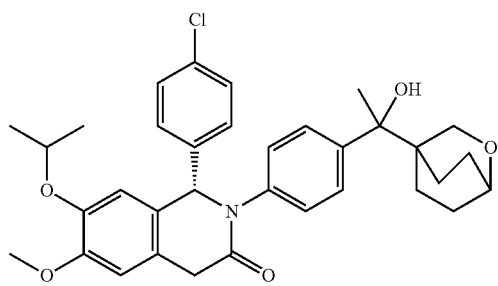 [SMILES: COc1cc2c(cc1OC(C)C)[C@H](c1ccc(Cl)cc1)N(c1ccc(C(C)(O)C34CCC(CC3)OC4)cc1)C(=O)C2]

A dry microwave vial was charged with $K_3PO_4$ (255 mg, 1.203 mmol), (S)-1-(4-chlorophenyl)-7-isopropoxy-6-methoxy-1,2-dihydroisoquinolin-3(4H)-one (208 mg, 0.601 mmol), 1-(4-bromo-phenyl)-1-(2-oxa-bicyclo[2.2.2]oct-4-yl)ethanol (225 mg, 0.722 mmol) and dioxane (1.9 ml). The reaction mixture was degassed with argon, then trans-1,2-diaminocyclohexane (69 mg, 0.072 ml, 0.601 mmol) and copper(I)iodide (115 mg, 0.601 mmol) were added. The vial was sealed and heated for 17 hrs to 97° C. in an oil bath. The reaction mixture was diluted with dioxane, filtered through a pad of hyflo, the residue was washed with dioxane and the filtrate concentrated to dryness. The crude product was purified by silica gel column chromatography (eluting with a gradient of DCM:DCM/EtOH (9/1) 95:05 to 50:50) yielding the title example (223 mg, 0.387 mmol, 64%) as a beige resin.

HPLC: $^Bt_{Ret}$=7.59; HPLC/MS: $^At_{Ret}$=1.21 min: LC-MS: m/z 576.3 [M+H]⁺.

1H-NMR (600 MHz, DMSO-d₆): δ 1.19 (d, J=6.02 Hz, 3H), 1.23 (d, J=6.02 Hz, 3H), 1.27-1.56 (m, 8H), 1.62-1.79 (m, 3H), 3.48-3.56 (m, 2H), 3.59 (d, J=19.76 Hz, 1H), 3.65 (dd, J=8.56, 2.54 Hz, 1H), 3.71 (s, 3H), 3.84 (dd, J=19.67, 4.05 Hz, 1H), 4.45 (quind, J=6.07, 6.07, 6.07, 6.07, 3.58 Hz, 1H), 4.85 (d, J=0.94 Hz, 1H), 6.09 (s, 0.5H), 6.10 (s, 0.5H), 6.84 (s, 1H), 7.08 (dd, J=8.66, 4.52 Hz, 2H), 7.11 (d, J=5.83 Hz, 1H), 7.29 (d, J=8.47 Hz, 2H), 7.35 (s, 4H).

Intermediate 178.1

1-(4-Bromo-phenyl)-1-(2-oxa-bicyclo[2.2.2]oct-4-yl)ethanol

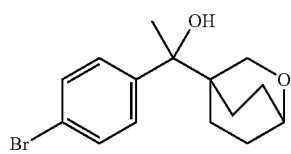 [SMILES: CC(O)(c1ccc(Br)cc1)C12CCC(CC1)OC2]

To a solution of (4-Bromo-phenyl)-(2-oxa-bicyclo[2.2.2]oct-4-yl)-methanone (218 mg, 0.739 mmol) in THF (2 ml) at 8° C. to 10° C. was added methylmagnesium bromide 1.4M in toluene/THF 3/1 (1.06 ml, 1.48 mmol). The reaction mixture was stirred at 10° C. for 1 hr. The solution was cooled with an ice bath and quenched with a saturated aqueous solution of NH₄Cl and water 1/1, diluted and extracted with ethyl acetate. The organic phases were combined, washed with brine, dried using Na₂SO₄, filtered and concentrated in vacuo. The crude solid product (227 mg, 0.729 mmol, 99%) was used in the next step without further purification.

HPLC: $^Bt_{Ret}$=7.04; HPLC/MS: $^At_{Ret}$=1.08 min: LC-MS: m/z 328.1 [M+NH₃]⁺.

1H-NMR (600 MHz, DMSO-d₆): δ 1.32 (tt, J=11.90, 3.50 Hz, 1H), 1.35-1.42 (m, 5H), 1.42-1.48 (m, 1H), 1.52 (tt, J=11.62, 3.72 Hz, 1H), 1.62-1.78 (m, 3H), 3.50-3.57 (m, 2H), 3.65 (dd, J=8.47, 2.82 Hz, 1H), 4.94 (s, 1H), 7.28 (d, J=8.66 Hz, 2H), 7.46 (d, J=8.66 Hz, 2H).

Intermediate 178.2

(4-Bromo-phenyl)-(2-oxa-bicyclo[2.2.2]oct-4-yl)methanone

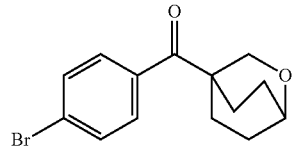 [SMILES: O=C(c1ccc(Br)cc1)C12CCC(CC1)OC2]

To a solution of (4-Bromo-phenyl)-(2-oxa-bicyclo[2.2.2]oct-4-yl)methanol (224 mg, 0.821 mmol) in DCM (13 ml) was added a total of manganese dioxide (1.414 g, 16.264 mmol) at RT and the reaction mixture was stirred for 20 hrs. The suspension was filtered through a pad of hyflo and the residue was washed with DCM, dried in vacuo to yield the title intermediate (220 mg, 0.745 mmol, 91%) as a colourless solid.

HPLC: $^Bt_{Ret}$=7.29;

1H-NMR (600 MHz, DMSO-d₆): δ 1.63-1.70 (m, 2H), 1.83-1.96 (m, 4H), 2.07-2.14 (m, 2H), 3.74-3.77 (m, 1H), 3.90 (s, 2H), 7.67 (s, 4H).

Intermediate 178.3

(4-Bromo-phenyl)-(2-oxa-bicyclo[2.2.2]oct-4-yl)methanol

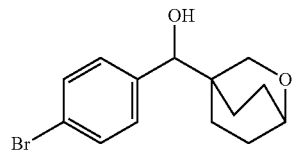

To a solution of 1-bromo-4-iodobenzene (0.777 g, 2.75 mmol) in THF (6.5 ml) at −30° C. to −25° C. was added isopropylmagnesium chloride 2M in THF (1.50 ml, 3.00 mmol). The reaction mixture was stirred at −25° C. for 2 hrs, allowed to warm to 4° C., 2-oxabicyclo[2.2.2]octane-4-carboxaldehyde (350 mg, 2.497 mmol) was added, the syringe was rinsed with THF (1 ml) and the mixture was stirred for 1.5 hrs while cooled in an ice bath. The reaction mixture was quenched at 0° C. with an aqueous saturated solution of NH₄Cl and water 2/1 (7.5 ml), diluted with ethyl acetate and extracted with ethyl acetate. The organic phases were combined, washed with brine, dried using Na₂SO₄, filtered and concentrated in vacuo. The crude product was crystallized with DCM and the remaining mother liqueur was purified by silica gel column chromatography (eluting with a gradient of hexanes:MTBE 100:0 to 0:100) yielding the title intermediate (246 mg, 0.828 mmol, 33%) as a colourless solid.

HPLC: $^B t_{Ret}$=6.82; HPLC/MS: $^A t_{Ret}$=1.02 min: LC-MS: m/z 314.1 [M+NH$_3$]$^+$.

1H-NMR (600 MHz, DMSO-d$_6$): δ 1.17-1.24 (m, 1H), 1.31-1.39 (m, 1H), 1.40-1.48 (m, 2H), 1.50-1.60 (m, 2H), 1.76 (td, J=10.92, 3.95 Hz, 2H), 3.46 (dd, J=8.38, 2.92 Hz, 1H), 3.58 (dt, J=3.58, 1.98 Hz, 1H), 3.74 (dd, J=8.38, 2.92 Hz, 1H), 4.18 (d, J=3.95 Hz, 1H), 5.33 (d, J=3.95 Hz, 1H), 7.15 (d, J=8.47 Hz, 2H), 7.45-7.50 (m, 2H).

Example 179

(S)-3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carboxylic acid tert-butyl ester

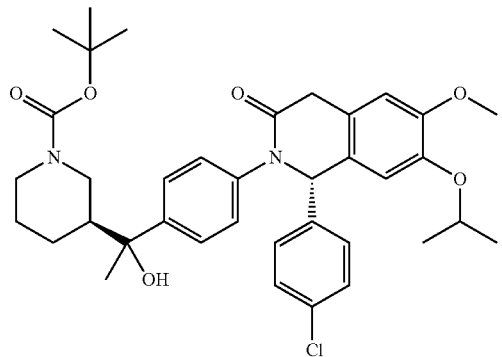 [SMILES: COc1cc2c(cc1OC(C)C)[C@H](c1ccc(Cl)cc1)N(c1ccc(C(C)(O)[C@H]3CCCN(C(=O)OC(C)(C)C)C3)cc1)C(=O)C2]

Example 179 was obtained analogously to example 1 except that intermediate 179.1 was used instead of 1-(4-iodophenyl)-1-(3-methoxyphenyl)ethanol (step 1.1).

HPLC: $^A t_{Ret}$=1.32 min; LC-MS: m/z 649.3 [M+H]$^+$

Intermediate 179.1

(S)-3-[1-(4-Bromo-phenyl)-1-hydroxy-ethyl]-piperidine-1-carboxylic acid tert-butyl ester

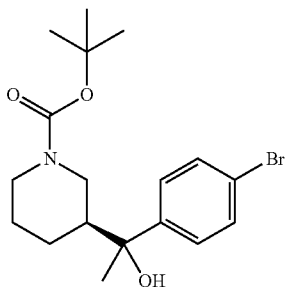 [SMILES: CC(C)(C)OC(=O)N1CCC[C@H](C(C)(O)c2ccc(Br)cc2)C1]

Intermediate 179.1 was synthesized according the general synthesis scheme B. (S)-3-Acetyl-piperidine-1-carboxylic acid tert-butyl ester was obtained following the procedures from intermediate 49.2 and intermediate 49.1 (methyl ketone). The applied Grignard procedure is described in intermediate 29.1.

HPLC: $^A t_{Ret}$=1.23 min; LC-MS: m/z 384.2 [M+H]$^+$

Example 180

(S)-1-(4-Chloro-phenyl)-2-[4-((S)-1-hydroxy-1-piperidin-3-yl-ethyl)-phenyl]-7-isopropoxy-6-methoxy-1,4-dihydro-2H-isoquinolin-3-one

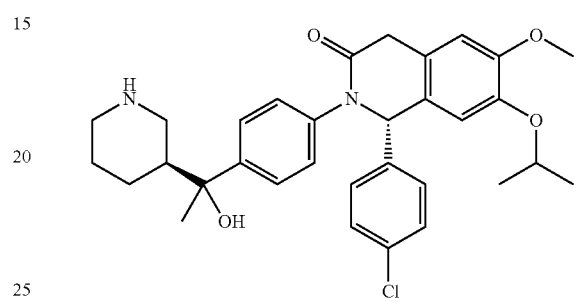

Example 180 was obtained from example 179 by using TFA (5 eq) in dichloromethane. The reaction was stirred 3 hrs at r.t. and after completion diluted with ice/saturated aq. sodium hydrogencarbonate solution and extracted with DCM. The organic phase was separated, dried over sodium sulfate, filtered and concentrated in vacuo to obtain the crude product which was purified by preparative HPLC (reversed phase). Fractions containing the product were pooled and worked up (addition of NaHCO$_3$, removal of acetonitrile followed by extraction with DCM) to obtain the title compound as slightly yellowish solid.

HPLC: $^A t_{Ret}$=0.90 min; LC-MS: m/z 549.4 [M+H]$^+$

Example 181

(S)-1-(4-Chloro-phenyl)-2-{4-[1-hydroxy-1-((S)-1-methyl-piperidin-3-yl)-ethyl]-phenyl}-7-isopropoxy-6-methoxy-1,4-dihydro-2H-isoquinolin-3-one

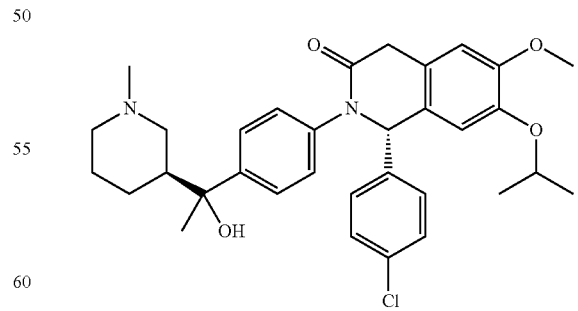

Example 181 was obtained from example 180 analogously to example 69 except that formaldehyde was used instead of 3,3,3-trifluoropropanal.

HPLC: $^A t_{Ret}$=0.92 min; LC-MS: m/z 563.3 [M+H]$^+$

Example 182

(S)-3-(1-{4-[(S)-1-(4-Chloro-phenyl)-7-isopropoxy-6-methoxy-3-oxo-3,4-dihydro-1H-isoquinolin-2-yl]-phenyl}-1-hydroxy-ethyl)-piperidine-1-carbaldehyde

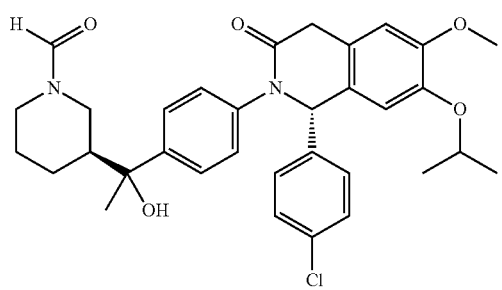 [SMILES: COc1cc2c(cc1OC(C)C)[C@H](c1ccc(Cl)cc1)N(c1ccc(C(C)(O)[C@H]3CCCN(C=O)C3)cc1)C(=O)C2]

Example 182 (white solid) was obtained from example 180 analogously to the procedure used in example 89.

HPLC: $^A t_{Ret}$=1.05 min; LC-MS: m/z 577.4 [M+H]$^+$

Example 183

(S)-1-(4-Chloro-phenyl)-2-{4-[1-hydroxy-1-((S)-1-oxetan-3-yl-piperidin-3-yl)-ethyl]-phenyl}-7-isopropoxy-6-methoxy-1,4-dihydro-2H-isoquinolin-3-one

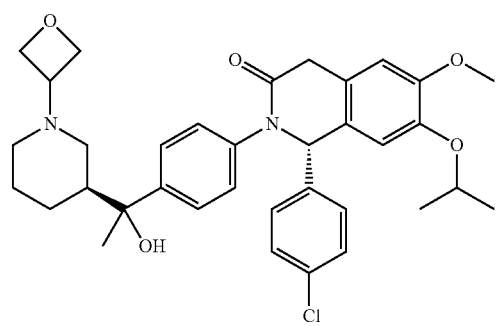 [SMILES: COc1cc2c(cc1OC(C)C)[C@H](c1ccc(Cl)cc1)N(c1ccc(C(C)(O)[C@H]3CCCN(C4COC4)C3)cc1)C(=O)C2]

Example 183 (white solid) was obtained from example 180 analogously to the procedure described in example 96.

HPLC: $^A t_{Ret}$=0.91 min; LC-MS: m/z 605.4 [M+H]$^+$

Another embodiment of the invention provides the compounds shown below, which may be useful as intermediates in the synthesis of compounds of formula (I):

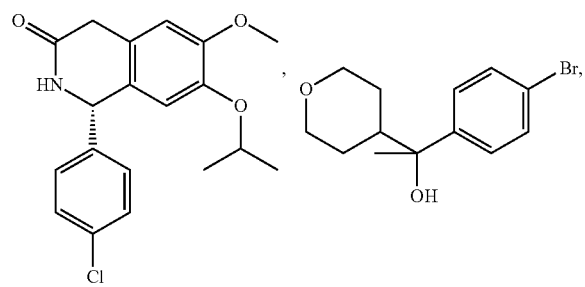

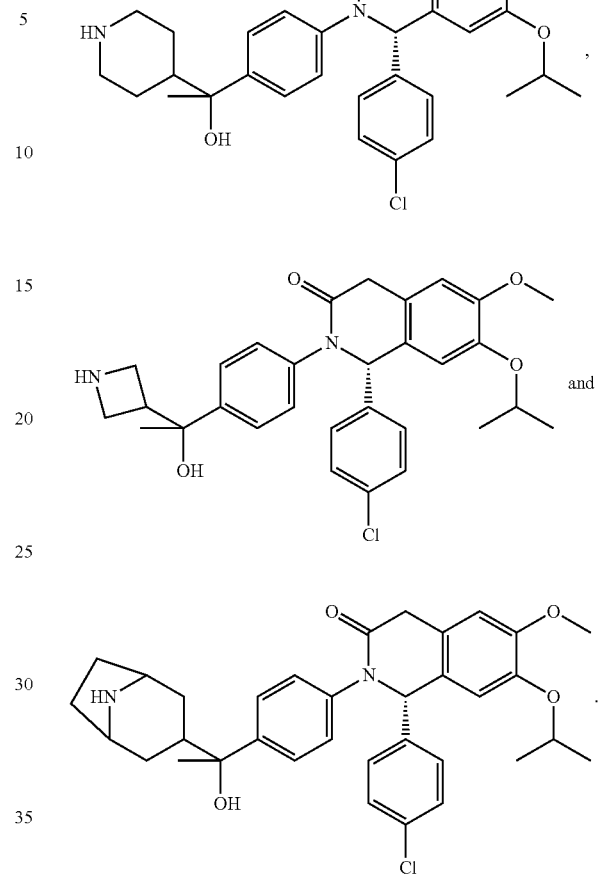

The following additional compounds of formula (I) can be made using the methods described herein, and using methods known to the skilled person:

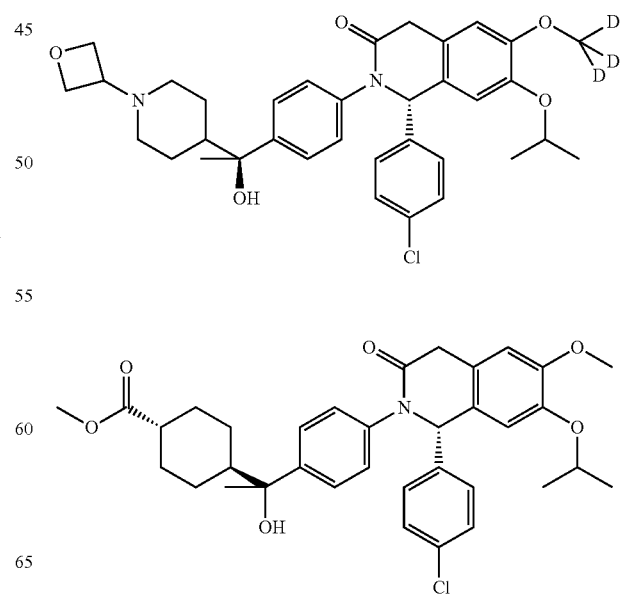

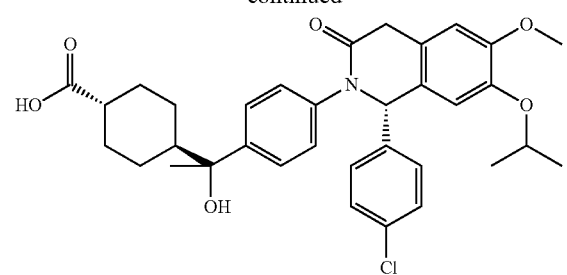
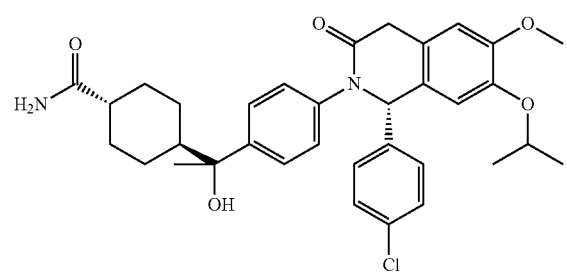
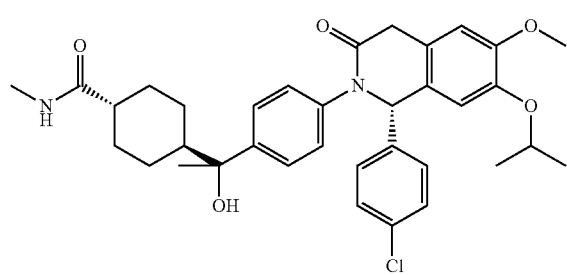
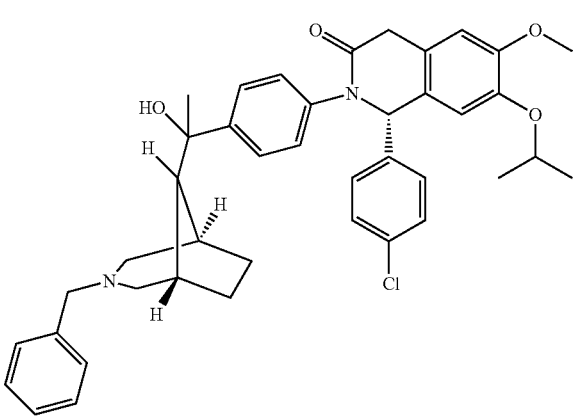
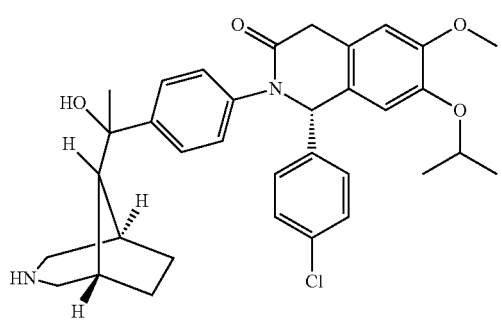
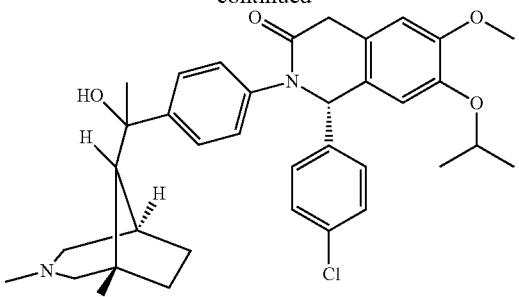
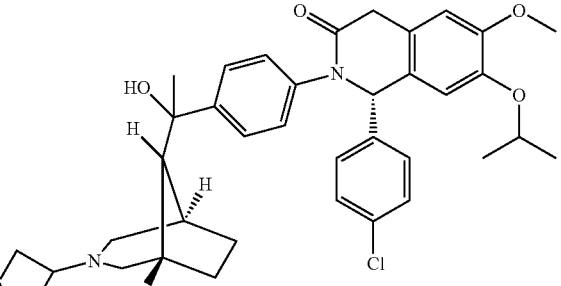
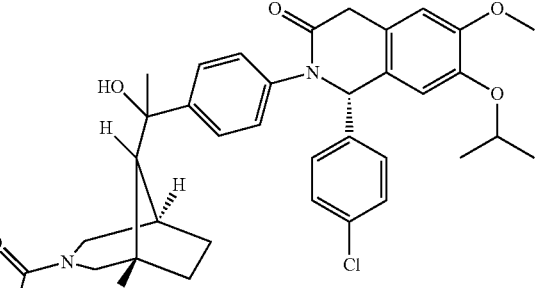
| Example | IC$_{50}$ (μM) of p53-Hdm2 inhibition (TR-FRET) Assay 1 | IC$_{50}$ (nM) of p53-Hdm2 inhibition (TR-FRET) Assay 2 | IC$_{50}$ (μM) of p53-Hdm4 inhibition (TR-FRET) Assay 1 |
|---|---|---|---|
| 1 | 0.0432 | nd | 70.75 |
| 2 | 0.0868 | nd | 87.04 |
| 3 | 0.0267 | nd | 18.91 |
| 4 | 0.0107 | nd | 17.31 |
| 5 | 0.0082 | nd | 10.50 |
| 6 | 0.0343 | nd | 61.82 |
| 7 | 0.1319 | nd | 49.29 |
| 8 | 0.0316 | nd | 61.32 |
| 9 | 0.4594 | nd | nd |
| 10 | 0.2473 | nd | nd |
| 11 | 0.0555 | nd | 51.56 |
| 12 | 0.0195 | nd | 23.85 |
| 13 | 0.0608 | nd | 82.70 |
| 14 | 0.0494 | nd | 53.72 |
| 15 | 0.0404 | nd | 61.09 |
| 16 | 0.0058 | nd | 8.42 |
| 17 | 0.0068 | nd | 7.73 |
| 18 | 0.0368 | nd | 37.20 |
| 19 | 0.0446 | nd | 87.25 |
| 20 | 0.0723 | nd | nd |
| 21 | 0.0071 | nd | 10.44 |
| 22 | 0.0225 | nd | 21.66 |
| 23 | 0.0159 | nd | 24.69 |
| 24 | 0.0544 | nd | 61.32 |
| 25 | 0.0112 | nd | 19.53 |
| 26 | 0.0043 | nd | 8.25 |
| 27 | 0.0458 | nd | 36.28 |

-continued

| Example | IC$_{50}$ (μM) of p53-Hdm2 inhibition (TR-FRET) Assay 1 | IC$_{50}$ (nM) of p53-Hdm2 inhibition (TR-FRET) Assay 2 | IC$_{50}$ (μM) of p53-Hdm4 inhibition (TR-FRET) Assay 1 |
|---|---|---|---|
| 28 | 0.0066 | nd | 9.70 |
| 29 | 0.1433 | nd | 39.66 |
| 30 | 0.0037 | nd | 4.06 |
| 31 | 0.0023 | nd | 2.31 |
| 32 | 0.0023 | nd | 2.19 |
| 33 | 0.2158 | nd | 67.79 |
| 34 | 0.0051 | nd | 5.23 |
| 35 | 0.0025 | nd | 1.48 |
| 36 | 0.0051 | nd | 6.03 |
| 37 | 0.0117 | nd | 13.77 |
| 38 | 0.3834 | nd | 83.98 |
| 39 | 0.0023 | nd | 1.52 |
| 40 | 0.0328 | nd | 31.64 |
| 41 | 0.247 | nd | nd |
| 42 | 0.0091 | nd | 14.91 |
| 43 | 0.0041 | nd | 4.99 |
| 44 | 0.0982 | nd | nd |
| 45 | 0.0089 | nd | 17.43 |
| 46 | 0.4224 | nd | nd |
| 47 | 0.005 | nd | 7.17 |
| 48 | 0.0432 | nd | 44.47 |
| 49 | 0.011 | nd | 8.07 |
| 50 | 0.2463 | nd | 90.19 |
| 51 | 0.0731 | nd | 45.30 |
| 52 | 0.0018 | 1.98 | 2.32 |
| 53 | 0.0017 | nd | 1.62 |
| 54 | 0.1045 | nd | 36.67 |
| 55 | 0.0926 | nd | 26.29 |
| 56 | 0.8111 | nd | nd |
| 57 | 0.2621 | nd | nd |
| 58 | 0.2046 | nd | nd |
| 59 | 0.1668 | nd | nd |
| 60 | 0.1862 | nd | 88.39 |
| 61 | 0.1558 | nd | nd |
| 62 | 0.3416 | nd | 77.00 |
| 63 | 0.0154 | nd | 40.53 |
| 64 | 0.0072 | nd | 10.58 |
| 65 | 0.0423 | nd | 41.16 |
| 66 | 0.0146 | nd | 13.49 |
| 67 | 0.0152 | nd | 16.71 |
| 68 | 0.0152 | nd | 15.02 |
| 69 | 0.0363 | nd | 40.51 |
| 70 | 0.0547 | nd | 60.08 |
| 71 | 0.026 | nd | 30.13 |
| 72 | 0.0234 | nd | 18.44 |
| 73 | 0.0179 | nd | 18.93 |
| 74 | 0.0179 | nd | 17.99 |
| 75 | 0.0043 | nd | 4.95 |
| 76 | 0.0017 | 2.344 | 1.91 |
| 77 | 0.011 | nd | 13.53 |
| 78 | 0.0043 | nd | 3.18 |
| 79 | 0.0052 | nd | 5.63 |
| 80 | 0.0052 | nd | 5.11 |
| 81 | 0.0057 | nd | 5.11 |
| 82 | 0.0032 | nd | 2.90 |
| 83 | 0.0069 | nd | 7.54 |
| 84 | 0.0056 | nd | 5.91 |
| 85 | 0.0048 | nd | 4.94 |
| 86 | 0.0058 | nd | 6.45 |
| 87 | 0.0287 | nd | 23.87 |
| 88 | 0.0114 | nd | 10.78 |
| 89 | 0.0028 | nd | 2.39 |
| 90 | 0.0026 | 1.38 | 2.31 |
| 91 | 0.0023 | 1.855 | 2.16 |
| 92 | 0.0036 | 1.84 | 2.71 |
| 93 | 0.0027 | 2.304 | 3.35 |
| 94 | 0.0016 | 1.057 | 1.75 |
| 95 | 0.1289 | nd | 49.89 |
| 96 | 0.0021 | 1.349 | 2.18 |
| 97 | 0.0025 | 2.402 | 2.43 |
| 98 | 0.0342 | nd | 34.67 |
| 99 | 0.0279 | nd | 24.60 |
| 100 | 0.0082 | nd | 9.66 |
| 101 | 0.0085 | nd | 9.21 |
| 102 | 0.0078 | nd | 7.38 |
| 103 | nd | 9.184 | nd |
| 104 | 0.01325 | nd | 14.18 |
| 105 | 0.0043 | 2.246 | 4.12 |
| 106 | 0.0049 | 1.966 | 8.84 |
| 107 | 0.0028 | 1.548 | 2.48 |
| 108 | 0.0027 | 2.069 | 1.99 |
| 109 | 0.0024 | 1.704 | 2.50 |
| 110 | 0.0049 | nd | 4.23 |
| 111 | 0.0021 | 1.502 | 2.55 |
| 112 | 0.003 | 2.764 | 3.46 |
| 113 | 0.0048 | 2.519 | 4.45 |
| 114 | 0.0045 | 4.763 | 4.92 |
| 115 | 0.0051 | 5.114 | 5.39 |
| 116 | 0.0036 | 3.397 | 3.93 |
| 117 | 0.0028 | 1.601 | 2.88 |
| 118 | 0.0129 | 13.653 | 25.09 |
| 119 | nd | 1.465 | nd |
| 120 | nd | 4.672 | nd |
| 121 | nd | 3.439 | nd |
| 122 | nd | 2.309 | nd |
| 123 | nd | 4.2 | nd |
| 124 | nd | 149.617 | nd |
| 125 | nd | 0.746 | nd |
| 126 | nd | 58.603 | nd |
| 127 | nd | 0.935 | nd |
| 128 | nd | 1.338 | nd |
| 129 | nd | 99.77 | nd |
| 130 | nd | 2.081 | nd |
| 131 | nd | 1.424 | nd |
| 132 | nd | 25.254 | nd |
| 133 | nd | 1.62 | nd |
| 134 | nd | 141.373 | nd |
| 135 | 0.00815 | nd | 7.61 |
| 136 | 0.0025 | nd | 2.96 |
| 137 | 0.1449 | nd | 25.74 |
| 138 | 0.0062 | nd | 7.54 |
| 139 | nd | 2.72 | nd |
| 140 | nd | 304.694 | nd |
| 141 | 0.02515 | nd | nd |
| 142 | 0.0054 | nd | 13.19 |
| 143 | 2.3066 | nd | nd |
| 144 | 0.1232 | nd | nd |
| 145 | 0.0083 | nd | 3.00 |
| 146 | 0.005 | nd | 1.19 |
| 147 | 0.0086 | nd | 3.05 |
| 148 | 0.0067 | nd | 2.64 |
| 149 | 0.0101 | nd | 5.53 |
| 150 | nd | 4.429 | nd |
| 151 | nd | 2.086 | nd |
| 152 | nd | 152.013 | nd |
| 153 | nd | 3.163 | nd |
| 154 | nd | 78.714 | nd |
| 155 | nd | 1.228 | nd |
| 156 | nd | 12.6 | nd |
| 157 | nd | 4.887 | nd |
| 158 | 0.0028 | 1.202 | 2.84 |
| 159 | nd | 0.894 | nd |
| 160 | nd | 41.852 | nd |
| 161 | 0.0041 | 3.722 | 4.52 |
| 162 | 0.0065 | nd | 5.53 |
| 163 | nd | 1.256 | nd |
| 164 | nd | 508.805 | nd |
| 165 | nd | 11.951 | nd |
| 166 | 0.00735 | nd | 7.78 |
| 167 | 0.1246 | nd | 51.14 |
| 168 | 0.0015 | 1.248 | 1.96 |
| 169 | 0.0096 | nd | 8.30 |
| 170 | 0.1681 | nd | 62.52 |
| 171 | 0.0031 | nd | 4.40 |
| 172 | 0.0079 | nd | 8.05 |
| 173 | 0.0943 | nd | 41.37 |
| 174 | 0.0009 | 0.9608 | 1.17 |
| 175 | 0.0028 | 1.918 | 3.58 |

-continued

| Example | IC$_{50}$ (µM) of p53-Hdm2 inhibition (TR-FRET) Assay 1 | IC$_{50}$ (nM) of p53-Hdm2 inhibition (TR-FRET) Assay 2 | IC$_{50}$ (µM) of p53-Hdm4 inhibition (TR-FRET) Assay 1 |
|---|---|---|---|
| 176 | nd | 97.994 | nd |
| 177 | nd | 1.15 | nd |
| 178 | nd | 1.591 | nd |
| 179 | nd | 1.277 | nd |
| 180 | nd | 2.248 | nd |
| 181 | nd | 5.129 | nd |
| 182 | nd | 0.329 | nd |
| 183 | nd | 8.775 | nd | nd = not determined.

The invention claimed is:

1. A compound of formula (I):

(I)

wherein either X is N and Y is CH, or X is CH and Y is N, or both X and Y are CH;

$R^1$ is halogen or cyano;

q is 0, 1 or 2;

$R^2$ is selected from phenyl, wherein said phenyl is optionally substituted with from 1 to 4 substituents independently selected from $(C_1-C_4)$alkyl, $(C_1-C_4)$alkoxy-, $(C_1-C_4)$alkylC(O)—, $(C_1-C_4)$alkoxyC(O)—, halo, CN, OH, —$(CH_2)_v$—N($R^8$)C(O)—$(C_1-C_7)$alkyl and $R^8(R^9)$N—C(O)—, wherein v is 0, 1 or 2, —$(CH_2)_b$—N($R^8$)C(O)—$(C_1-C_7)$alkyl, wherein b is 0, 1 or 2, $(C_1-C_7)$alkyl, wherein said $(C_1-C_7)$alkyl is optionally substituted with from 1 to 4 substituents independently selected from hydroxy, halo, CN and OH, $(C_3-C_{10})$cycloalkyl$^1$, wherein said $(C_3-C_{10})$cycloalkyl$^1$ is optionally substituted with from 1 to 4 substituents independently selected from halo, =O, —$(C_1-C_7)$alkyl, $(C_1-C_4)$alkoxy-, $(C_1-C_4)$alkylC(O)—, $(C_1-C_4)$alkoxyC(O)—, HO—C(O)—, halo-C(O)—, $R^8(R^9)$N—C(O)—, or heterocyclyl$^1$, said heterocyclyl$^1$ being optionally substituted by 1 or 2 —$(C_1-C_4)$alkyl substituents, heteroaryl$^1$, wherein said heteroaryl$^1$ is optionally substituted with from 1 to 4 substituents independently selected from $(C_1-C_4)$alkyl, $(C_1-C_4)$alkoxy-, $(C_1-C_4)$alkylC(O)—, $(C_1-C_4)$alkoxyC(O)—, halo, CN, OH, —$(CH_2)_v$—N($R^8$)C(O)—$(C_1-C_7)$alkyl and $R^8(R^9)$N—C(O)—, heterocyclyl$^3$, wherein said heterocyclyl$^3$ is optionally substituted by 1, 2, 3 or 4 $(C_1-C_3)$alkyl substituents, and is optionally substituted at 1 or 2 ring C atoms with =O, and wherein when heterocyclyl$^3$ contains a S atom in the ring, said S atom may optionally be substituted with 1 or 2 =O substituents, and heterocyclyl$^2$, wherein said heterocyclyl$^2$ is optionally substituted at a ring N atom with a substituent selected from:

$(C_1-C_7)$alkyl, $(C_1-C_4)$alkoxy-, $(C_1-C_4)$alkylC(O)—, or $(C_1-C_4)$alkoxyC(O)—, wherein said $(C_1-C_7)$alkyl, $(C_1-C_4)$alkoxy-, $(C_1-C_4)$alkylC(O)— and $(C_1-C_4)$alkoxyC(O)— are each optionally substituted at alkyl by from 1 to 4 substituents independently selected from halo, —CN, OH, $(C_1-C_4)$alkoxy-, $(C_1-C_4)$alkylC(O)—, $(C_1-C_4)$alkoxyC(O)— and $(C_1-C_4)$alkyl-C(O)—O—, HC(O)—, halo-C(O)—, $R^8(R^9)$N—C(O)—, $(C_3-C_7)$cycloalkyl-C(O)—, $(C_1-C_4)$alkylS(O)$_t$—, OH, CN, =O, heterocyclyl$^1$, said heterocyclyl$^1$ being optionally substituted by 1 or 2 $(C_1-C_4)$alkyl substituents, $(C_4-C_6)$cycloalkyl$^2$, said $(C_4-C_6)$cycloalkyl$^2$ being optionally substituted with one or two substituents independently selected from halo, $(C_1-C_4)$alkyl, =O, OH, and —$(CH_2)_r$-phenyl, wherein r is 1 or 2, and wherein said heterocyclyl$^2$ is optionally further substituted at a ring C atom with 1, 2 or 3 $(C_1-C_3)$alkyl substituents and wherein said heterocyclyl$^2$ is optionally substituted at 1 or 2 ring C atoms with =O, or optionally substituted at a ring S atom with 1 or 2 =O;

$R^3$ is $(C_1-C_3)$alkyl or H, wherein said $(C_1-C_3)$alkyl is optionally substituted with from one to 3 substituents independently selected from halo and OH;

or $R^2$ and $R^3$ together with the carbon atom to which they are attached form:

a 4, 5 or 6 membered fully saturated carbocyclic ring, wherein said carbocyclic ring is optionally substituted with from 1 to 4 substituents independently selected from halo, =O, —$(C_1-C_3)$alkyl, $(C_1-C_3)$alkoxy-, $(C_1-C_3)$alkylC(O)—, $(C_1-C_3)$alkoxyC(O)—, or heterocyclic ring A, comprising 3 carbon atoms and one nitrogen atom, wherein the arrow indicates the point of attachment to the rest of the molecule, wherein $R^{10}$ is H, $(C_1-C_4)$alkylC(O)—, $(C_1-C_4)$alkoxyC(O)—, $R^8(R^9)$N—C(O)—, $(C_3-C_7)$cycloalkyl-C(O)—, $(C_1-C_4)$alkylS(O)$_t$—, $(C_1-C_7)$alkyl, (said $(C_1-C_7)$alkyl being optionally substituted by from 1 to 4 substituents independently selected from halo and OH);

t is 0, 1 or 2;

$R^4$ is halo, methyl or methoxy;

p is 0, 1 or 2;

$R^5$ is halo or cyano;

$R^6$ is $(C_1-C_7)$alkyl, wherein optionally one, several, or all of the hydrogen atoms are replaced with deuterium, and wherein said $(C_1-C_7)$alkyl is optionally substituted with from 1 to 4 halo substituents, $(C_1-C_4)$alkoxy$(C_1-C_4)$alkyl-, heteroaryl$^1$$(C_1-C_7)$alkyl-, heterocyclyl$^1$$(C_1-C_7)$alkyl-, $R^8(R^9)N-C(O)-(CH_2)_n-$,
$R^8(R^9)N-(CH_2)_n-$, n is 1 or 2;

$R^7$ is $(C_1-C_7)$alkyl wherein optionally one, several, or all of the hydrogen atoms are replaced with deuterium;

$R^8$ is H or $(C_1-C_4)$alkyl;

$R^9$ is H or $(C_1-C_4)$alkyl;

$(C_3-C_{10})$cycloalkyl$^1$ is a fully saturated ring or ring system containing 3, 4, 5, 6, 7, 8, 9 or 10 ring carbon atoms, which can comprise fused and/or bridged rings;

$(C_4-C_6)$cycloalkyl$^2$ is a fully saturated monocyclic ring containing 4, 5 or 6 ring carbon atoms;

heterocyclyl$^1$ is a 4, 5 or 6 membered saturated or partially unsaturated monocyclic group comprising ring carbon atoms and 1 or 2 ring heteroatoms independently selected from N, O and S;

heteroaryl$^1$ is a 5 or 6 membered fully unsaturated or partially unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;

heterocyclyl$^2$ is a 4, 5, 6, 7, 8 or 9 membered fully saturated or partially unsaturated monocyclic, bicyclic or multicyclic group, which can comprise fused and/or bridged rings, and which comprises 1 ring N atom and optionally 1 ring S atom or optionally 1 ring O atom;

heterocyclyl$^3$ is a 4, 5, 6, 7, 8 or 9 membered fully saturated or partially unsaturated monocyclic, bicyclic or multicyclic group, which can comprise fused and/or bridged rings, and which comprises 1 ring S heteroatom or 1 ring O heteroatom;

with the proviso that the compound of formula (I) is not 7-((R)-sec-Butoxy)-1-(4-chloro-phenyl)-2-[4-(1-hydroxy-ethyl)-phenyl]-6-methoxy-1,4-dihydro-2H-isoquinolin-3-one:

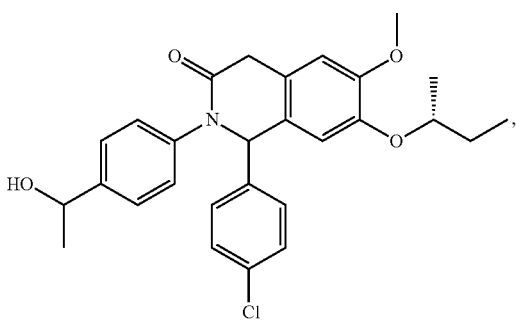 [SMILES: CC[C@@H](C)Oc1cc2c(cc1OC)CC(=O)N(c1ccc(C(C)O)cc1)C2c1ccc(Cl)cc1]

or a salt thereof.

2. The compound of formula (I) or salt thereof as claimed in claim 1, wherein both X and Y are CH.

3. The compound of formula (I) or salt thereof as claimed in claim 1, wherein $R^2$ is:

phenyl, wherein said phenyl is optionally substituted with from 1 to 4 substituents independently selected from $(C_1-C_4)$alkoxy-, halo and $-(CH_2)_v-N(R^8)C(O)-(C_1-C_7)$alkyl, $-(CH_2)-N(R^8)C(O)-(C_1-C_4)$alkyl, $(C_1-C_2)$alkyl, wherein said $(C_1-C_2)$alkyl is optionally substituted with a hydroxy substituent, $(C_3-C_{10})$cycloalkyl$^1$, wherein said $(C_3-C_{10})$cycloalkyl$^1$ is optionally substituted with from 1 to 4 substituents independently selected from halo, =O, $(C_1-C_4)$alkoxyC(O)-, HO-C(O)-, $R^8(R^9)N-C(O)-$, heteroaryl$^1$, wherein said heteroaryl$^1$ is optionally substituted with from 1 substituent selected from methyl and methoxy, optionally substituted heterocyclyl$^2$ or optionally substituted heterocyclyl$^3$, wherein the substituents of heterocyclyl$^2$ or heterocyclyl$^3$, are as claimed in claim 1.

4. The compound of formula (I) or salt thereof as claimed in claim 1 wherein $R^2$ is heterocyclyl$^2$, wherein said heterocyclyl$^2$ is optionally substituted at a ring N atom with a substituent selected from:

$(C_1-C_4)$alkyl, $(C_1-C_4)$alkylC(O)- or $(C_1-C_4)$alkoxyC(O)-, wherein said $(C_1-C_7)$alkyl, $(C_1-C_4)$alkylC(O)- and $(C_1-C_4)$alkoxyC(O)- are each optionally substituted at alkyl by from 1 to 4 substituents independently selected from halo, -CN, OH, $(C_1-C_4)$alkylC(O)-, $(C_1-C_4)$alkoxyC(O)- and $(C_1-C_4)$alkyl-C(O)-O-;

HC(O)-, halo-C(O)-, $R^8(R^9)N-C(O)-$, $(C_3-C_7)$cycloalkyl-C(O)-, $(C_1-C_4)$alkylS(O)$_t-$, =O;

heterocyclyl$^1$, said heterocyclyl$^1$ being optionally substituted by 1 or 2 $(C_1-C_4)$alkyl substituents;

$(C_4-C_6)$cycloalkyl$^2$, said $(C_4-C_6)$cycloalkyl$^2$ being optionally substituted with one or two substituents independently selected from halo, $(C_1-C_4)$alkyl or =O;

$-(CH_2)_r$-phenyl, wherein r is 1, and wherein said heterocyclyl$^2$ is optionally further substituted at a ring C atom with 1, 2 or 3 $(C_1-C_3)$alkyl substituents, and wherein said heterocyclyl$^2$ is optionally substituted at 1 or 2 ring C atoms with =O, or optionally substituted at a ring S atom with 1 or 2 =O;

or $R^2$ is heterocyclyl$^3$, wherein said heterocyclyl$^3$ is optionally substituted by 1, 2, 3 or 4 $(C_1-C_3)$alkyl substituents, and wherein when heterocyclyl$^3$ contains a S atom in the ring, said S atom may optionally be substituted with 1 or 2 =O substituents.

5. The compound of formula (I) or salt thereof as claimed in claim 1, wherein $R^2$ is heterocyclyl$^2$, wherein said heterocyclyl$^2$ is piperidinyl, azetidinyl, aza-bicyclooctyl, aza-bicyclononyl or oxa-aza-bicyclononyl, optionally substituted with:

$CH_3-C(O)-$, said $CH_3-C(O)-$, being optionally substituted with 1, 2 or 3 fluoro substituents, CN, or OH, $(C_1-C_4)$alkyl, said $(C_1-C_4)$alkyl optionally substituted with 1, 2 or 3 fluoro, 1 or 2 OH, piperidinyl, said piperidinyl being optionally substituted with methyl or ethyl, or t-butoxy-C(O)-, =O, $CH_3-NH-C(O)-$, $CH_3-N(CH_3)-C(O)-$, $NH_2-C(O)-$, $(C_1-C_2)$alkylS(O)$_2-$, methoxy-C(O)-, cyclopropyl-C(O)-, isopropoxy-C(O)-, isopropyl-NH-C(O)-, HC(O)-, FC(O)-, $CH_3-C(O)-O-CH_2-C(O)-$, oxetanyl, cyclobutanyl, tetrahydrofuranyl or cyclohexyl, or $R^2$ is heterocyclyl$^3$, wherein said heterocyclyl$^3$ is tetrahydropyranyl, said tetrahydropyranyl being optionally substituted by 1, 2, 3 or 4 methyl, or tetrahydrofuranyl, oxabicycloheptyl, dioxohydrothiopyranyl, oxohydrothiopyranyl, oxabicyclooctyl, oxabicyclononyl, dioxo-thia-bicyclooctyl, dioxo-thia-bicyclononyl or oxa-bicyclooctyl.

6. The compound of formula (I) or salt thereof as claimed in claim 1 wherein $R^2$ is piperidinyl substituted at N by $CH_3-C(O)-$, said $CH_3-C(O)-$, being optionally substituted with 1, 2 or 3 fluoro substituents, ($C_1$-$C_4$)alkyl, said ($C_1$-$C_4$)alkyl optionally substituted with 1, 2 or 3 fluoro, 1 or 2 OH, wherein ($C_1$-$C_4$)alkyl is in particular t-butyl, isopropyl, n-propyl, ethyl or methyl, or t-butoxy-C(O)—, =O, $CH_3$—NH—C(O)—, $CH_3$—N($CH_3$)—C(O)— or $NH_2$—C(O)—, ($C_1$-$C_2$)alkylS(O)$_2$—, methoxy-C(O)—, cyclopropyl-C(O)—, isopropoxy-C(O)—, isopropyl-NH—C(O)—, HC(O)—, FC(O)—, $CH_3$—C(O)—O—$CH_2$—C(O)—, oxetanyl, cyclobutanyl, tetrahydrofuranyl or cyclohexyl, or $R^2$ is tetrahydropyranyl.

7. The compound of formula (I) or salt thereof as claimed in claim 1, wherein $R^3$ is ($C_1$-$C_3$)alkyl.

8. The compound of formula (I) or salt thereof as claimed in claim 1, wherein $R^2$ and $R^3$ together with the carbon atom to which they are attached form:
a 4 or 5 membered fully saturated carbocyclic ring, or
heterocyclic ring A, wherein $R^{10}$ is H, t-butoxy-C(O)—, $CH_3$—C(O)—, $CH_3$—O—C(O)—, $CH_3$—NH—C(O)—, $CH_3$—N($CH_3$)—C(O)—, $NH_2$—C(O)—, cyclopropyl-C(O)— or ($C_1$-$C_2$)alkylS(O)$_2$—.

9. The compound of formula (I) or salt thereof as claimed in claim 1 wherein $R^5$ is chloro.

10. The compound of formula (I) or salt thereof as claimed in claim 1 wherein $R^6$ is methyl and $R^7$ is isopropyl.

11. The compound of formula (I) or salt thereof as claimed in claim 1 wherein the stereochemistry of the compound of formula (I) is as shown in formula (Ia) below:

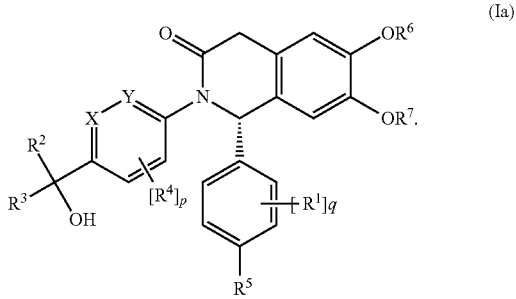

(Ia)

12. The compound of formula (I) or salt thereof as claimed in claim 1, with the proviso that $R^2$ is not:
($C_1$-$C_7$)alkyl or ($C_1$-$C_2$)alkyl, wherein said ($C_1$-$C_7$)alkyl or ($C_1$-$C_2$)alkyl are optionally substituted with from 1 to 4 substituents independently selected from hydroxy, halo, CN and OH.

13. The compound of formula (I) or salt thereof as claimed in claim 1, wherein $R^3$ is methyl, and $R^2$ is as claimed in claim 1, with the proviso that $R^2$ is not:
($C_1$-$C_7$)alkyl or ($C_1$-$C_2$)alkyl, wherein said ($C_1$-$C_7$)alkyl or ($C_1$-$C_2$)alkyl are optionally substituted with from 1 to 4 substituents independently selected from hydroxy, halo, CN and OH.

14. A pharmaceutical composition comprising a therapeutically effective amount of a compound of formula (I) or salt thereof as defined in claim 1, and one or more pharmaceutically acceptable carriers.

15. A method of inhibiting MDM2 and/or MDM4 activity in a subject, comprising the step of administering to a subject a therapeutically effective amount of a compound of formula (I) or salt thereof of claim 1.

16. A method for the treatment of cancer mediated by the activity of MDM2 and/or MDM4 comprising the step of administering to a subject a therapeutically effective amount of a compound of formula (I) or salt thereof as defined in claim 1.

17. A compound of the formula (I) or salt thereof as claimed in claim 1, in combination with one or more therapeutically active agents.

18. A compound selected from (S)-1-(4-chloro-phenyl)-2-{4-[(S)-1-hydroxy-1-(tetrahydro-pyran-4-yl)-ethyl]-phenyl}-7-isopropoxy-6-methoxy-1,4-dihydro-2H-isoquinolin-3-one and a pharmaceutically acceptable salt thereof.

* * * * *